United States Patent
Hawley et al.

(10) Patent No.: US 11,230,532 B2
(45) Date of Patent: *Jan. 25, 2022

(54) PYRIMIDINES AND VARIANTS THEREOF, AND USES THEREFOR

(71) Applicant: Afferent Pharmaceuticals Inc., San Mateo, CA (US)

(72) Inventors: Ronald Charles Hawley, Oakland, CA (US); Prabha Ibrahim, Mountainview, CA (US); Anthony P. Ford, Palo Alto, CA (US); Joel R. Gever, Los Altos, CA (US)

(73) Assignee: AFFERENT PHARMACEUTICALS, INC., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/846,452

(22) Filed: Apr. 13, 2020

(65) Prior Publication Data

US 2020/0239421 A1 Jul. 30, 2020

Related U.S. Application Data

(63) Continuation of application No. 16/080,840, filed as application No. PCT/US2017/023126 on Mar. 20, 2017, now Pat. No. 10,662,162.

(60) Provisional application No. 62/313,334, filed on Mar. 25, 2016.

(51) Int. Cl.
  *C07D 239/48* (2006.01)
  *C07D 401/12* (2006.01)
  *C07D 403/12* (2006.01)

(52) U.S. Cl.
  CPC ......... *C07D 239/48* (2013.01); *C07D 401/12* (2013.01); *C07D 403/12* (2013.01)

(58) Field of Classification Search
  CPC .. C07D 239/48; C07D 401/12; C07D 403/12; A61P 11/14; A61P 29/00
  USPC ....................................................... 544/298
  See application file for complete search history.

(56) References Cited

U.S. PATENT DOCUMENTS

| | | | |
|---|---|---|---|
| 2,953,567 A | 9/1960 | Hitchings et al. | |
| 8,003,788 B2 | 8/2011 | Dvorak et al. | |
| 8,846,705 B2 | 9/2014 | Broka et al. | |
| 9,724,346 B2 | 8/2017 | Ford et al. | |
| 10,195,198 B2 | 2/2019 | Ford et al. | |
| 10,206,922 B2 | 2/2019 | Ford et al. | |
| 10,662,162 B2 * | 5/2020 | Hawley ................ | C07D 239/48 |
| 10,822,311 B2 * | 11/2020 | Hawley ................ | C07D 405/12 |
| 2004/0157893 A1 | 8/2004 | Bebbington et al. | |
| 2007/0049610 A1 | 3/2007 | Dillon et al. | |
| 2008/0207655 A1 | 8/2008 | Dillon et al. | |
| 2010/0286390 A1 | 11/2010 | Shigeta et al. | |
| 2011/0077242 A1 | 3/2011 | Broka et al. | |
| 2012/0135993 A1 | 5/2012 | Leach et al. | |

FOREIGN PATENT DOCUMENTS

| | | |
|---|---|---|
| CN | 108834412 A | 11/2018 |
| KR | 20080049802 A | 6/2008 |
| KR | 20180122406 A | 11/2018 |
| MX | 2018011136 A | 1/2019 |
| WO | 2000059893 A1 | 10/2000 |
| WO | 2005095359 A1 | 10/2005 |
| WO | 2007025899 A1 | 3/2007 |
| WO | 2007025900 A1 | 3/2007 |
| WO | 2007025901 A1 | 3/2007 |
| WO | 2007025925 A1 | 3/2007 |
| WO | 2008104472 A1 | 9/2008 |
| WO | 2008104474 A1 | 9/2008 |
| WO | 2014200078 A1 | 12/2014 |
| WO | 2017165255 A1 | 9/2017 |
| WO | WO2017160569 A1 | 9/2017 |

OTHER PUBLICATIONS

NPL-PUBCHEM-CID608444-2005.
Bredereck, H., Mechanism of the new purine synthesis, Justus Llebigs Annalen der Chemie, 1964, 88-92, 673.
Bredereck, Hellmut, Mechanism of the new purine synthesis, Justus Llebigs Annalen der Chemie, 1964, 88-92, 673.

(Continued)

*Primary Examiner* — Tracy Vivlemore
*Assistant Examiner* — Ebenezer O Sackey
(74) *Attorney, Agent, or Firm* — Yong Zhao; Catherine D. Fitch

(57) ABSTRACT

The present disclosure provides pyrimidine compounds of Formula 1 and uses thereof, for example, for the potential treatment of diseases associated with P2X purinergic receptors:

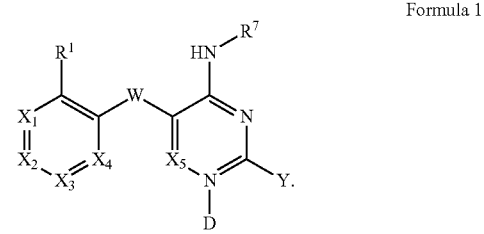

Formula 1

In certain aspects, the present disclosure provides P2X3 and/or P2X2/3 antagonists which are useful, for example, for the potential treatment of visceral organ, cardiovascular and pain-related diseases, conditions and disorders.

12 Claims, No Drawings

(56) References Cited

OTHER PUBLICATIONS

Carter, Identification and SAR of novel diaminopyrimidines. Part 1: The discovery of RO-4, a dual P2X3/PsX2/3 antagonist for the treatment of pain, Bioorganic& Medicinal Chemistry Letters, 2009, 1628-1631, 19.
Falco, Elvira A., 5-Arylthiopyrimidines. I. 2,4-Diamino Derivatives, Journal of Organic Chemistry, 1961, 1143-1146, 26.
Jahangir, Alam, Identification and SAR of novel diaminopyrimidines. Part 2: The discovery of RO-51, a potent and selective, dual P2X3/P2X2/3 antagonist for the treatment of pain, Bioorganic & Medicinal Chemistry Letters, 2009, 1632-1635, 19.
NPL-PubChem-CID18762697-2007.
Zhao, Synthesis and antibacterial activity of 2, 4-diamino-5-(substituted aniline)pyrimidines, Yaoxue Xuebao (Acta Pharmaceutica Sinica), 1987, 541-547, 22(7).
Zhao, Synthesis and antibacterial activity of 2, 4-diamino-5-(substituted aniline)pyrimidines, Yaoxue Xuebao, 1987, 541-547, 22(7).
Registry [online], Columbus, Ohio, US, Nov. 16, 1984 [4 pages].
Chinese Search Report, Application 2017800195340, datred Oct. 30, 2020, 4 pages.
Chinese Search Report, Application 2017800195340, dated Oct. 30, 2020, 3 pages. English Translation.
U.S. Appl. No. 16/080,840, filed Aug. 29, 2018.

* cited by examiner

PYRIMIDINES AND VARIANTS THEREOF, AND USES THEREFOR

CROSS-REFERENCE TO RELATED APPLICATIONS

The present application is a continuation of application Ser. No. 16/080,840, filed Aug. 29, 2018, which is a 371 national phase application of international application no. PCT/US2017/023126, filed Mar. 20, 2017, which claims the benefit of U.S. Provisional Application No. 62/313,334, filed Mar. 25, 2016; hereby incorporated by reference in its entirety.

FIELD OF THE INVENTION

The present disclosure pertains to pyrimidine compounds and variants thereof, as well as the use thereof, for example, for the potential treatment of diseases associated with P2X purinergic receptors, and more particularly to P2X3 and/or P2X2/3 antagonists usable for the potential treatment of visceral, cardiovascular and pain-related diseases, conditions and disorders.

BACKGROUND OF THE INVENTION

The information provided herein and references cited are provided solely to assist the understanding of the reader, and does not constitute an admission that any of the references or information is prior art to the present invention.

Purines, acting via cell surface purinoceptors, have been implicated as having a variety of physiological and pathological roles. ATP, and to a lesser extent, adenosine, can stimulate sensory nerve endings resulting in intense pain and irritation and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoceptors are G-protein coupled receptors, while the P2X-purinoceptors are a family of ATP-gated cation channels. Purinergic receptors, in particular, P2X receptors, are known to form homomultimers or heteromultimers. To date, cDNAs for seven P2X subunits have been cloned, (P2X1, P2X2, P2X3, P2X4, P2X5, P2X6 and P2X7), each able to produce homotrimeric channels and some able to form heterotrimeric receptors (e.g. P2X2/3, P2X4/6 and P2X1/5). The structure and chromosomal mapping of mouse and human genomic P2X3 receptor subunits have also been described. In vitro, co-expression of P2X2 and P2X3 receptor subunits is necessary to produce ATP-gated currents with the properties seen in some sensory neurons.

P2X3 receptor subunits are found on primary sensory afferents innervating rodent and human organs and tissues. Data exist suggesting that ATP may be released from epithelial/endothelial cells of the hollow organs or from muscle beds as a result of distention, movement, injury infection and inflammation. ATP released in this manner may serve a role in conveying information to nearby sensory neurons located. P2X receptors have been studied in a number of neurons, including sensory, sympathetic, parasympathetic, mesenteric, and central neurons. Some studies indicate that P2X purinergic receptors play a role in afferent neurotransmission from the many organ systems and tissues, and that modulators of P2X receptors are potentially useful in the treatment of functional organ or tissue disorders and attenuate common chronic symptoms and signs of important diseases or conditions.

Evidence also suggests a role of endogenous ATP and purinergic receptors in nociceptive responses in mice. ATP-induced activation of P2X3 receptors on dorsal root ganglion nerve terminals in the dorsal horn of the spinal cord has been shown to stimulate release of glutamate, a key neurotransmitter involved in nociceptive signalling. P2X3 receptors have been identified on nociceptive neurons in the tooth pulp. ATP released from distressed or damaged cells in many tissue systems may thus lead to pain by activating P2X3 containing receptors on nociceptive sensory nerve endings. This is consistent with observations of the induction of pain and discomfort by intradermally applied ATP in the human blister-base model or following its infusion into a muscle bed. P2X antagonists have been shown to be analgesic in many animal models. This evidence suggests that P2X3 containing channels are involved in the sensitization of nerves that drives and maintains heightened nociception signalling, and that modulators of P2X receptors are potentially useful as inhibitors of sensitization and may have applicability as analgesics, anti-pruritics, antitussives and treatments for autonomic hyperresponsiveness.

The use of antagonists of P2X2 and P2X2/3 for the treatment of pain was discussed by Carter, et al., (*Bioorganic and Medical Chemistry Letters*, 2009, 19(6), 1628-1635; doi:10.1016/j.bmcl.2009.02.003). The structure-activity relationship of a series of diaminopyrimidines was studied. The selectivity of these compounds for P2X3 and P2X2/3 vs. other P2X purinoceptors was also discussed.

Vandenbeuch et al. (*J. Physiol*, 2015, 593(5), 1113-1125; doi: 10/1113/jphysiol.2014.281014) discuss the role of both P2X3 and P2X2/3 channels in taste transduction.

SUMMARY OF THE INVENTION

Described herein are compounds of Formula 1 or their pharmaceutically acceptable salts which are inhibitors of P2X3 and/or P2X2/3 receptors. Also described herein are uses of these compounds in the potential treatment or prevention of a P2X3- and/or P2X2/3-associated disease or disorder. Also disclosed herein are compositions comprising one or more of these compounds. Further disclosed herein are uses of these compositions in the potential treatment or prevention of a P2X3- and/or P2X2/3-associated disease or disorder.

DETAILED DESCRIPTION OF THE INVENTION

In a first aspect of the present disclosure, there are provided compounds of Formula 1:

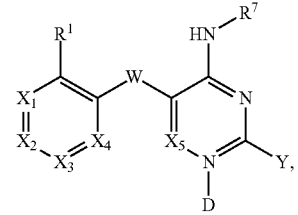

Formula 1 or a pharmaceutically acceptable salt thereof, wherein:

W is selected from CH$_2$, O, S and NR, wherein R is H, or C$_{1-3}$ alkyl;

X$_1$ is N or CR$^2$;

X$_2$ is N or CR$^3$;

X$_3$ is N or CR$^4$;

X$_4$ is N or CR$^5$, provided, however not more than two of X$_1$, X$_2$, X$_3$, or X$_4$ are N at the same time;

X$_5$ is N or CR$^6$, provided, however, when X$_1$ is CR$^2$, X$_2$ is CR$^3$, X$_3$ is CR$^4$ and X$_4$ is CR$^5$, W is not O or —CH$_2$—;

Y is selected from hydrogen and —NHR$^d$, wherein R$^d$ is selected from: hydrogen; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalkyl; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{1-12}$-hydroxycarbonylalkyl; C$_{2-12}$-hydroxylalkyloxycarbonylalkyl; C$_{5-12}$-aryl; C$_{6-12}$-arylalkyl; C$_{5-12}$-aryl sulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl;

D is an optional oxygen;

R$^1$ is selected from C$_{1-12}$-alkyl; C$_{2-12}$-alkenyl; C$_{2-12}$-alkynyl; C$_{3-12}$-cycloalkyl; C$_{3-12}$-cycloalkenyl; halo; C$_{1-12}$-haloalkyl; and C$_{1-12}$-hydroxyalkyl;

R$^2$, R$^3$, R$^4$ and R$^5$ are each independently selected from hydrogen; C$_{1-12}$-alkyl; C$_{2-12}$-alkenyl; C$_{2-12}$-alkynyl; amino; halo; amido; C$_{1-12}$-haloalkyl; C$_{1-12}$-alkoxy; hydroxy; C$_{1-12}$-haloalkoxy; nitro; C$_{1-12}$-hydroxyalkyl; C$_{2-12}$-alkoxyalkyl; C$_{1-12}$-hydroxyalkoxy; C$_{3-12}$-alkynylalkoxy; C$_{1-12}$-alkylsulfonyl; C$_{5-12}$-arylsulfonyl; cyano; C$_{6-12}$-aryl; C$_{5-12}$-heteroaryl; C$_{3-12}$-heterocyclyl; C$_{4-12}$-heterocyclylalkoxy; C$_{6-12}$-aryloxy; C$_{5-12}$-heteroaryloxy; C$_{7-12}$-arylalkyloxy; C$_{6-12}$-heteroaralkyloxy; optionally substituted phenoxy; —(CH$_2$)$_m$—(Z)$_n$—(CO)—R$^f$ and —(CH$_2$)$_m$—(Z)$_n$—SO$_2$—(NR$^g$)$_{n'}$—R$^f$, where m, n and n' are each independently 0 or 1, Z is O or NR$^g$, R$^f$ is selected from hydrogen, C$_{1-12}$-alkyl, hydroxy, C$_{1-12}$-alkoxy, amino, C$_{1-12}$-hydroxyalkyl and C$_{2-12}$-alkoxyalkyl and each R$^g$ is independently hydrogen or C$_{1-12}$-alkyl;

or R$^3$ and R$^4$ together with the atoms to which they are attached may form a five or six-membered ring that optionally includes one or two heteroatoms selected from O, S and N;

or R$^2$ and R$^3$ may together form an alkylene dioxy; or R$^2$ and R$^3$ together with the atoms to which they are attached may form a five or six-membered ring that optionally includes one or two heteroatoms selected from O, S and N;

R$^6$ is selected from hydrogen and C$_{1-12}$-alkyl; and

R$^7$ is selected from hydrogen; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalky; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{2-12}$-hydroxycarbonylalkyl; C$_{3-12}$-hydroxyalkyloxycarbonylalkyl; C$_{6-12}$-aryl; C$_{7-12}$-arylalkyl; C$_{6-12}$-aryl sulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl.

In certain aspects of the present disclosure, compounds of Formula 1 have greater than ten-fold (10×) selectivity for the P2X3 homotrimeric receptor compared to the P2X2/3 heterotrimeric receptor. In another aspect, compounds of Formula 1 have greater than 20× selectivity for P2X3 receptor compared to P2X2/3 receptor. In another aspect, compounds of Formula 1 have greater than 30× selectivity for P2X3 receptor compared to P2X2/3 receptor. In another aspect, compounds of Formula 1 have greater than 40× selectivity for P2X3 receptor compared to P2X2/3 receptor. In another aspect, compounds of Formula 1 have greater than 50× selectivity for P2X3 receptor compared to P2X2/3 receptor. In another aspect, compounds of Formula 1 have greater than 1×, but less than 10× selectivity for P2X3 receptor compared to P2X2/3 receptor.

In a second aspect, the present disclosure provides methods for treating a disease mediated by a P2X3 receptor antagonist, a P2X2/3 receptor antagonist, or both, said method comprising administering to a subject in need thereof an effective amount of a compound of Formula 1:

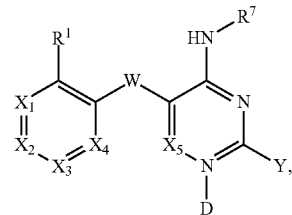

Formula 1 or a pharmaceutically acceptable salt thereof, wherein:

W is CH$_2$, NR (where R is H, or C$_{1-3}$ alkyl), O or S;

X$_1$ is N or CR$^2$;

X$_2$ is N or CR$^3$;

X$_3$ is N or CR$^4$;

X$_4$ is N or CR$^5$, provided, however not more than two of X$_1$, X$_2$, X$_3$, or X$_4$ are N at the same time;

X$_5$ is N or CR$^6$, provided, however, when X$_1$ is C—R$^2$, X$_2$ is C—R$^3$, X$_3$ is C—R$^4$ and X$_4$ is C—R$^5$, W is not O or —CH$_2$—;

Y is selected from hydrogen and —NHR$^d$, wherein R$^d$ is selected from; C$_{1-12}$-alkyl; C$_{3-12}$-cycloalkyl; C$_{4-12}$-cycloalkylalkyl; C$_{1-12}$-haloalkyl; C$_{1-12}$-haloalkoxy; C$_{1-12}$-hydroxyalkyl; C$_{2-12}$-alkoxyalkyl; acetyl; C$_{1-12}$-alkylsulfonyl; C$_{2-12}$-alkylsulfonylalkyl; C$_{2-12}$-aminocarbonyloxyalkyl; C$_{1-12}$-hydroxycarbonylalkyl; C$_{2-12}$-hydroxylalkyloxycarbonylalkyl; C$_{5-12}$-aryl; C$_{6-12}$-arylalkyl; C$_{5-12}$-aryl sulfonyl; C$_{5-12}$-heteroaryl; C$_{6-12}$-heteroarylalkyl; C$_{5-12}$-heteroarylsulfonyl; C$_{3-12}$-heterocyclyl; and C$_{4-12}$-heterocyclylalkyl;

D is an optional oxygen;

R$^1$ is selected from C$_{1-12}$-alkyl; C$_{2-12}$-alkenyl; C$_{2-12}$-alkynyl; C$_{3-12}$-cycloalkyl; C$_{3-12}$-cycloalkenyl; halo; C$_{1-12}$-haloalkyl; and C$_{1-12}$-hydroxyalkyl;

R$^2$, R$^3$, R$^4$ and R$^5$ are each independently selected from hydrogen; C$_{1-12}$-alkyl; C$_{2-12}$-alkenyl; C$_{2-12}$-alkynyl; amino; halo; amido; C$_{1-12}$-haloalkyl; C$_{1-12}$-alkoxy; hydroxy; C$_{1-12}$-haloalkoxy; nitro; C$_{1-12}$-hydroxyalkyl; C$_{2-12}$-alkoxyalkyl; C$_{1-12}$-hydroxyalkoxy; C$_{3-12}$-alkynylalkoxy; C$_{1-12}$-alkylsulfonyl; C$_{5-12}$-arylsulfonyl; cyano; C$_{6-12}$-aryl; C$_{5-12}$-heteroaryl; C$_{3-12}$-heterocyclyl; C$_{4-12}$-heterocyclylalkoxy; C$_{6-12}$-aryloxy; C$_{5-12}$-heteroaryloxy; C$_{7-12}$-arylalkyloxy; C$_{6-12}$-heteroaralkyloxy; optionally substituted phenoxy; —(CH$_2$)$_m$—(Z)$_n$—(CO)—R$^f$ and —(CH$_2$)$_m$—(Z)$_n$—SO$_2$—(NR$^g$)$_{n'}$—R$^f$, where m, n and n' are each independently 0 or 1, Z is O or NR$^g$, R$^f$ is selected from hydrogen, C$_{1-12}$-alkyl, hydroxy, C$_{1-12}$-alkoxy, amino, C$_{1-12}$-hydroxyalkyl and C$_{2-12}$-alkoxyalkyl and each $R^g$ is independently hydrogen or $C_{1-12}$-alkyl;

or $R^3$ and $R^4$ together with the atoms to which they are attached may form a five or six-membered ring that optionally includes one or two heteroatoms selected from O, S and N;

or $R^2$ and $R^3$ may together form an alkylene dioxy; or $R^2$ and $R^3$ together with the atoms to which they are attached may form a five or six-membered ring that optionally includes one or two heteroatoms selected from O, S and N;

$R^6$ is selected from hydrogen and $C_{1-12}$-alkyl; and $R^7$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{3-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl and $C_{4-12}$-heterocyclylalkyl.

Exemplary diseases and conditions that are rationally treated by a P2X3 receptor antagonist, or a P2X2/3 receptor antagonist, or antagonist at both channels, contemplated herein include disorders of the urinary tract (aka uropathy), disease states associated with the urinary tract (aka urinary tract disease states), overactive bladder (aka detrusor hyperactivity or urge incontinence), outlet obstruction (aka benign prostatic hypertrophy), outlet insufficiency, pelvic hypersensitivity, bladder pain syndrome, endometriosis, respiratory symptoms, cough or urge to cough associated with a respiratory disease, asthma, hypertension, heart failure, dyspnea (aka shortness of breath), sleep apnea, signs and symptoms of carotid body hypertonicity and hyperreflexia (such as breathlessness and fatigue), sympathetic overactivity in a subject, and the like. Additionally, signs and symptoms of upper respiratory tract infection, including the cold and flu symptoms of pharyngitis, rhinitis, nasal congestion, hypertussivity, rhinorrhea and sneezing targeted conditions for treatment with an antagonist for P2X3 containing receptors.

In other instances the disease may be a disease associated with pain. The disease associated with pain may be: inflammatory pain; surgical pain; visceral pain; dental pain; premenstrual pain; central pain; pain due to burns; migraine or cluster headaches; nerve injury; neuropathy; neuritis; neuralgias; poisoning; ischemic injury; interstitial cystitis; cancer pain; pain of viral, parasitic or bacterial infection; post-traumatic injury pain; or pain associated with irritable bowel syndrome and inflammatory bowel diseases.

In additional instances the disorders or disease states may include hepatocellular carcinoma, tinnitus, migraine, itch (pruritus), diabetes mellitus, endometriosis and dysmenorrhea, peripheral artery occlusive disease (PAOD), intermittent claudication, acute and chronic heart failure, metabolic syndrome, chronic obstructive pulmonary disease (COPD), atopic dermatitis and other forms of eczema or dermatitis, prurigo nodularis, bursitis, tendonitis, fibromyalgia, gout, joint replacement, lichen sclerosus, psoriasis and psoriatic arthritis, cold sores, kidney stones, gall stones, smell disorders, taste disorders including dysgeusia or burning mouth syndrome, binge eating disorders, hyperphagia, obesity, gastro esophageal reflux disease (GERD), or pain from sickle cell anemia and ischemia.

The present disclosure also provides pharmaceutical compositions comprising the compounds, methods of using the compounds, and methods of preparing the compounds.

Unless otherwise stated, the following terms used in this Application, including the specification and claims, have the definitions given herein.

It must be noted that, as used in the specification and the appended claims, the singular forms "a", "an", and "the" include plural referents unless the context clearly dictates otherwise.

"Agonist" refers to a compound that enhances the activity of another compound or receptor site.

"Antagonist" refers to a compound that diminishes or prevents the action of another compound or receptor site. Antagonist selectivity for P2X3 subunit containing trimeric channel types, for example, is of increasing interest in the search for therapeutically preferred medicines. This is due to increased understanding, driven by clinical experience with first generation antagonists, of the potential contribution of blockade of distinct trimers with desirable (e.g., efficacy as antitussive, antihypertensive and antihyperalgesic) and less desirable (e.g., tolerability events such as hypogeusia, oropharyngeal dysesthesia) outcomes in treated patients.

Improved clinical effectiveness (efficacy vs. tolerability profile) is expected based on findings suggesting that channels formed solely from P2X3 subunits (homomeric P2X3 or P2X3.3.3) are found in nociceptive sensory fibers responsible for mediating irritative, painful and bothersome ("targeted") pathological symptoms such as cough, emanating mostly from neural crest derived sensory neurons of DRG and certain cranial (trigeminal, jugular) ganglia. In contrast, P2X channels involved in ATP mediation of the sense of taste, innervating the gustatory papillae of the tongue and oropharynx, are formed in placodally derived sensory neurons, notably from geniculate, petrosal and nodose cranial ganglia, as the heterotrimeric P2X2/3 (i.e., P2X2.3.3 and P2X2.2.3) channels found to be expressed in these cells.

Accordingly, antagonists with increased potency ($pIC_{50}$) at P2X3 homotrimers relative to P2X2/3 heterotrimers achieve greater attenuation of nociceptor sensitization and symptoms of pain, urgency, irritation, dyspnea, fatigue and autonomic hyperreflexia, before exposures are reached that introduce gustatory disturbance and raise issues of tolerability and patient compliance.

"Alkyl" means the monovalent linear or branched saturated hydrocarbon moiety, consisting solely of carbon and hydrogen atoms, having from one to twelve carbon atoms.

"Lower alkyl" refers to an alkyl group of one to six carbon atoms, i.e. $C_{1-6}$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear or branched saturated divalent hydrocarbon radical of one to twelve carbon atoms or a branched saturated divalent hydrocarbon radical of three to six carbon atoms, e.g., methylene, ethylene, 2,2-dimethylethylene, propylene, 2-methylpropylene, butylene and pentylene.

"Alkenyl" means a linear monovalent hydrocarbon radical of two to twelve carbon atoms or a branched monovalent hydrocarbon radical of three to twelve carbon atoms, containing at least one double bond. Examples of alkenyl groups include, but are not limited to, ethenyl (vinyl, —CH=CH$_2$), 1-propenyl (—CH=CH—CH$_3$), 2-propenyl (allyl, —CH—CH=CH$_2$) and isopropenyl (1-methylvinyl, —C(CH$_3$)=CH$_2$).

"Alkynyl" means a linear monovalent hydrocarbon radical of two to twelve carbon atoms or a branched monovalent hydrocarbon radical of three to twelve carbon atoms, containing at least one triple bond. Examples of alkynyl groups include, but are not limited to, ethynyl (—C≡CH) and 2-propynyl (propargyl, —CH$_2$C≡CH).

"Alkoxy" means a moiety of the formula —OR, wherein R is an alkyl moiety as defined herein. Examples of alkoxy moieties include, but are not limited to, methoxy, ethoxy, and iso-propoxy.

"Alkoxyalkyl" means a moiety of the formula R$^a$—O—R$^b$—, where R$^a$ is alkyl and R$^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxy-propyl, and 1-(2-methoxyethyl)-3-methoxypropyl.

"Alkoxyalkoxyalkl" means a group of the formula —R—O—R'—O—R" wherein R and R' each are alkylene and R" is alkyl as defined herein.

"Alkylcarbonyloxyalkyl" means a group of the formula —R—O—C(O)—R' wherein R is alkylene and R' is alkyl as defined herein.

"Alkylcarbonyl" means a moiety of the formula —R'—R", where R' is —C(=O)— and R" is alkyl as defined herein.

"Alkylsulfonyl" means a moiety of the formula —R'—R", where R' is —SO$_2$— and R" is alkyl as defined herein.

"Alkylsulfonylalkyl" means a moiety of the formula —R'—R"—R" where R' is alkyl, R" is —SO$_2$— and R" is alkyl as defined herein.

"Alkylamino" means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkali metal ion" means a monovalent ion of a group I metal such as lithium, sodium, potassium, rubidium or cesium, preferably sodium or potassium.

"Alkaline earth metal ion" means a divalent ion of a group II metal such as berylium, magnesium, calcium, strontium or barium, preferably magnesium or calcium.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, and ethylaminoethyl.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl and N-methyl-N-ethylaminoethyl.

"Aminoalkyl" means a group —R—R' wherein R' is amino and R is alkylene as defined herein. "Aminoalkyl" includes aminomethyl, aminoethyl, 1-aminopropyl, and 2-aminopropyl.

"Aminoalkoxy" means a group —OR—R$^1$ wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a groups —R—O—C(=O)—R' wherein R' is amino and R is alkylene as defined herein.

"Aminosulfonyl" means a group —SO$_2$—NR'R" wherein R' and R" each independently is hydrogen or alkyl. "Aminosulfonyl" as used herein thus encompasses "alkylaminosulfonyl" and "dialkylaminosulfonyl".

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenyl sulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl and ethylenedioxyphenyl, including partially hydrogenated derivatives thereof.

"Arylalkyl" and "Aralkyl", which may be used interchangeably, mean a radical —R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" or "Arylalkyloxy" means a group of the formula —O—R—R" wherein R is alkylene and R' is aryl as defined herein.

"Cyanoalkyl" "means a moiety of the formula —R'—R", where R' is alkylene as defined here-in and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl and cycloheptyl, including partially unsaturated derivatives thereof.

"Cycloalkenyl" means a monovalent unsaturated carbocyclic moiety consisting of mono- or bicyclic rings containing at least one double bond. Cycloalkenyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkenyl moieties include, but are not limited to, cyclopropenyl, cyclobutenyl, cyclopentenyl, cyclohexenyl, cycloheptenyl.

"Cycloalkylalkyl" means a moiety of the formula —R'—R", where R' is alkylene and R" is cycloalkyl as defined herein.

"Cycloalkylene" means a divalent saturated carbocyclic radical consisting of mono- or bi-cyclic rings. Cycloalkylene can optionally be substituted with one or more substituents, wherein each substituent is independently hydroxy, alkyl, alkoxy, halo, haloalkyl, amino, monoalkylamino, or dialkylamino, unless otherwise specifically indicated.

"Cycloalkylalkylene" means a moiety of the formula —R'—R"—, where R' is alkylene and R" is cycloalkylene as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl and methylaminosulfonylpropyl.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl and acridinyl, including partially hydrogenated derivatives thereof.

Heteroarylalkyl" or "heteroaralkyl" means a group of the formula —R—R' wherein R is alkylene and R' is heteroaryl as defined herein.

"Heteroarylsulfonyl" means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

"Heterocyclylalkoxy means a group of the formula —O—R—R' wherein R is alkylene and R' is heterocyclyl as defined herein.

The terms "halo", "halogen" and "halide", which may be used interchangeably, refer to a substituent fluoro, chloro, bromo, or iodo. In some embodiments, halo refers to a fluoro substituent.

"Haloalkyl" means alkyl as defined herein in which one or more hydrogen has been replaced with same or different halogen. In some embodiments, haloalkyl is a fluoroalkyl; in some embodiments, the haloalkyl is a perfluoroalkyl. Exemplary haloalkyls include, but are not limited to, —CH$_2$Cl, —CH$_2$CF$_3$, —CH$_2$CCl$_3$ and perfluoroalkyl (e.g., —CF$_3$).

"Haloalkoxy" means a moiety of the formula —OR, wherein R is a haloalkyl moiety as defined herein. In some embodiments, haloalkoxy is a fluoroalkoxy; in some embodiments, the haloalkoxyl is a perfluoroalkoxy. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl and tetrahydroisoquinolinyl.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxy-propyl, 2-hydroxy-1-hydroxymethylethyl, 2,3-dihydroxybutyl, 3,4-dihydroxybutyl and 2-(hydroxymethyl)-3-hydroxypropyl.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxyl-5-methyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

"Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxy-cyclohexyl.

"Urea" or "ureido" means a group of the formula —NR'—C(O)—NR"R'" wherein R, R" and R" each independently is hydrogen or alkyl.

"Carbamate" means a group of the formula —O—C(O)—NR'R" wherein R' and R" each independently is hydrogen or alkyl.

"Carboxy" means a group of the formula —C(O)OH.

"Sulfonamido" means a group of the formula —SO$_2$—NR'R" wherein R', R" and R" each independently is hydrogen or alkyl.

"Nitro" means —NO$_2$.

"Cyano" mean —CN.

"Phenoxy" means a phenyl ring that is substituted with at least one —OH group.

"Acetyl" means —C(=O)—CH$_3$.

"C$_{n-m}$" is used as a prefix before a functional group wherein 'n' and 'm' are recited as integer values (i.e. 0, 1, 2, 12), for example C$_{1-12}$-alkyl or C$_{5-12}$-heteroaryl. The prefix denotes the number, or range of numbers, of carbons atoms present in the functional group. In the case of ring systems the prefix denotes the number of ring atoms, or range of the number of ring atoms, whether the ring atoms are carbon atoms or heteroatoms. In the case of functional groups made up a ring portion and a non-ring portion (i.e. "arylalkyl" is made up of an aryl portion and an alkyl portion) the prefix is used to denote how many carbon atoms and ring atoms are present in total. For example, with arylalkyl, "C$_7$-arylalkyl" may be used to denote "phenyl-CH$_2$—". In the case of some functional groups zero carbon atoms may be present, for example C$_0$-aminosulfonyl (i.e. —SO$_2$—NH$_2$, with both potential R groups as hydrogen) the '0' indicates that no carbon atoms are present.

"Peptide" means an amide derived from two or more amino acids by combination of the amino group of one acid with the carboxyl group. "Monopeptide" means a single amino acid, "dipeptide" means an amide compound comprising two amino acids, "tripeptide" means an amide compound comprising three amino acids, and so on. The C-terminus of a "peptide" may be joined to another moiety via an ester functionality.

"Optionally substituted", when used in association with "aryl", phenyl", "heteroaryl" "cyclo-hexyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy and acyloxy.

"Modulator" means a molecule that interacts with a target. The interactions include, but are not limited to, agonist and antagonist, as defined herein.

"Optional" or "optionally" means that the subsequently described event or circumstance may but need not occur, and that the description includes instances where the event or circumstance occurs and instances in which it does not.

"Disease" and "disease state" means any disease, condition, symptom, disorder or indication.

"Inert organic solvent" or "inert solvent" means the solvent is inert under the conditions of the reaction being described in conjunction therewith, including, e.g., benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present disclosure are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalene-sulfonic acid, propionic acid, salicylic acid, succinic acid, tartaric acid, p-toluenesulfonic acid and trimethylacetic acid; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, trimethylamine and tromethamine. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound.

Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, N-acyl derivatives (e.g. N-acetyl)N-Mannich bases, Schiff bases and enaminones of amino functional groups, oximes, acetals, ketals and enol esters of ketone and aldehyde functional groups in compounds of Formula I, see Bundegaard, "Design of Prodrugs" p1-92, Elsevier, New York-Oxford (1985).

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of the present disclosure rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, and tert-butoxycarbonyl (BOC). The person skilled in the art will know how to choose a group for the ease of removal and for the ability to withstand the following reactions.

"Solvates" means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such com-bination being able to form one or more hydrate.

"Subject" means mammals and non-mammals. Mammals means any member of the mammalia class including, but not limited to, humans; non-human primates such as chimpanzees and other apes and monkey species; farm animals such as cows, horses, sheep, goats, and swine; domestic animals such as rabbits, dogs, and cats; laboratory animals in-eluding rodents, such as rats, mice, and guinea pigs; and the like. Examples of non-mammals include, but are not limited to, birds. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis and idiophatic bladder hypersensitivity.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, low micturition threshold, unstable bladder contractions, sphincteric spasticity, detrusor hyperreflexia (neurogenic bladder; dyssynergia) and detrusor instability.

"Outlet obstruction" includes, but is not limited to, benign prostatic hypertrophy (BPH), urethral stricture disease, tumors, low flow rates, difficulty in initiating urination, urgency and suprapubic pain.

"Outlet insufficiency" includes, but is not limited to, urethral hypermobility, intrinsic sphincteric deficiency, mixed incontinence and stress incontinence.

"Pelvic Hypersensitivity" includes, but is not limited to, pelvic pain, interstitial (cell) cystitis, prostatodynia, prostatitis, vulvadynia, urethritis, orchidalgia and overactive bladder.

"Cough" includes acute, sub-acute and chronic cough, treatment-resistant cough, idiopathic chronic cough, post-viral cough, iatrogenic cough, cough associated with postnasal drip, cough associated with upper respiratory infection, asthma and/or COPD, cough associated with interstitial disease, cough associated with gastroesophageal reflux disease (GERD), cough associated with smoking or a form of bronchitis, and neuronal hypeersensitivity underlying acute, sub-acute or chronic cough.

The term "hypertension" as used herein refers to a condition or disease well known in the art in which the blood pressure in a mammal is chronically elevated. In certain embodiments hypertension may refer to a condition in which a subject's resting systolic blood pressure is above about 120 mmHg and/or diastolic pressure is above about 80 mmHg. In certain embodiments hypertension may refer to a condition in which a subject's resting systolic blood pressure is above about 115 mmHg; or above about 120 mmHg; or above about 125 mmHg; or above about 130 mmHg; or above about 135 mmHg; or above about 140 mmHg; or above about 145 mmHg; or above about 150 mmHg; or above about 155; or above about 160; or above about 165; or above about 170 and/or resting diastolic pressure is above about 75 mmHg; or above about 80 mmHg; or above about 85 mmHg; or above about 90 mmHg; or above about 95 mmHg; or above about 100 mmHg; or above about 105 mmHg; or above about 110 mmHg. In some embodiments hypertension may be primary or secondary hypertension. In some embodiments hypertension may be chronic treatment resistant hypertension, defined as persistent hypertension (resting office blood pressure >140/90 [SBP/DBP]) despite use of 2 or 3 antihypertensive medications including a diuretic, as well as hypertension in patients unable to tolerate currently preferred antihypertensive medications, or in whom approved medications cannot achieve recommended levels of BP control. Diagnosis of hypertension in a subject may in various embodiments be performed by an individual qualified to make such diagnosis in a particular jurisdiction.

The term "heart failure" as used herein refers to a condition or disease well known in the art which is associated with the heart being unable to maintain blood flow sufficient to maintain the needs of the body. Diagnosis of heart failure may in certain embodiments be based on echocardiography results characteristic of heart failure. In some embodiments, heart failure may refer to a condition often referred to as congestive heart failure. In some embodiments, heart failure may refer to systolic heart failure, also called heart failure due to reduced ejection fraction (HFREF) or heart failure due to left ventricular systolic dysfunction. In some embodiments, heart failure may refer to heart failure with preserved ejection fraction (HFPEF) also known as diastolic heart failure or heart failure with normal ejection fraction (HF-NEF). In some embodiments, heart failure may be chronic heart failure and in other embodiments the heart failure may be acute heart failure. Diagnosis of heart failure in a subject may in various embodiments be performed by an individual qualified to make such diagnosis in a particular jurisdiction.

The term "dyspnea" as used herein refers to a condition or disease well known in the art in which a subject experiences feelings or sensations associated with impaired breathing. In some embodiments dyspnea may refer to a condition consistent with the America Thoracic Society definition of dyspnea, i.e., "a subjective experience of breathing discomfort that consists of qualitatively distinct sensations that vary in intensity". In some embodiments dyspnea may refer to sensations of inadequate breathing, uncomfortable awareness of breathing and/or breathlessness. Diagnosis of dyspnea in a subject may in various embodiments be performed by an individual qualified to make such diagnosis in a particular jurisdiction.

The term "sleep apnea" as used herein refers to a condition or disease well known in the art characterized by disruptions in breathing (e.g., pauses in breathing or instances of shallow or infrequent breathing, accompanied by ischemia/hypoxemia) during sleep. In some aspects sleep apnea is central sleep apnea, obstructive sleep apnea, or mixed sleep apnea. In some embodiments, sleep apnea may be characterized by more than about 5 apneic events per hour of sleep; or more than about 10 apneic events per hour of sleep; or more than about 15 apneic events per hour sleep; or more than about 20 apneic events per hour of sleep, or more than about 25 apneic events per hour of sleep, or more than about 30 apneic sleep events per hour sleep; or more than about 35 apneic sleep events per hour sleep. Diagnosis of dyspnea in a subject may in various embodiments be performed by an individual qualified to make such diagnosis in a particular jurisdiction.

The term "carotid body" as used herein refers to a small cluster of chemoreceptors and supporting cells located near the fork (bifurcation) of the carotid artery. The carotid body is also referred in the art as carotid *glomus* or *glomus caroticum*. The term "altering carotid body tonicity" or activity as used herein means modifying the level of excitation of carotid sinus nerve chemoreceptor afferents that are discharging excessively in response to dysregulated levels of arterial chemicals (hyperreflexia), as well as attenuating the aberrant, spontaneous discharge of such nerve fibers that can occur in the absence of chemical dysregulation (hypertonoicity).

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, ie., arresting the development of the disease state or its clinical symptoms, or (iii) relieving the disease state, ie., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Any open valency appearing on a carbon, oxygen, sulfur or nitrogen atom in the structures herein indicates the presence of a hydrogen atom.

All patents and publications identified herein are incorporated herein by reference in their entirety.

In certain embodiments, $X_1$ in Formula 1 is C—$R^2$ and W is S, providing compounds of Formula 1a as follows:

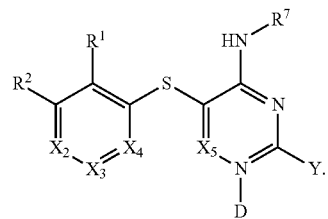

Formula 1a

In certain embodiments, $X_1$ in Formula 1 is N, providing compounds of the Formula 1b, as follows:

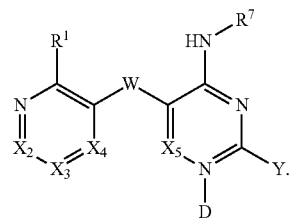

Formula 1b

In some embodiments of Formula 1b, W is O. In some embodiments of Formula 1b, W is S. In some embodiments of Formula 1b, W is $CH_2$. In some embodiments of Formula 1b, W is NR.

In certain embodiments, $X_1$ in Formula 1 is C—$R^2$ and $X_2$ is N, providing compounds of Formula 1c, as follows:

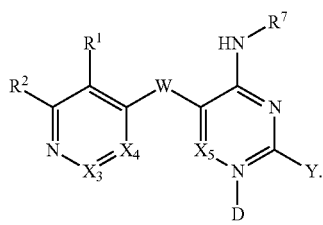

Formula 1c

In some embodiments of Formula 1c, W is O. In some embodiments of Formula 1c, W is S. In some embodiments of Formula 1c, W is CH$_2$. In some embodiments of Formula 1c, W is NR.

In certain embodiments, $X_1$ in Formula 1 is C—R$^2$ and $X_3$ is N, providing compounds of Formula 1d, as follows:

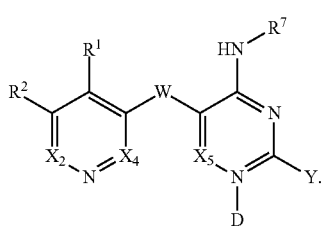

Formula 1d

In some embodiments of Formula 1d, W is O. In some embodiments of Formula 1d, W is S. In some embodiments of Formula 1d, W is CH$_2$. In some embodiments of Formula 1d, W is NR.

In certain embodiments, $X_1$ in Formula 1 is C—R$^2$ and $X_4$ is N, providing compounds of Formula 1e, as follows:

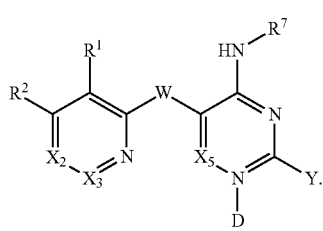

Formula 1e

In some embodiments of Formula 1e, W is O. In some embodiments of Formula 1e, W is S. In some embodiments of Formula 1e, W is CH$_2$. In some embodiments of Formula 1e, W is NR.

In certain embodiments, $X_1$ in Formula 1 is C—R$^2$ and both $X_2$ and $X_3$ are N, providing compounds of Formula 1f, as follows:

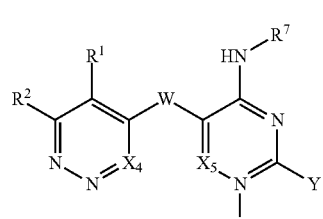

Formula 1f

In some embodiments of Formula 1f, W is O. In some embodiments of Formula 1f, W is S. In some embodiments of Formula 1f, W is CH$_2$. In some embodiments of Formula 1f, W is NR.

In certain embodiments, $X_1$ in Formula 1 is C—R$^2$ and both $X_2$ and $X_4$ are N, providing compounds of Formula 1g, as follows:

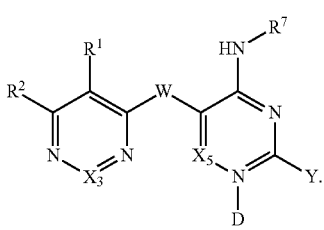

Formula 1g

In some embodiments of Formula 1g, W is O. In some embodiments of Formula 1g, W is S. In some embodiments of Formula 1g, W is CH$_2$. In some embodiments of Formula 1g, W is NR.

In certain embodiments, $X_1$ in Formula 1 is C—R$^2$ and both $X_3$ and $X_4$ are N, providing compounds of Formula 1h, as follows:

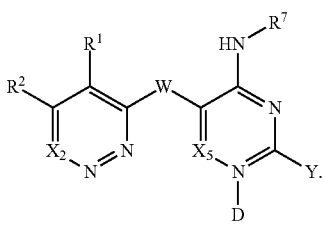

Formula 1h

In some embodiments of Formula 1h, W is O. In some embodiments of Formula 1h, W is S. In some embodiments of Formula 1h, W is CH$_2$. In some embodiments of Formula 1h, W is NR.

In certain embodiments, both $X_1$ and $X_2$ of Formula I are N, providing compounds of Formula 1i as follows:

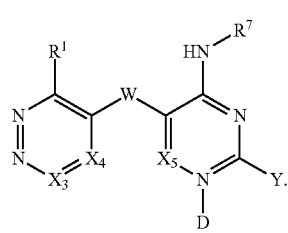

Formula 1i

In some embodiments of Formula 1i, W is O. In some embodiments of Formula 1i, W is S. In some embodiments of Formula 1i, W is CH$_2$. In some embodiments of Formula 1i, W is NR.

In certain embodiments, both $X_1$ and $X_3$ of Formula I are N, providing the compounds of Formula 1j, as follows:

Formula 1j

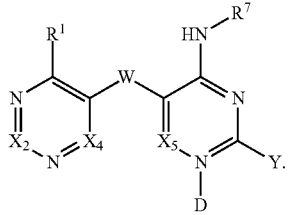

In some embodiments of Formula 1j, W is O. In some embodiments of Formula 1j, W is S. In some embodiments of Formula 1j, W is CH$_2$. In some embodiments of Formula 1j, W is NR.

In certain embodiments, both $X_1$ and $X_4$ of Formula I are N, providing compounds of Formula 1k, as follows:

Formula 1k

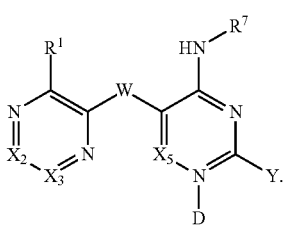

In some embodiments of Formula 1k, W is O. In some embodiments of Formula 1k, W is S. In some embodiments of Formula 1k, W is CH$_2$. In some embodiments of Formula 1k, W is NR.

In certain embodiments, $X_5$ of Formula I is N, providing compounds of Formula 1l, as follows:

Formula 1l

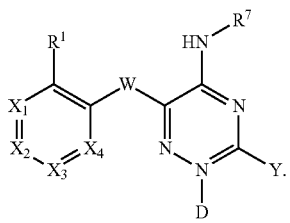

In some embodiments of Formula 1l, W is O. In some embodiments of Formula 1l, W is S. In some embodiments of Formula 1l, W is CH$_2$. In some embodiments of Formula 1l, W is NR.

In certain embodiments, $X_5$ of Formula I is C—R$^6$, providing compounds of Formula 1m, as follows:

Formula 1m

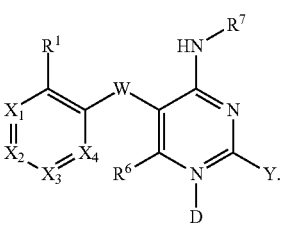

In some embodiments of Formula 1m, W is O. In some embodiments of Formula 1m, W is S. In some embodiments of Formula 1m, W is CH$_2$. In some embodiments of Formula 1m, W is NR. In certain embodiments of Formula 1m, when $X_1$ is C—R$^2$, $X_2$ is C—R$^3$, $X_3$ is C—R$^4$ and $X_4$ is C—R$^5$, W is not O or —CH$_2$—.

In certain embodiments of any one of Formulae 1-1m, R$^5$ and R$^6$ are hydrogen.

In certain embodiments of any one of Formulae 1-1m, R$^6$ is hydrogen or methyl.

In certain embodiments of any one of Formulae 1-1m, R$^2$ is hydrogen.

In certain embodiments of any one of Formulae 1-1m, D is absent.

In certain embodiments of any one of Formulae 1-1m, R$^1$ is selected from $C_{1-12}$-alkyl, $C_{2-12}$-alkenyl and $C_{3-12}$-cycloalkyl. In some of these embodiments, R$^1$ is selected from ethyl, cyclopropyl, isopropenyl and isopropyl. In particular embodiments, R$^1$ is isopropyl. In particular embodiments, R$^1$ is ethyl. In particular embodiments, R$^1$ is cyclopropyl.

In certain embodiments of any one of Formulae 1-1m, R$^7$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of any one of Formulae 1-1m, R$^7$ is selected from $C_{1-12}$-alkyl, $C_{1-12}$-hydroxyalkyl and $C_{1-12}$-haloalkyl.

In certain embodiments of any one of Formulae 1-1m, Y is —NHR$^d$. In some of these embodiments of formula 1, R$^d$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl. In particular embodiments, R$^d$ is selected from $C_{1-12}$-alkyl, $C_{1-12}$-hydroxyalkyl and $C_{1-12}$-haloalkyl.

In certain embodiments of any one of Formulae 1-1m, R$^3$ and R$^4$ each independently is $C_{1-12}$-alkyl, $C_{2-12}$-alkynyl, cyano, $C_{0-12}$-sulfonamido, —COOH, $C_{5-12}$-heteroaryl, halo, $C_{1-12}$-alkoxy, $C_{1-12}$-halo-alkoxy or $C_{1-12}$-alkylsulfonyl.

In certain embodiments of any one of Formulae 1-1m, R$^3$ is halo, $C_{1-12}$-alkoxy, $C_{1-12}$-haloalkoxy or hydroxy. In further embodiments, R$^3$ is methoxy, fluoro, or chloro. In particular embodiments, R$^3$ is methoxy. In certain embodiments R$^3$ is hydroxy.

In certain embodiments of any one of Formulae 1-1m, R$^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl. In further embodiments, R$^4$ is methoxy, iodo, methanesulfonyl or $C_{5-12}$-heteroaryl. In particular embodiments, R$^4$ is methoxy, methyl, cyano, bromo, chloro, iodo, —C≡C—CH$_3$, —C≡CH, —COOH, —S(O)$_2$CH$_3$, —S(O)$_2$NH$_2$ or tetrazolyl. In specific embodiments R$^4$ is methoxy, while in other embodiments R$^4$ is iodo.

In certain embodiments of any one of Formulae 1-1m, R$^7$, R$^d$ and R$^e$ are hydrogen.

In certain embodiments of any one of Formulae 1-1m, R$^3$ and R$^4$ together with the atoms to which they are attached form a five or six-membered ring that optionally includes one or two heteroatoms selected from O, S and N. In many such embodiments R3 and R4 together with the atoms to which they are attached form: a five membered aromatic with one nitrogen, i.e. a pyrrol ring; a five membered aromatic with two nitrogens, i.e., a pyrazol or imidazol ring; a five membered aromatic with one nitrogen and one oxygen, i.e., an ox-azole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In certain embodiments of any one of Formulae 1-1m, $R^2$ and $R^3$ together with the atoms to which they are attached form a five or six-membered ring that optionally includes one or two heteroatoms selected from O, S and N. In many such embodiments $R^3$ and $R^4$ together with the atoms to which they are attached form: a five membered aromatic with one nitrogen, i.e. a pyrrol ring; a five membered aromatic with two nitrogens, i.e. a pyrazol or imidazole ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In some embodiments of the present disclosure, the compounds are of Formula 2:

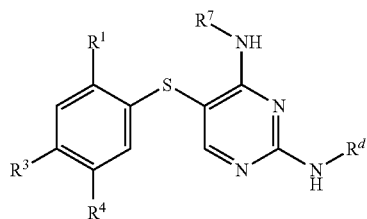

Formula 2 wherein:

$R^1$ is $C_{1-12}$-alkyl; $C_{2-12}$-alkenyl; $C_{3-12}$-cycloalkyl; or $C_{3-12}$-cycloalkenyl; or halo;

$R^3$ and $R^4$ each independently is: hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{2-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroarylalkyloxy; optionally substituted phenoxy; —$(CH_2)_m$—$(Z)_n$—(CO)—$R^f$ or —$(CH_2)_m$—$(Z)_n$—$SO_2$—$(NR^g)_{n'}$—$R^f$, where m, n and n' are each independently 0 or 1, Z is O or $NR^g$, $R^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl, and each $R^g$ is independently hydrogen or $C_{1-12}$-alkyl; or $R^3$ and $R^4$ together with the atoms to which they are attached may form a five or six-membered ring that optionally includes one or two heteroatoms selected from O, S and N;

$R^7$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalkyl; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl; and $R^d$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 2, $R^1$ is selected from $C_{1-12}$-alkyl, $C_{2-12}$-alkenyl and $C_{3-12}$-cycloalkyl. In some of these embodiments, $R^1$ is selected from ethyl, cyclopropyl, isopropenyl and isopropyl. In particular embodiments, $R^1$ is isopropyl. In particular embodiments, $R^1$ is ethyl. In particular embodiments, $R^1$ is cyclopropyl.

In certain embodiments of Formula 2, $R^7$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 2, $R^7$ is selected from $C_{1-12}$-alkyl, $C_{1-12}$-hydroxyalkyl and $C_{1-12}$-haloalkyl.

In certain embodiments of Formula 2, $R^d$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl. In further embodiments, $R^d$ is selected from $C_{1-12}$-alkyl, $C_{1-12}$-hydroxyalkyl and $C_{1-12}$-haloalkyl.

In certain embodiments of Formula 1, $R^3$ and $R^4$ each independently is $C_{1-12}$-alkyl, $C_{2-12}$-alkynyl, cyano, $C_{0-12}$-sulfonamido, —COOH, $C_{5-12}$-heteroaryl, halo, $C_{1-12}$-alkoxy, $C_{1-12}$-halo-alkoxy or $C_{1-12}$-alkylsulfonyl.

In certain embodiments of Formula 1, $R^3$ is halo, $C_{1-12}$-alkoxy, $C_{1-12}$-haloalkoxy or hydroxy. In further embodiments, $R^3$ is methoxy, fluoro, or chloro. In particular embodiments, $R^3$ is methoxy. In certain embodiments $R^3$ is hydroxy.

In certain embodiments of Formula 1, $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl. In further embodiments, $R^4$ is methoxy, iodo, methanesulfonyl or $C_{5-12}$-heteroaryl. In particular embodiments, $R^4$ is methoxy, methyl, cyano, bromo, chloro, iodo, —C≡C—$CH_3$, —C≡CH, —COOH, —$S(O)_2CH_3$, —$S(O)_2NH_2$ or tetrazolyl. In specific embodiments $R^4$ is methoxy, while in other embodiments $R^4$ is iodo.

In certain embodiments of Formula 2, $R^7$, $R^d$ and $R^e$ are hydrogen. In certain embodiments of Formula 2, $R^4$ is $C_{5-12}$-heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, ox-azol-5-yl, imidazol-2-yl, thiazol-2-yl, thiazol-4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thiophen-3-yl, oxazol-4-yl, furan-3-yl, 4-methyl-thiophen-2-yl, thiazol-5-yl, tetrazol-1-yl, [1,2,4]

triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

In certain embodiments of Formula 2, $R^3$ and $R^4$ together with the atoms to which they are attached form a five or six-membered ring that optionally includes one or two heteroatoms selected from O, S and N. In many such embodiments $R^3$ and $R^4$ together with the atoms to which they are attached form: a five membered aromatic with one nitrogen, i.e. a pyrrol ring; a five membered aromatic with two nitrogens, i.e., a pyrazol or imidazol ring; a five membered aromatic with one nitrogen and one oxygen, i.e., an ox-azole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In a further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, and $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl.

In another further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, and $R^4$ is $C_{1-12}$-alkyl, $C_{2-12}$-alkynyl, cyano, $C_{0-12}$-sulfonamido, —COOH, halo, $C_{1-12}$-alkoxy or $C_{1-12}$-alkylsulfonyl.

In another further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, and $R^4$ is $C_{5-12}$-heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl.

In another further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, $R^4$ is $C_{1-12}$-alkyl, $C_{2-12}$-alkynyl, cyano, $C_{0-12}$-sulfonamido, —COOH, halo, $C_{1-12}$-alkoxy or $C_{1-12}$-alkylsulfonyl, $R^7$ is hydrogen, and $R^d$ is hydrogen, $C_{1-12}$-alkyl, $C_{1-12}$-hydroxyalkyl or $C_{1-12}$-haloalkyl.

In another further embodiment of Formula 2, $R^1$ is $C_{1-12}$-alkyl, $C_{2-12}$-alkenyl, $C_{3-12}$-cycloalkyl, or halo, $R^3$ is $C_{1-12}$-alkoxy, hydroxy or halo, $R^4$ is $C_{5-12}$-heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl, $R^7$ is hydrogen, and $R^d$ is hydrogen, $C_{1-12}$-alkyl, acetyl, $C_{1-12}$-hydroxyalkyl or $C_{1-12}$-haloalkyl.

In another further embodiment of Formula 2, $R^1$ is isopropyl, isopropenyl, cyclopropyl or iodo, $R^3$ is $C_{1-12}$-alkoxy, hydroxy or halo, and $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl.

In another further embodiment of Formula 2, $R^1$ is isopropyl, isopropenyl, cyclopropyl or iodo, $R^3$ is $C_{1-12}$-alkoxy, hydroxy or halo, $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl, $R^7$ is hydrogen, and $R^d$ is hydrogen, $C_{1-12}$-alkyl, $C_{1-12}$-hydroxyalkyl or $C_{1-12}$-haloalkyl.

In another further embodiment of Formula 2, $R^1$ is isopropyl or iodo, $R^3$ is methoxy, hydroxy, chloro, bromo or iodo, and $R^4$ is methoxy, methyl, cyano, bromo, chloro, iodo, —C≡C—$CH_3$, —C≡CH, —COOH, —$S(O)_2CH_3$, —$S(O)_2NH_2$ or tetrazolyl.

In another further embodiment of Formula 2, $R^1$ is isopropyl or iodo, $R^3$ is methoxy, hydroxy, chloro, bromo or iodo, $R^4$ methoxy, methyl, cyano, bromo, chloro, iodo, —C≡C—$CH_3$, —C≡CH, —COOH, —$S(O)_2CH_3$, —$S(O)_2NH_2$ or tetrazolyl, $R^7$ is hydrogen, and $R^d$ is hydrogen, $C_{1-12}$-alkyl, $C_{1-12}$-hydroxyalkyl or $C_{1-12}$-haloalkyl.

In another further embodiment of Formula 2, $R^1$ is isopropyl, $R^3$ is methoxy, hydroxy, chloro, bromo or iodo, and $R^4$ is methoxy, methyl, cyano, bromo, chloro, iodo, —COOH, —$S(O)_2CH_3$, —$S(O)_2NH_2$ or tetrazolyl.

In another further embodiment of Formula 2, $R^1$ is isopropyl, $R^3$ is methoxy, hydroxy, chloro, bromo or iodo, $R^4$ methoxy, methyl, cyano, bromo, chloro, iodo, —C≡C—$CH_3$, —C≡CH, —COOH, —$S(O)_2CH_3$, —$S(O)_2NH_2$ or tetrazolyl, $R^7$ is hydrogen, and $R^d$ is hydrogen, $C_{1-12}$-alkyl, $C_{1-12}$ hydroxyalkyl or $C_{1-12}$-haloalkyl.

In other embodiments of the present disclosure, the compounds are of Formula 3:

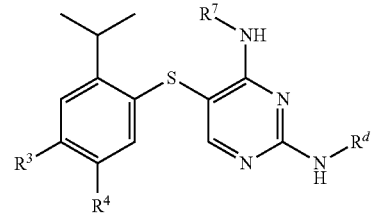

Formula 3 wherein:
$R^3$ and $R^4$ each independently is: hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_{n'}$—$R^f$, where m, n and n' are each independently 0 or 1, Z is O or $NR^g$, $R^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl, and each $R^g$ is independently hydrogen or $C_{1-12}$-alkyl;

$R^3$ and $R^4$ together with the atoms to which they are attached may form a five or six-membered ring that optionally includes one or two heteroatoms selected from O, S and N;

$R^7$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl; and $R^d$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl;

$C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments Formula 3, $R^7$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 3, $R^7$ is selected from $C_{1-12}$-alkyl, $C_{1-12}$-hydroxyalkyl and $C_{1-12}$-haloalkyl.

In certain embodiments of Formula 3, $R^d$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 3, $R^d$ is selected from: $C_{1-12}$-alkyl, $C_{1-12}$-hydroxyalkyl and $C_{1-12}$-haloalkyl.

In certain embodiments of Formula 3, $R^3$ and $R^4$ each independently is $C_{1-12}$-alkyl, $C_{2-12}$-alkynyl, cyano, $C_{0-12}$-sulfonamido, —COOH, $C_{5-12}$-heteroaryl, halo, $C_{1-12}$-alkoxy, $C_{1-12}$-halo-alkoxy or $C_{1-12}$-alkylsulfonyl.

In certain embodiments of Formula 3, $R^3$ is halo, $C_{1-12}$-alkoxy, $C_{1-12}$-haloalkoxy or hydroxy. In further embodiments, $R^3$ is methoxy, fluoro, or chloro. In particular embodiments, $R^3$ is methoxy. In certain embodiments $R^3$ is hydroxy.

In certain embodiments of Formula 3, R4 is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl. In further embodiments, $R^4$ is methoxy, iodo, methanesulfonyl or $C_{5-12}$-heteroaryl. In particular embodiments, $R^4$ is methoxy, methyl, cyano, bromo, chloro, iodo, —C≡C—CH$_3$, —C≡CH, —COOH, —S(O)$_2$CH$_3$, —S(O)$_2$NH$_2$ or 5-tetrazolyl. In specific embodiments $R^4$ may be methoxy, while in other embodiments $R^4$ may be iodo.

In certain embodiments of Formula 3, $R^7$ and $R^d$ are hydrogen.

In certain embodiments of Formula 3, $R^4$ is $C_{5-12}$-heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol-4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxa-diazol-3-yl, benzo[b]thiophen-3-yl, oxazol-4-yl, furan-3-yl, 4-methyl-thiophen-2-yl, thi-azol-5-yl, tetrazol-1-yl, [1,2,4]triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

In certain embodiments of Formula 3, $R^3$ and $R^4$ together with the atoms to which they are attached form a five or six-membered ring that optionally includes one or two heteroatoms selected from O, S and N; as shown in Formula 4:

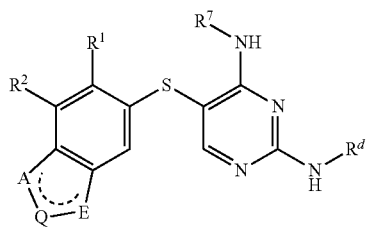

Formula 4 wherein:
$R^1$ is $C_{1-12}$-alkyl; $C_{2-12}$-alkenyl; $C_{3-12}$-cycloalkyl; or $C_{3-12}$-cycloalkenyl; or halo;
$R^2$ is hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroarylalkyloxy; optionally substituted phenoxy; or —(CH$_2$)$_m$—(Z)$_n$—(CO)—R$^f$ or —(CH$_2$)$_m$—(Z)$_n$—SO$_2$—(NR$^g$)$_{n'}$—R$^f$, where m, n and n' are each independently 0 or 1,
Z is O or NR$^g$,
R$^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl, and each R$^g$ is independently hydrogen or $C_{1-12}$-alkyl;
$R^7$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;
$R^d$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;
Q is (CR$^9$)$_x$, one of A and E is O, S or NR$^{10}$ and the other is (CR$^9$)$_x$ or N, wherein each x is independently 1 or 2; or
Q is N, one of A and E is NR$^{10}$ and the other is (CR$^9$)$_x$;
each R$^9$ is independently hydrogen, $C_{1-12}$-alkyl, halo or $C_{1-12}$-alkoxy; and
R$^{10}$ is hydrogen, $C_{1-12}$-alkyl, $C_{1-12}$-hydroxyalkyl, $C_{2-12}$-alkoxyalkyl, —(CH$_2$)$_m$—(Z)$_n$—(CO)—R$^f$, or —(CH$_2$)$_m$—(Z)$_n$—SO$_2$—(NR$^g$)$_{n'}$—R$^f$.

In many such embodiments $R^3$ and $R^4$ together with the atoms to which they are attached form: a five membered aromatic with one nitrogen, i.e. a pyrrole ring; a five membered aromatic with two nitrogens, i.e. a pyrazole or imidazole ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In additional embodiments, $R^3$ and $R^4$ together with the atoms to which they are attached form a six membered cycloalkyl, heterocyclic, aromatic or heteroaromatic ring, e.g., a heterocycle or heteroaromatic with one nitrogen (e.g., a tetrahydroquinoline or a quinoline) a six membered heterocycle or heteroaromatic with two nitrogens, e.g., a tetrahydrocinnoline/tetrahydroquinazoline/tetrahydroquinoxaline or a cinnoline/quinazoline/quinoxaline ring; a six membered heterocycle with one nitrogen and one oxygen, i.e., a benzoxazine ring; a six membered heterocycle or with one nitrogen and one sulfur, i.e., a benzothiazine ring; a six membered heterocycle with one oxygen, i.e., a chromane ring; or a six membered heterocycle with one sulfur, i.e., a thiochromane ring.

In certain embodiments of Formula 4, A is $NR^{10}$, Q and E are $CR^9$, and x=1; in certain embodiments of Formula 4, A is $NR^{10}$, Q and E are $CR^9$, and x=2.

In certain embodiments of Formula 4, E is $NR^{10}$, A and Q are $CR^9$, and x=1; in certain embodiments of Formula 4, E is $NR^{10}$, A and Q are $CR^9$, and x=2.

In certain embodiments of Formula 4, Q is $NR^{10}$, A and E are CR, and x=1; in certain embodiments of Formula 4, Q is $NR^{10}$, A and E are CR, and x=2.

In certain embodiments of Formula 4, A is O, E is N, Q is $CR^9$, and x=1; in certain embodiments of Formula 4, A is O, E is N, Q is $CR^9$, and x=2.

In certain embodiments of Formula 4, A is N, E is O, Q is $CR^9$, and x=1; in certain embodiments of Formula 4, A is N, E is O, Q is $CR^9$, and x=2.

In certain embodiments of Formula 4, A is S, E is N, Q is $CR^9$, and x=1; in certain embodiments of Formula 4, A is S, E is N, Q is $CR^9$, and x=2.

In certain embodiments of Formula 4, A is N, E is S, Q is $CR^9$, and x=1; in certain embodiments of Formula 4, A is N, E is S, Q is $CR^9$, and x=2.

In certain embodiments of Formula 4, E is S, A and Q are $CR^9$, and x=1; in certain embodiments of Formula 4, E is S, A and Q are $CR^9$, and x=2.

In certain embodiments of Formula 4, E is O, A and Q are $CR^9$, and x=1; in certain embodiments of Formula 4, E is O, A and Q are $CR^9$, and x=2.

In certain embodiments of Formula 4, A is S, E and Q are $CR^9$, and x=1; in certain embodiments of Formula 4, A is S, E and Q are $CR^9$, and x=2.

In certain embodiments of Formula 4, A is O, E and Q are $CR^{9'}$ and x=1; in certain embodiments of Formula 4, A is O, E and Q are $CR^9$, and x=2.

In certain embodiments of Formula 4, A is $NR^{10}$, Q is N, E is $CR^9$, and x=1; in certain embodiments of Formula 4, A is $NR^{10}$, Q is N, E is $CR^9$, and x=2.

In certain embodiments of Formula 4, E is $NR^{10}$, Q is N, A is $CR^9$, and x=1; in certain embodiments of Formula 4, E is $NR^{10}$, Q is N, A is $CR^9$, and x=2.

In certain embodiments of Formula 4, $R^2$ is hydrogen.

In certain embodiments of Formula 4, $R^1$ is $C_{1-12}$-alkyl, $C_{2-12}$-alkenyl or $C_{3-12}$-cycloalkyl. In further embodiments, $R^1$ is ethyl, cyclopropyl, isopropenyl or isopropyl. In particular embodiments, $R^1$ is isopropyl. In particular embodiments, $R^1$ is ethyl. In particular embodiments, $R^1$ is cyclopropyl.

In certain embodiments of Formula 4, $R^7$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 4, $R^7$ is selected from: $C_{1-12}$-alkyl, $C_{1-12}$-hydroxyalkyl and $C_{1-12}$-haloalkyl.

In certain embodiments of Formula 4, $R^d$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 4, $R^d$ is selected from: $C_{1-12}$-alkyl, $C_{1-12}$-hydroxyalkyl and $C_{1-12}$-haloalkyl.

In certain embodiments of Formula 4, $R^7$ and $R^d$ are hydrogen.

In some embodiments of the present disclosure, the compounds are of Formula 5:

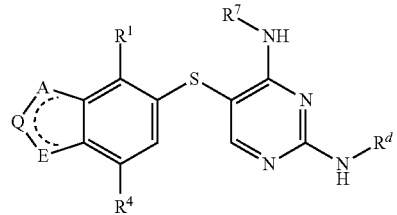

Formula 5 wherein:
$R^1$ is: $C_{1-12}$-alkyl; $C_{2-12}$-alkenyl; $C_{3-12}$-cycloalkyl; or $C_{3-12}$-cycloalkenyl; or halo;

$R^4$ is: hydrogen; $C_{1-12}$-alkyl; $C_{2-12}$-alkenyl; $C_{2-12}$-alkynyl; amino; halo; amido; $C_{1-12}$-haloalkyl; $C_{1-12}$-alkoxy; hydroxy; $C_{1-12}$-haloalkoxy; nitro; $C_{1-12}$-hydroxyalkyl; $C_{2-12}$-alkoxyalkyl; $C_{1-12}$-hydroxyalkoxy; $C_{3-12}$-alkynylalkoxy; $C_{1-12}$-alkylsulfonyl; $C_{6-12}$-arylsulfonyl; cyano; $C_{6-12}$-aryl; $C_{5-12}$-heteroaryl; $C_{3-12}$-heterocyclyl; $C_{4-12}$-heterocyclylalkoxy; $C_{6-12}$-aryloxy; $C_{5-12}$-heteroaryloxy; $C_{7-12}$-arylalkyloxy; $C_{6-12}$-heteroarylalkyloxy; optionally substituted phenoxy; or —$(CH_2)_m$—$(Z)_n$—(CO)—$R^f$ or —$(CH_2)_m$—$(Z)_n$—$SO_2$—$(NR^g)_{n'}$—$R^f$, where m, n and n' are each independently 0 or 1, Z is O or $NR^g$, $R^f$ is hydrogen, $C_{1-12}$-alkyl, hydroxy, $C_{1-12}$-alkoxy, amino, $C_{1-12}$-hydroxyalkyl or $C_{2-12}$-alkoxyalkyl, and each $R^g$ is independently hydrogen or alkyl;

$R^7$ is selected from hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;

$R^d$ is selected from: hydrogen; $C_{1-12}$-alkyl; $C_{3-12}$-cycloalkyl; $C_{4-12}$-cycloalkylalkyl; $C_{1-12}$-haloalkyl; $C_{1-12}$-haloalkoxy; $C_{1-12}$-hydroxyalky; $C_{2-12}$-alkoxyalkyl; acetyl; $C_{1-12}$-alkylsulfonyl; $C_{2-12}$-alkylsulfonylalkyl; $C_{2-12}$-aminocarbonyloxyalkyl; $C_{2-12}$-hydroxycarbonylalkyl; $C_{2-12}$-hydroxyalkyloxycarbonylalkyl; $C_{6-12}$-aryl; $C_{7-12}$-arylalkyl; $C_{6-12}$-aryl sulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl;

Q is $(CR^9)_x$, one of A and E is O, S or $NR^{10}$ and the other is $(CR^9)_x$ or N, wherein each x is independently 1 or 2; or Q is N, one of A and E is $NR^{10}$ and the other is $(CR^9)_x$;
each $R^9$ is independently hydrogen, $C_{1-12}$-alkyl, halo or $C_{1-12}$-alkoxy; and
$R^{10}$ is hydrogen, $C_{1-12}$-alkyl, $C_{1-12}$-hydroxyalkyl, $C_{2-12}$-alkoxyalkyl, —$(CH_2)_m$—$(Z)_n$—$(CO)$—$R^f$, or —$(CH_2)_m$—$(Z)_n$—$SO_2$—$(NR^g)_{n'}$—$R^f$.

In certain embodiments of Formula 5, A is $NR^{10}$, Q and E are $CR^9$ and x=1; in certain embodiments of Formula 5, A is $NR^{10}$, Q and E are $CR^9$ and x=2.

In certain embodiments of Formula 5 E is $NR^{10}$, A and Q are $CR^9$, and x=1; in certain embodiments of Formula 5, E is $NR^{10}$, A and Q are $CR^9$, and x=2.

In certain embodiments of Formula 5, Q is $NR^{10}$, A and E are $CR^9$, and x=1; in certain embodiments of Formula 5, Q is $NR^{10}$, A and E are $CR^9$, and x=2.

In certain embodiments of Formula 5, A is O, E is N, Q is $CR^9$, and x=1; in certain embodiments of Formula 5, A is O, E is N, Q is $CR^9$, and x=2.

In certain embodiments of Formula 5, A is N, E is O, Q is $CR^9$, and x=1; in certain embodiments of Formula 5, A is N, E is O, Q is $CR^9$, and x=2.

In certain embodiments of Formula 5, A is S, E is N, Q is $CR^9$, and x=1; in certain embodiments of Formula 5, A is N, E is O, Q is $CR^9$, and x=2.

In certain embodiments of Formula 5, A is N, E is S, Q is $CR^9$, and x=1; in certain embodiments of Formula 5, A is N, E is S, Q is $CR^9$, and x=2.

In certain embodiments of Formula 5, E is S, A and Q are $CR^9$, and x=1; in certain embodiments of Formula 5, E is S, A and Q are $CR^9$, and x=2.

In certain embodiments of Formula 5, E is O, A and Q are $CR^9$ and x=1; in certain embodiments of Formula 5, E is O, A and Q are $CR^9$, and x=2.

In certain embodiments of Formula 5, A is S, E and Q are $CR^9$, and x=1; in certain embodiments of Formula 5, A is S, E and Q are $CR^9$, and x=2.

In certain embodiments of Formula 5, A is O, E and Q are $CR^9$, and x=1; in certain embodiments of Formula 5, A is O, E and Q are $CR^9$, and x=2.

In certain embodiments of Formula 5, A is $NR^{10}$, Q is N, E is $CR^9$, and x=1; in certain embodiments of Formula 5, A is $NR^{10}$, Q is N, E is $CR^9$, and x=2.

In certain embodiments of Formula 5, E is $NR^{10}$, Q is N, A is $CR^9$, and x=1; in certain embodiments of Formula 5, E is $NR^{10}$, Q is N, A is $CR^9$, and x=2.

In certain embodiments of Formula 5, $R^7$ is $C_{1-12}$-alkyl, $C_{2-12}$-alkenyl or $C_{3-12}$-cycloalkyl. Preferably, $R^1$ is ethyl, cyclopropyl, isopropenyl or isopropyl. In certain embodiments, $R^1$ is isopropyl. In particular embodiments, $R^1$ is ethyl. In particular embodiments, $R^1$ is cyclopropyl.

In certain embodiments of Formula 5, $R^7$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 5, $R^7$ is selected from $C_{1-12}$-alkyl, $C_{1-12}$-hydroxyalkyl and $C_{1-12}$-haloalkyl.

In certain embodiments of Formula 5, $R^d$ is selected from: $C_{1-12}$-alkyl, $C_{3-12}$-cycloalkyl; $C_{4-12}$-cycloalkylalkyl; $C_{1-12}$-haloalkyl; $C_{1-12}$-hydroxyalky; $C_{2-12}$-alkoxyalkyl; $C_{2-12}$-alkylsulfonylalkyl; acetyl; $C_{1-12}$-alkylsulfonyl; $C_{6-12}$-aryl; $C_{7-12}$-arylalkyl; $C_{6-12}$-arylsulfonyl; $C_{5-12}$-heteroaryl; $C_{6-12}$-heteroarylalkyl; $C_{5-12}$-heteroarylsulfonyl; $C_{3-12}$-heterocyclyl; and $C_{4-12}$-heterocyclylalkyl.

In certain embodiments of Formula 5, $R^d$ is selected from $C_{1-12}$-alkyl, $C_{1-12}$-hydroxyalkyl and $C_{1-12}$-haloalkyl.

In certain embodiments of Formula 5, $R^7$ and $R^d$ are hydrogen.

In certain embodiments of Formula 1, $R^4$ is $C_{1-12}$-alkyl, $C_{2-12}$-alkynyl, cyano, $C_{0-12}$-sulfonamido, —COOH, halo, $C_{1-12}$-alkoxy, $C_{1-12}$-alkylsulfonyl or $C_{5-12}$-heteroaryl. In further embodiments, $R^4$ is methoxy, iodo, methanesulfonyl or $C_{5-12}$-heteroaryl. In particular embodiments, $R^4$ is methoxy, methyl, cyano, bromo, chloro, iodo, —C≡C—$CH_3$, —C≡CH, —COOH, —$S(O)_2CH_3$, —$S(O)_2NH_2$ or tetrazolyl. In specific embodiments $R^4$ is methoxy, while in other embodiments $R^4$ is iodo.

In certain embodiments of Formula 5, $R^4$ is $C_{5-12}$-heteroaryl. The $C_{5-12}$-heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol-4-yl, thiophen-3-yl, 5-chloro-thio-phen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxa-diazol-3-yl, benzo [b] thiophen-3-yl, oxazol-4-yl, furan-3-yl, 4-methyl-thiophen-2-yl, thiazol-5-yl, tetrazol-1-yl, [1, 2,4] triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

In embodiments of the present disclosure, where any of $R^7$ or $R^d$ are $C_{3-12}$-heterocyclyl or a group that includes a heterocyclyl moiety, such heterocyclyl or heterocyclyl moiety is piperidinyl, piperazinyl, tetrahydrofuranyl, tetrahydrothiopyranyl, or 1,1-dioxotetrahydrothio-pyranyl. More preferably, such heterocyclyl or heterocyclyl moiety is piperidin-4-yl, 1-methyl-piperidine-4-yl, 1-methanesulfonyl-piperidin-4-yl, tetrahydropyran-4-yl, tetra-hydrothiopyran-4-yl, or 1,1-dioxotrahydrothiopyran-4-yl.

Where any of $R^1$, $R^2$, $R^3$, $R^4$, $R^5$, $R^6$, $R^7$, $R^9$, $R^{10}$, $R^c$, $R^d$, $R^f$, $R^g$, or $R^h$ is $C_{1-12}$-alkyl or contains an alkyl moiety, such alkyl is preferably lower alkyl, i.e. $C_{1-6}$-alkyl, and more preferably $C_{1-4}$-alkyl.

In one embodiment of Formula 1, the compound is selected from the group consisting of Compounds 1-47 as exemplified in Examples 1-49.

The present disclosure also provides methods for treating a disease or condition by using a P2X3 receptor antagonist, a P2X2/3 receptor antagonist, or both, the method comprising administering to a subject in need thereof an effective amount of a compound of any of Formulae 1 to 5. The disease may be genitorurinary disease or urinary tract disease. In other instances the disease may be a disease is associated with pain. The urinary tract disease may be: reduced bladder capacity; frequent micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitits; pelvic pain syndrome; prostatodynia; cystitis; or idiophatic bladder hypersensitivity.

The disease associated with pain may be: inflammatory pain; surgical pain; visceral pain; dental pain; premenstrual pain; central pain; pain due to burns; migraine or cluster headaches; nerve injury; neuritis; neuralgias; neuropathy; poisoning; ischemic injury; interstitial cystitis; cancer pain; viral, parasitic or bacterial infection; post-traumatic injury; pain associated with irritable bowel syndrome and inflammatory bowel disease.

In certain aspects, the present disclosure also provides methods for treating cough or urge to cough associated with a respiratory disease, hypertension, heart failure, dyspnea, sleep apnea, fatigue, exercise intolerance, by altering carotid body tonicity or activity in a subject, and the like. In additional instances the disorders or disease states may include hepatocellular carcinoma, tinnitus, migraine, itch, diabetes, endometriosis and dysmenorrhea, peripheral artery occlusive disease (PAOD), chronic obstructive pulmonary disease (COPD), atopic dermatitis and other forms of eczema or dermatitis, bursitis, tendonitis, fibromyalgia, gout, joint replacement, lichen sclerosus, psoriasis and psoriatic arthritis, cold sores, kidney stones, gall stones, smell disorders, taste disorders including dysgeusia or burning mouth syndrome, gastro esophageal reflux disease (GERD), binge-eating disorders and obesity, or pain from sickle cell anemia and ischemia.

In some embodiments of the method for treating a disease mediated by a P2X3 receptor antagonist, a P2X2/3 receptor antagonist, or both, comprises administering to a subject in need thereof an effective amount of a compound of any one of Formulae 1 to 5 which shows selectivity for P2X3 vs P2X2/3. For example when the disease to be treated is medicated by at least the P2X3 receptor, the compound may show greater selectivity for P2X3 than P2X2/3.

In this way the present disclosure may provide a treatment which has reduced side effects, for example reduced taste effects.

EXPERIMENTAL

The following examples are intended to be illustrative only and not limiting in any way. Abbreviations used are those conventional in the art or the following.

ACN acetonitrile
° C. degree Celsius
DCM dichloromethane
DMF N,N-dimethylformamide
DMSO dimethylsulfoxide
EtOAc ethyl acetate
EtOH ethanol
g gram
h hour(s)
HPLC high pressure liquid chromatography
kg kilogram
L liter
LC liquid chromatography
LCMS liquid chromatography and mass spectrometry
MeOH methanol
MS mass spectrometry
MTBE methyl tert-butyl ether
min minutes
mL milliliter(s)
m/z mass to charge ratio
nm nanometer
nM nanomolar
N normal
RT or rt room temperature
sat. saturated
TFA trifluoroacetic acid
THF tetrahydrofuran

GENERAL SYNTHETIC SCHEMES

Compounds of the present disclosure can be made by a variety of methods depicted in the illustrative synthetic reaction schemes shown and described herein.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40. The following synthetic reaction schemes are merely illustrative of some methods by which the compounds of the present disclosure can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature (RT), e.g., about 20° C.

Scheme A illustrates one synthetic procedure usable to prepare specific compounds of Formula (1):

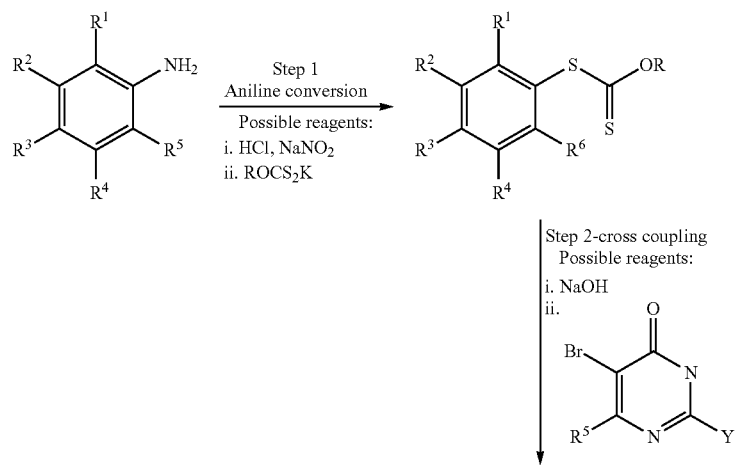

Scheme A

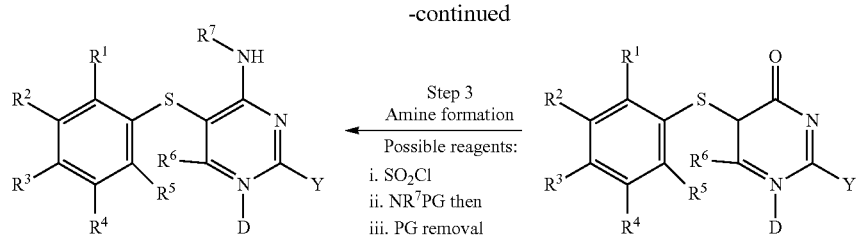
Generally speaking, Scheme A contemplates: (a) reaction of an optionally substituted aniline with $ROCS_2K$; (b) reaction of the resulting thioester with a bromo-pyrimidine oxide; and (c) aminating the resulting polycyclic compound.
Scheme B illustrates another synthetic procedure usable to prepare specific compounds of Formula (1):
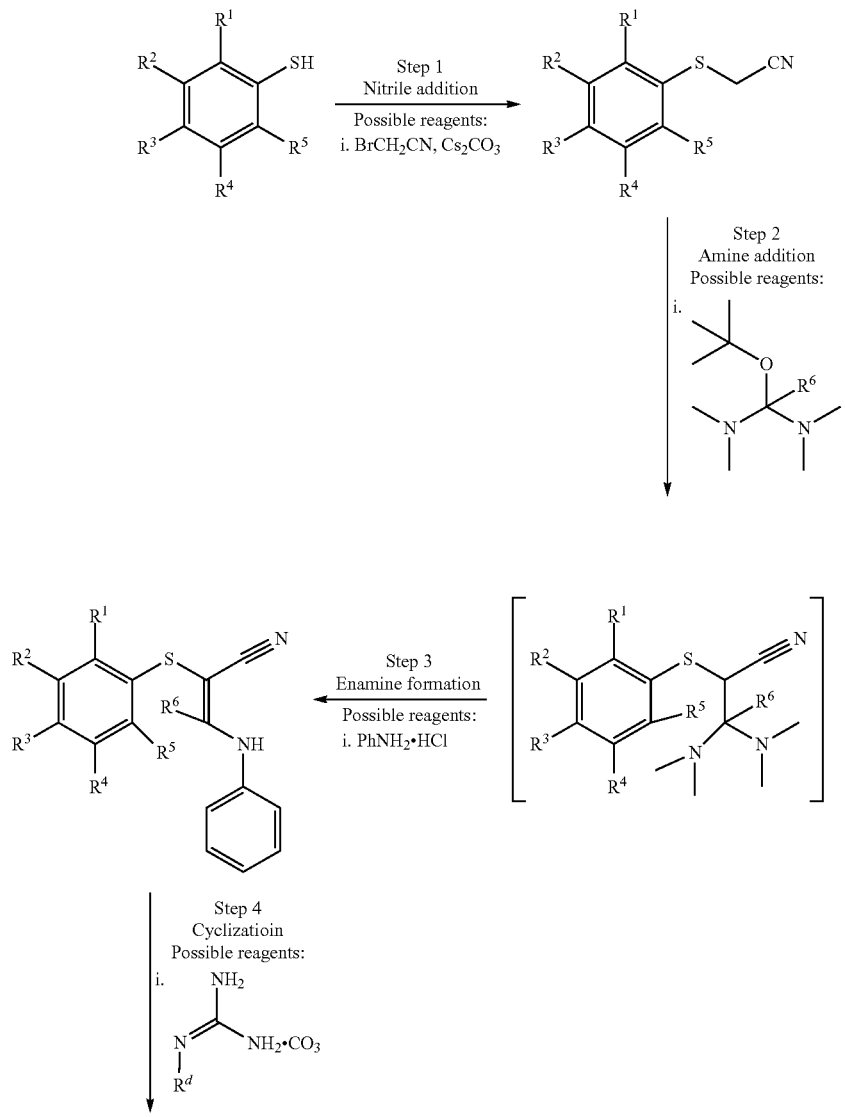

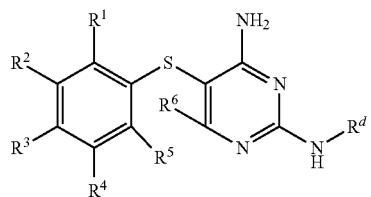
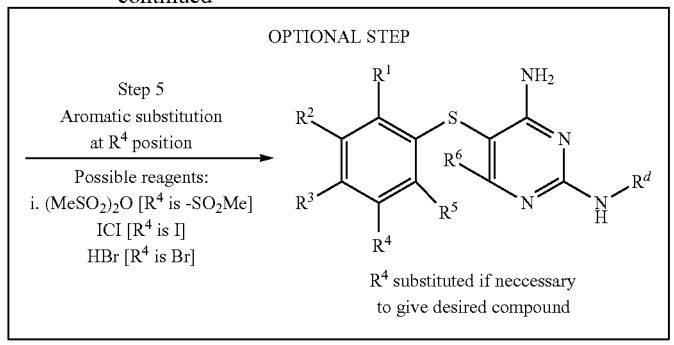

Generally speaking, Scheme B contemplates: (a) reaction of an optionally substituted thiophenol with $BrCH_2CN$ and $Cs_2CO_3$; (b) amine addition to the resulting thioether; (c) enamine formation from the resulting amine; and (d) cyclization of the resulting compound to produce a compound of Formula 1.

In Scheme B further additional steps may be used to manipulate the substitution on the phenyl ring. For example, when $R^4$ is methyl or alkynyl, these compounds may be provided via the corresponding compound wherein $R^4$ is iodo e.g. by cross-coupling chemistry to exchange the iodo group for a methyl or alkynyl group.

Scheme C illustrates yet another synthetic procedure usable to prepare specific compounds of Formula (1):

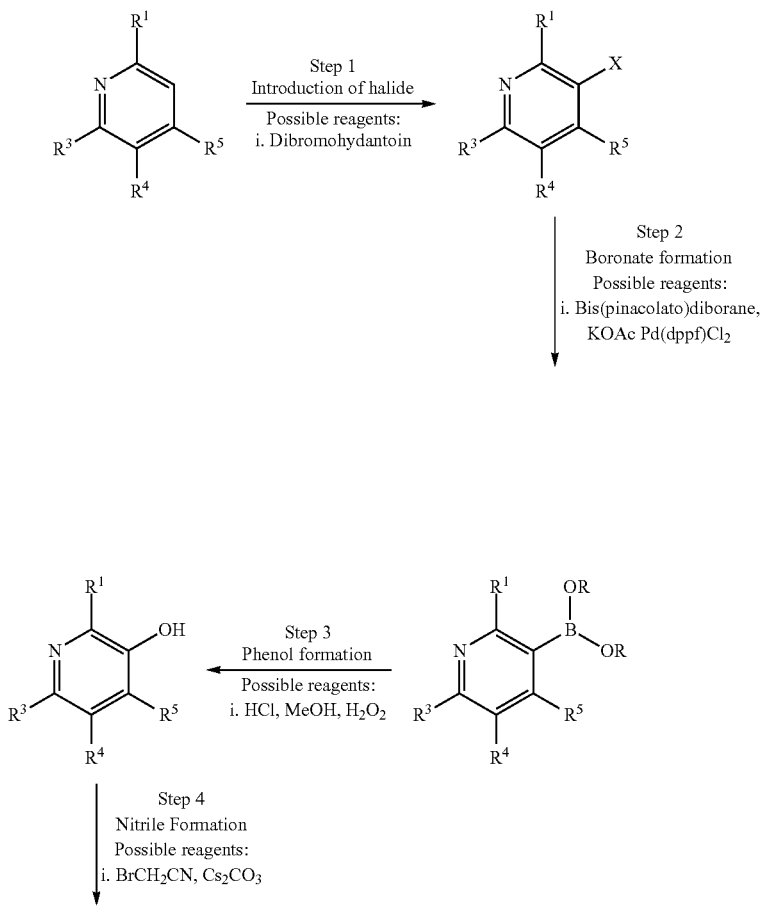

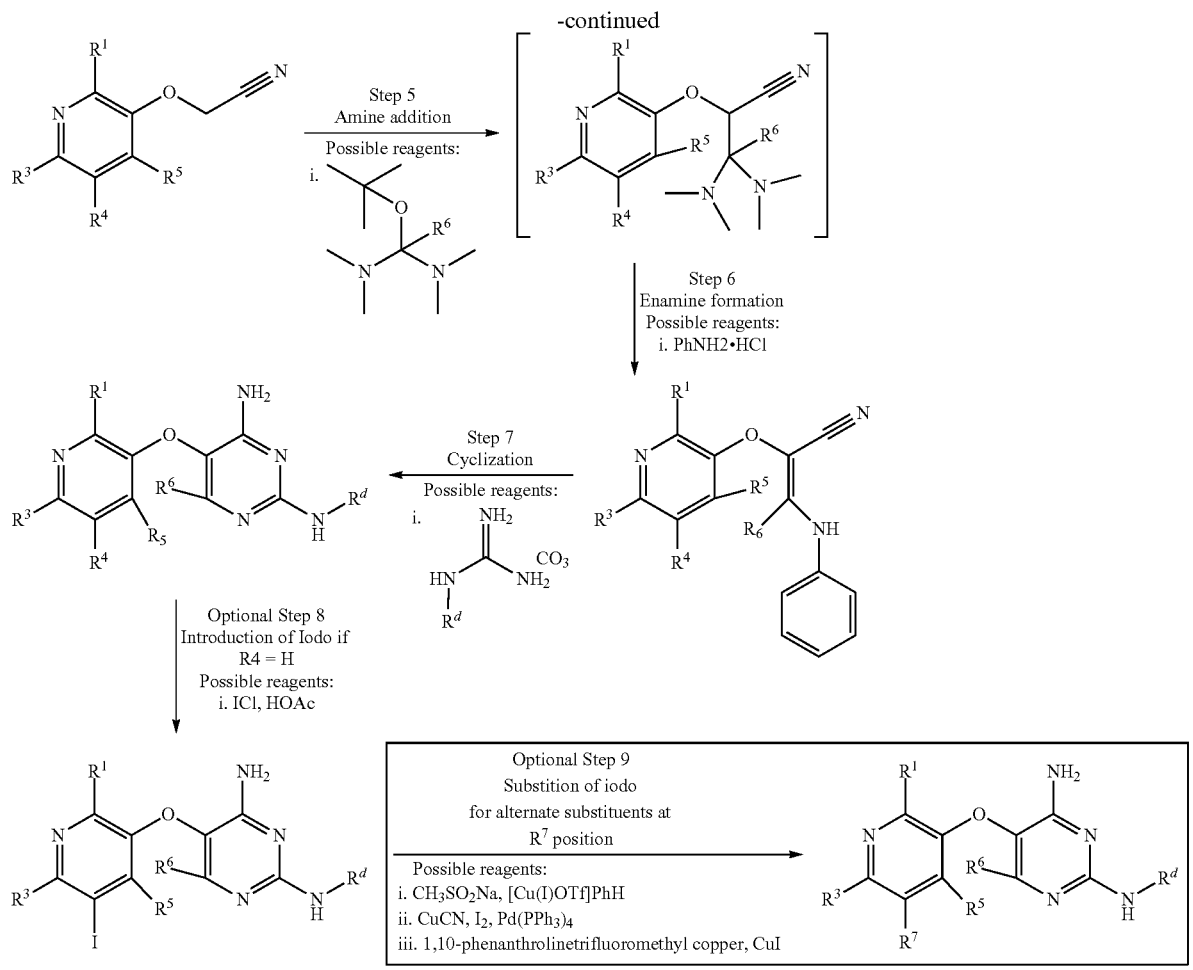

Generally speaking, Scheme C contemplates: (a) halogenation of an optionally substituted pyridine; (b) boronating the resulting halogenated pyridine; (c) converting the boronate to an hydroxy pyridine; (d) reaction of the hydroxy pyridine with BrCH$_2$CN and Cs$_2$CO$_3$; (e) amine addition to the resulting nitrile ether; (f) enamine formation from the resulting amine; and (g) cyclization of the resulting compound to produce a compound of Formula 1.

Scheme D illustrates still another synthetic procedure usable to prepare specific compounds of Formula (1):

Scheme D

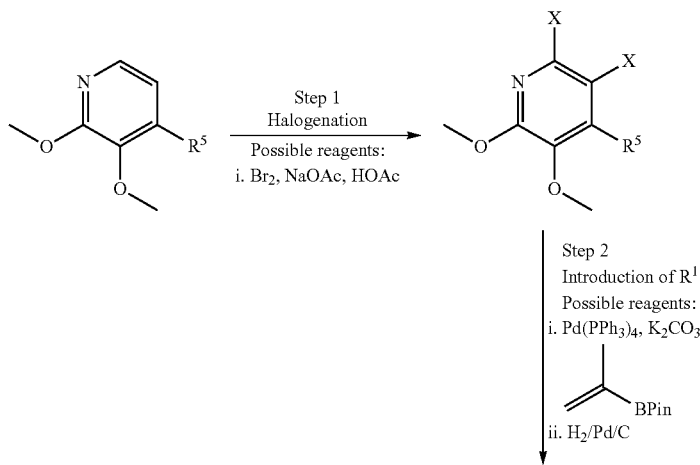

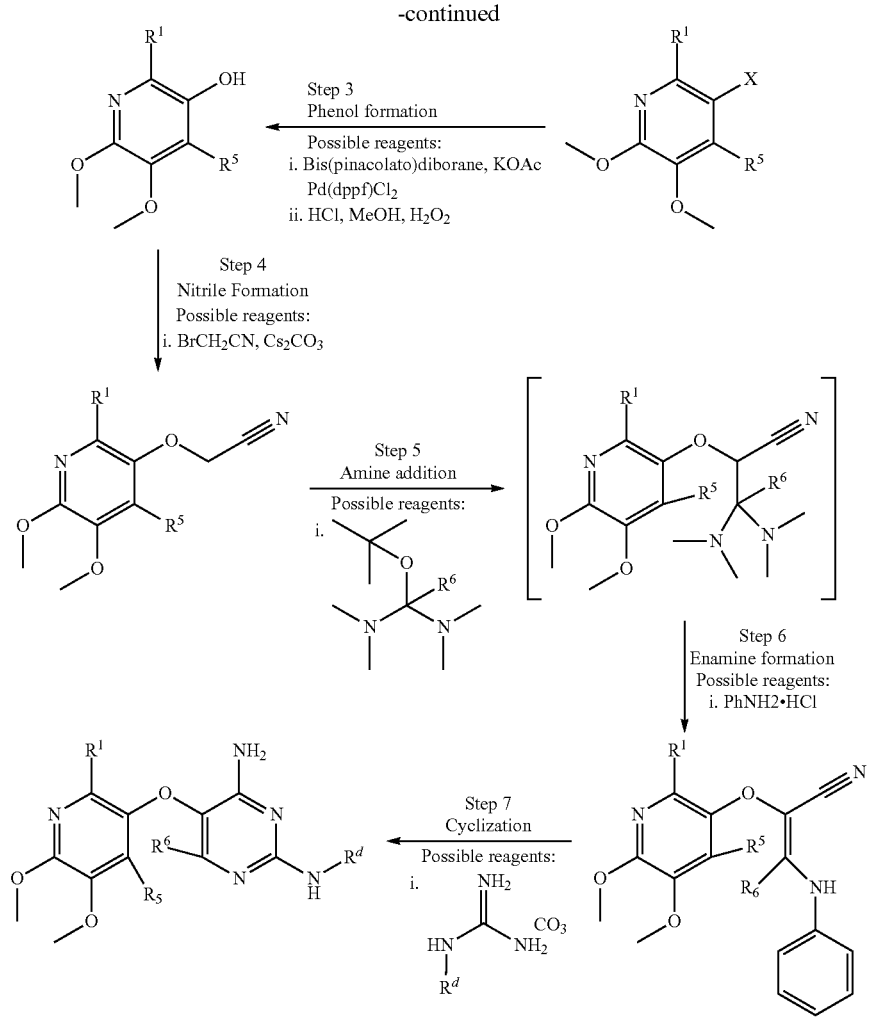

Generally speaking, Scheme D contemplates: (a) halogenation of a dimethoxypyridine; (b) introduction of $R^1$ into the halogenated dimethoxypyridine; (c) converting the resulting compound into an hydroxy pyridine; (d) reaction of the hydroxy pyridine with $BrCH_2CN$ and $Cs_2CO_3$; (e) amine addition to the resulting cyano ether; (f) enamine formation from the resulting amine; and (g) cyclization of the resulting compound to produce a compound of Formula 1.

Scheme D is especially applicable to compounds wherein $R^4=OCH_3$. The first two steps are a variation on the general scheme set forth above.

The compounds of the present disclosure are usable for the treatment of a wide range of genitourinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The compounds of the present disclosure are also useful for the treatment of cough or urge to cough associated with a respiratory disease, hypertension, heart failure, dyspnea, sleep apnea, altering carotid body tonicity or activity in a subject.

The compounds of the present disclosure are also expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The present disclosure includes pharmaceutical compositions comprising at least one compound of the present disclosure, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present disclosure will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present disclosure for a given disease.

Compounds of the present disclosure may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by in-halation or insufflation. The preferred manner of administration is generally oral using a convenient daily dosage regimen which can be adjusted according to the degree of affliction.

A compound or compounds of the present disclosure, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present disclosure may be formulated in a wide variety of oral administration dosage forms. The pharmaceutical compositions and dosage forms may comprise a compound or compounds of the present disclosure or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, e.g., in aqueous propylene glycol solutions or may contain emulsifying agents, e.g., such as lecithin, sorbitan monooleate, or acacia. Aqueous solutions can be prepared by dissolving the active component in water and adding suitable colorants, flavours, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavours, stabilizers, buffers, artificial and natural sweeteners, dispersants, thickeners and solubilizing agents.

The compounds of the present disclosure may be formulated for parenteral administration (e.g., by injection, e.g. bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, e.g. solutions in aqueous polyethylene glycol.

Examples of oily or non-aqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present disclosure may be formulated for topical administration to the epidermis as ointments, creams or lotions, or as a transdermal patch. Ointments and creams may, e.g., be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouth-washes comprising the active ingredient in a suitable liquid carrier.

The compounds of the present disclosure may be formulated for administration as suppositories. A low melting wax, such as a mixture of fatty acid glycerides or cocoa butter is first melted and the active component is dispersed homogeneously, e.g., by stirring. The molten homogeneous mixture is then poured into convenient sized molds, allowed to cool, and to solidify.

The compounds of the present disclosure may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or sus-pensions are applied directly to the nasal cavity by conventional means, e.g., with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved e.g. by means of a metering atomizing spray pump.

The compounds of the present disclosure may be formulated for aerosol administration, particularly to the respiratory tract and including intranasal administration. The compound will generally have a small particle size e.g. of the order of five (5) microns or less. Such a particle size may be obtained by means known in the art, e.g. by micronization. The active ingredient is provided in a pressurized pack with a suitable propellant such as a chlorofluoro-carbon (CFC), e.g., dichlorodifluoromethane, trichlorofluoromethane, or dichlorotetra-fluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, e.g. a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form e.g. in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present disclosure can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted sub-cutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy, 1995, edited by Martin, Mack Publishing Company, 19th edition, Easton, Pa. Representative pharmaceutical formulations containing a compound of the present disclosure are described herein.

EXAMPLES

Representative compounds disclosed herein are shown in Table 1. Detailed experimental steps and conditions for making these compounds are provided below.

TABLE 1

| Compound # | Structure | MW Found [M + H]$^+$ |
|---|---|---|
| 1 | 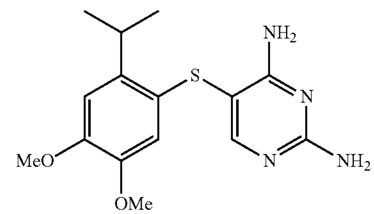 [SMILES: COc1cc(Sc2cnc(N)nc2N)c(C(C)C)cc1OC] | 321.2 |
| 2 | 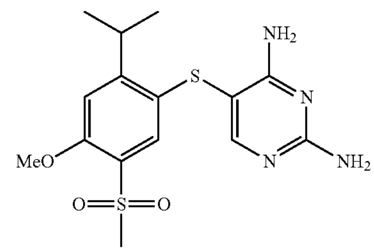 [SMILES: COc1cc(C(C)C)c(Sc2cnc(N)nc2N)cc1S(C)(=O)=O] | 369.0 |
| 3 | 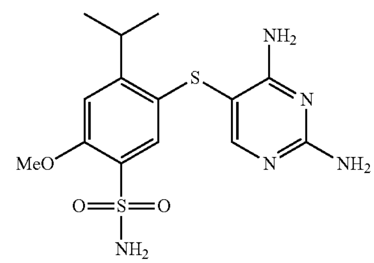 [SMILES: COc1cc(C(C)C)c(Sc2cnc(N)nc2N)cc1S(N)(=O)=O] | 370.0 |
| 4 | 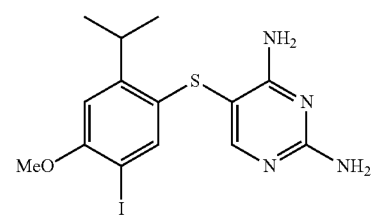 [SMILES: COc1cc(C(C)C)c(Sc2cnc(N)nc2N)cc1I] | 417.0 |
| 5 | 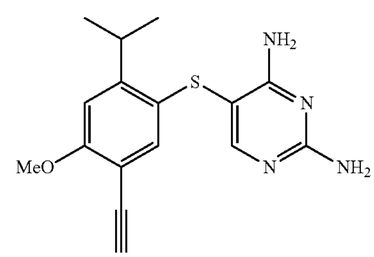 [SMILES: C#Cc1cc(Sc2cnc(N)nc2N)c(C(C)C)cc1OC] | 315.0 |

TABLE 1-continued

| Compound # | Structure | MW Found [M + H]+ |
|---|---|---|
| 6 | 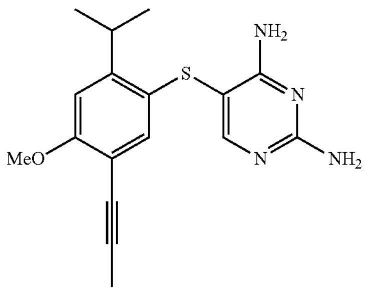 [SMILES: CC#Cc1cc(Sc2cnc(N)nc2N)c(C(C)C)cc1OC] | 329.1 |
| 7 | 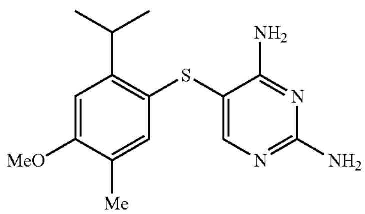 [SMILES: COc1cc(C(C)C)c(Sc2cnc(N)nc2N)cc1C] | 305.0 |
| 8 | 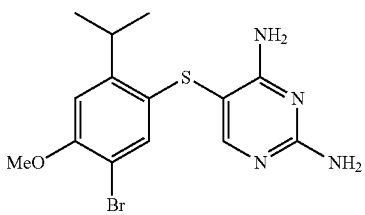 [SMILES: COc1cc(C(C)C)c(Sc2cnc(N)nc2N)cc1Br] | 368.9 |
| 9 | 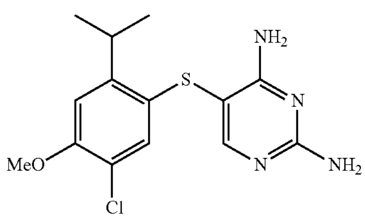 [SMILES: COc1cc(C(C)C)c(Sc2cnc(N)nc2N)cc1Cl] | 325.0 |
| 10 | 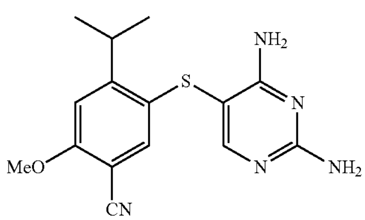 [SMILES: COc1cc(C(C)C)c(Sc2cnc(N)nc2N)cc1C#N] | 316.1 |
| 11 | 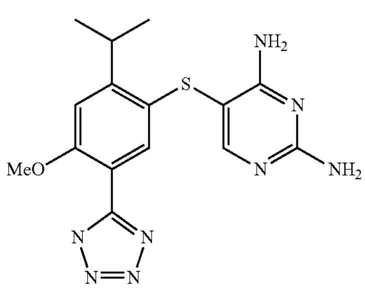 [SMILES: COc1cc(C(C)C)c(Sc2cnc(N)nc2N)cc1-c1nnn[nH]1] | 359.1 |
| 12 | | 335.1 |
| 13 | | 306.0 |
| 14 | | 276.1 |
| 15 | | 401.9 |
| 16 | | 354.1 |
| 17 | | 301.1 |

TABLE 1-continued
| Compound # | Structure | MW Found [M + H]+ |
|---|---|---|
| 18 | 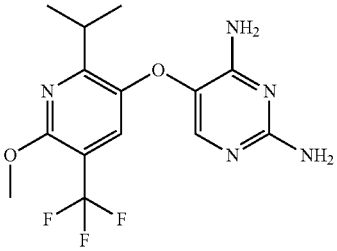 [SMILES: COc1nc(C(C)C)c(Oc2cnc(N)nc2N)cc1C(F)(F)F] | 344.2 |
| 19 | 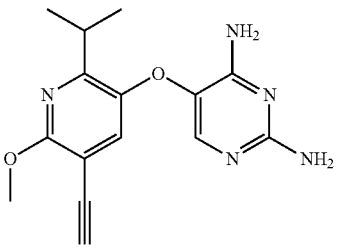 [SMILES: C#Cc1cc(Oc2cnc(N)nc2N)c(C(C)C)nc1OC] | 300.1 |
| 20 | 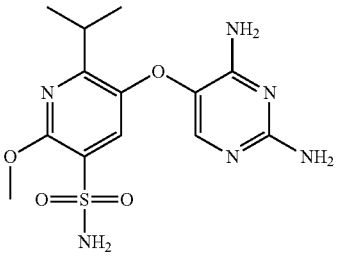 [SMILES: COc1nc(C(C)C)c(Oc2cnc(N)nc2N)cc1S(N)(=O)=O] | 355.0 |
| 21 | 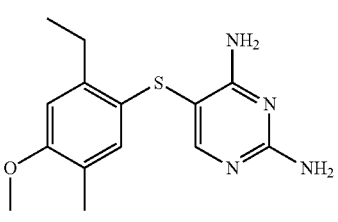 [SMILES: CCc1cc(OC)c(C)cc1Sc1cnc(N)nc1N] | 403.0 |
| 22 | 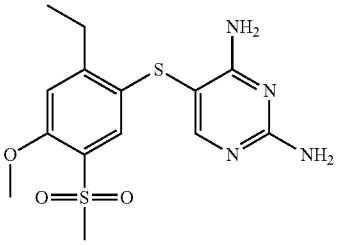 [SMILES: CCc1cc(OC)c(S(C)(=O)=O)cc1Sc1cnc(N)nc1N] | 355.1 |
| 23 | 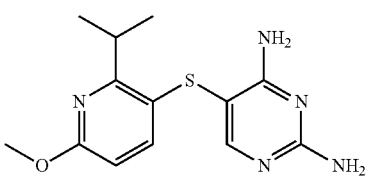 [SMILES: COc1ccc(Sc2cnc(N)nc2N)c(C(C)C)n1] | 292.0 |
| 24 | 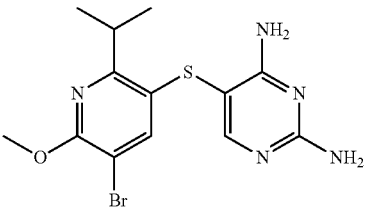 | 369.9 |
| 25 | 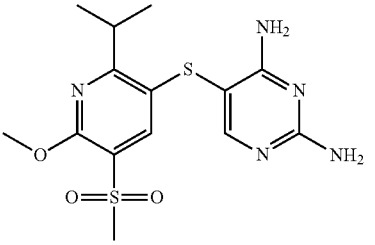 [SMILES: COc1nc(C(C)C)c(Sc2cnc(N)nc2N)cc1S(C)(=O)=O] | 370.0 |
| 26 | 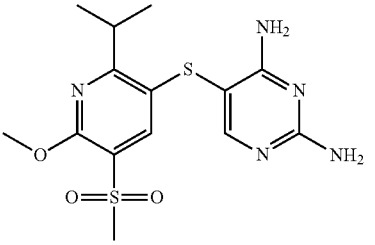 [SMILES: COc1nc(C(C)C)c(Sc2cnc(N)nc2N)cc1S(C)(=O)=O] | 317.0 |
| 27 | 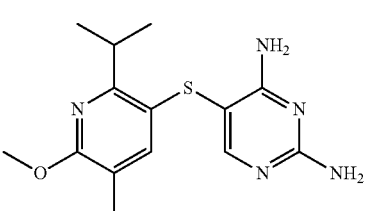 | 371.1 |
| 28 | 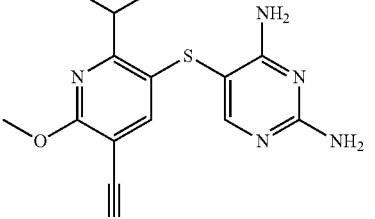 | 330.0 |
| 29 | 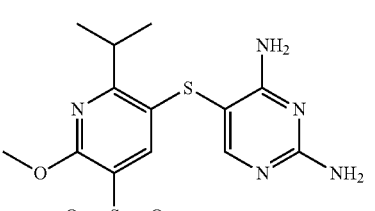 | 316.1 |

TABLE 1-continued

| Compound # | Structure | MW Found [M + H]+ |
|---|---|---|
| 30 | 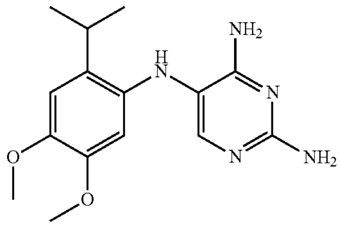 [SMILES: COc1cc(Nc2cnc(N)nc2N)c(C(C)C)cc1OC] | 304.1 |
| 31 | 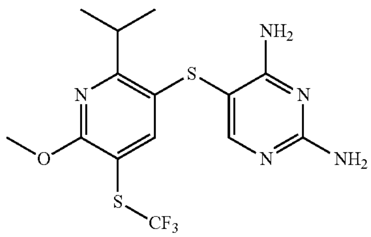 [SMILES: COc1nc(C(C)C)c(Sc2cnc(N)nc2N)cc1SC(F)(F)F] | 392.1 |
| 32 | 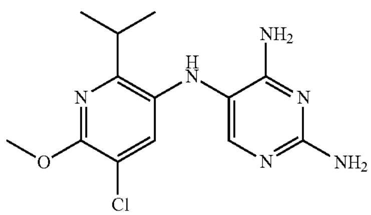 [SMILES: COc1nc(C(C)C)c(Nc2cnc(N)nc2N)cc1Cl] | 309.1 |
| 33 | 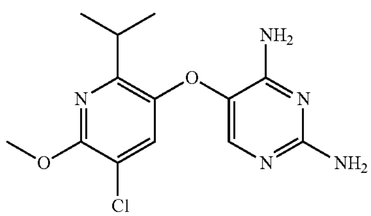 | 310.1 |
| 34 | 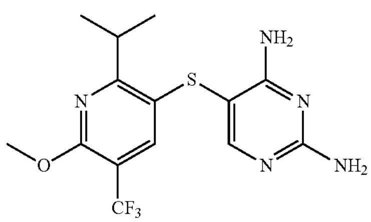 [SMILES: COc1nc(C(C)C)c(Sc2cnc(N)nc2N)cc1C(F)(F)F] | 360.0 |
| 35 | 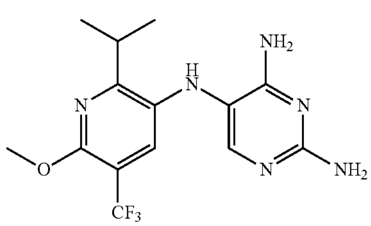 [SMILES: COc1nc(C(C)C)c(Nc2cnc(N)nc2N)cc1C(F)(F)F] | 343.2 |
| 36 | | 353.1 |
| 37 | | 352.0 |
| 38 | | 325.9 |
| 39 | | 308.1 |
| 40 | | 342.1 |
| 41 | | 322.0 |

TABLE 1-continued
| Compound # | Structure | MW Found [M + H]+ |
|---|---|---|
| 42 | 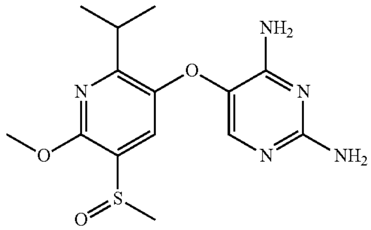 [SMILES: COc1nc(C(C)C)c(Oc2cnc(N)nc2N)cc1S(C)=O] | 338.0 |
| 43 | 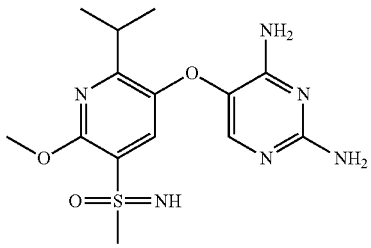 [SMILES: COc1nc(C(C)C)c(Oc2cnc(N)nc2N)cc1S(C)(=N)=O] | 353.0 |
| 44 | 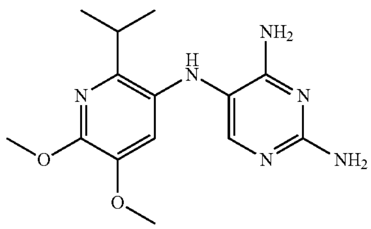 [SMILES: COc1cc(Nc2cnc(N)nc2N)c(C(C)C)nc1OC] | 305.2 |
| 45 | 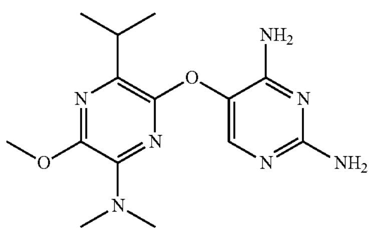 [SMILES: COc1nc(C(C)C)c(Oc2cnc(N)nc2N)nc1N(C)C] | 320.1 |
| 46 | 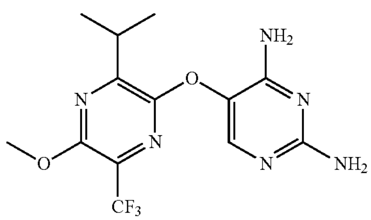 [SMILES: COc1nc(C(C)C)c(Oc2cnc(N)nc2N)nc1C(F)(F)F] | 345.0 |
| 47 | 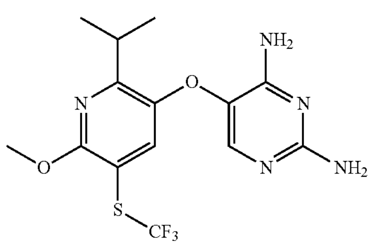 [SMILES: COc1nc(C(C)C)c(Oc2cnc(N)nc2N)cc1SC(F)(F)F] | 376.1 |
Example 1: Synthesis of Compound 1
Compound 1 was made by the synthetic method outlined in Scheme E:
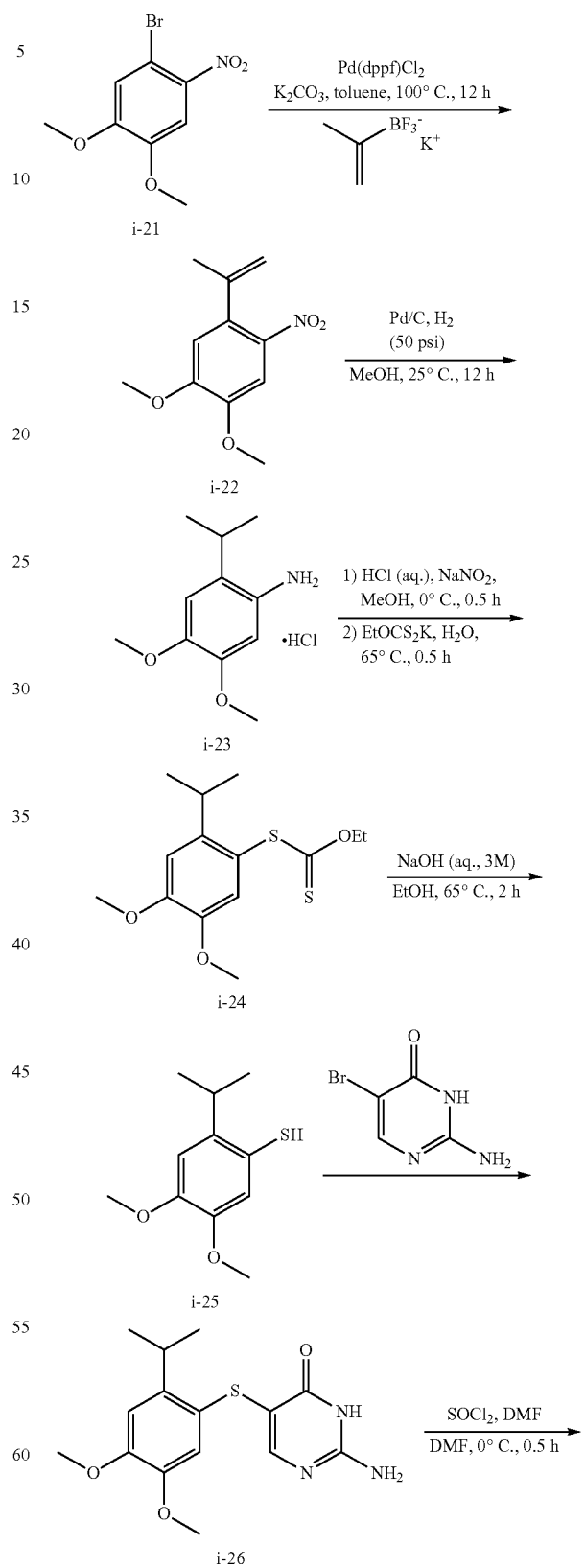
Scheme E

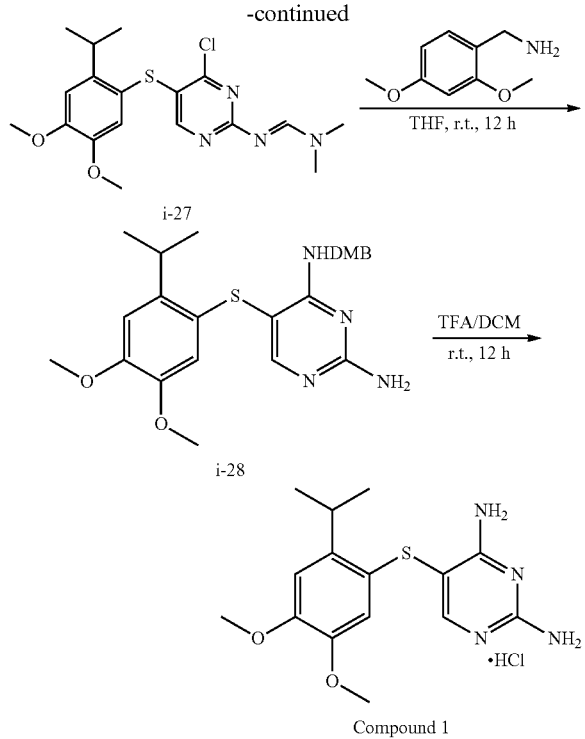

General Procedure for Preparation of Compound i-22:

To a solution of compound i-21 (2.0 g, 7.6 mmol, 1.0 eq) and potassium difluoro(isopropenyl)borane fluoride (4.5 g, 30 mmol, 4.0 eq) in toluene was added $K_2CO_3$ (3.16 g, 22 mmol, 3.0 eq) and Pd(dppf)$Cl_2$ (558 mg, 763 µmol, 0.1 eq) at 25° C. under $N_2$. The mixture was heated to 100° C. and stirred for 12 h. The reaction mixture was directly concentrated under reduced pressure to give a residue. The residue was further purified by column chromatography eluted with petroleum ether:ethyl acetate to give compound i-22 (1.6 g, 6.4 mmol, 90% TLC purity) as a solid, which was used directly in the next step.

General Procedure for Preparation of Compound i-23:

A mixture of compound i-22 (1.6 g, 7.1 mmol, 1.0 eq) in MeOH was hydrogenated under $H_2$ (50 psi) with catalyst Pd/C (100 mg) at 25° C. for 12 h. The mixture was filtered through celite, washed with methanol (200 mL). The filtrate was added concentrated HCl (1.0 mL), and then concentrated to give compound i-23 (1.4 g crude) as a solid, which was used directly in the next step. $^1$H NMR: (400 MHz MeOD-$d_4$) δ 7.00 (s, 1H), 6.92 (s, J=4.0 Hz, 1H), 3.88 (s, 3H), 3.86 (s, 3H), 3.08-3.02 (m, 1H), 1.31 (d, J=6.4 Hz, 6H.

General Procedure for Preparation of Compound i-24:

To a solution of compound i-23 (1.3 g, 6.6 mmol, 1.0 eq) in MeOH (6.5 mL) and aq.HCl (1.0 M, 13 mL, 2.0 eq) was added dropwise a solution of $NaNO_2$ (716 mg, 10 mmol, 564 µL, 1.5 eq) in $H_2O$ (13 mL) at 0° C., then the mixture was stirred for 0.5 h. After this time, the mixture was added to solution of ethoxycarbothioylsulfanylpotassium (2.1 g, 13 mmol, 2.0 eq) in $H_2O$ (32 mL) at 65° C. Then mixture was stirred for 0.5 h at 65° C. The mixture was poured into water (150 mL). EtOAc (150 mL) was added and the organic layer was separated. The aqueous layer was extracted with EtOAc (150 mL). The extractions were combined, dried over anhydrous $Na_2SO_4$, and filtered. The filtrate was concentrated to give crude product, which was further purified by silica gel column to give compound i-24 (800 mg) as an oil.

$^1$H NMR: (400 MHz CDCl$_3$) δ 6.95 (s, 1H), 6.86 (s, 1H), 4.61 (q, J=7.2 Hz, 2H), 3.94 (s, 3H), 3.86 (s, 3H), 3.41-3.83 (m, 1H), 1.35 (t, J=7.2 Hz, 3H), 1.20 (d, J=6.8 Hz, 6H).

General Procedure for Preparation of Compound i-25:

To a solution of compound i-24 (700 mg, 2.3 mmol, 1.0 eq) in EtOH (8.0 mL) was added aq.NaOH (3 M, 8.5 mL, 11 eq) at 25° C. Then the mixture was heated to 65° C. and stirred for 2 h. The mixture was cooled to RT and 1,4-dithioerythritol (CAS: 6892-68-8, 20 mg) was added. The mixture was adjusted to pH=5 with 10% aq. HCl, then extracted with EtOAc (100 mL×2). The organic layer was dried over anhydrous $Na_2SO_4$, filtered. The filtrate was concentrated to give compound i-25 (500 mg, crude) as an oil, which was directly used without further purification.

General Procedure for Preparation of Compound i-26:

To a solution of compound i-25 (400 mg, 1.8 mmol, 1.0 eq) in DMF (5.0 mL) was added 2-amino-5-bromo-1H-pyrimidin-6-one (357 mg, 1.8 mmol, 1.0 eq) and $K_2CO_3$ (779 mg, 5.6 mmol, 3.0 eq) at 25° C. Then the mixture was heated to 80° C. in a sealed tube and stirred for 1 h under microwave. The mixture was filtered. The filter cake was washed with DMF (1 mL). The DMF solution was collected and combined and purified by prep-HPLC to give i-26 (220 mg) as a solid. $^1$H NMR: (400 MHz DMSO-$d_6$) δ 11.16 (br.s, 1H), 7.66 (s, 1H), 6.84-6.77 (m, 4H), 3.76 (s, 3H), 3.64 (s, 3H), 3.53-3.33 (m, 1H), 1.18 (d, J=6.8 Hz, 6H). LCMS: [M+H] 321.1.

General procedure for preparation of compound i-27:

To a solution of DMF (143 mg, 1.9 mmol, 151 µL, 4.8 eq) was added dropwise $SOCl_2$ (246 mg, 2.0 mmol, 150 µL, 5.1 eq) with cooling bath at 0° C. The resulting mixture was added to a solution of i-26 (130 mg, 404 µmol, 1.0 eq) in DMF (3.0 mL) at 0° C. The mixture was stirred for 0.5 h at 0° C. The reaction was concentrated to give compound i-27 (160 mg, crude) as an oil, which was directly used without further purification. LCMS: [M+H] 395.2.

General procedure for preparation of compound i-28:

To a solution of compound i-27 (160 mg, 405 µmol, 1.0 eq) in THF (4.0 mL) was added 2,4-DMBNH$_2$ (2,4-Dimethoxybenzylamine, 3.4 g, 20 mmol, 50 eq) at 25° C. The resulting mixture was stirred for 12 h at 25° C. The mixture was diluted with brine (50 mL), and then extracted with EtOAc (100 mL). The organic layer was dried over anhydrous $Na_2SO_4$, filtered, and the filtrate was concentrated to give crude product, which was further purified by prep-HPLC to give compound i-28 (120 mg, 85% LCMS purity) as an oil, which was used directly in the next step. LCMS: [M+H] 471.2.

General Procedure for Preparation of Compound 1:

To a solution of compound i-28 (120 mg, 255 µmol, 1.0 eq) in DCM (4.0 mL) was added TFA (6.1 g, 54 mmol, 4.0 mL, 211 eq) at 25° C., the mixture was stirred for 12 h at 25° C. The mixture was concentrated to give crude product, which was purified by prep-HPLC to give Compound 1 (15 mg, 100% LCMS purity) as a solid. $^1$H NMR: (400 MHz MeOD-$d_4$) 7.78 (s, 1H), 6.95 (s, 1H), 6.88 (s, 1H), 3.86 (s, 3H), 3.78 (s, 3H), 3.61-3.53 (m, 1H), 1.26 (d, J=6.8 Hz, 6H). LCMS: [M+H]$^+$ 321.2.

Example 2: Synthesis of Compound 2

Compound 2 was made by the synthetic method outlined in Scheme F:

Scheme F

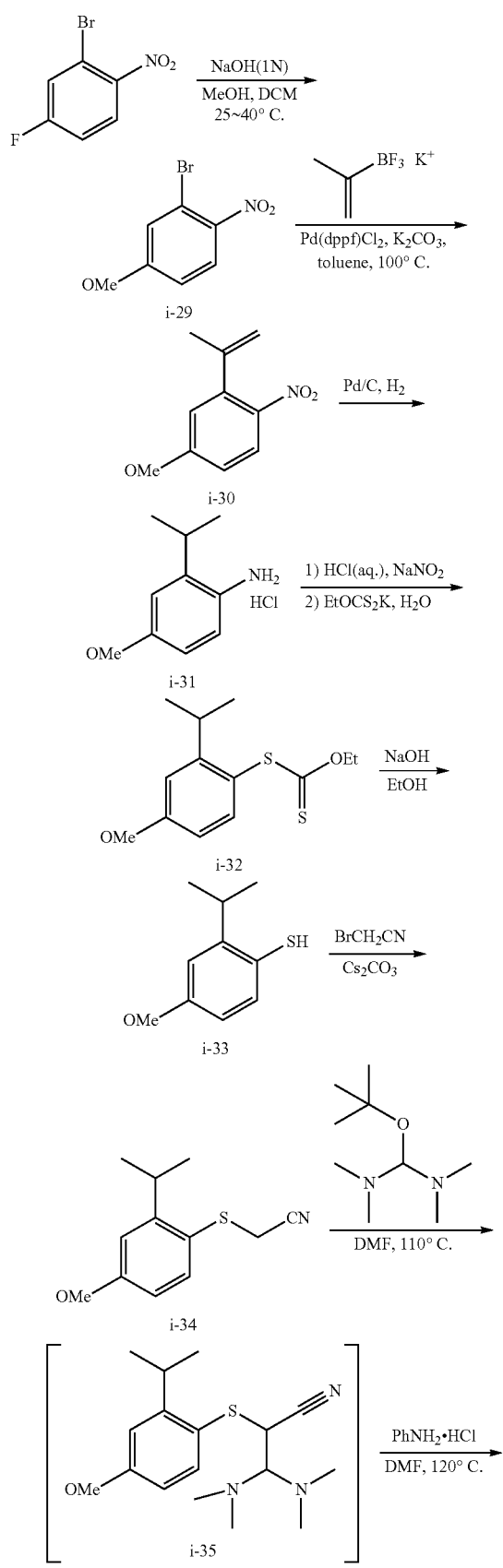

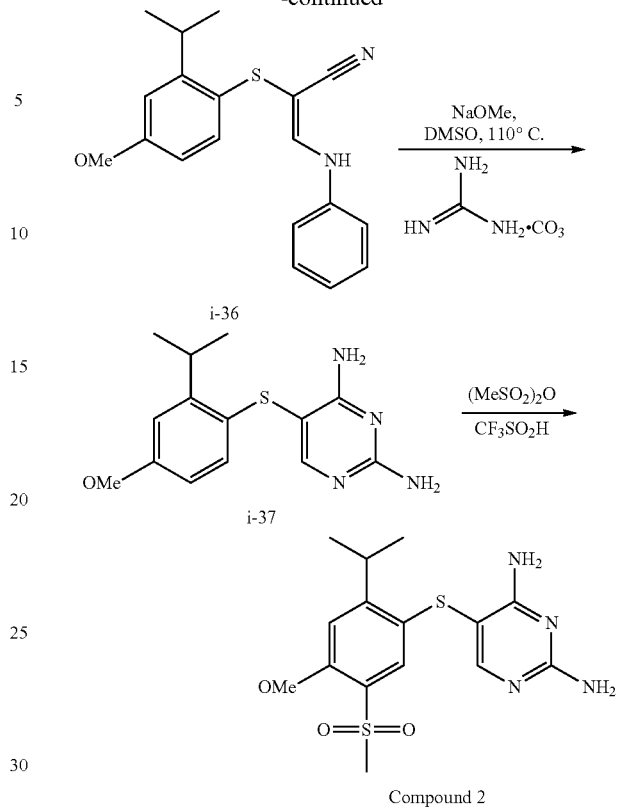

General Procedure for Preparation of Compound i-29:

To a solution of 2-bromo-4-fluoro-1-nitro-benzene (60.0 g, 273 mmol, 1.00 eq) in the mixture of dichloromethane (400 mL) and methanol (440 mL) was added 1 M NaOH aqueous solution (1.00 L). Then a catalytic amount of TBAB (tetrabutylammonium bromide, 360 mg, 1.26 mmol) was added. The reaction was stirred at 40° C. for 16 h. The reaction mixture was partitioned between DCM and water. Then the aqueous layer was extracted with dichloromethane (3×300 mL). The combined organic layers were dried over $Na_2SO_4$, filtered and concentrated under reduced pressure. The crude product was purified by column chromatography on silica gel to give compound i-29 (43.1 g, 186 mmol) as a solid. $^1$H NMR: (400 MHz, Chloroform-d) 8.00 (d, J=9.3 Hz, 1H), 7.23 (d, J=2.6 Hz, 1H), 6.93 (dd, J=2.6, 9.3 Hz, 1H), 3.90 (s, 3H).

General Procedure for Preparation of Compound i-30:

Two parallel reactions were set up as follows and subsequently combined for extraction and purification.

To a solution of i-29 (40.0 g, 172 mmol, 1.00 eq) and potassium difluoro(isopropenyl)borane fluoride (51.0 g, 344 mmol, 2.00 eq) in toluene (200 mL) was added Pd(dppf)Cl$_2$ (12.6 g, 17.2 mmol, 0.10 eq) and K$_2$CO$_3$ (71.5 g, 517 mmol, 3.00 eq). The reaction mixture was stirred at 100° C. for 12 h under N$_2$ atmosphere.

The two reaction mixtures were combined and were partitioned between ethyl acetate (200 mL) and water (200 mL). The aqueous layer was extracted with ethyl acetate (3×200 mL). Then the combined organic layers were dried over Na$_2$SO$_4$, filtered and concentrated under reduced pressure. The residue was purified by column chromatography on silica gel to give compound i-30 (45.0 g, 233 mmol) as an oil. $^1$H NMR: (400 MHz, Chloroform-d) 8.01 (d, J=8.8

Hz, 1H), 6.86 (dd, J=2.9, 9.0 Hz, 1H), 6.76 (d, J=2.6 Hz, 1H), 5.17-5.14 (m, 1H), 4.93 (s, 1H), 3.90 (s, 3H), 2.08 (s, 3H).

General Procedure for Preparation of Compound i-31:

To a solution of i-30 (45.0 g, 233 mmol, 1.00 eq) in methanol (800 mL) was added Pd/C (4.18 g, 1.97 mmol, 5% w.t.). The mixture was stirred at 25° C. under H2 (50 psi) for 12 h. The reaction mixture was filtered through celite and washed with methanol (300 mL). To the filtrate was added 12M HCl (40.0 mL). Then the mixture was concentrated to give compound i-31 (53.7 g, crude, HCl) as a solid which was used for the next step directly. $^1$H NMR: (400 MHz, DMSO-$d_6$) 10.16 (br. s., 3H), 7.38-7.32 (m, 1H), 6.91 (d, J=2.6 Hz, 1H), 6.86-6.80 (m, 1H), 3.73 (s, 3H), 3.08 (td, J=6.7, 13.6 Hz, 1H), 1.16 (d, J=7.1 Hz, 6H).

General Procedure for Preparation of Compound i-32:

Two parallel reactions were set up as follows and subsequently combined for extraction and purification.

To a solution of i-31 (19.4 g, 95.9 mmol, 1.00 eq) in methanol (70.0 mL) and HCl (1M, 193 mL, 56.4 eq) was added dropwise a solution of NaNO$_2$ (7.94 g, 115 mmol, 6.25 mL, 1.20 eq) in H$_2$O (80.0 mL) at 0° C. The mixture was stirred at 0° C. for 0.5 h. Then the mixture was added dropwise to a solution of EtOCS$_2$K (30.7 g, 192 mmol, 2.00 eq) in H$_2$O (500 mL) at 25° C. The mixture was stirred at 25° C. for 0.5 h. The two reaction mixtures were combined and partitioned between ethyl acetate (500 mL) and water (500 mL). The aqueous layer was extracted with ethyl acetate (3×300 mL). The combined organic layers were dried over Na$_2$SO$_4$, filtered and concentrated under reduced pressure. The residue was purified by column chromatography on silica gel to give compound i-32 (22.0 g, 81.4 mmol) as an oil which was used for the next step directly. $^1$H NMR: (400 MHz, Chloroform-d) 7.43-7.38 (m, 1H), 6.93 (d, J=2.6 Hz, 1H), 6.78 (dd, J=2.6, 8.4 Hz, 1H), 4.61 (q, J=7.1 Hz, 2H), 3.86 (s, 3H), 3.38 (td, J=6.8, 13.7 Hz, 1H), 1.34 (t, J=7.1 Hz, 3H), 1.21 (d, J=7.1 Hz, 6H).

General Procedure for Preparation of Compound i-33:

To a solution of i-32 (22.0 g, 81.4 mmol, 1.00 eq) in EtOH (200.00 mL) was added NaOH (3M, 298 mL, 11.0 eq). Then the mixture was stirred at 65° C. for 2 h. 1,4-dithioerythritol (200 mg) was added. The mixture was adjusted to pH=5 with 3M HCl (290 mL). Then the mixture was partitioned between ethyl acetate (300 mL) and water (300 mL). The aqueous layer was extracted with ethyl acetate (3×300 mL). The combined organic layers were dried over Na$_2$SO$_4$, filtered and concentrated under reduced pressure to give compound i-33 (13.3 g, crude) as an oil which was used for the next step directly. $^1$H NMR: (400 MHz, DMSO-$d_6$) 7.27 (d, J=8.4 Hz, 1H), 6.78 (d, J=2.2 Hz, 1H), 6.70-6.65 (m, 1H), 4.80 (s, 1H), 3.69 (s, 3H), 3.11 (td, J=6.9, 13.5 Hz, 1H), 1.15 (d, J=6.6 Hz, 6H).

General Procedure for Preparation of Compound i-34:

To a solution of i-33 (13.3 g, 72.9 mmol, 1.00 eq) in CH$_3$CN (100 mL) was added BrCH$_2$CN (13.1 g, 109 mmol, 1.50 eq) and Cs$_2$CO$_3$ (35.6 g, 109 mmol, 1.50 eq). The mixture was stirred at 80° C. for 12 h. The reaction mixture was partitioned between ethyl acetate (100 mL) and water (100 mL). The aqueous layer was extracted with ethyl acetate (3×80 mL). The combined organic layers were dried over Na$_2$SO$_4$, filtered and concentrated under reduced pressure. The residue was purified by column chromatography on silica gel to give compound i-34 (10.6 g, 47.9 mmol) as an oil. $^1$H NMR: (400 MHz, DMSO-$d_6$) 7.54 (d, J=8.8 Hz, 1H), 6.91 (d, J=3.1 Hz, 1H), 6.86 (dd, J=2.9, 8.6 Hz, 1H), 3.96 (s, 2H), 3.78 (s, 3H), 3.50 (td, J=7.0, 13.8 Hz, 1H), 1.19 (d, J=6.6 Hz, 6H).

General Procedure for Preparation of Compound i-35:

To a solution of i-34 (10.6 g, 47.9 mmol, 1.00 eq) in DMF (80.0 mL) was added 1-tert-butoxy-N,N,N',N'-tetramethylmethanediamine (16.7 g, 95.8 mmol, 2.00 eq). Then the mixture was stirred at 110° C. for 1 h. The reaction mixture was used directly in the next step.

General Procedure for Preparation of Compound i-36:

To a solution of i-35 (15.4 g, 47.9 mmol, 1.00 eq) in DMF (150 mL) was added aniline hydrochloride (31.0 g, 240 mmol, 30.4 mL, 5.00 eq). The mixture was stirred at 120° C. for 12 h. The reaction mixture was partitioned between toluene (100 mL) and water (100 mL). Then the aqueous layer was extracted with toluene (3×80 mL). The combined organic layers were dried over Na$_2$SO$_4$, filtered and concentrated under reduced pressure to give compound i-36 (32.3 g, crude) as an oil which was used in the next step directly. $^1$H NMR: (400 MHz, Chloroform-d) 7.34 (dt, J=3.5, 7.1 Hz, 5H), 7.15 (d, J=7.9 Hz, 3H), 6.98 (d, J=7.9 Hz, 2H), 6.71 (s, 1H), 3.80 (s, 3H), 3.49 (d, J=6.6 Hz, 1H), 1.29 (d, J=7.1 Hz, 6H).

General Procedure for Preparation of Compound i-37:

To a solution of i-36 (32.3 g, 100 mmol, 1.00 eq) in DMSO (300 mL) was added CH$_3$ONa (16.1 g, 299 mmol, 3.00 eq) and guanidine carbonate (26.9 g, 149 mmol, 1.50 eq). The mixture was stirred at 110° C. for 12 h. The reaction mixture was partitioned between ethyl acetate (200 mL) and water (200 mL). Then the aqueous layer was extracted with ethyl acetate (3×100 mL). The combined organic layer was dried over Na$_2$SO$_4$, filtered and concentrated under reduced pressure. The residue was purified by column chromatography on silica gel and prep-HPLC to give Compound i-37 (4.00 g, 13.8 mmol) as a solid which was used for the next step directly. $^1$H NMR: (400 MHz, DMSO-$d_6$) 7.82 (s, 1H), 6.79 (d, J=2.6 Hz, 1H), 6.73 (s, 1H), 6.69-6.66 (m, 1H), 6.31 (br. s., 2H), 3.66 (s, 3H), 3.40-3.35 (m, 1H), 1.17 (d, J=6.6 Hz, 6H). LCMS: [M+H]$^+$ 291.1

General Procedure for Preparation of Compound 2:

To a mixture of i-37 (200 mg, 689 µmol, 1.00 eq) and methylsulfonyl methanesulfonate (480 mg, 2.76 mmol, 4.00 eq) was added CF$_3$SO$_3$H (310. mg, 2.07 mmol, 3.00 eq). Then the mixture was stirred at 80° C. for 12 h. The mixture was adjusted to pH=8 with sat. NaHCO$_3$ (10 mL). The mixture was partitioned between ethyl acetate (30 mL) and water (30 mL). Then the aqueous layer was extracted with ethyl acetate (3×30 mL). The combined organic layers were dried over Na$_2$SO$_4$, filtered and concentrated under reduced pressure. The residue was purified by prep-HPLC to give Compound 2 (46.0 mg, 125 µmol) as a solid. $^1$H NMR: (400 MHz, DMSO-$d_6$) 7.84 (s, 1H), 7.19 (s, 1H), 7.12 (s, 1H), 6.36 (br. s., 2H), 3.91 (s, 3H), 3.46-3.39 (m, 1H), 3.13 (s, 3H), 1.26 (d, J=6.6 Hz, 6H). LCMS: [M+H]$^+$ 369.0.

Example 3: Synthesis of Compound 3

Compound 3 was made by the synthetic method outlined in Scheme G:

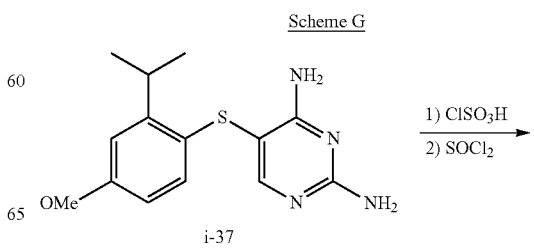

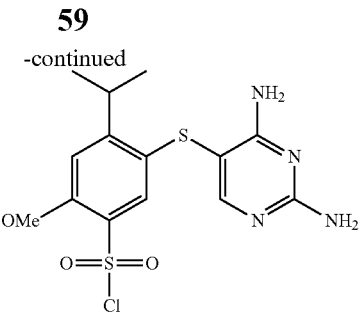

i-38

↓ NH₃, THF

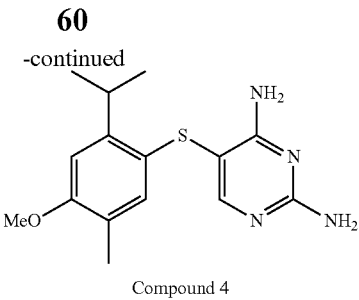

Compound 3

Compound i-37 was prepared as outlined above in Example 2.

General Procedure for Preparation of Compound i-38:

A mixture of i-37 (200 mg, 689 µmol, 1.00 eq) and sulfurochloridic acid (802 mg, 6.89 mmol, 458 µL, 10.0 eq) was stirred at 20° C. for 2.5 h. Then SOCl₂ (164 mg, 1.38 mmol, 99.9 µL, 2.00 eq) was added. The mixture was stirred at 20° C. for 1 h. The mixture was used for the next step directly without work up and purification.

General Procedure for Preparation of Compound 3:

Compound i-38 was added to a cooled solution of NH₃ (10 mol/L, 1.38 mL, 20.0 eq) in THF (1.38 mL) slowly at 0° C. The reaction mixture was stirred at 20° C. for 12 h. The mixture was filtered and washed with CH₃OH (30 mL). The filtrate was concentrated and the residue was purified by prep-HPLC to give Compound 3 (37.0 mg, 100 µmol) as a solid. ¹H NMR: (400 MHz, DMSO-d₆) 7.87 (s, 1H), 7.22 (s, 1H), 7.06 (s, 1H), 6.96 (s, 2H), 6.41 (br. s., 2H), 3.89 (s, 3H), 3.45 (td, J=6.7, 13.6 Hz, 1H), 2.07 (s, 2H), 1.27 (d, J=7.1 Hz, 6H). LCMS: [M+H]⁺ 370.0.

Example 4: Synthesis of Compound 4

Compound 4 was made by the synthetic method outlined in Scheme H

Scheme H

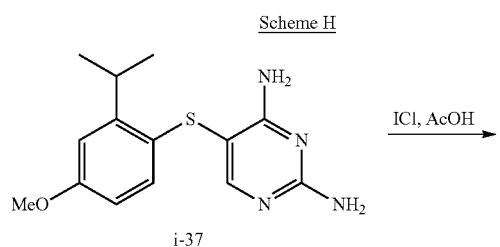

i-37

↓ ICl, AcOH

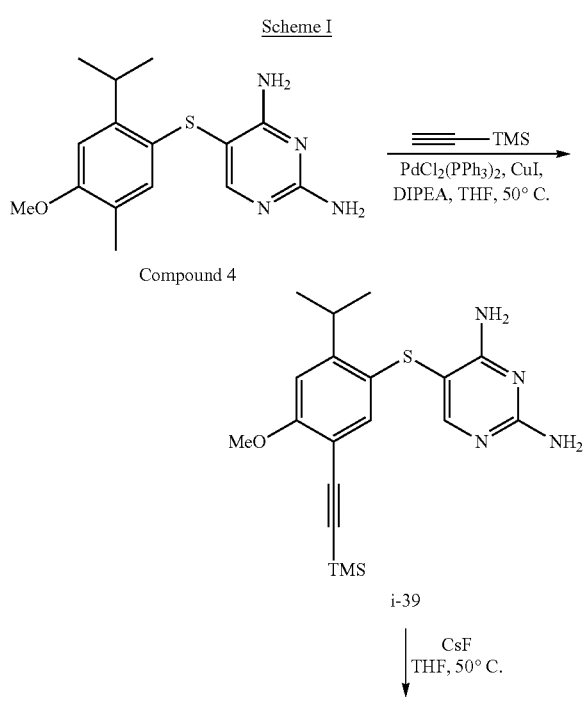

Compound 4

Compound i-37 was prepared as outlined above in Example 2.

General Procedure for Preparation of Compound 4:

To a solution of i-37 (1.50 g, 5.17 mmol, 1.00 eq) in HOAc (15.00 mL) was added ICl (1.01 g, 6.20 mmol, 316 µL, 1.20 eq) and H₂O (93.1 mg, 5.17 mmol, 1.80 mL, 1.00 eq). The mixture was stirred at 25° C. for 12 h. Then ICl (1.01 g, 6.20 mmol, 316 µL, 1.20 eq) was added and the mixture was stirred at 40° C. for 12 h. Another portion of ICl (1.01 g, 6.20 mmol, 316 µL, 1.20 eq) was added. The mixture was stirred at 40° C. for another 12 h. The mixture was adjusted to pH=7 with sat. NaHCO₃ (40 mL). Then the mixture was partitioned between ethyl acetate (50 mL) and water (50 mL). The aqueous layer was extracted with ethyl acetate (3×30 mL). The combined organic layers were dried over Na₂SO₄, filtered and concentrated. The residue was purified by column chromatography on silica gel to give Compound 4 (1.00 g, 2.40 mmol). 100 mg of the solid was further purified by SFC separation to give 25 mg Compound 4 as a solid. ¹H NMR: (400 MHz, DMSO-d₆) 7.89 (s, 1H), 7.13 (s, 1H), 6.88 (s, 1H), 6.53 (br.s., 2H), 3.81 (s, 3H), 3.44-3.36 (m, 1H), 1.24 (d, J=6.6 Hz, 6H). LCMS: [M+H]⁺ 417.0.

Example 5: Synthesis of Compound 5

Compound 5 was made by the synthetic method outlined in Scheme I:

Scheme I

Compound 4

≡—TMS
PdCl₂(PPh₃)₂, CuI,
DIPEA, THF, 50° C.

i-39

↓ CsF
THF, 50° C.

-continued

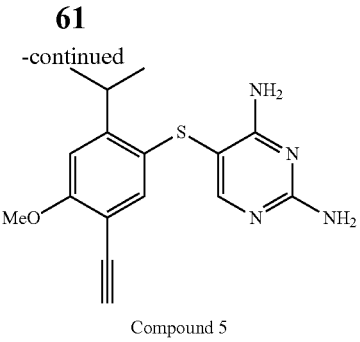

Compound 5

Compound 4 was prepared as outlined above in Example 4.

General Procedure for Preparation of Compound i-39:

To a solution of Compound 4 (300 mg, 721 μmol, 1.00 eq) in THF (3.00 mL) was added Pd(PPh$_3$)$_2$Cl$_2$ (202 mg, 288 μmol, 0.400 eq) and CuI (27.4 mg, 144 μmol, 0.200 eq) under N$_2$. Then ethynyl(trimethyl)silane (177 mg, 1.80 mmol, 2.50 eq) and diisopropylethylamine (745 mg, 5.77 mmol, 8.00 eq) was added. The mixture was heated to 50° C. for 12 h under N$_2$. The reaction mixture was poured into aq. NH$_4$Cl (15% w.t., 3 mL) and extracted with ethyl acetate (4×6 mL). The combined organic layers were concentrated under reduced pressure to give an oil. The residue was purified by prep-TLC to give i-39 (110 mg, 284 μmol) as a solid. $^1$H NMR: (400 MHz, Methanol-d$_4$) 7.92-7.90 (m, 1H), 6.91-6.87 (m, 2H), 3.85 (s, 3H), 3.56-3.49 (m, 1H), 1.31-1.26 (m, 6H), 0.19 (s, 9H).

General Procedure for Preparation of Compound 5:

To a mixture of i-39 (95.0 mg, 246 μmol, 1.00 eq) in THF (2.00 mL) was added CsF (373 mg, 2.46 mmol, 90.6 10.0 eq) in one portion. The mixture was stirred at 50° C. for 2 h under N$_2$. The mixture was poured into H$_2$O (5 mL). The aqueous phase was extracted with ethyl acetate (4×10 mL). The combined organic phase was washed with brine (10 mL), dried over anhydrous Na$_2$SO$_4$, filtered and concentrated in vacuum to give a solid. The residue was purified by prep-HPLC to give Compound 5 (15.0 mg, 47.7 μmol) as a solid.

$^1$H NMR: (400 MHz, DMSO-d$_6$) 7.87 (s, 1H), 6.93 (s, 1H), 6.75 (s, 1H), 6.43 (br. s., 2H), 4.13 (s, 1H), 3.81 (s, 3H), 3.41 (td, J=6.8, 13.7 Hz, 1H), 1.24 (d, J=6.6 Hz, 6H). LCMS: [M+H]$^+$ 315.0.

Example 6: Synthesis of Compound 6

Compound 6 was made by the synthetic method outlined in Scheme J

Scheme J

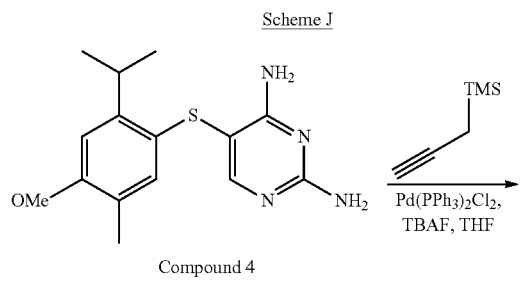

-continued

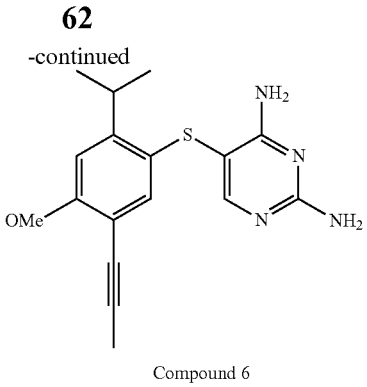

Compound 6

Starting material Compound 4 was prepared as outlined above in Example 4.

General Procedure for Preparation of Compound 6:

To a mixture of Compound 4 (200 mg, 480 μmol, 1.00 eq) in THF (4.00 mL) was added trimethyl(prop-2-ynyl)silane (135 mg, 1.20 mmol, 179 μL, 2.50 eq), Pd(PPh$_3$)$_2$Cl$_2$ (169 mg, 240 μmol, 0.5 eq) and tetrabutyl ammonium fluoride (1 mol/L, 1.44 mL, 3.00 eq). The mixture was de-gassed and then heated to 50° C. for 12 h under N$_2$. The residue was poured into H$_2$O (5 mL). The aqueous phase was extracted with ethyl acetate (3×8 mL). The combined organic phase was washed with brine (10 mL), dried over anhydrous Na$_2$SO$_4$, filtered and concentrated in vacuum to give a light yellow solid. The solid was purified by prep-HPLC to give Compound 6 (16.0 mg, 48.7 μmol) as a solid. $^1$H NMR: (400 MHz, DMSO-d$_6$) 7.86 (s, 1H), 6.88 (s, 1H), 6.66 (s, 1H), 6.42 (br. s., 2H), 3.78 (s, 3H), 3.43-3.36 (m, 1H), 1.99 (s, 3H), 1.24 (d, J=7.1 Hz, 6H). LCMS: [M+H]$^+$ 329.1.

Example 7: Synthesis of Compound 7

Compound 7 was made by the synthetic method outlined in Scheme K.

Scheme K

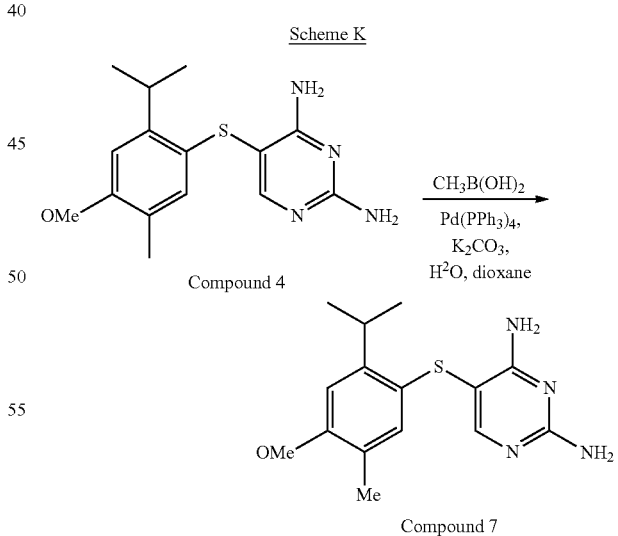

Compound 4 was prepared as outlined above in Example 4.

General Procedure for Preparation of Compound 7:

To a solution of Compound 4 (200 mg, 480 μmol, 1.00 eq) in dioxane (14.0 mL)/H$_2$O (2.00 mL) was added methylboronic acid (152 mg, 2.55 mmol, 5.30 eq), K$_2$CO$_3$ (265 mg, 1.92 mmol, 4.00 eq) and Pd(PPh$_3$)$_4$ (55.5 mg, 48.0 μmol, 0.100 eq). The mixture was de-gassed and then heated to 100° C. for 12 h under N$_2$. The mixture was cooled to RT and then poured into water (10 mL). The aqueous phase was extracted with ethyl acetate (4×20 mL). The combined organic phase was dried over anhydrous Na$_2$SO$_4$, filtered and concentrated in vacuum to give crude product Compound 7 as light yellow solid. The residue was purified by prep-HPLC and further purified by SFC separation to give Compound 7 (26.0 mg, 85.4 μmol) as a solid. $^1$H NMR: (400 MHz, DMSO-d$_6$) 7.85 (s, 1H), 6.81 (s, 1H), 6.68 (s, 1H), 6.34 (br. s., 2H), 3.76 (s, 3H), 3.46 (quin, J=6.7 Hz, 1H), 2.00 (s, 3H), 1.21 (d, J=6.8 Hz, 6H). LCMS: [M+H]$^+$ 305.0.

Example 8: Synthesis of Compound 8

Compound 8 was made by the synthetic method outlined in Scheme L:

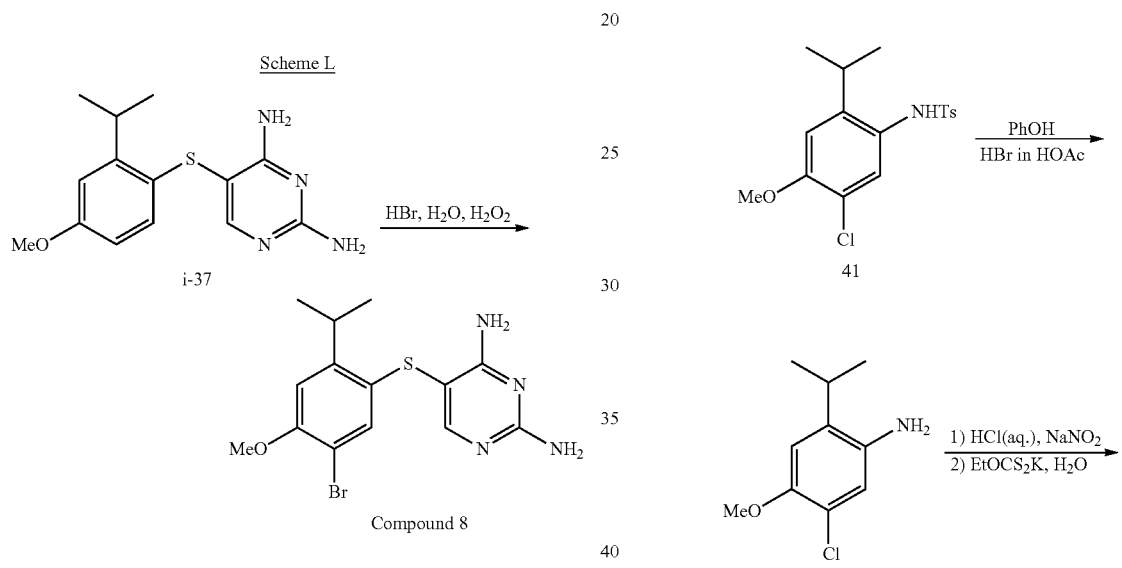

Starting material compound i-37 was prepared as outlined above in Example 2.

General Procedure for Preparation of Compound 8:

To a solution of i-37 (200 mg, 689 μmol, 1.00 eq) in aqueous HBr (697 mg, 40% w.t., 5.00 eq) was added aqueous H$_2$O$_2$ (156 mg, 1.38 mmol, 30% w.t., 2.00 eq). Then the mixture was stirred at 25° C. for 12 h. Another portion of aqueous HBr (111 mg, 1.38 mmol, 74.8 μL, 2.00 eq) and aqueous H$_2$O$_2$ (46.9 mg, 1.38 mmol, 39.7 μL, 2.00 eq) was added. Then the mixture was stirred at 25° C. for 12 h. H$_2$O (5 mL) and sat. NaHSO$_4$ (5 mL) were added and the mixture was partitioned between ethyl acetate (10 mL) and water (10 mL). Then the aqueous layer was extracted with ethyl acetate (3×10 mL). The combined organic layers were dried over Na$_2$SO$_4$, filtered and concentrated under reduced pressure. The residue was purified by prep-HPLC to give Compound 8 (18.0 mg, 48.7 μmol) as a solid. $^1$H NMR: (400 MHz, Methanol-d$_4$) 7.90 (s, 1H), 6.99 (s, 1H), 6.92 (s, 1H), 3.84 (s, 3H), 3.51-3.46 (m, 1H), 1.28 (d, J=6.6 Hz, 6H). LCMS: [M+H]$^+$ 368.9.

Example 9: Synthesis of Compound 9

Compound 9 was made by the synthetic method outlined in Scheme M:

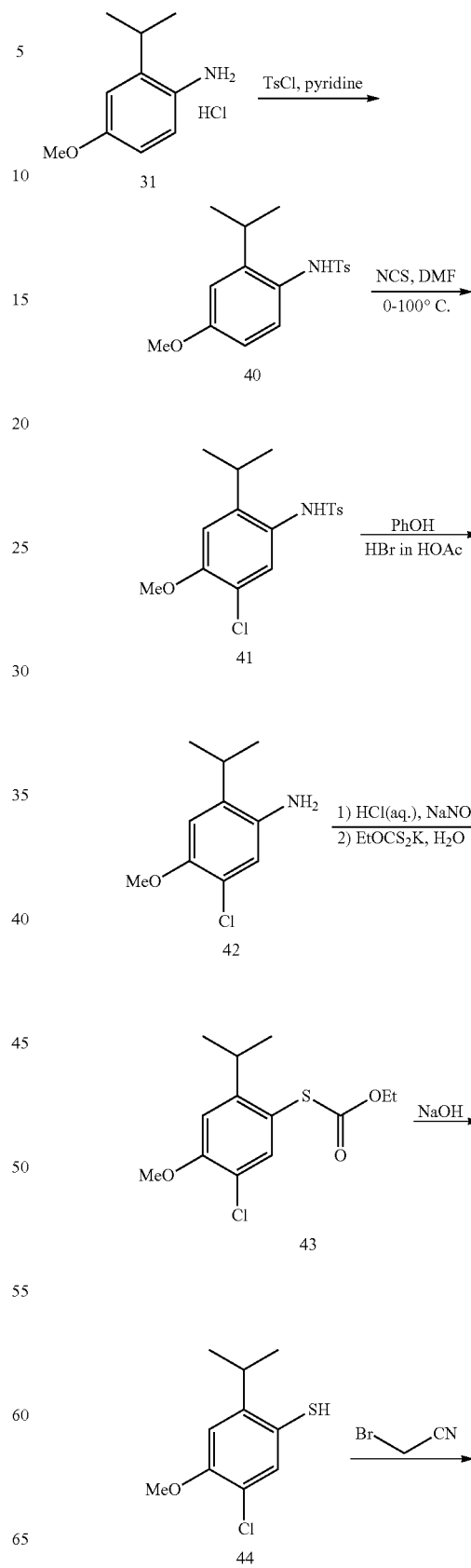

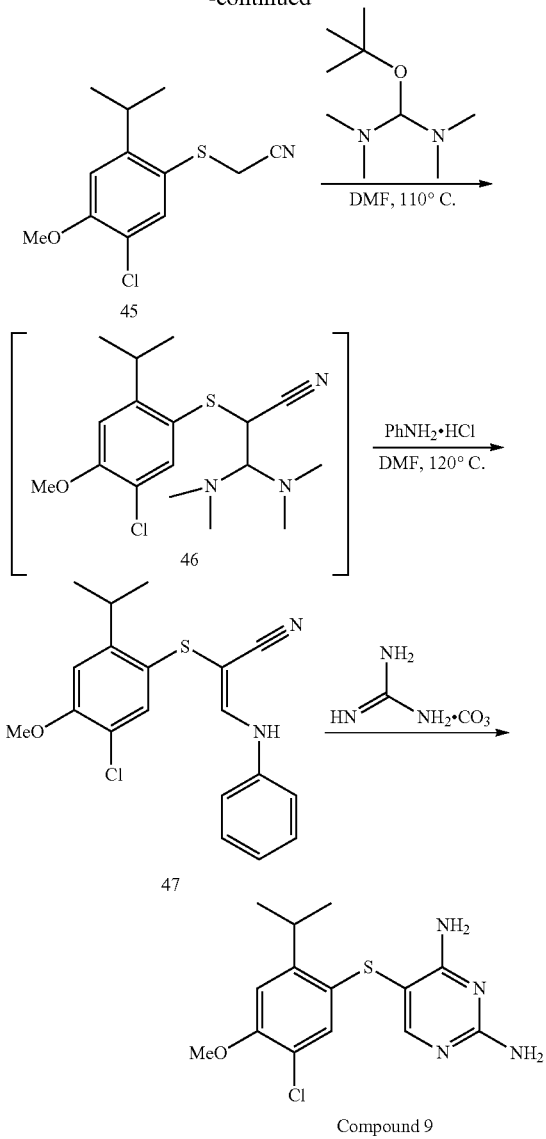

Compound i-31 was prepared according to the procedure outlined in Example 2.

General Procedure for Preparation of Compound 40:

A solution of i-31 (3.00 g, 14.8 mmol, 1.00 eq) and TosCl (3.69 g, 19.3 mmol, 1.30 eq) in pyridine (30 mL) was stirred at 80° C. for 5 h. The reaction mixture was partitioned between ethyl acetate (30 mL) and water (30 mL) and the aqueous layer was extracted with ethyl acetate (3×30 mL). The combined organic layer was washed with 0.5 M HCl (3×50 mL), dried over $Na_2SO_4$, filtered and concentrated under reduced pressure to give i-40 (4.06 g, 12.7 mmol) as a solid which was used in the next step directly. $^1$H NMR: (400 MHz, Chloroform-d) 7.59-7.54 (m, 2H), 7.23 (d, J=7.9 Hz, 2H), 7.10 (d, J=8.4 Hz, 1H), 6.71 (d, J=3.1 Hz, 1H), 6.68-6.63 (m, 1H), 6.12 (s, 1H), 3.79 (s, 3H), 2.88-2.77 (m, 1H), 2.40 (s, 3H), 0.96 (d, J=6.6 Hz, 6H).

General Procedure for Preparation of Compound i-41:

To a solution of i-40 (3.56 g, 11.15 mmol, 1.00 eq) in $CH_3CN$ (30.0 mL) was added TFA (1.75 g, 15.4 mmol, 1.38 eq) and NCS (1.49 g, 11.1 mmol) at 0° C. Then the mixture was stirred at 80° C. for 1 h. The reaction mixture was partitioned between ethyl acetate (50 mL) and water (50 mL). Then the aqueous layer was extracted with ethyl acetate (3×50 mL). The combined organic layer was dried over $Na_2SO_4$, filtered and concentrated under reduced pressure to give a crude product. The crude product was purified by column chromatography on silica gel to give i-41 (3.59 g, 10.1 mmol) as a solid which was used in the next step. $^1$H NMR: (400 MHz, chloroform-d) 7.58-7.54 (m, 2H), 7.24-7.21 (m, 2H), 7.13 (s, 1H), 6.68 (s, 1H), 3.85 (s, 3H), 2.87 (quin, J=6.8 Hz, 1H), 2.39 (s, 3H), 0.95 (d, J=6.6 Hz, 6H).

General Procedure for Preparation of Compound i-42:

To a mixture of i-41 (2.70 g, 7.63 mmol, 1.00 eq) and phenol (1.53 g, 16.25 mmol, 1.43 mL, 2.13 eq) was added hydrogen bromide in HOAc (22.5 g, 97.4 mmol, 15.1 mL, 35% w.t., 12.8 eq). The mixture was stirred for 12 h at 40° C. The reaction mixture was adjusted to pH=9 by progressively adding aq. NaOH (6 mol/L, 50 mL). Then $H_2O$ (40 mL) was added. The mixture was extracted with methyl tert-butyl ether (4×100 mL). The combined organic phases were dried over anhydrous $Na_2SO_4$, filtered and concentrated in vacuum. The residue was purified by prep-HPLC to give i-42 (1.20 g, 6.01 mmol) as an oil.

$^1$H NMR: (400 MHz, Chloroform-d) 6.75 (s, 1H), 6.72 (s, 1H), 3.84 (s, 3H), 3.44 (br. s., 2H), 2.93-2.84 (m, 1H), 1.25 (d, J=7.1 Hz, 6H).

General Procedure for Preparation of Compound i-43:

To a solution of i-42 (600 mg, 3.00 mmol, 1.00 eq) in $CH_3OH$ (25.0 mL) and HCl (1 mol/L, 9.00 mL, 3.00 eq.) was added drop-wise a solution of $NaNO_2$ (311 mg, 4.51 mmol, 245 μL, 1.50 eq) in $H_2O$ (6.00 mL) within 0.5 h at 0° C. Then the mixture was added to a solution of potassium ethylxanthate (962 mg, 6.00 mmol, 2.00 eq) in $H_2O$ (14.00 mL) at 65° C. Then the mixture was stirred for 0.5 h at 65° C. Ethyl acetate (20 mL) was added. The organic layer was separated. The aqueous layer was extracted with ethyl acetate (3×30 mL). The extractions were combined, dried over anhydrous $Na_2SO_4$ and filtered. The filtrate was concentrated to give i-43 (700 mg, 2.30 mmol) as an oil which was used in the next step directly. $^1$H NMR: (400 MHz, DMSO-$d_6$) 7.45 (s, 1H), 6.96 (s, 1H), 3.99-3.83 (m, 5H), 3.38-3.36 (m, 1H), 1.35-1.19 (m, 9H).

General Procedure for Preparation of Compound i-44:

To a solution of i-43 (700 mg, 2.30 mmol, 1.00 eq) in EtOH (8.40 mL) was added NaOH (3 mol/L, 8.43 mL, 11.0 eq) at 10° C. Then mixture was heated to 65° C. and stirred for 2 h. The mixture was cooled to RT. 1,4-Dithioerythritol (70 mg, 0.45 mmol) was added. The mixture was adjusted to pH=5 with aq. HCl (1 mol/L, 25 mL). The mixture was extracted with ethyl acetate (3×60 mL). The extractions were combined, dried over anhydrous $Na_2SO_4$ and filtered. The filtrate was concentrated to give i-44 (630 mg, crude) as an oil which was used in the next step directly. $^1$H NMR: (400 MHz, Chloroform-d) 7.36-7.34 (m, 1H), 6.81 (s, 1H), 3.90 (s, 3H), 3.54-3.41 (m, 1H), 1.25 (d, J=7.1 Hz, 6H).

General Procedure for Preparation of Compound i-45:

To a mixture of i-44 (630 mg, 2.91 mmol, 1.00 eq) in acetonitrile (6.30 mL) was added $Cs_2CO_3$ (1.42 g, 4.37 mmol, 1.50 eq) and 2-bromoacetonitrile (349 mg, 2.91 mmol, 194 μL, 1.00 eq) in one portion. The mixture was stirred at 80° C. for 12 h. $H_2O$ (50 mL) was added and the mixture was extracted with ethyl acetate (3×50 mL). The combined organic phase was washed with brine (50 mL), dried over anhydrous $Na_2SO_4$, filtered and concentrated in vacuum to give brownish dark oil. The residue was purified by silica gel chromatography to give i-45 (210 mg, 821 μmol) as an oil. $^1$H NMR: (400 MHz, Chloroform-d) 7.62 (s, 1H), 6.89 (s, 1H), 3.95 (s, 3H), 3.67 (td, J=6.7, 13.9 Hz, 1H), 3.46 (s, 2H), 1.27 (d, J=7.1 Hz, 6H).

General Procedure for Preparation of Compound i-46:

To a mixture of i-45 (210 mg, 821 µmol, 1.00 eq) in N,N-dimethylformamide (2.10 mL) was added 1-tert-butoxy-N,N,N',N'-tetramethyl-methanediamine (286 mg, 1.64 mmol, 340 µL, 2.00 eq). The mixture was stirred at 110° C. for 1.5 h. The mixture was used in the next step directly without work up and purification.

General Procedure for Preparation of Compound i-47:

To a mixture of i-46 (255 mg, 820 µmol, 1.00 eq) in N,N-dimethylformamide (2.10 mL) was added aniline (532 mg, 4.10 mmol, 521 µL, 5.00 eq, HCl) at 120° C. The mixture was stirred at 120° C. for 5 h. $H_2O$ (30 mL) was added and the mixture was extracted with ethyl acetate (3×30 mL). The combined organic phase was dried over anhydrous $Na_2SO_4$, filtered and concentrated in vacuum to give i-47 (650 mg, crude) as an oil which was used in the next step directly. $^1$H NMR: (400 MHz, Chloroform-d) 7.55 (d, J=7.9 Hz, 5H), 7.00 (s, 1H), 6.99 (m, 1H), 6.86 (s, 1H), 3.95 (br. s., 1H), 3.91 (s, 3H), 3.53-3.45 (m, 1H), 1.28 (d, J=7.1 Hz, 5H).

General Procedure for Preparation of Compound 9:

To a solution of i-47 (785 mg, 2.19 mmol, 1.00 eq) in dimethylsulfoxide (2.30 mL) was added guanidine carbonate (11.6 g, 64.3 mmol, 1.20 eq) and sodium methoxide (473 mg, 2.63 mmol, 2.50 eq). Then the mixture was heated to 110° C. and stirred for 12 h. $H_2O$ (50 mL) was added and the mixture was extracted with ethyl acetate (3×70 mL). The combined organic phase was dried over anhydrous $Na_2SO_4$, filtered and concentrated to give light yellow solid. The solid was purified by prep-HPLC to give Compound 9 (40.0 mg, 123 µmol) as a solid. $^1$H NMR: (400 MHz, DMSO-$d_6$) 7.88 (s, 1H), 7.01 (s, 1H), 6.73 (s, 1H), 6.40 (br. s., 2H), 3.84 (s, 3H), 3.44-3.37 (m, 1H), 1.25 (d, J=7.1 Hz, 6H). LCMS: $[M+H]^+$ 325.0.

Example 10: Synthesis of Compound 10

Compound 10 was made by the synthetic method outlined in Scheme N:

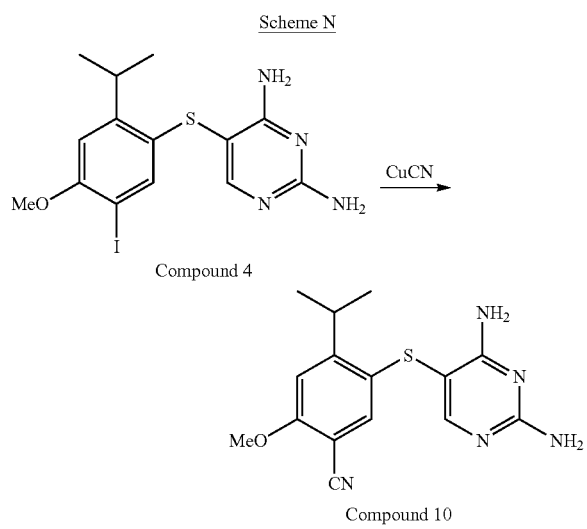

Compound 4 was prepared as outlined above in Example 4.

General Procedure for Preparation of Compound 10:

To a solution of Compound 4 (500 mg, 1.20 mmol, 1.00 eq) in DMF (5.00 mL) was added CuCN (215 mg, 2.40 mmol, 2.00 eq). Then the mixture was stirred at 120° C. for 2 h. The mixture was cooled to RT, concentrated under reduced pressure and directly purified by prep-HPLC and SFC separation to give Compound 10 (29.0 mg, 91.9 µmol) as a solid. $^1$H NMR: (400 MHz, DMSO-$d_6$) 7.95 (br. s., 1H), 7.12 (s, 1H), 7.05 (s, 1H), 6.65 (br. s., 2H), 3.92 (s, 3H), 3.49-3.43 (m, 1H), 1.26 (d, J=6.6 Hz, 6H). LCMS: $[M+H]^+$ 316.1.

Example 11: Synthesis of Compound 11

Compound 11 was made by the synthetic method outlined in Scheme 0:

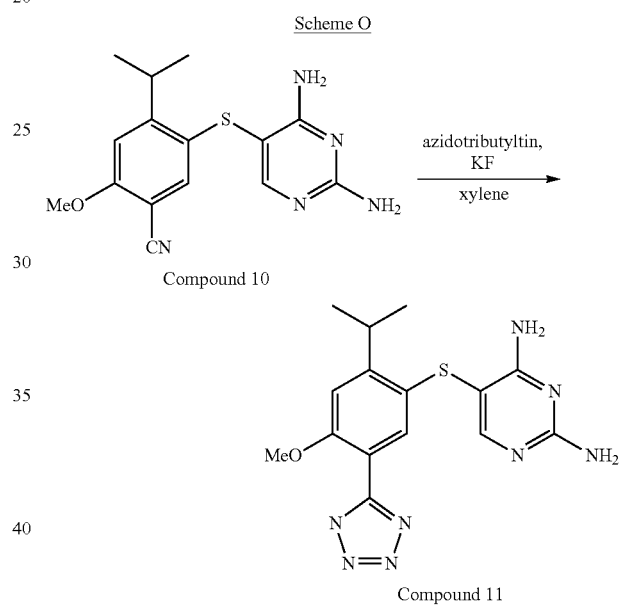

Compound 10 was prepared as outlined above in Example 10.

General Procedure for Preparation of Compound 11:

To a solution of Compound 10 (200 mg, 634 µmol, 1.00 eq) in xylene (2.00 mL) was added azidotributyltin (3.37 g, 10.1 mmol, 16.0 eq) at 120° C. The mixture was stirred at 120° C. for 12 h. The mixture was cooled to RT and KF (737 mg, 12.7 mmol, 297 µL, 20.00 eq) was added. Then the mixture was concentrated under reduced pressure to give a residue which was purified by prep-HPLC to give Compound 11 (35.0 mg, 97.6 µmol) as a solid.

$^1$H NMR: (400 MHz, DMSO-$d_6$) 7.90 (br. s., 1H), 7.53 (br. s., 1H), 7.11 (br. s., 1H), 6.42 (br. s., 2H), 3.95 (br. s., 3H), 3.46 (d, J=6.1 Hz, 1H), 1.30 (d, J=5.9 Hz, 6H). LCMS: $[M+H]^+$ 359.1 $(M+1)^+$.

Example 12: Synthesis of Compound 12

Compound 12 was made by the synthetic method outlined in Scheme P:

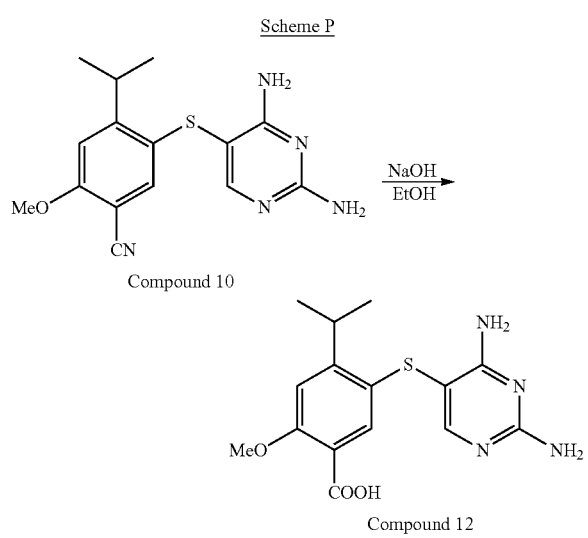

Compound 10 was prepared as outlined above in Example 10.

General Procedure for Preparation of Compound 12:

To a solution of Compound 10 (100 mg, 317.07 µmol, 1.00 eq) in EtOH (1.0 mL) was added NaOH (317 mg, 7.93 mmol, 25.00 eq) in H$_2$O (1.0 mL). Then the mixture was stirred at 80° C. for 12 h. The mixture was adjusted to pH=7 with aqueous HCl (1 M) and the mixture was purified by prep-HPLC to give Compound 12 (15.0 mg, 44.8 µmol) as a solid.

$^1$H NMR: (400 MHz, DMSO-d$_6$) 7.86 (br. s., 1H), 7.01 (br. s., 1H), 6.92 (br. s., 1H), 6.37 (br. s., 2H), 3.76 (br. s., 3H), 3.43 (br. s., 1H), 1.24 (d, J=6.6 Hz, 6H). LCMS: [M+H]$^+$ 335.1.

Example 13: Synthesis of Comparative Compound 1

Comparative compound 1 was made by the synthetic method shown in Scheme Q:

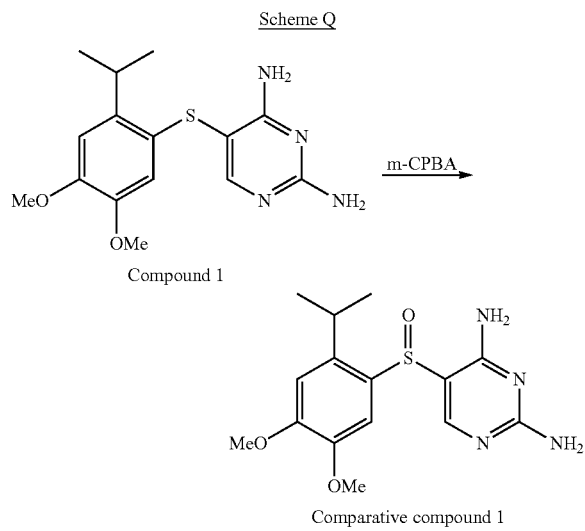

Compound 1 was prepared as outlined above in Example 1.

General Procedure for Preparation of Comparative Compound 1:

Batch 1: To a solution of Compound 1 (20.0 mg, 62.4 µmol, 1.00 eq) in dichloromethane (1.00 mL) was added a solution of m-CPBA (13.5 mg, 62.4 µmol, 80.0% purity, 1.00 eq) in dichloromethane (1.00 mL) at 0° C. The reaction mixture was stirred at 25° C. for 0.5 h.

Batch 2: To a solution of Compound 1 (100 mg, 312 µmol, 1.00 eq) in dichloromethane (5.00 mL) was added a solution of m-CPBA (67.3 mg, 312 µmol, 80.0% purity, 1.00 eq) in dichloromethane (1.00 mL) at 0° C. The reaction mixture was stirred at 0° C. for 0.5 h.

The above two mixtures from Batch 1 and Batch 2 were combined, washed with sat. Na$_2$SO$_3$ (10 mL) and sat. Na$_2$CO$_3$ (2×10 mL). The combined organic layers were washed with brine (20 mL), dried over anhydrous Na$_2$SO$_4$, filtered and concentrated in vacuum. The residue was purified by prep-TLC to give Comparative compound 1 (60.0 mg, 178 µmol) as a solid. $^1$H NMR: (400 MHz, Methanol-d$_4$) 7.81 (s, 1H), 7.52 (s, 1H), 6.99 (s, 1H), 3.89 (d, J=7.06 Hz, 6H), 3.04-3.13 (m, 1H), 1.28 (d, J=6.62 Hz, 3H), 0.95 (d, J=6.62 Hz, 3H). LCMS: [M+H]$^+$ 337.0.

Example 14: Synthesis of Comparative Compound 2

Comparative compound 2 was made by the synthetic method shown in Scheme R:

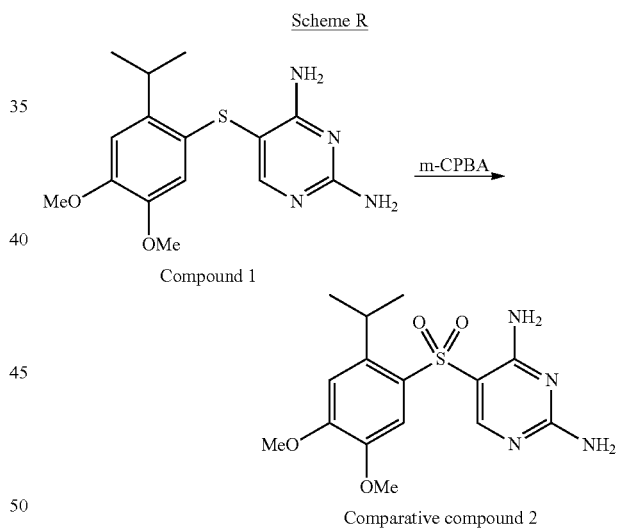

Starting material Compound 1 was prepared as outlined above in Example 1.

General Procedure for Preparation of Comparative Compound 2:

To a solution of Compound 1 (400 mg, 1.25 mmol, 1.00 eq) in dichloromethane (5.00 mL) was added m-CPBA (539 mg, 2.50 mmol, 80.0% purity, 2.00 eq) at 0° C. The reaction mixture was stirred at 20° C. for 12 h. Dichloromethane (10 mL) was added. The mixture was washed with sat. Na$_2$SO$_3$ (10 mL), sat. Na$_2$CO$_3$ (2×10 mL) and brine (10 mL) in sequence. Then the organic layer was dried over anhydrous Na$_2$SO$_4$, filtered and concentrated in vacuum. The residue was purified by prep-HPLC to give Comparative compound 2 (27.0 mg, 76.6 µmol) was obtained as a solid. $^1$H NMR: (400 MHz, Methanol-d$_4$) 8.23 (s, 1H), 7.63 (s, 1H), 7.01 (s, 1H), 3.90 (s, 6H), 3.65 (dt, J=13.56, 6.67 Hz, 1H), 1.11 (d, J=6.62 Hz, 6H). LCMS: [M+H]⁺ 353.1.

Example 15: Synthesis of Compound 13

Compound 13 was made by the synthetic method outlined in Scheme S:

Scheme S

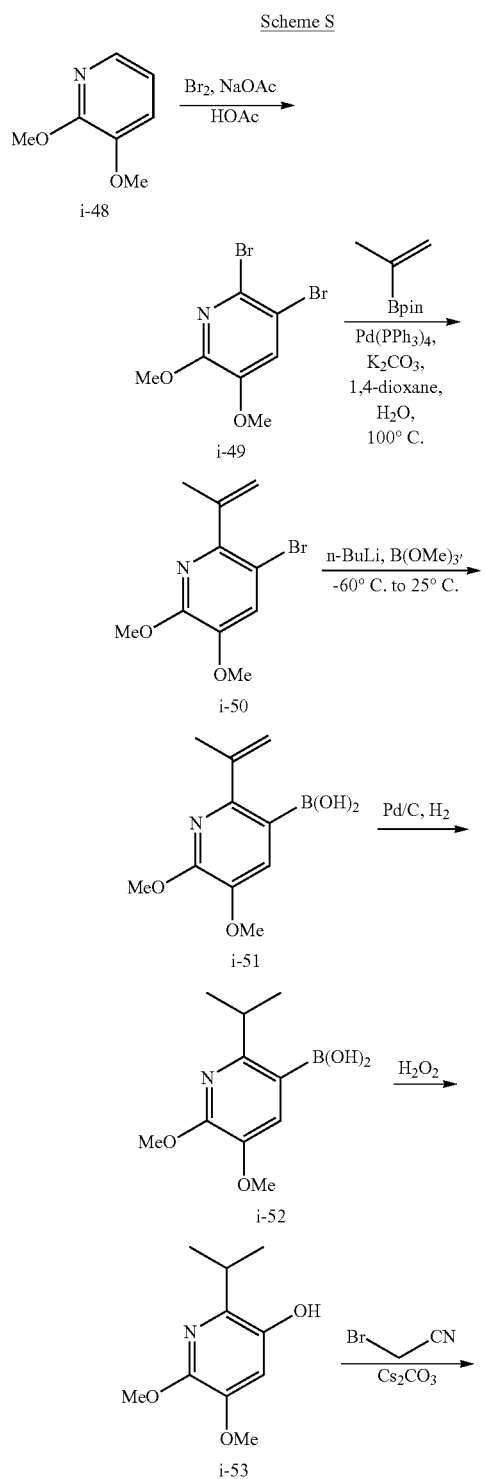

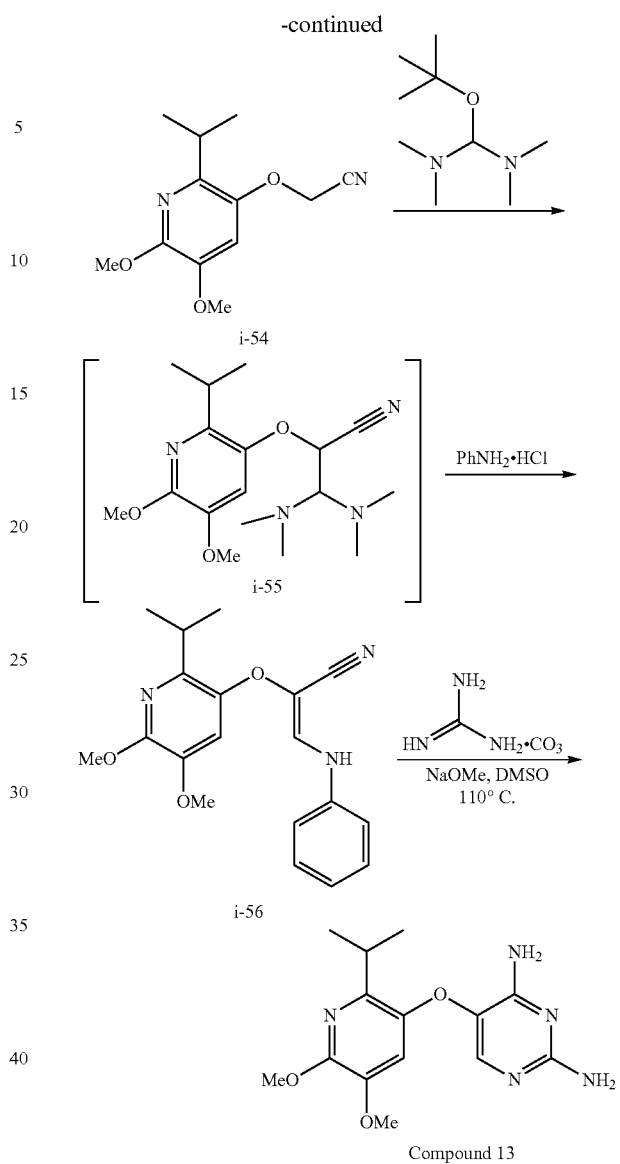

Compound 13

General Procedure for Preparation of Compound i-49:

To the solution of compound i-48 (5.00 g, 35.9 mmol, 1.00 eq), NaOAc (8.84 g, 107 mmol, 3.00 eq) in HOAc (65.0 mL) was added $Br_2$ (20.1 g, 125 mmol, 6.48 mL, 3.50 eq), while maintaining the inner temperature below 25° C. The mixture was stirred at 25° C. for 20 h. The mixture was poured into ice water and neutralized to pH=7 with 25% aq. NaOH solution. The aqueous phase was extracted with $CH_2Cl_2$ (3×100 mL). The organic phases were combined and washed with brine (100 mL), dried over anhydrous $Na_2SO_4$, filtered and concentrated to give compound i-49 (9.20 g, 30.9 mmol) as a solid, which was used in the next step without purification. ¹H NMR (400 MHz, Chloroform-d) δ=7.22 (s, 1H), 4.01 (s, 3H), 3.87 (s, 3H).

General Procedure for Preparation of Compound i-50:

The mixture of compound i-49 (9.00 g, 30.3 mmol, 1.00 eq), isopropenylboronic acid pinacol ester (5.09 g, 30.3 mmol, 1.00 eq), $K_2CO_3$ (8.38 g, 60.6 mmol, 2.00 eq) and $Pd(PPh_3)_4$ (4.20 g, 3.64 mmol, 0.12 eq) in 1,4-dioxane (100 mL) and $H_2O$ (25.0 mL) was stirred at 100° C. under $N_2$ atmosphere for 6 h. The mixture was filtered and washed with ethyl acetate (20 mL). To the filtrate was added ethyl acetate (50 mL) and brine (30 mL). The aqueous phase was separated and extracted with ethyl acetate (3×100 mL). The organic phases were combined and dried over anhydrous $Na_2SO_4$, filtered and concentrated. The residue was purified via column chromatography on silica gel to give compound i-50 (4.00 g, 15.5 mmol) as a liquid. 1H NMR (400 MHz, Chloroform-d) δ=7.20 (s, 1H), 5.39 (s, 1H), 5.33 (s, 1H), 3.99 (s, 3H), 3.88 (s, 3H), 2.14 (s, 3H).

General Procedure for Preparation of Compound i-51:

To the solution of compound i-50 (3.00 g, 11.6 mmol, 1.00 eq) in THF (80.0 mL) was added n-BuLi (2.5 M, 9.30 mL, 2.00 eq) at −60° C. under Na atmosphere. The mixture was stirred at −60° C. for 1 h. Then $B(OMe)_3$ (3.62 g, 34.9 mmol, 3.00 eq) was added. The mixture was allowed to warm to 20° C. and stirred for 13 h. The reaction mixture was quenched with $H_2O$ (20 mL) at 0° C. and then was adjusted to pH=4 with 1 N HCl (30 mL). Two phases were separated and the aqueous phase was extracted with ethyl acetate (3×100 mL). The organic phases were combined, dried over anhydrous $Na_2SO_4$, filtered and concentrated. The residue was purified via column chromatography on silica gel to give compound i-51 (1.10 g, 4.93 mmol) as a liquid, which was used in the next step without purification.

$^1$H NMR (400 MHz, Chloroform-d) δ=7.45 (s, 1H), 5.37 (br. s., 1H), 5.15 (br. s., 1H), 4.02 (br. s., 3H), 3.91 (s, 3H), 3.73 (s, 2H), 2.22 (br. s., 3H).

General Procedure for Preparation of Compound i-52:

A mixture of compound i-51 (1.10 g, 4.93 mmol, 1.00 eq) and Pd/C (524.87 mg, 4.93 mmol, 5% w.t., 1.00 eq) in MeOH (50.00 mL) was stirred at 20° C. under $H_2$ balloon for 15 h. The mixture was filtered through a pad of celite and the filter cake was washed with MeOH (150 mL). The combined filtrates were concentrated to give compound i-52 (800 mg, 3.55 mmol) as a liquid, which was used in the next step without purification.

$^1$H NMR (400 MHz, Chloroform-d) δ=7.75 (s, 1H), 4.22-4.15 (m, 1H), 4.11 (s, 3H), 3.95 (s, 3H), 3.78-3.73 (m, 2H), 1.35 (d, J=6.7 Hz, 6H).

General Procedure for Preparation of Compound i-53:

To the solution of compound i-52 (290 mg, 1.29 mmol, 1.00 eq) in $CH_3CN$ (9.00 mL) was added $H_2O_2$ (292 mg, 2.58 mmol, 30% w.t., 2.00 eq). The mixture was stirred at 20° C. for 0.5 h. To the mixture was added saturated aqueous $Na_2SO_3$ (5 mL) at 0° C. Then the mixture was stirred at 20° C. for 5 min. To the mixture was added ethyl acetate (20 mL) and $H_2O$ (5 mL). The aqueous phase was separated and extracted with ethyl acetate (3×20 mL). The organic phases were combined, dried over anhydrous $Na_2SO_4$ and concentrated to give compound i-53 (240 mg, 1.22 mmol) as a liquid which was used in the next step without purification.

$^1$H NMR (400 MHz, Chloroform-d) δ=6.68 (s, 1H), 4.27 (br. s., 1H), 3.98 (s, 3H), 3.83 (s, 3H), 3.12 (td, J=6.8, 13.7 Hz, 1H), 1.25 (d, J=6.7 Hz, 6H).

General Procedure for Preparation of Compound i-54:

To compound i-53 (120 mg, 608 umol, 1.00 eq) in $CH_3CN$ (3.00 mL) was added $Cs_2CO_3$ (297 mg, 912 umol, 1.50 eq) and $BrCH_2CN$ (109.47 mg, 912.65 umol, 1.50 eq). The mixture was stirred at 80° C. for 15 h. To the reaction mixture was added ethyl acetate (10 mL) and water (4 mL). The aqueous phase was separated and extracted with ethyl acetate (3×10 mL). The organic phases were combined, dried over anhydrous $Na_2SO_4$, filtered and concentrated to give compound i-54 (135 mg, 571 umol) as a solid which was used in the next step without purification. $^1$H NMR (400 MHz, DMSO-$d_6$) δ=7.28 (s, 1H), 5.16 (s, 2H), 3.84 (s, 3H), 3.78 (s, 3H), 3.22-3.25 (m, 1H), 1.15 (d, J=7.0 Hz, 6H).

General Procedure for Preparation of Compound i-55:

The mixture of compound i-54 (200 mg, 846 umol, 1.00 eq) and 1-tert-butoxy-N,N,N',N'-tetramethyl-methanediamine (295 mg, 1.69 mmol, 2.00 eq) in DMF (2.00 mL) was stirred at 110° C. for 3 h. The reaction mixture was used in the next step directly.

General Procedure for Preparation of Compound i-56:

To the solution of compound i-55 (284 mg, 846 umol, 1.00 eq) in DMF (2.00 mL) was added $PhNH_2$ (219 mg, 1.69 mmol, 2.00 eq, HCl). The mixture was stirred at 120° C. for 3 h. LCMS showed the starting material was consumed completely. To the mixture was added toluene (30 mL) and $H_2O$ (6 mL). The two phases were separated and the aqueous phase was extracted with toluene (3×15 mL). The organic phases were combined, dried over anhydrous $Na_2SO_4$, filtered and concentrated to give compound i-56 (280 mg, 825 umol) as a liquid which was used in the next step without purification. $^1$H NMR (400 MHz, Chloroform-d) δ=7.37-7.34 (m, 2H), 7.16 (d, J=5.7 Hz, 2H), 6.95 (d, J=7.9 Hz, 1H), 6.80 (s, 1H), 6.70 (d, J=7.5 Hz, 1H), 4.69 (s, 1H), 4.02 (s, 3H), 3.85 (s, 3H), 3.37-3.25 (m, 1H), 1.28 (d, J=7.1 Hz, 6H).

General Procedure for Preparation of Compound 13:

A mixture of compound i-56 (140 mg, 412 umol, 1.00 eq), guanidine carbonate (111 mg, 618 umol, 1.50 eq) and NaOMe (66.8 mg, 1.24 mmol, 3.00 eq) in DMSO (1.50 mL) was stirred at 110° C. for 1 h. One additional vial was set up as described above. The two reaction mixtures were combined and filtered. The filtrate was purified via prep-HPLC to give Compound 13 (46.00 mg, 148 umol) as a solid. $^1$H NMR (400 MHz, DMSO-$d_6$) δ=7.18 (s, 1H), 6.81 (s, 1H), 6.44 (br. s., 2H), 5.72 (s, 2H), 3.86 (s, 3H), 3.68 (s, 3H), 3.24 (td, J=6.7, 13.6 Hz, 1H), 1.16 (d, J=6.6 Hz, 6H). LCMS: 98.2% purity, m/z=306.0 $(M+1)^+$ Example 16: Synthesis of Compound 14

Compound 14 was made by the synthetic method outlined in Scheme T:

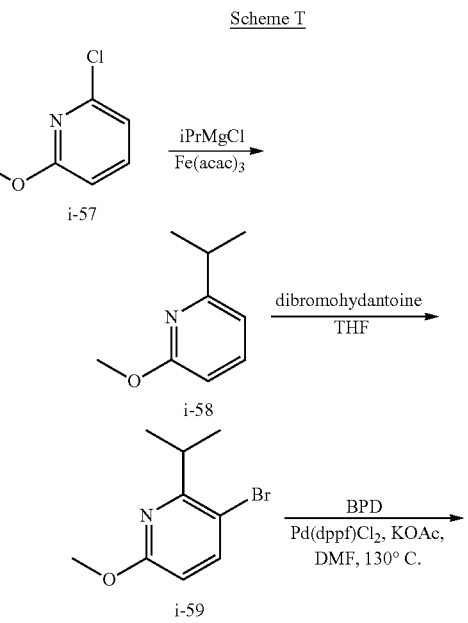

Scheme T

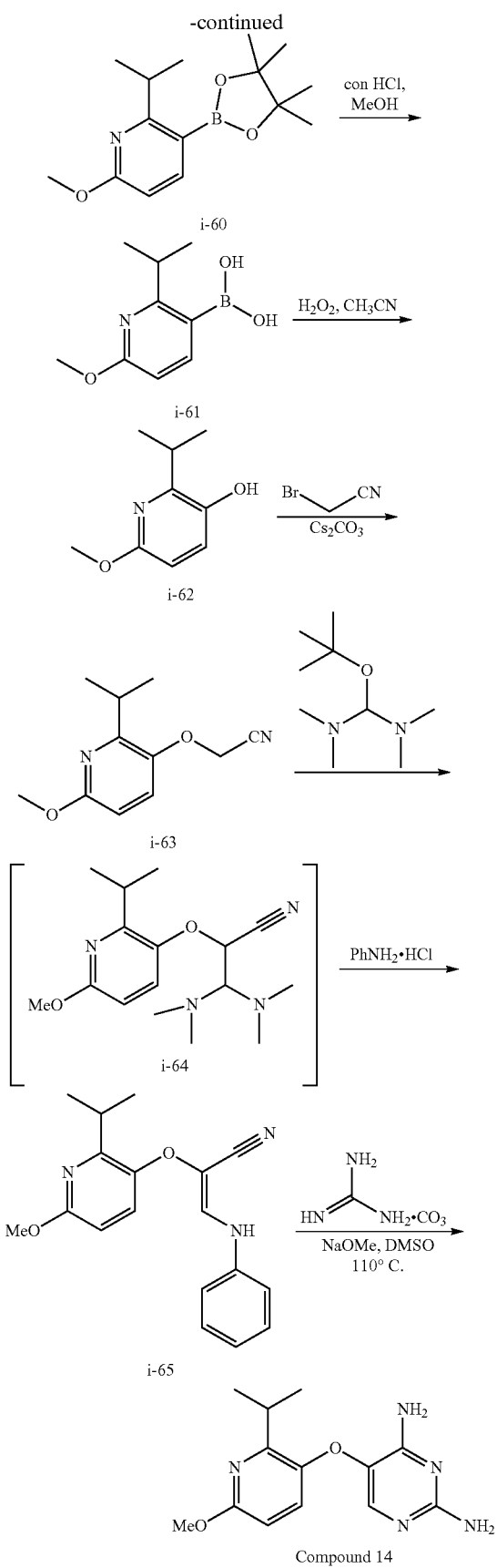

General Procedure for Preparation of Compound i-58:

To the solution of compound i-57 (10.0 g, 69.6 mmol, 1.00 eq) in THF (200 mL) and NMP (20.0 mL) was added Fe(acac)$_3$ (1.23 g, 3.48 mmol, 0.05 eq). Then i-PrMgCl (2 M, 41.79 mL, 1.20 eq) was added dropwise at −30° C. within 30 min. The mixture was stirred at 0° C. for 1 h. The reaction mixture was quenched with saturated aqueous NH$_4$Cl (80 mL) at 0° C. Then the two phases were separated and the aqueous phase was extracted with methyl t-butyl ether (80 mL). The combined organic phases were washed with water (4×50 mL). Then the organic phase was dried over anhydrous Na$_2$SO$_4$, filtered and concentrated to give compound i-58 (7.10 g, 46.9 mmol) as a liquid which was used for the next step without purification.

$^1$H NMR (400 MHz, Chloroform-d) δ=7.48 (t, J=7.7 Hz, 1H), 6.72 (d, J=7.1 Hz, 1H), 6.54 (d, J=7.9 Hz, 1H), 3.93 (s, 3H), 2.95 (td, J=6.8, 13.7 Hz, 1H), 1.28 (d, J=7.1 Hz, 6H).

General Procedure for Preparation of Compound i-59:

To the solution of compound i-58 (8.50 g, 56.2 mmol, 1.00 eq) in THF (85.0 mL) was added 1,3-dibromo-5,5-dimethyl-imidazolidine-2,4-dione (16.1 g, 56.2 mmol, 1.00 eq). The mixture was stirred at 20° C. for 3 h. To the mixture was added water (50 mL) and ethyl acetate (30 mL). The two phases were separated and the aqueous phase was extracted with ethyl acetate (3×40 mL). The combined organic phases were dried over anhydrous Na$_2$SO$_4$, filtered and concentrated. The residue was purified via column chromatography on silica gel to give compound i-59 (7.10 g, 30.8 mmol) as a liquid. $^1$H NMR (400 MHz, Chloroform-d) δ=7.58 (d, J=8.8 Hz, 1H), 6.42 (d, J=8.4 Hz, 1H), 3.89 (s, 3H), 3.42 (td, J=6.8, 13.3 Hz, 1H), 1.23 (d, J=7.1 Hz, 6H).

General Procedure for Preparation of Compound i-60:

The mixture of compound i-59 (7.10 g, 30.8 mmol, 1.00 eq), BPD (Bis(pinacolato)diboron, 11.7 g, 46.3 mmol, 1.50 eq), Pd(dppf)Cl$_2$ (1.13 g, 1.54 mmol, 0.05 eq) and KOAc (6.06 g, 61.7 mmol, 2.00 eq) in DMF (71.0 mL) was stirred at 130° C. under N$_2$ atmosphere for 0.5 h. To the mixture was added water (30 mL) and ethyl acetate (30 mL). The two phases were separated and the aqueous phase was extracted with ethyl acetate (2×30 mL). The combined organic phases were dried over anhydrous Na$_2$SO$_4$, filtered and concentrated. The residue was purified via column chromatography on silica gel to give compound i-60 (4.30 g, 15.5 mmol) as a liquid. $^1$H NMR (400 MHz, Chloroform-d) δ=7.90 (d, J=8.2 Hz, 1H), 6.50 (d, J=8.2 Hz, 1H), 3.95 (s, 3H), 3.74 (td, J=6.7, 13.3 Hz, 1H), 1.37-1.31 (m, 12H), 1.24 (d, J 6.7 Hz, 6H).

General Procedure for Preparation of Compound i-61:

To a solution of compound i-60 (4.60 g, 16.6 mmol, 1.00 eq) in MeOH (8.00 mL) was added HCl (12 M, 46.1 mL, 33.3 eq). The mixture was stirred at 65° C. for 2 h. The mixture was cooled to RT, and was adjusted to pH=5 with 10 N NaOH (60 mL). To the mixture was added ethyl acetate (100 mL). The aqueous phase was separated and extracted with ethyl acetate (3×50 mL). The organic phases were combined and dried over anhydrous Na$_2$SO$_4$. Then filtered and concentrated to give i-61 (3.20 g, 16.4 mmol) as a liquid which was used for the next step without purification. $^1$H NMR (400 MHz, Chloroform-d) δ=8.29 (d, J=8.4 Hz, 1H), 6.68-6.63 (m, 1H), 4.13 (td, J=6.6, 13.2 Hz, 1H), 4.03 (s, 3H), 1.37 (d, J=7.1 Hz, 6H).

General Procedure for Preparation of Compound i-62:

To a solution of compound i-61 (3.20 g, 16.4 mmol, 1.00 eq) in CH$_3$CN (50.0 mL) was added hydrogen peroxide (3.72 g, 32.8 mmol, 30% w.t., 2.00 eq). The mixture was stirred at 20° C. for 0.5 h. To the mixture was added saturated Na$_2$SO$_3$ solution (50 mL) at 0° C. Then the mixture was stirred at 20° C. for 10 min. To the mixture was added ethyl acetate (100 mL) and H$_2$O (10 mL). The aqueous phase was separated and extracted with ethyl acetate (3×50 mL). The organic phases were combined, washed with brine (50 mL) and dried over anhydrous Na$_2$SO$_4$. Then the solution was filtered and concentrated to give i-62 (2.50 g, 14.95 mmol) as a liquid which was used for the next step without purification. $^1$H NMR (400 MHz, Chloroform-d) δ=7.05 (d, J=8.8 Hz, 1H), 6.45 (d, J=8.8 Hz, 1H), 4.45 (br. s., 1H), 3.89 (s, 3H), 3.31-3.20 (m, 1H), 1.27 (d, J=6.6 Hz, 6H).

General Procedure for Preparation of Compound i-63:

To compound i-62 (2.50 g, 14.95 mmol, 1.00 eq) in CH$_3$CN (30.00 mL) was added Cs$_2$CO$_3$ (7.31 g, 22.43 mmol, 1.50 eq) and BrCH$_2$CN (2.69 g, 22.4 mmol, 1.50 eq). The mixture was stirred at 80° C. for 13 h. To the reaction mixture was added ethyl acetate (60 mL) and water (30 mL). The aqueous phase was separated and extracted with ethyl acetate (3×50 mL). The organic phases were combined and washed with brine (50 mL). Then the solution was dried over anhydrous Na$_2$SO$_4$, filtered and concentrated to give i-63 (2.90 g, 14.1 mmol) as a solid which was used for the next step without purification. $^1$H NMR (400 MHz, DMSO-d$_6$) δ=7.56 (d, J=8.8 Hz, 1H), 6.67 (d, J=8.8 Hz, 1H), 5.14 (s, 2H), 3.82 (s, 3H), 3.36-3.27 (m, 1H), 1.17 (d, J=7.1 Hz, 6H).

General Procedure for Preparation of Compound i-64:

A mixture of compound i-63 (2.90 g, 14.1 mmol, 1.00 eq) and 1-tert-butoxy-N,N,N',N'-tetramethyl-methanediamine (4.90 g, 28.1 mmol, 5.83 mL, 2.00 eq) in DMF (30.0 mL) was stirred at 110° C. for 2 h. The reaction mixture was used in the next step directly.

General Procedure for Preparation of Compound i-65:

To the solution of compound i-64 (4.31 g, 14.07 mmol, 1.00 eq) in DMF (30.00 mL) was added PhNH$_2$ (4.56 g, 35.2 mmol, 4.47 mL, 2.50 eq), HCl). The mixture was stirred at 120° C. for 3 h. To the mixture was added toluene (80 mL) and H$_2$O (30 mL). The two phases were separated and the aqueous was extracted with toluene (3 30 mL). The organic phases were combined, washed with brine (30 mL). Then the solution was dried over anhydrous Na$_2$SO$_4$, filtered and concentrated to give compound i-65 (5.00 g, crude) as a liquid which contained PhNH$_2$ and DMF. The crude product was used for the next step without purification.

$^1$H NMR (400 MHz, Chloroform-d) δ=7.33 (t, J=7.3 Hz, 3H), 7.18-7.13 (m, 3H), 6.94 (d, J 7.9 Hz, 2H), 6.76 (t, J=7.3 Hz, 2H), 6.69 (d, J=7.9 Hz, 2H), 6.54 (d, J=8.8 Hz, 1H), 3.93 (s, 3H), 3.46-3.38 (m, 1H), 1.30 (d, J=7.1 Hz, 6H).

General Procedure for Preparation of Compound 14:

A mixture of compound i-65 (2.50 g, 8.08 mmol, 1.00 eq), guanidine carbonate (2.18 g, 12.1 mmol, 1.50 eq) and NaOMe (1.31 g, 24.2 mmol, 3.00 eq) in DMSO (25.00 mL) was stirred at 110° C. for 1 h. One additional reaction was set up with the same amounts and conditions, and the two reaction mixtures were combined at the end of the heating period. To the mixture was added ethyl acetate (100 mL) and water (40 mL). The two phases were separated and the aqueous phase was extracted with ethyl acetate (2×50 mL). The organic phases were combined and washed with brine (30 mL), dried over anhydrous Na$_2$SO$_4$, filtered and concentrated. The residue was purified via prep-HPLC to give Compound 14 (1.20 g, 4.36 mmol) as a solid. $^1$H NMR (400 MHz, DMSO-d$_6$) δ=7.26 (s, 1H), 7.08 (d, J=8.8 Hz, 1H), 6.58 (d, J=8.8 Hz, 1H), 6.44 (br. s., 2H), 5.80 (s, 2H), 3.82 (s, 3H), 3.43-3.35 (m, 1H), 1.21 (d, J 6.6 Hz, 6H). LCMS: 99.7% purity, m/z=276.1 (M+1)$^+$ Example 17: Synthesis of Compound 15

Compound 15 was made by the synthetic method outlined in Scheme U:

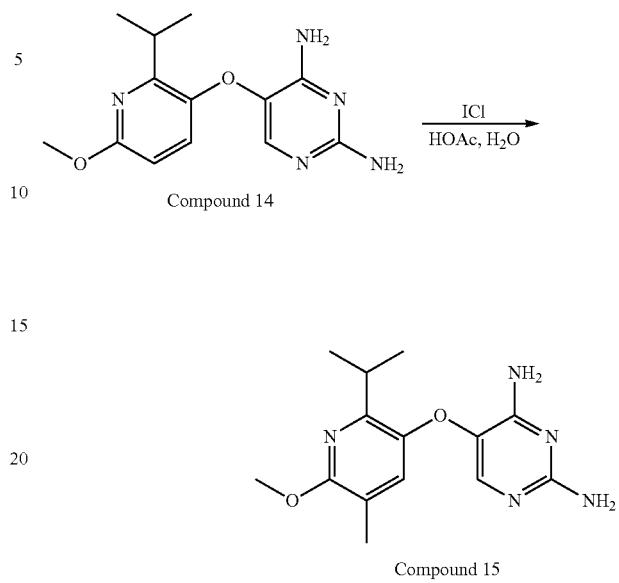

Starting material Compound 14 was prepared as outlined above in Example 16.

General Procedure for Preparation of Compound 15

To a solution of Compound 14 (250 mg, 908 umol, 1.00 eq) in HOAc (2.5 mL) was added a solution of ICl (295 mg, 1.82 mmol, 2.00 eq) in HOAc (2.5 mL). Then H$_2$O (4.00 mL) was added. The mixture was stirred at 90° C. for 2 h. Then a second portion of ICl (442 mg, 2.72 mmol, 3.00 eq) was added. The mixture was stirred at 90° C. for 4 h. The reaction mixture was adjusted to pH=8 with 1 N NaOH (2 mL) and saturated NaHCO$_3$ (3 mL). The mixture was extracted with ethyl acetate (3×15 mL). The combined organic phases were washed with saturated Na$_2$CO$_3$ (10 mL) and brine (10 mL), dried over anhydrous Na$_2$SO$_4$, filtered and concentrated. The residue was purified via prep-TLC (CH$_2$Cl$_2$:CH$_3$OH=20:1) to give Compound 15 (40.0 mg, 99.7 umol) as a solid. $^1$H NMR (400 MHz, DMSO-d$_6$) δ=7.38 (s, 1H), 7.33 (s, 1H), 6.47 (br. s., 2H), 5.89 (s, 2H), 3.86 (s, 3H), 3.40-3.34 (m, 1H), 1.22 (d, J=6.6 Hz, 6H). LCMS: 97.4% purity, m/z=401.9 (M+1)$^+$ Example 18: Synthesis of Compound 16

Compound 16 was made by the synthetic method outlined in Scheme V:

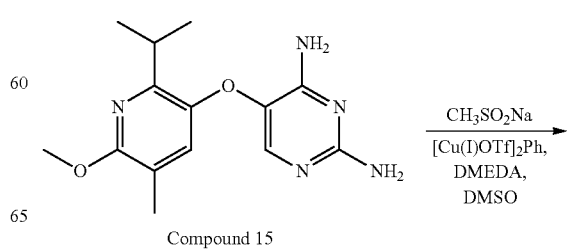

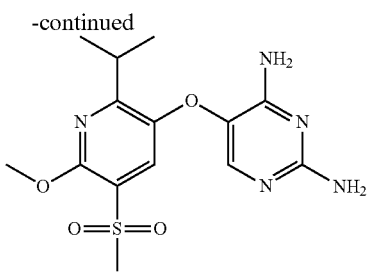

Compound 16

Compound 15 was prepared as outlined above in Example 17.

To a solution of Compound 15 (400 mg, 997 umol, 1.00 eq), CH$_3$SO$_2$Na (254 mg, 2.49 mmol, 2.50 eq) and copper (I) trifluoromethanesulfonate-benzene complex (75.28 mg, 150 umol, 0.15 eq) in DMSO (8.00 mL) was added DMEDA (26.4 mg, 299 umol, 32.2 uL, 0.30 eq). The mixture was stirred at 120° C. under N$_2$ atmosphere for 4 h. To the mixture was added ethyl acetate (20 mL) and H$_2$O (10 mL). The two phases were separated and the aqueous phase was extracted with ethyl acetate (3×15 mL). The combined organic phases were washed with brine (10 mL), dried over anhydrous Na$_2$SO$_4$, filtered and concentrated. The residue was purified via prep-HPLC to give Compound 16 (280 mg) as a solid.

$^1$H NMR (400 MHz, DMSO-d$_6$) δ=7.51 (br. s., 1H), 7.28 (s, 1H), 6.53 (br. s., 2H), 5.98 (br. s., 2H), 4.02 (s, 3H), 3.59-3.48 (m, 1H), 3.25 (s, 3H), 1.27 (d, J=6.6 Hz, 6H). LCMS: 99.8% purity, m/z=354.1 (M+1)$^+$ Example 19: Synthesis of Compound 17

Compound 17 was made by the synthetic method outlined in Scheme W:

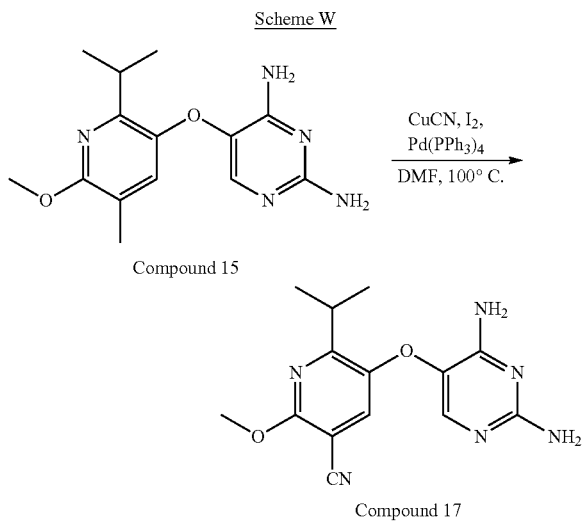

Compound 15 was prepared as outlined above in Example 17.

A solution of Compound 15 (100 mg, 249 umol, 1.00 eq), CuCN (51.3 mg, 573 umol, 2.30 eq), Pd(PPh$_3$)$_4$ (57.6 mg, 49.8 umol, 0.20 eq), I$_2$ (25.3 mg, 99.7 umol, 0.40 eq) in DMF (2.00 mL) was stirred at 100° C. under N$_2$ atmosphere for 12 h. To the reaction mixture was added ethyl acetate (10 mL), saturated NH$_4$Cl (3 mL) and NH$_3$.H$_2$O (0.5 mL). The two phases were separated and the aqueous phase was extracted with ethyl acetate (3×5 mL). The combined organic phases were dried over anhydrous Na$_2$SO$_4$, filtered and concentrated. The residue was purified via prep TLC and then purified via prep-HPLC to give Compound 17 (15.0 mg, 48.9 umol) as a solid. $^1$H NMR (400 MHz, DMSO-d$_6$) δ=7.50 (s, 1H), 7.44 (s, 1H), 6.46 (br. s., 2H), 5.90 (s, 2H), 3.97 (s, 3H), 3.46 (quin, J=6.7 Hz, 1H), 1.24 (d, J=6.6 Hz, 6H). LCMS: 97.9% purity, m/z=301.1 (M+1)$^+$ Example 20: Synthesis of Compound 18

Compound 18 was made by the synthetic method outlined in Scheme X:

Scheme X

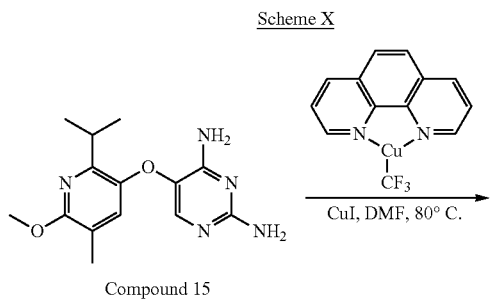

Compound 15

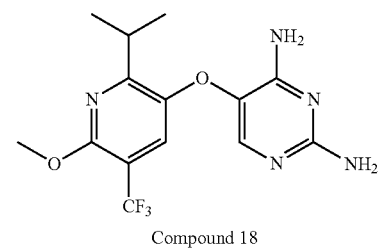

Compound 18

Starting material Compound 15 was prepared as outlined above in Example 17.

A solution of Compound 15 (100 mg, 249 umol, 1.00 eq), 1,10-phenanthrolinetrifluoromethyl copper (624 mg, 1.99 mmol, 8.00 eq) and CuI (94.9 mg, 498 umol, 2.00 eq) in DMF (2.00 mL) was stirred at 80° C. under N$_2$ atmosphere for 6 h. The mixture was filtered and ethyl acetate (10 mL) and H$_2$O (4 mL) were added to the filtrate. The two phases were separated and the aqueous phase was extracted with ethyl acetate (3×10 mL). The combined organic phases were dried over anhydrous Na$_2$SO$_4$, filtered and concentrated. The residue was purified via prep-HPLC to give Compound 18 (13.0 mg, 37.3 umol) as a solid. $^1$H NMR (400 MHz, DMSO-d$_6$) δ=7.46 (s, 1H), 7.16 (s, 1H), 6.51 (br. s., 2H), 5.93 (br. s., 2H), 3.96 (s, 3H), 3.54-3.42 (m, 1H), 1.26 (d, J=6.6 Hz, 6H). LCMS: 98.5% purity, m/z=344.2 (M+1)$^+$ Example 21: Synthesis of Compound 19

Compound 19 was made by the synthetic method outlined in Scheme Y:

Scheme Y

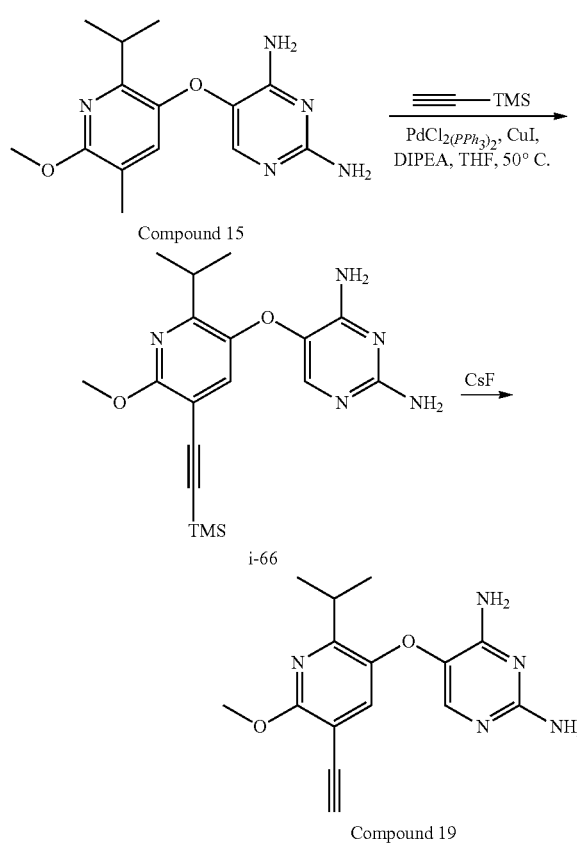

Compound 15 was prepared as outlined above in Example 17.

General Procedure for Preparation of Compound i-66:

To a solution of Compound 15 (100 mg, 249 umol, 1.00 eq), Pd(PPh$_3$)$_2$Cl$_2$ (35.0 mg, 49.8 umol, 0.20 eq) and CuI (4.75 mg, 24.9 umol, 0.10 eq) in THF (2.00 mL) was added ethynyl (trimethyl)silane (49.0 mg, 498 umol, 2.00 eq) and DIPEA (258 mg, 2.00 mmol, 8.00 eq). The mixture was stirred at 50° C. for 12 h. To the mixture was added ethyl acetate (4 mL) and saturated NH$_4$Cl (2 mL). The two phases were separated and the aqueous phase was extracted with ethyl acetate (3×3 mL). The combined organic phases were washed with brine (2 mL), dried with anhydrous Na$_2$SO$_4$, filtered and concentrated. The residue was purified via prep-TLC to give compound i-66 (80.0 mg, 215 umol) as a solid. $^1$H NMR (400 MHz, METHANOL-d$_4$) δ=7.24 (s, 1H), 7.12 (s, 1H), 3.96 (s, 3H), 3.43-3.36 (m, 1H), 1.26 (d, J=6.7 Hz, 6H), 0.21 (s, 9H).

General Procedure for Preparation of Compound 19:

To the solution of i-66 (75.0 mg, 201 umol, 1.00 eq) in THF (1.60 mL) was added CsF (153 mg, 1.01 mmol, 5.00 eq). The mixture was stirred at 50° C. for 5 h. Another portion of CsF (153 mg, 1.01 mmol, 5.00 eq) was added in. The mixture was stirred at 50° C. for 13 h. To the mixture was added ethyl acetate (10 mL) and saturated NH$_4$Cl (5 mL). The two phases were separated and the aqueous phase was extracted with ethyl acetate (4×10 mL). The combined organic phase was washed with brine (10 mL), dried over anhydrous Na$_2$SO$_4$, filtered and concentrated. The residue was purified via prep-HPLC to give Compound 19 (26.0 mg, 84.9 umol) as a solid. $^1$H NMR (400 MHz, DMSO-d$_6$) δ=7.38 (s, 1H), 7.02 (s, 1H), 6.46 (br. s., 2H), 5.88 (s, 2H), 4.33 (s, 1H), 3.89 (s, 3H), 3.40 (quin, J=6.8 Hz, 1H), 1.22 (d, J=7.1 Hz, 6H). LCMS: 97.7% purity, m/z=300.1 (M+1)$^+$ Example 22: Synthesis of Compound 20

Compound 20 was made by the synthetic method outlined in Scheme Z:

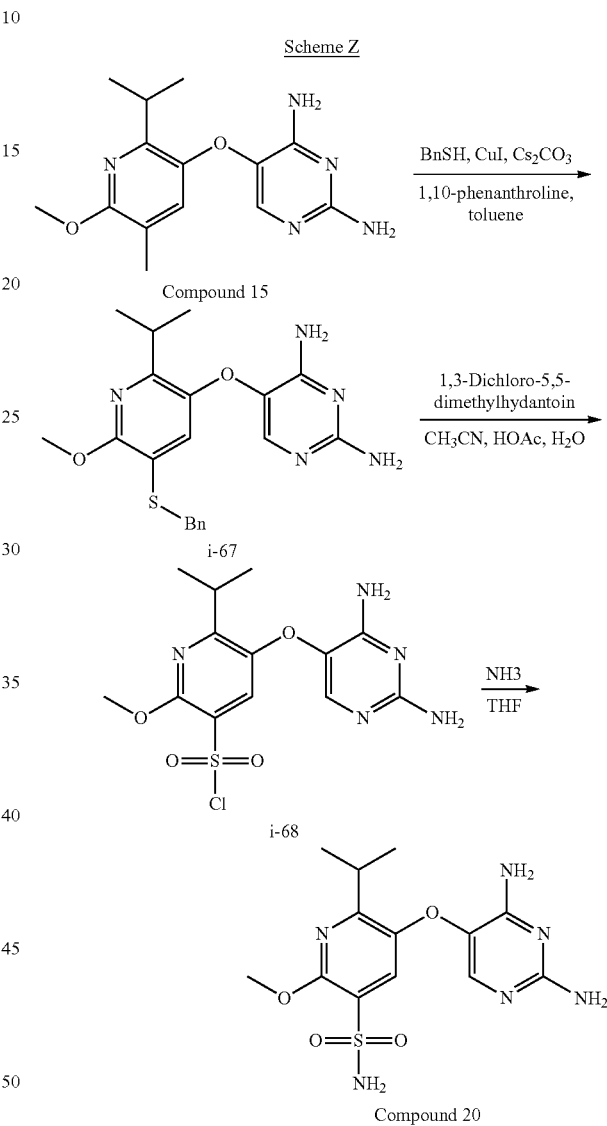

Compound 15 was prepared as outlined above in Example 17.

General Procedure for Preparation of Compound i-67:

To the mixture of Compound 15 (1.00 g, 2.49 mmol, 1.00 eq), CuI (213 mg, 1.12 mmol, 0.45 eq), 1,10-phenanthroline (202 mg, 1.12 mmol, 0.45 eq) and Cs$_2$CO$_3$ (1.22 g, 3.74 mmol, 1.50 eq) was added toluene (20.0 mL) and phenyl-methanethiol (3.09 g, 24.9 mmol, 2.92 mL, 10.0 eq). The mixture was stirred at 80° C. under N$_2$ atmosphere for 12 h. To the mixture was added water (10 mL) and ethyl acetate (20 mL). The two phases were separated and the aqueous phase was extracted with ethyl acetate (3×20 mL). The organic phases were combined, dried over anhydrous Na$_2$SO$_4$, filtered and concentrated. To the residue was added petroleum (20 mL) and ethyl actetate (3 mL). The mixture was stirred at 15° C. for 30 min. During this time a pink solid precipitated. The solid was filtered and further purified via prep-HPLC to give compound i-67 (520 mg, 1.31 mmol) as a solid. $^1$H NMR (400 MHz, DMSO-d$_6$) δ=7.30-7.16 (m, 6H), 7.01 (s, 1H), 6.40 (br. s., 2H), 5.85 (s, 2H).

General Procedure for Preparation of Compound i-68:

To the solution of i-67 (300 mg, 755 umol, 1.00 eq) in HOAc (4.20 mL) and H$_2$O (1.40 mL) was added 1,3-dichloro-5,5-dimethylhydantoin (297 mg, 1.51 mmol, 2.00 eq) at 0-5° C. The mixture was stirred at 0-5° C. for 1 h, and then stirred at 20° C. for 3 h. The reaction mixture was used in the next step directly without purification.

General Procedure for Preparation of Compound 20:

To a solution of NH$_3$ (1.03 g, 60.4 mmol, 80.0 eq) in THF (6.00 mL) was added dropwise the solution of i-68 (282 mg, 755 umol, 1.00 eq) in HOAc (4.20 mL) and H$_2$O (1.40 mL) at 0° C. The mixture was stirred at 20° C. for 12 h. To the mixture was added ethyl acetate (15 mL) and water (6 mL). The two phases were separated and the aqueous phase was extracted with ethyl acetate (2×10 mL). The organic phases were combined and concentrated. The residue was purified via prep-HPLC to give Compound 20 (92.0 mg, 259 umol, 99.7% purity) as a solid. $^1$H NMR (400 MHz, DMSO-d$_6$) δ=7.45 (s, 1H), 7.27 (s, 3H), 6.52 (br. s., 2H), 5.94 (s, 2H), 3.97 (s, 3H), 3.51 (td, J=6.6, 13.5 Hz, 1H), 1.26 (d, J=6.6 Hz, 6H. LCMS: 99.7% purity, m/z=355.0 (M+1).

Example 23: Synthesis of Compound 21

Compound 21 was made by the synthetic method outlined in Scheme AA:

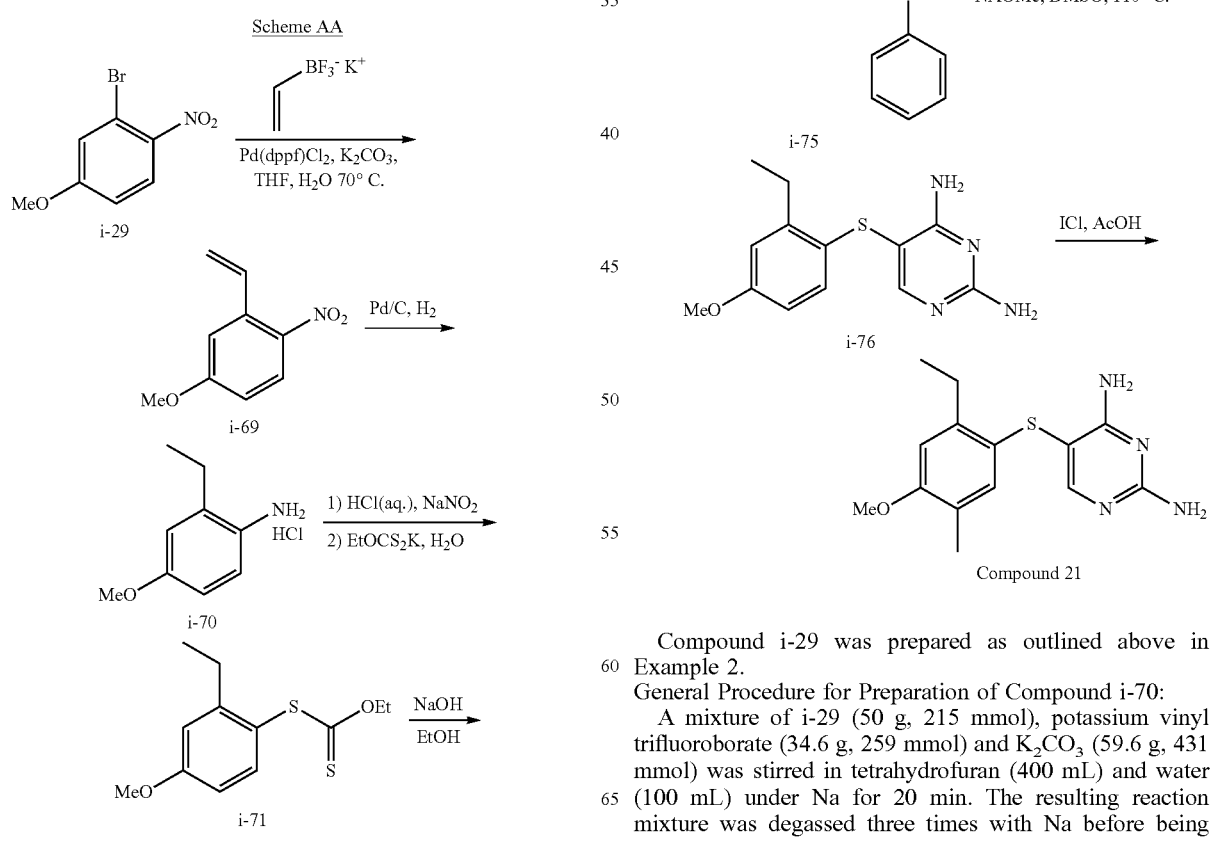
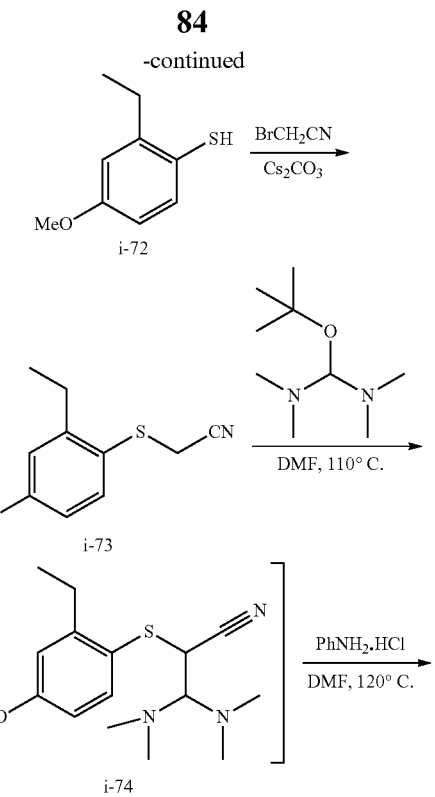
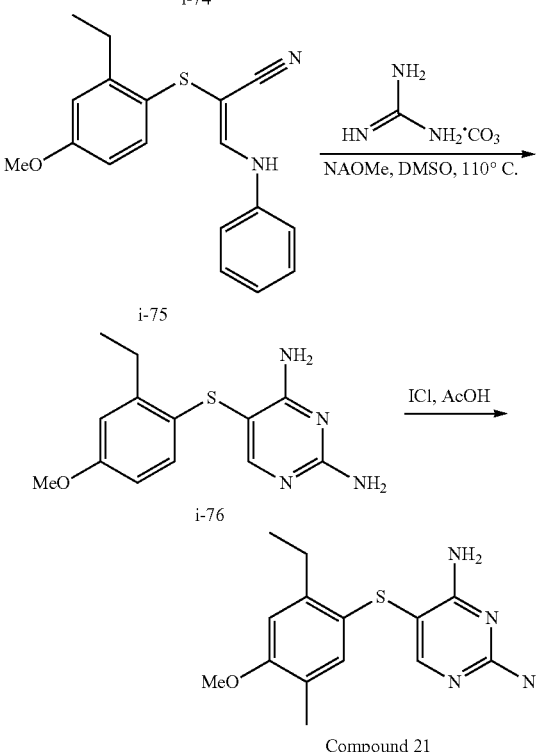

Compound i-29 was prepared as outlined above in Example 2.

General Procedure for Preparation of Compound i-70:

A mixture of i-29 (50 g, 215 mmol), potassium vinyl trifluoroborate (34.6 g, 259 mmol) and K$_2$CO$_3$ (59.6 g, 431 mmol) was stirred in tetrahydrofuran (400 mL) and water (100 mL) under Na for 20 min. The resulting reaction mixture was degassed three times with Na before being charged with Pd(dppf)Cl$_2$ (1.57 g, 2.10 mmol). The resulting reaction mixture was degassed again with Na and the mixture was stirred at 70° C. for 15 h. Two additional vials were set up as described above. All three reaction mixtures were combined and were partitioned between ethyl acetate (1.5 L) and water (1.5 L). The aqueous layer was extracted with ethyl acetate (3×1.0 L). The combined organic layers were dried over $Na_2SO_4$, filtered and concentrated under reduced pressure. The residue was purified by column chromatography on silica gel to give i-69 (90.0 g, 502 mmol) as an oil. $^1H$ NMR (400 MHz, Chloroform-d) δ=8.09-8.01 (m, 1H), 7.31-7.24 (m, 1H), 7.01 (d, J=2.6 Hz, 1H), 6.87 (dd, J=2.6, 9.0 Hz, 1H), 5.68 (d, J=17.4 Hz, 1H), 5.47 (d, J=11.0 Hz, 1H), 3.91 (s, 3H).

General Procedure for Preparation of Compound i-70:

A mixture of i-69 (90.0 g, 502 mmol, 1.00 eq) and Pd/C (9.01 g) in MeOH (900 mL) was stirred under $H_2$ (50 psi) at 25° C. for 12 h. The reaction mixture was filtered through celite and washed with MeOH (300 mL). To the filtrate was added 12 M HCl (90.0 mL). Then the mixture was concentrated to give i-70 (92.0 g, 490 mmol) as a solid which was used in the next step directly. $^1H$ NMR (400 MHz, DMSO-$d_6$) δ=10.18 (br. s., 3H), 7.39 (d, J=8.3 Hz, 1H), 6.91-6.83 (m, 2H), 3.76 (s, 3H), 2.67 (q, J=7.5 Hz, 2H), 1.19 (t, J=7.5 Hz, 3H).

General Procedure for Preparation of Compound i-71:

To a solution of i-70 (50.0 g, 266 mmol, 1.00 eq) in MeOH (300 mL) and HCl (1 M, 501 mL, 1.88 eq) was added dropwise a solution of $NaNO_2$ (27.6 g, 400 mmol, 1.50 eq) in $H_2O$ (100 mL) at 0° C. The mixture was stirred at 0° C. for 1 h. Then the mixture was added dropwise to a solution of $EtOCS_2K$ (85.4 g, 533 mmol, 2.00 eq) in $H_2O$ (700 mL). The mixture was stirred at 25° C. for 2 h. The mixture was partitioned between ethyl acetate (300 mL) and water (100 mL). The aqueous layer was extracted with ethyl acetate (3×200 mL). The combined organic layers were dried over $Na_2SO_4$, filtered and concentrated under reduced pressure to give a residue. The residue was purified by column chromatography on silica gel to give i-71 (40.0 g, 156 mmol) as an oil which was used in the next step directly. $^1H$ NMR (400 MHz, DMSO-$d_6$) δ=7.39 (d, J=8.8 Hz, 1H), 6.97 (br. s., 1H), 6.89-6.84 (m, 1H), 4.57 (q, J=6.9 Hz, 2H), 3.80 (s, 3H), 2.65 (q, J=7.5 Hz, 2H), 1.35 (t, J=7.1 Hz, 3H), 1.12 (t, J=7.5 Hz, 3H).

General Procedure for Preparation of Compound i-72:

To a solution of i-71 (40.0 g, 156 mmol, 1.00 eq) in EtOH (280 mL) was added aqueous NaOH (3 M, 572 mL, 11.0 eq). Then the mixture was stirred at 65° C. for 1 h. TLC showed the reaction was completed. 1, 4-Dithioerythritol (100 mg) was added in and the mixture was adjusted to pH=5 with aqueous HCl (3 M, 140 mL). Then the mixture was partitioned between ethyl acetate (100 mL) and water (100 mL). The aqueous layer was extracted with ethyl acetate (3×100 mL). The combined organic layers were dried over $Na_2SO_4$, filtered and concentrated under reduced pressure to give i-72 (18.0 g, 107 mmol) as an oil which was used in the next step directly. $^1H$ NMR (400 MHz, DMSO-$d_6$) δ=7.31-7.25 (m, 1H), 6.78 (d, J=2.2 Hz, 1H), 6.69 (dd, J=2.4, 8.6 Hz, 1H), 4.85 (s, 1H), 3.73-3.67 (m, 3H), 2.63-2.56 (m, 2H), 1.14 (t, J=7.5 Hz, 3H).

General Procedure for Preparation of Compound i-73:

To a solution of i-72 (18.0 g, 107 mmol, 1.00 eq) in $CH_3CN$ (120 mL) was added $Cs_2CO_3$ (52.3 g, 160 mmol, 1.50 eq) and 2-bromoacetonitrile (19.3 g, 160 mmol, 1.50 eq). Then the mixture was stirred at 80° C. for 12 h. The reaction mixture was partitioned between ethyl acetate (100 mL) and water (100 mL). The aqueous layer was extracted with ethyl acetate (3×80 mL). The combined organic layers were dried over $Na_2SO_4$, filtered and concentrated under reduced pressure. The residue was purified by column chromatography on silica gel to give i-73 (7.40 g, 35.7 mmol) as an oil. $^1H$ NMR (400 MHz, DMSO-$d_6$) δ=7.51 (d, J=8.4 Hz, 1H), 6.91 (d, J=2.2 Hz, 1H), 6.86 (dd, J=2.4, 8.6 Hz, 1H), 3.98 (s, 2H), 3.77 (s, 3H), 2.77 (q, J=7.5 Hz, 2H), 1.16 (t, J=7.5 Hz, 3H).

General Procedure for Preparation of Compound i-75:

To a solution of i-73 (2.70 g, 13.0 mmol, 1.00 eq) in DMF (27.0 mL) was added 1-tert-butoxy-N,N,N',N'-tetramethylmethanediamine (4.54 g, 26.1 mmol, 5.41 mL, 2.00 eq). The mixture was stirred at 110° C. for 1 h. The reaction mixture was cooled to RT, and used in the next step directly without characterization.

To the crude reaction mixture was added aniline hydrochloride (8.43 g, 65.1 mmol, 5.00 eq). The mixture was stirred at 120° C. for 12 h and then cooled to RT. The reaction mixture was partitioned between toluene (50 mL) and water (50 mL). The aqueous layer was extracted with toluene (3×40 mL). The combined organic layers were dried over $Na_2SO_4$, filtered and concentrated under reduced pressure to give i-75 9.00 g, (crude) as a an oil which was used in the next step directly. $^1H$ NMR (400 MHz, Chloroform-d) δ=7.38-7.32 (m, 7H), 6.99 (s, 1H), 6.71 (s, 1H), 3.80 (s, 3H), 2.87-2.81 (m, 2H), 1.32-1.26 (m, 3H).

General Procedure for Preparation of Compound i-76:

To a solution of i-75 (9.00 g, 29.0 mmol, 1.00 eq) in DMSO (90.0 mL) was added guanidine carbonate (7.84 g, 43.5 mmol, 1.50 eq) and $CH_3ONa$ (4.70 g, 87.0 mmol, 3.00 eq). The mixture was stirred at 110° C. for 12 h and then cooled to RT. The reaction mixture was partitioned between ethyl acetate (100 mL) and water (100 mL). The aqueous layer was extracted with ethyl acetate (3×80 mL). The combined organic layers were dried over $Na_2SO_4$, filtered and concentrated under reduced pressure. The residue was purified by prep-HPLC to give i-76 (676 mg, 2.45 mmol) as a solid. $^1H$ NMR (400 MHz, DMSO-$d_6$) δ=7.85 (s, 1H), 6.79 (s, 1H), 6.77-6.69 (m, 2H), 6.34 (br. s., 2H), 3.69 (s, 3H), 2.77-2.70 (m, 2H), 1.20 (t, J=7.5 Hz, 3H) LCMS: $[M+H]^+$ 277.0

General Procedure for Preparation of Compound 21:

First batch: To a solution of i-76 (25.0 mg, 90.5 umol, 1.00 eq) in HOAc (0.1 mL) was added a solution of ICl (29.4 mg, 181 umol, 2.00 eq) in HOAc (0.1 mL). Then $H_2O$ (25.0 uL) was added. The mixture was stirred at 20° C. for 14 h. Another portion of ICl (29.4 mg, 181 umol, 2.00 eq) was added. Then the mixture was stirred at 40° C. for 2 h, and then cooled to RT. The reaction mixture was adjust to pH=8 with 4 M NaOH and saturated $Na_2CO_3$. The mixture was extracted with ethyl acetate (2×5 mL), the combined organic phases were washed with saturated $Na_2CO_3$ (5 mL), dried over anhydrous $Na_2SO_4$, filtered and concentrated.

Second batch: To a solution of i-76 (300 mg, 1.09 mmol, 1.00 eq) in HOAc (3 mL) was added a solution of ICl (354 mg, 2.18 mmol, 2.00 eq) in HOAc (3 mL). Then $H_2O$ (500 uL) was added in. The mixture was stirred at 40° C. for 2 h. Another portion of ICl (177 mg, 1.09 mmol, 1.00 eq) was added. Then the mixture was stirred at 40° C. for 12 h. The reaction mixture was adjust to pH=8 with 4 M NaOH and saturated $Na_2CO_3$. The mixture was extracted with ethyl acetate (2×10 mL). Then the combined organic phases were washed with saturated $Na_2CO_3$ (5 mL), dried over anhydrous $Na_2SO_4$, filtered and concentrated.

The above two residues from the first batch and the second batch were combined. This was purified via prep-HPLC to give Compound 21 (200 mg, 472 umol) as a solid.

$^1$H NMR (400 MHz, DMSO-d$_6$) δ=7.88 (s, 1H), 7.08 (s, 1H), 6.88 (s, 1H), 6.46 (s, 2H), 3.79 (s, 3H), 2.74 (q, J=7.5 Hz, 2H), 1.21 (t, J=7.5 Hz, 3H) LCMS: [M+H]$^+$ 403.0

Example 24: Synthesis of Compound 22

Compound 22 was made by the synthetic method outlined in Scheme AB:

Scheme AB

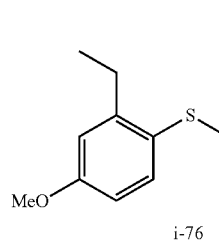
i-76

Compound 22

Compound i-76 was prepared as outlined above in Example 23.

General Procedure for Preparation of Compound 22:

First batch: To a mixture of i-76 (25.0 mg, 90.5 umol, 1.00 eq) and methylsulfonyl methanesulfonate (63.0 mg, 361 umol, 4.00 eq) was added trifluoromethanesulfonic acid (40.7 mg, 271 umol, 3.00 eq). The mixture was heated at 80° C. for 12 h and cooled to RT. To the mixture was added ethyl acetate (2 mL) and H$_2$O (0.5 mL). Then the mixture was adjusted to pH=8 with 4 M NaOH and saturated Na$_2$CO$_3$. The two phases were separated and the aqueous phase was extracted with ethyl acetate (2×10 mL). The organic phases were combined, dried over anhydrous Na$_2$SO$_4$ and concentrated.

Second batch: To a mixture of i-76 (300 mg, 1.09 mmol, 1.00 eq) and methylsulfonyl methanesulfonate (756 mg, 4.34 mmol, 4.00 eq) was added trifluoromethanesulfonic acid (489 mg, 3.26 mmol, 3.00 eq). The mixture was heated at 80° C. for 12 h and cooled to RT. To the mixture was added ethyl acetate (10 mL) and H$_2$O (5 mL). Then the mixture was adjusted to pH=8 with 4 M NaOH and saturated Na$_2$CO$_3$. The two phases were separated and the aqueous phase was extracted with ethyl acetate (2×10 mL). The organic phases were combined, dried over anhydrous Na$_2$SO$_4$ and concentrated.

The above two residues from the two batches were combined. The mixture was purified via prep-HPLC to give Compound 22 (68.0 mg, 188 umol) as a solid.

$^1$H NMR (400 MHz, DMSO-d$_6$) δ=7.88 (s, 1H), 7.20 (s, 1H), 7.17 (s, 1H), 6.42 (br. s., 2H), 3.92 (s, 3H), 3.16 (s, 3H), 2.82 (q, J=7.5 Hz, 2H), 1.26 (t, J=7.5 Hz, 3H) LCMS: [M+H]$^+$ 355.1

Example 25: Synthesis of Compound 23

Compound 23 was made by the synthetic method outlined in Scheme AC:

Scheme AC

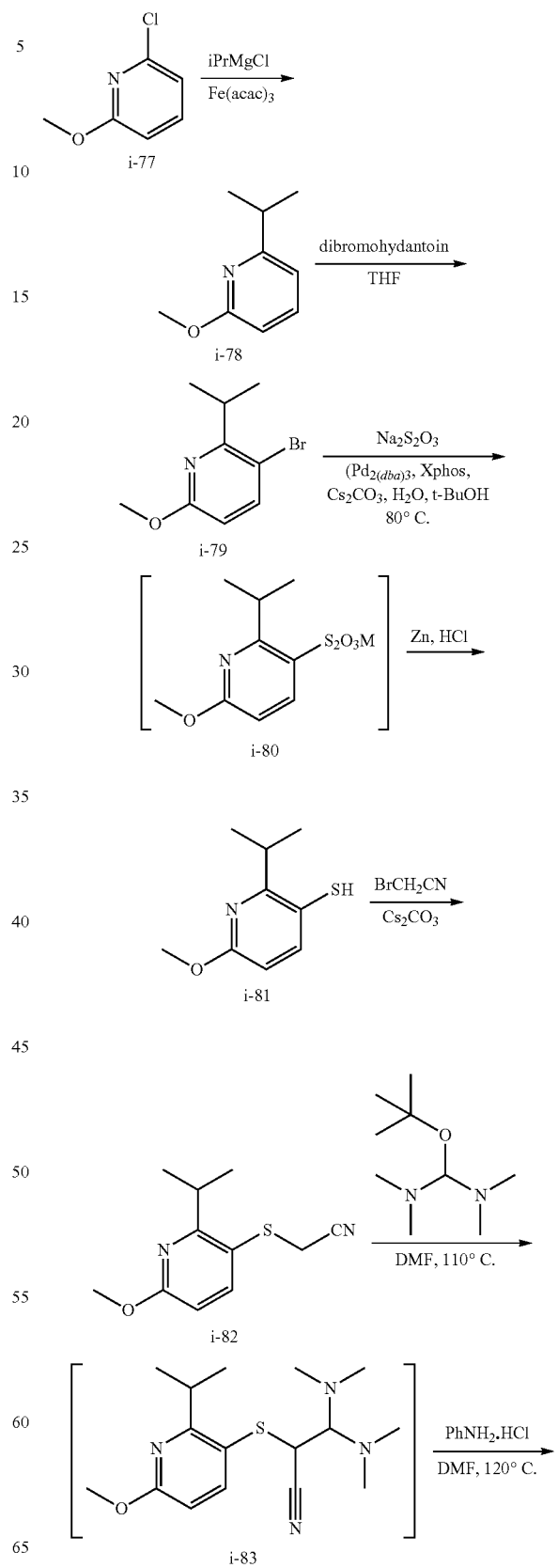

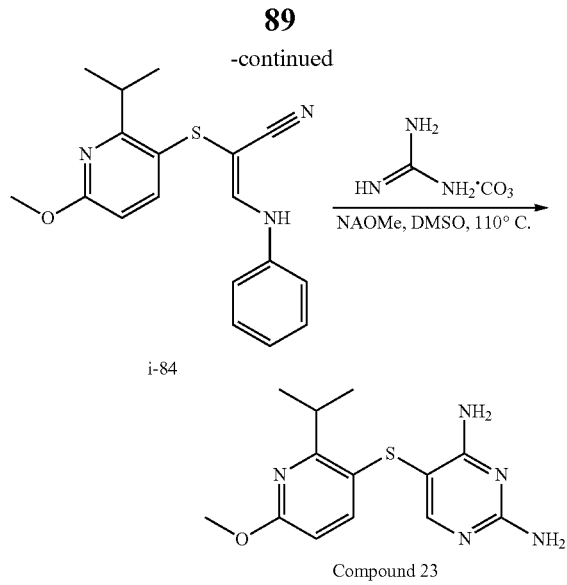

General Procedure for Preparation of Compound i-78:

Compound i-77 (60 g, 417 mmol, 50 mL, 1.00 eq) and Fe(AcAc)$_3$ (7.38 g, 20.9 mmol, 0.05 eq) were dissolved in THF (2 L) and NMP (200 mL). The suspension was cooled to −30° C. i-PrMgCl (250 mL, 1.20 eq) was added into above suspension while keeping the internal temperature between −30° C. to −40° C. The suspension was warmed to 0° C. and was stirred for 1 h. Two additional reactions were set up as described above. All three reaction mixtures were combined. The reaction solution was quenched with saturated aqueous NH$_4$Cl (500 mL) and was extracted with ethyl acetate (3×500 mL). The organic layer was combined, washed with H$_2$O (5×250 mL), dried over Na$_2$SO$_4$ and concentrated under vacuum to give i-78 (53.0 g, 350 mmol) which was used in next step without purification. $^1$H NMR (400 MHz, CDCl$_3$-D$_6$) δ=7.46 (t, J=7.6 Hz, 1H), 6.71 (d, J=9.2 Hz, 1H), 6.52 (d, J=8.0 Hz, 1H), 3.92 (s, 3H), 2.95 (m, 1H), 1.27 (d, J=7.2 Hz, 6H).

General Procedure for Preparation of Compound i-79:

To the solution of compound i-78 (120 g, 794 mmol, 1.00 eq) in THF (1.2 L) was added 1,3-dibromo-5,5-dimethyl-imidazolidine-2,4-dione (205 g, 794 mmol, 1.00 eq) at 0° C. in portions during 0.5 h. The mixture was stirred at 20° C. for 3 h. To the mixture was added ice water (500 mL) and ethyl acetate (300 mL). The two phases were separated and the aqueous phase was extracted with ethyl acetate (3×400 mL). The combined organic phase was dried over anhydrous Na$_2$SO$_4$, filtered and concentrated. The residue was purified via column chromatography on silica gel to give i-79 (96 g, 417 mmol) as an oil. $^1$H NMR (400 MHz, CDCl$_3$-D$_6$) δ=7.61 (d, J=8.60 Hz, 1H), 6.45 (d, J=8.60 Hz, 1H), 3.39-3.49 (m, 1H), 3.92 (s, 3H), 1.25 (d, J=6.84 Hz, 6H).

General Procedure for Preparation of Compound i-81:

A mixture of compound i-79 (50.0 g, 217 mmol, 1.00 eq), Na$_2$S$_2$O$_3$ (85.9 g, 543 mmol, 2.50 eq) and Cs$_2$CO$_3$ (142 g, 434 mmol, 2.00 eq) in t-BuOH (250 mL) and toluene (250 mL) was degassed three times back filling with N$_2$ each time before being charged with Pd$_2$(dba)$_3$ (3.98 g, 4.35 mmol, 0.02 eq). The resulting reaction mixture was degassed twice back filling with N$_2$ each time and then warmed to 80° C. for 15 h. The reaction mixture was cooled to 20° C. Three additional vials were set up as described above. All the four reaction mixtures were combined. The reaction mixture was concentrated to dryness to give a residue which was crushed in MTBE (500 mL). The mixture was filtered and the filter cake was washed with MTBE (200 mL) to give crude compound i-80.

The combined dried filter cake was added into HCl (4 M, 200 mL) at 0° C., and Zn dust (20 g) was added into the mixture. Gas evolution occurred, and the mixture was stirred for 1 h. The reaction mixtures were poured into ice-water (w/w=1/1) (2 L) and stirred for 20 min. The aqueous phase was extracted with ethyl acetate (3×2 L). The combined organic phase was washed with brine (2×500 mL), dried with anhydrous Na$_2$SO$_4$, filtered and concentrated in vacuum to give i-81 (160 g, crude) as an oil. $^1$H NMR (400 MHz, CDCl$_3$-D$_6$) δ=7.48 (d, J=8.4 Hz, 1H), 6.45-6.48 (d, J=8.4 Hz, 1H), 3.91 (s, 1H), 3.37-3.49 (m, 1H), 1.25 (d, J=6.84 Hz, 6H).

General Procedure for Preparation of Compound i-82:

To compound i-81 (80 g, 436.51 mmol, 1.00 eq) in CH$_3$CN (1.6 L) was added Cs$_2$CO$_3$ (213 g, 655 mmol, 1.50 eq) and BrCH$_2$CN (87.7 g, 53.8 mmol, 1.50 eq). The mixture was stirred at 80° C. for 15 h. One additional vial was set up as described above. The two reaction mixtures were combined. The reaction mixture was filtered and the filtrate was concentrated to give a residue which was purified by silica column chromatography on silica to give i-82 (81 g, 364 mmol, 41% yield) as an oil which was used for the next step without next purification. $^1$H NMR (400 MHz, CDCl$_3$-D$_6$) δ=7.77 (d, J=8.38 Hz, 1H), 6.58 (d, J=8.38 Hz, 1H), 3.87-4.00 (m, 3H), 3.64-3.80 (m, 1H), 3.30-3.46 (m, 2H), 1.26 (d, J=6.62 Hz, 6H).

General Procedure for Preparation of Compound i-83:

Crude i-82 (20.0 g, 90.0 mmol, 1.00 eq) and 1-tert-butoxy-N,N,N',N'-tetramethyl-methane diamine (31.2 g, 179 mmol, 37.3 mL, 2.00 eq) were dissolved in DMF (200 mL). The solution was heated to 110° C. for 4 h and cooled to RT to give a solution of crude i-83. The solution was used for next step without purification.

General Procedure for Preparation of Compound i-84:

The solution of crude i-83 (29 g, 90.0 mmol, 1.00 eq) and aniline hydrochloride (23.3 g, 180 mmol, 2.00 eq) were dissolved in DMF (200 mL). The reaction solution was heated to 120° C. for 2 h. Aniline hydrochloride (23.3 g, 180 mmol, 2.00 eq) was added into the above solution. The solution was heated at 120° C. for 16 and cooled to RT. To the mixture was added ethyl acetate (200 mL) and water (100 mL). The two phases were separated and the aqueous phase was extracted with ethyl acetate (3×100 mL). The organic phases were combined and washed with brine (200 mL), dried over anhydrous Na$_2$SO$_4$, filtered and concentrated to give i-84 (29.3 g, crude) which was used directly in next step without characterization.

General Procedure for Preparation of Compound 23:

Crude i-84 (29.3 g, 90.0 mmol, 1.00 eq, crude) and guanidine carbonate (24.3 g, 135 mmol, 1.50 eq) were dissolved in DMSO (200 mL). To the reaction solution was added into NaOMe (14.6 g, 269 mmol, 3.00 eq). The solution was heated to 110° C. for 16 h and cooled to RT. Two additional reactions were set up as described above. All the three reaction mixtures were combined. To the mixture was added ethyl acetate (500 mL) and water (200 mL). The two phases were separated and the aqueous phase was extracted with ethyl acetate (3×150 mL). The organic phases were combined and washed with brine (200 mL), dried over anhydrous Na$_2$SO$_4$, filtered and concentrated. The residue was purified by column chromatography on silica gel to give crude product. The crude product was washed with MTBE (100 mL) to give Compound 23 (3.3 g, 37.8 mmol) as a solid. $^1$H NMR (400 MHz, CDCl$_3$-D$_6$) δ=7.87 (s, 1H), 7.14

(d, J=8.4 Hz, 1H), 6.56 (d, J=7.6 Hz, 1H), 6.47-6.43 (br. m., 4H), 3.80 (s, 3H), 3.47 (m, 1H), 1.20 (d, J=6.4 Hz, 6H) LCMS: [M+H]+ 292.0

Example 26: Synthesis of Compound 24

Compound 24 was made by the synthetic method outlined in Scheme AD:

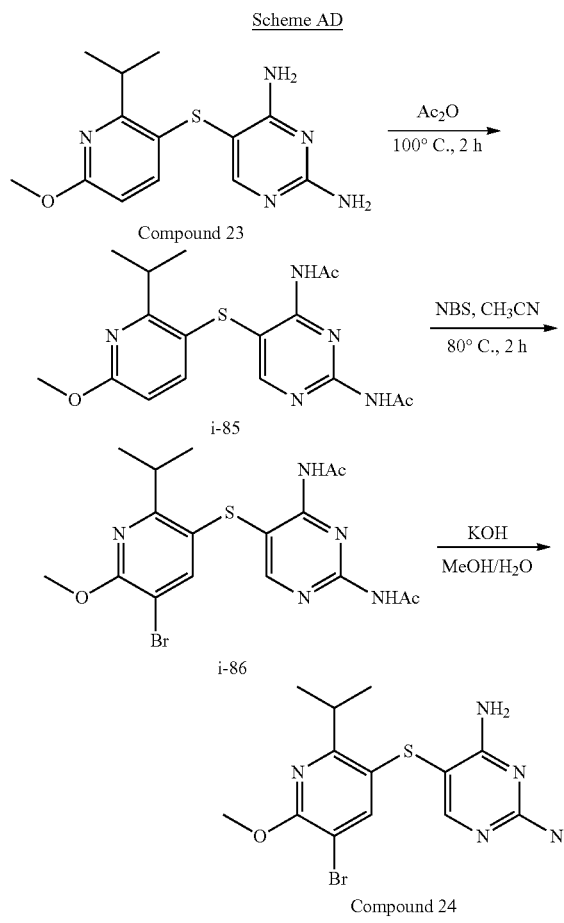

Scheme AD

General Procedure for Preparation of Compound i-85:
Compound 23 (6.50 g, 22.3 mmol, 1.00 eq) was dissolved in Ac$_2$O (42 mL, 20.0 eq). The solution was heated to 100° C. for 2 h, cooled to RT, and the solvent was removed. The residue was added into saturated aqueous Na$_2$CO$_3$. The aqueous layer was extracted with ethyl acetate (3×10 mL). The combined organic layer was combined, dried over Na$_2$SO$_4$ and concentrated. The residue was purified by silica column to give i-85 (5.00 g).
$^1$H NMR (400 MHz, CDCl$_3$-D$_6$) δ=9.22 (br s, 1H), 8.72 (s, 1H), 8.42 (s, 1H), 7.22 (d, J=8.6 Hz, 1H), 6.46 (d, J=8.6 Hz, 1H), 3.89 (s, 3H), 3.57 (m, J=6.7 Hz, 1H), 2.46 (d, J=6.2 Hz, 6H), 1.23-1.19 (m, 6H).
General Procedure for Preparation of Compound i-86:
Compound i-85 (4.80 g, 12.8 mmol, 1.00 eq) and NBS (3.41 g, 19.1 mmol, 1.50 eq.) were dissolved in CH$_3$CN (40 mL). The suspension was heated to 80° C. for 1.5 h and cooled to RT. The solvent was removed. The residue was added into saturated Na$_2$CO$_3$. The aqueous layer was extracted with ethyl acetate (3×20 mL). The combined organic layers were dried over Na$_2$SO$_4$ and concentrated. The residue was purified by prep-HPLC to give i-85 (2.00 g, 4.40 mmol). $^1$H NMR (400 MHz, CDCl$_3$-D$_6$) δ=8.52 (d, J=14.8 Hz, 2H), 8.42 (s, 1H), 7.37 (s, 1H), 3.98 (s, 3H), 3.53 (m, 1H), 2.53 (s, 3H), 2.46 (s, 3H), 1.24 (J=6.4 Hz, 6H).
General Procedure for Preparation of Compound 24:
Compound i-86 (600 mg, 1.32 mmol, 1.00 eq) and KOH (296 mg, 5.28 mmol, 4.00 eq) were dissolved in MeOH (5 mL) and H$_2$O (5 mL). The solution was heated to 50° C. for 2 h. The solvent was removed. H$_2$O (10 mL) was added into the solution. The aqueous layer was extracted with ethyl acetate (3×20 mL). The combined organic layers were dried over Na$_2$SO$_4$ and concentrated. The residue was purified by silica column chromatography on silica gel (petroleum ether:ethyl acetate=10:1 to 1:1) to give Compound 24 (300 mg, crude) as a solid. 100 mg of Compound 24 was purified by Prep-HPLC to give 26 mg of Compound 24.
$^1$H NMR (400 MHz, CDCl$_3$-D$_6$) δ=8.10 (s, 1H), 7.27 (s, 1H), 5.23 (s, 2H), 4.95 (s, 2H), 3.98 (s, 3H), 3.46 (m, 1H), 1.27 (d, J=6.4 Hz, 6H) LCMS: [M+H]+ 369.9

Example 27: Synthesis of Compound 25

Compound 25 was made by the synthetic method outlined in Scheme AE:

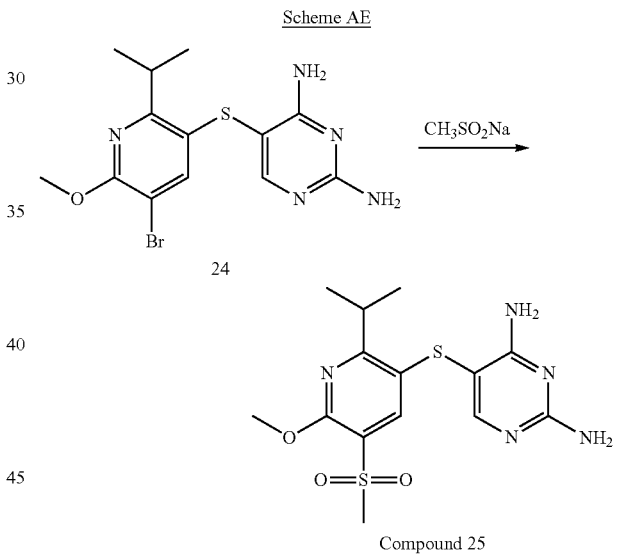

Scheme AE

General Procedure for Preparation of Compound 25:
A solution of Compound 24 (60.0 mg, 162 umol, 1.00 eq, prepared as described in Example 26), CH$_3$SO$_2$Na (41.4 mg, 405 umol, 2.50 eq), CuI (6.17 mg, 32.4 umol, 0.20 eq) and 1,2-diaminocyclohexane (7.40 mg, 64.8 umol, 0.40 eq) in DMSO (1.20 mL) was stirred at 120° C. under N$_2$ atmosphere for 4 h. Two additional vials were set up as described above. All the three reaction mixtures were combined and purified via prep-HPLC to give Compound 25 (55.0 mg, 149 umol) as a solid. $^1$H NMR (400 MHz, DMSO-d$_6$) δ=7.92 (s, 1H), 7.48 (s, 1H), 6.62 (br s, 1H), 6.45 (br s, 2H), 4.02 (s, 3H), 3.52-3.42 (m, 1H), 3.22 (s, 3H), 1.27 (br d, J=6.4 Hz, 6H) LCMS: [M+H]+ 370.0

Example 28: Synthesis of Compound 26

Compound 26 was made by the synthetic method outlined in Scheme AF:

Scheme AF

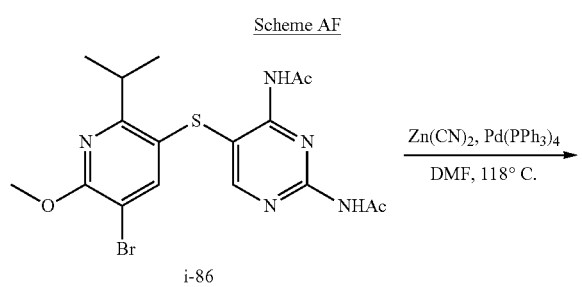

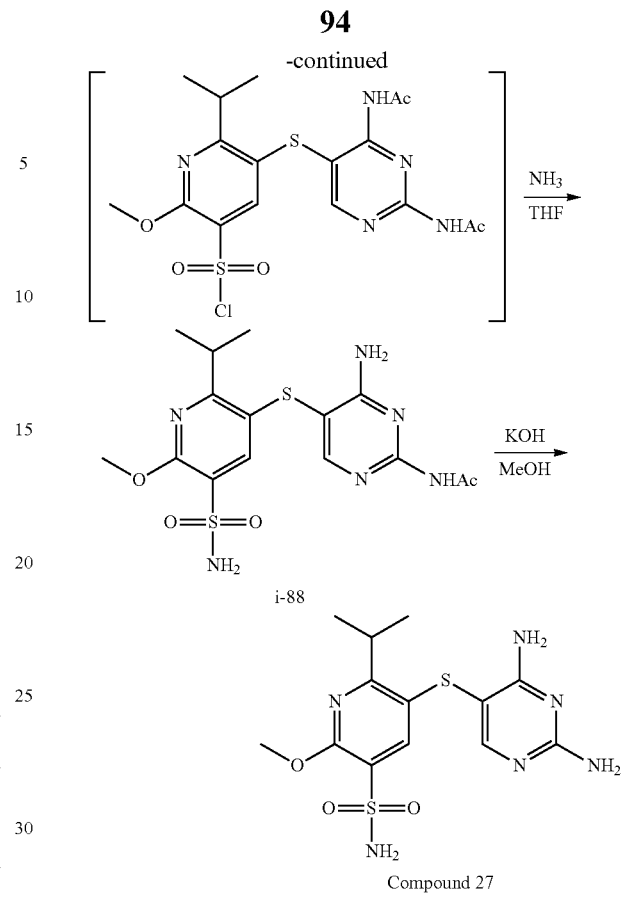

General Procedure for Preparation of Compound 26:

A mixture of i-86 (180 mg, 396 umol, 1.00 eq, prepared as described in example 26) and Zn(CN)$_2$ (93 mg, 792 umol, 2.00 eq) in DMF (4.00 mL) was protected by Argon. Then Pd(PPh$_3$)$_4$ (183 mg, 158 umol, 0.40 eq) was added in one portion. The resulted orange mixture was heated at 118° C. for 17 h to give a suspension. The reaction mixture was allowed to cool to ambient temperature gradually and stayed till all solid deposited. The clear solution was collected by a dropper and purified by prep-HPLC to give Compound 26 (30.0 mg) as a powder. $^1$H NMR (400 MHz, DMSO-d$_6$) δ=7.93 (s, 1H), 7.50 (s, 1H), 6.62 (brs, 2H), 6.47 (s, 2H), 3.97 (s, 3H), 3.50 (m, 1H), 1.23 (d, J=6.8 Hz, 6H) LCMS: [M+H]$^+$ 317.0

Example 29: Synthesis of Compound 27

Compound 27 was made by the synthetic method outlined in Scheme AG:

Scheme AG

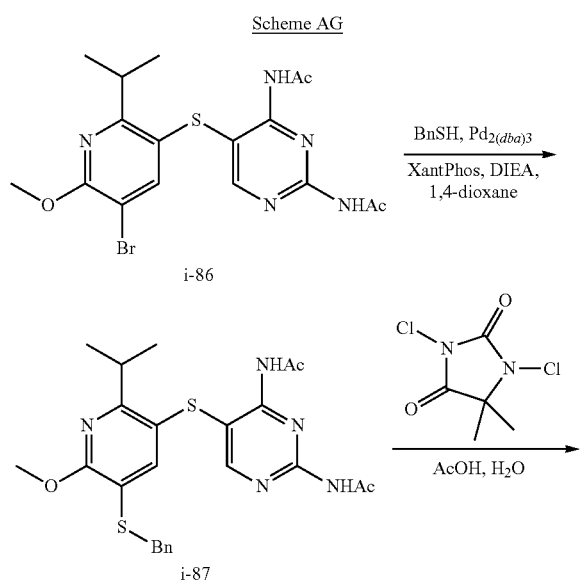

General Procedure for Preparation of Compound i-87:

Compound i-86 (300 mg, 660 umol, 1.00 eq, prepared as described in example 26), phenylmethanethiol (205 mg, 1.65 mmol, 2.50 eq), Pd$_2$(dba)$_3$ (242 mg, 264 umol, 0.40 eq), Xantphos (153 mg, 264 umol, 0.40 eq) and DIEA (171 mg, 1.32 mmol, 2.00 eq) were dissolved in 1,4-dioxane (8 mL). The suspension was heated to 100° C. for 16 h under N$_2$. The solvent was removed. The residue was added into water (30 mL). The aqueous layer was extracted with ethyl acetate (3×15 mL). The combined organic layers were dried over Na$_2$SO$_4$ and concentrate. The residue was purified by column to give i-87 (300 mg, crude) which was used in next step without purification. $^1$H NMR (400 MHz, CDCl$_3$-D$_6$) δ=8.25 (s, 1H), 7.21-7.16 (m, 5H), 7.02 (s, 1H), 4.01 (s, 3H), 3.99 (s, 2H), 3.52 (m, 1H), 2.50 (s, 3H), 2.48 (s, 3H), 1.23 (J=7.2 Hz, 6H).

General Procedure for Preparation of Compound i-88:

Compound i-87 (180 mg, 362 umol, 1.00 eq) was dissolved in AcOH (2.5 mL) and H$_2$O (1 mL). The solution was cooled to 0° C. 1, 3-Dichloro-5,5-dimethyl-imidazolidine-2,4-dione (143 mg, 723 umol, 2.00 eq) was added into the solution at 0° C. The suspension was warmed to RT and stirred for 2 h. A solution of NH$_3$ (629 mg, 36.9 mmol, 80.00 eq) in THF (10 mL) was added drop wise to the reaction solution of at 0° C. The mixture was stirred at 20° C. for 12 h. To the mixture was added ethyl acetate (15 mL) and water (6 mL). The two phases were separated and the aqueous phase was extracted with ethyl acetate (2×10 mL). The organic phases were combined and dried with anhydrous Na$_2$SO$_4$, filtered and concentrated to give i-88 (180 mg, crude) which was used in next step without purification.

General Procedure for Preparation of Compound 27:

Crude compound i-88 (180 mg, 436 umol, 1.00 eq) was dissolved in MeOH (3 mL) and H$_2$O (1 mL). KOH (97.9 mg, 1.75 mmol, 4.00 eq) was added into the solution. The suspension was stirred at RT for 2 h. To the mixture was added ethyl acetate (15 mL) and water (10 mL). The two phases were separated and the aqueous phase was extracted with ethyl acetate (4×10 mL). The organic phases were combined and dried with anhydrous Na$_2$SO$_4$, filtered and concentrated. The residue was purified via prep-HPLC to give Compound 27 (14.7 mg, 39.7 umol) as a solid. $^1$H NMR (400 MHz, DMSO-d$_6$)

δ=7.90 (s, 1H), 7.48 (s, 1H), 7.24 (s, 2H), 6.62-6.43 (br. m., 4H), 3.96 (s, 3H), 3.48 (m, 1H), 1.25 (d, J=6.4 Hz, 6H) LCMS: [M+H]$^+$ 371.1

Example 30: Synthesis of Compound 28

Compound 28 was made by the synthetic method outlined in Scheme AH:

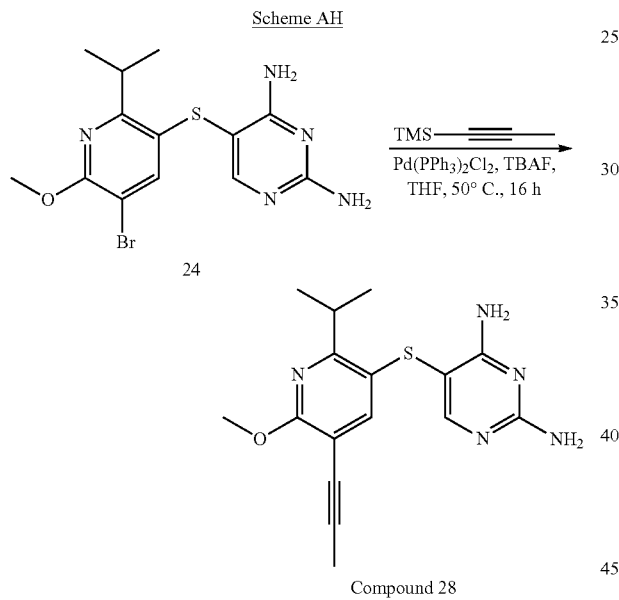

Compound 28

General Procedure for Preparation of Compound 28:

Compound 24 (200 mg, 540 umol, 1.00 eq prepared as described in Example 26), trimethyl(prop-2-ynyl)silane (485 mg, 4.32 mmol, 8.00 eq), Pd(PPh$_3$)$_2$Cl$_2$ (152 mg, 216 umol, 0.40 eq) and TBAF (1 M, 1.62 mL, 3.00 eq) were dissolved in THF (8 mL). The suspension was heated to 50° C. for 16 h under N$_2$. The reaction was cooled to RT. To the mixture was added ethyl acetate (20 mL) and saturated NH$_4$Cl (20 mL). The two phases were separated and the aqueous phase was extracted with ethyl acetate (3×15 mL). The combined organic phases were washed with brine (15 mL), dried with anhydrous Na$_2$SO$_4$, filtered and concentrated. The residue was dissolved in DMF (5 mL) and purified by prep-HPLC. MeCN was removed under reduced pressure and then water was removed by lyophillization to give Compound 28 (47.2 mg, 121 umol) as a solid. $^1$H NMR (400 MHz, CDCl$_3$-D$_6$) δ=8.10 (s, 1H), 7.12 (s, 1H), 5.28 (br. s., 2H), 5.03 (s, 2H), 3.97 (s, 3H) 3.46 (m, 1H), 2.07 (s, 3H), 1.27 (d, J=6.8 Hz, 6H) LCMS: [M+H]$^+$ 330.0

Example 31: Synthesis of Compound 29

Compound 29 was made by the synthetic method outlined in Scheme AH:

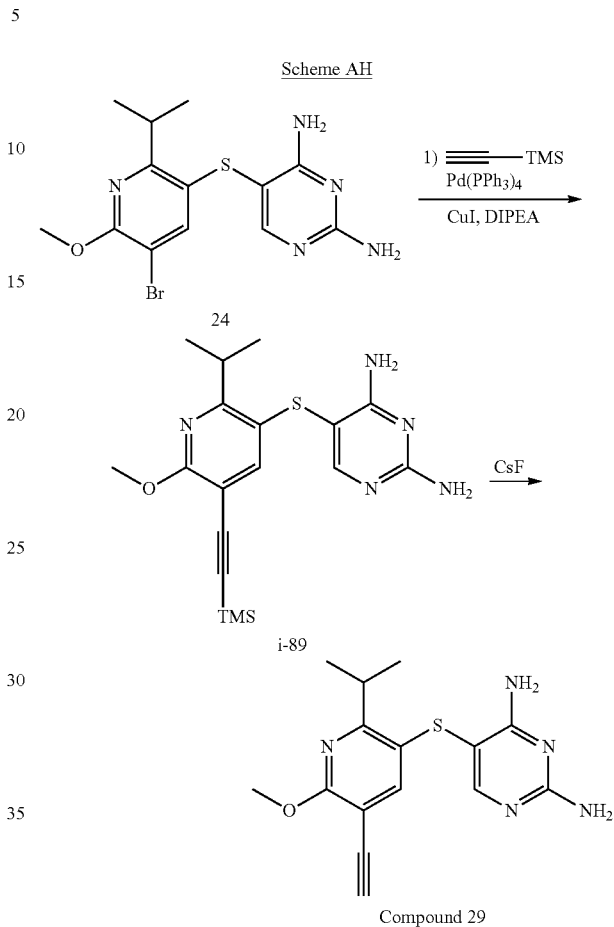

Compound 29

General Procedure for Preparation of Compound i-89:

Compound 24 (150 mg, 405 umol, 1.00 eq, prepared as described in Example 26), ethynyl(trimethyl)silane (318 mg, 3.24 mmol, 8.00 eq), Pd(PPh$_3$)$_2$Cl$_2$ (113 mg, 162 umol, 0.40 eq), CuI (15 mg, 81.0 umol, 0.20 eq) and DIPEA (419 mg, 3.24 mmol, 8.00 eq) were dissolved in THF (6 mL). The suspension was heated to 50° C. for 16 h. The solvent was removed in vacuo. To the residue was added ethyl acetate (10 mL) and saturated NH$_4$Cl (10 mL). The two phases were separated and the aqueous phase was extracted with ethyl acetate (3×10 mL). The combined organic phases were washed with brine (10 mL), dried with anhydrous Na$_2$SO$_4$, filtered and concentrated. The residue was purified via silica gel column to give i-89 (150 mg, crude) which was used in next step without further purification. $^1$H NMR (400 MHz, CDCl$_3$-d$_6$) δ=7.26 (s, 2H), 5.30-5.22 (m, 2H), 5.03 (br s, 2H), 3.96 (s, 3H), 3.48 (td, J=6.7, 13.3 Hz, 1H), 1.25 (d, J=6.6 Hz, 6H), 0.24 (s, 9H).

General Procedure for Preparation of Compound 29:

To a solution of i-89 (50 mg, 129 umol, 1.00 eq) in MeOH (3 mL) and DCM (3 mL) was added CsF (45 mg, 774 mmol, 6.00 eq). The mixture was stirred at RT for 2 h. Two additional reactions were set up as described above. All three reaction mixtures were combined. To the mixture was added ethyl acetate (5 mL) and saturated NH$_4$Cl (5 mL). The two phases were separated and the aqueous phase was extracted with ethyl acetate (4×5 mL). The combined organic phases were washed with brine (10 mL), dried over anhydrous Na$_2$SO$_4$, filtered and concentrated. The residue was purified via prep-HPLC to give Compound 29 (18.0 mg, 57.0 umol) as a solid. $^1$H NMR (400 MHz, CDCl$_3$-D$_6$) δ=8.10 (s, 1H), 7.21 (s, 1H), 5.24 (br. s., 2H), 4.97 (br. s., 2H), 4.00 (s, 3H), 3.47 (m, 1H), 3.28 (s, 1H), 1.28 (d, J=6.8 Hz, 6H) LCMS: [M+H]$^+$ 316.1

Example 32: Synthesis of Compound 30

Compound 30 was made by the synthetic method outlined in Scheme AI:

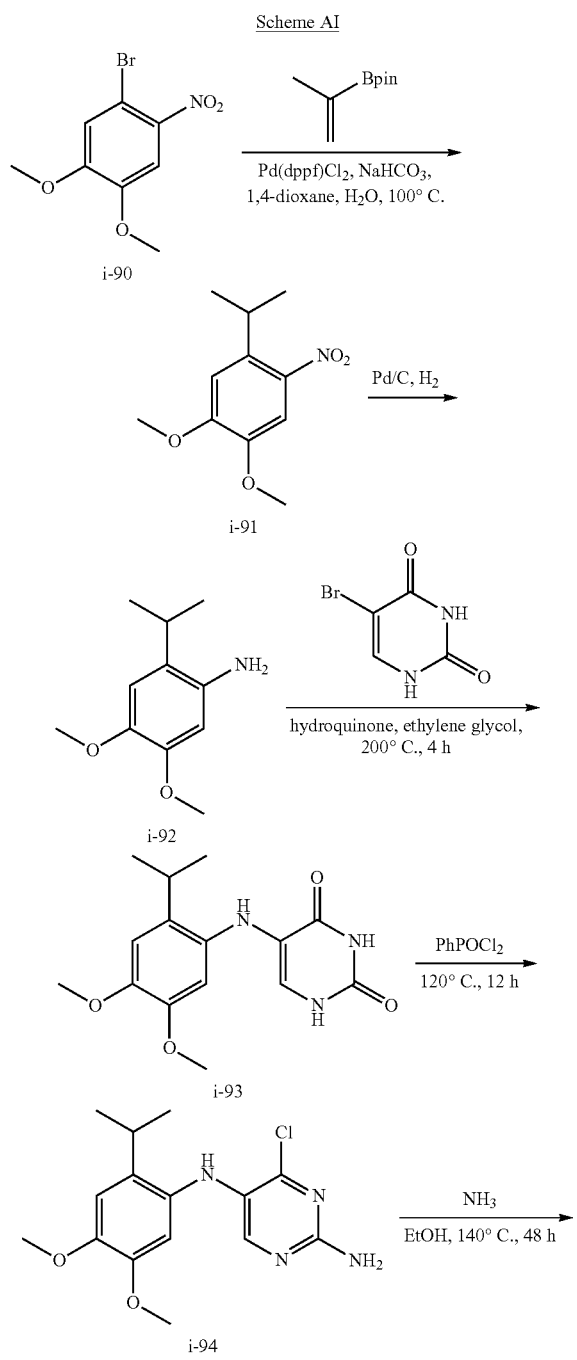

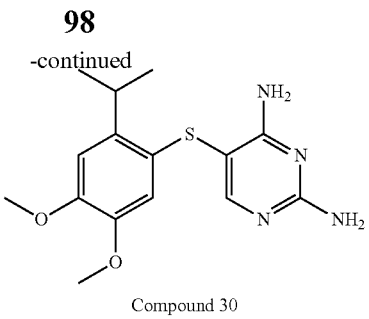

Compound 30

General Procedure for Preparation of Compound i-91:

A solution of i-90 (5.00 g, 19.1 mmol, 1.00 eq), isopropenylboronic acid pinacol ester (3.85 g, 22.9 mmol, 1.20 eq), Pd(dppf)Cl$_2$ (279 mg, 0.381 mmol, 0.02 eq) and NaHCO$_3$ (3.21 g, 38.2 mmol, 1.48 mL, 2.00 eq) in 1,4-dioxane (40.0 mL) and H$_2$O (8.0 mL) was heated at 100° C. for 12 h under Na atmosphere. To the mixture was added ethyl acetate (50 mL) and H$_2$O (20 mL). The two phases were separated and the aqueous phase was extracted with ethyl acetate (2×50 mL). The combined organic phases were dried, filtered and concentrated. The residue was purified via column chromatography on silica gel (eluting with petroleum to petroleum ether:ethyl acetate=5:1) to give i-91 (3.80 g, 17.0 mmol) as an oil. $^1$H NMR (400 MHz, DMSO-d$_6$) δ=7.55 (s, 1H), 6.90 (s, 1H), 5.16-5.08 (m, 1H), 4.90-4.83 (m, 1H), 3.88 (s, 3H), 3.85 (s, 3H), 2.02 (d, J=0.7 Hz, 3H).

General Procedure for Preparation of Compound i-92:

A solution of i-91 (3.80 g, 17.0 mmol, 1.00 eq) and Pd/C (906 mg, 8.51 mmol, 0.50 eq) in MeOH (80.00 mL) was stirred at 20° C. under H$_2$ (50 psi) for 12 h. The mixture was filtered and the solid was washed with MeOH (100 mL). Then the combined filtrates were concentrated to give i-92 (3.00 g, 15.4 mmol) as an oil which was used in the next step without purification. $^1$H NMR (400 MHz, DMSO-d$_6$) δ=6.59 (s, 1H), 6.31 (s, 1H), 4.45 (s, 2H), 3.64 (s, 3H), 3.62 (s, 3H), 2.88 (td, J=6.7, 13.8 Hz, 1H), 1.10 (d, J=6.6 Hz, 6H).

General Procedure for Preparation of Compound i-93:

The mixture of i-92 (1.02 g, 5.22 mmol, 3.50 eq), 5-bromopyrimidine-2,4 (1H,3H)-dione (285 mg, 1.49 mmol, 1.00 eq) and hydroquinone (16.4 mg, 149 umol, 0.10 eq) in ethylene glycol (6.00 mL) was stirred at 200° C. for 4 h and cooled to RT. One additional vial was set up as described above and heated at 200° C. for 4 h and cooled to RT. The two reaction mixtures were combined. To the mixture was added ethyl acetate (30 mL) and H$_2$O (10 mL). The aqueous phase was separated and extracted with ethyl acetate (2×20 mL). The organic phases were combined, dried over anhydrous Na$_2$SO$_4$, filtered and concentrated. The residue was purified via prep-HPLC to give i-93 (500 mg, 1.64 mmol) as a solid. $^1$H NMR (400 MHz, DMSO-d$_6$) δ=11.26 (s, 1H), 10.21 (br d, J=4.4 Hz, 1H), 6.80 (s, 1H), 6.53 (s, 1H), 6.38 (d, J=5.5 Hz, 1H), 5.92 (s, 1H), 3.73 (s, 3H), 3.66 (s, 3H), 3.01 (quin, J=6.8 Hz, 1H), 1.13 (d, J=6.8 Hz, 6H).

General Procedure for Preparation of Compound i-94:

A mixture of i-93 (500 mg, 1.64 mmol, 1.00 eq) in PhPOCl$_2$ (2.76 mL, 19.7 mmol, 12.00 eq) was degassed by sparging with Na for 3 times and then stirred at 120° C. for 12 h under Na atmosphere. The reaction mixture was poured over ice. Then ethyl acetate (30 mL) and H$_2$O (10 mL) were added in. The two phases were separated and the aqueous phase was extracted with ethyl acetate (2×15 mL). The combined organic phases were washed with saturated Na$_2$CO$_3$ (3×10 mL) and dried over anhydrous Na$_2$SO$_4$. Then filtered and concentrated to give i-94 (285 mg, 833 umol) as a solid which was used in the next step directly.

$^1$H NMR (400 MHz, CHLOROFORM-d) δ=7.76 (s, 1H), 6.86 (s, 1H), 6.66 (s, 1H), 5.67 (s, 1H), 3.94 (s, 3H), 3.83 (s, 3H), 3.04 (td, J=6.7, 13.7 Hz, 1H), 1.20 (d, J=7.1 Hz, 6H).

General Procedure for Preparation of Compound 30:

A solution of i-94 (285 mg, 833 umol, 1.00 eq) in NH$_3$/EtOH (20 N, 10 mL) in a sealed tube was placed in an autoclave. The mixture was stirred at 140° C. for 48 h. The mixture was cooled to RT and concentrated. The residue was purified via prep- to give 50 mg of desired product which was further purified via prep-HPLC to give Compound 30 (14.0 mg, 46.2 umol) as a solid. $^1$H NMR (400 MHz, CHLOROFORM-d) δ=7.76 (s, 1H), 6.80 (s, 1H), 6.09 (s, 1H), 4.91 (br s, 2H), 4.76 (s, 2H), 4.66 (s, 1H), 3.85 (s, 3H), 3.72 (s, 3H), 3.04 (spt, J=6.8 Hz, 1H), 1.31 (d, J=6.6 Hz, 6H) LCMS: [M+H]$^+$ 304.1

Example 33: Synthesis of Compound 31

Compound 31 was made by the synthetic method outlined in Scheme AJ:

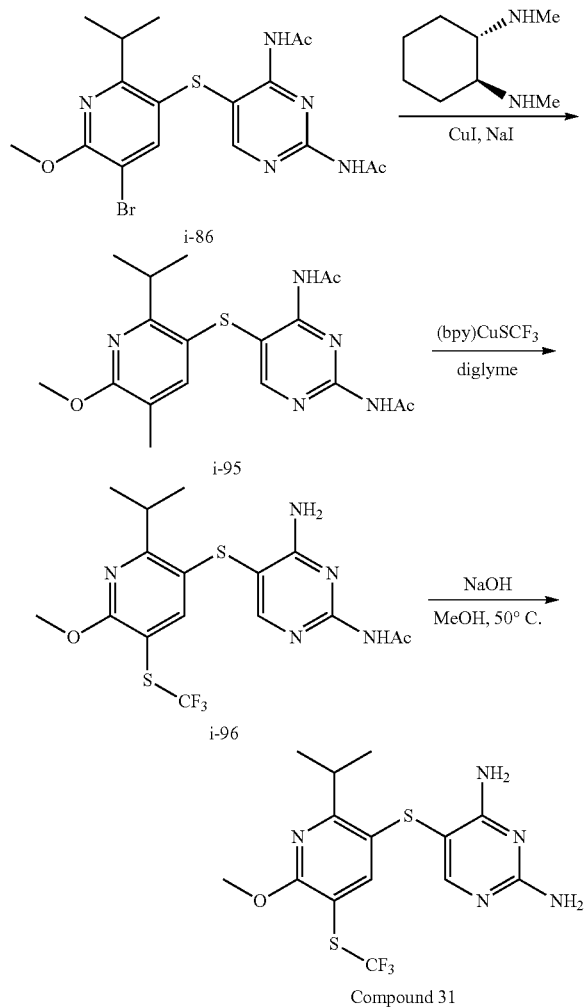

General Procedure for Preparation of Compound i-95:

A solution of i-86 (300 mg, 660 umol, 1.00 eq, prepared as described in Example 26), CuI (6.29 mg, 33.0 umol, 0.05 eq), NaI (198 mg, 1.32 mmol, 2.00 eq) and trans-N,N'-dimethyl-1,2-cyclohexanediamine (9.39 mg, 66.0 umol, 0.10 eq) in 1,4-dioxane (5.00 mL) was stirred at 110° C. for 18 h, and cooled to RT. The reaction mixture was filtered and the solid was washed with ethyl acetate (40 mL). The filtrate was concentrated and the residue was purified via column chromatography on silica gel (eluting with ethyl acetate) to give 360 mg of a solid which was a mixture of desired product, mono-Ac product and starting material. A second reaction was run exactly as described and the crude reaction products were combined to give 710 mg.

The solution of crude reaction mixture (710 mg) in Ac$_2$O (789 mg, 7.73 mmol, 5.00 eq) was stirred at 100° C. for 15 min. The mixture was adjusted to pH=7 with saturated Na$_2$CO$_3$ solution at 0° C. Then to the mixture was added ethyl acetate (20 mL) and H$_2$O (5 mL). The two phases were separated and the aqueous phase was extracted with ethyl acetate (3×15 mL). The combined organic phases were dried over anhydrous Na$_2$SO$_4$, filtered and concentrated. The residue was purified via prep-HPLC to give i-95 (220 mg, 439 umol) as a solid. $^1$H NMR (400 MHz, DMSO-d$_6$) δ=10.59 (s, 1H), 10.42 (s, 1H), 8.35 (s, 1H), 8.08 (s, 1H), 3.89 (s, 3H), 3.50-3.42 (m, 1H), 2.21 (s, 3H), 2.16 (s, 3H), 1.07 (d, J=6.6 Hz, 6H).

General Procedure for Preparation of Compound i-96:

A solution of i-95 (110 mg, 219 umol, 1.00 eq) and (bpy)CuSCF$_3$ (176 mg, 549 umol, 2.50 eq) in diglyme (2.00 mL) was stirred at 130° C. for 16 h and cooled to RT. One additional vial was set up as described above. The two cooled reaction mixtures were combined. To the mixture was added ethyl acetate (20 mL) and H$_2$O (10 mL). The two phases were separated and the aqueous phase was extracted with ethyl acetate (3×15 mL). The combined organic phases were dried over anhydrous Na$_2$SO$_4$ and then filtered and concentrated to give i-96 (180 mg, 415 umol) as a solid which was used in the next step directly.

General Procedure for Preparation of Compound 31:

To the solution of i-96 (180 mg, 415 umol, 1.00 eq) in MeOH (1.60 mL) and H$_2$O (1.60 mL) was added KOH (93.2 mg, 1.66 mmol, 4.00 eq). The solution was stirred at 50° C. for 2 h and cooled to RT. To the mixture was added ethyl acetate (10 mL) and H$_2$O (5 mL). The two phases were separated and the aqueous phase was extracted with ethyl acetate (3×10 mL). The combined organic phases were dried over anhydrous Na$_2$SO$_4$, filtered and concentrated. The residue was purified via prep-TLC (CH$_2$Cl$_2$/MeOH=20/1) to give Compound 31 (90.0 mg, 230 umol) as a solid. $^1$H NMR (400 MHz, CHLOROFORM-d) δ=8.11 (s, 1H), 7.35 (s, 1H), 5.23 (br s, 2H), 4.96 (s, 2H), 4.00 (s, 3H), 3.50 (quin, J=6.7 Hz, 1H), 1.31 (d, J=6.8 Hz, 6H) LCMS: [M+H]$^+$ 392.1

Example 34: Synthesis of Compound 32

Compound i-107 was made by the synthetic method outlined in Scheme AK:

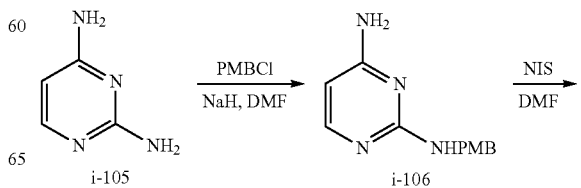

-continued

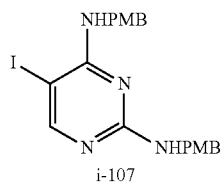
i-107

General Procedure for Preparation of Compound i-106:

To a mixture of i-105 (5 g, 45.4 mmol, 1.00 eq) in DMF (100 mL) was added NaH (5.45 g, 136 mmol, 60% purity, 3.00 eq) in portions at 0° C. The mixture was stirred at 25° C. for 1 h. The mixture was cooled to 0° C. and param-ethoxybenzyl chloride (17.8 g, 113 mmol, 2.50 eq) was added into the mixture at 0° C. The mixture was stirred for 13 h at 0° C. The mixture was poured into ice water (500 mL) and the mixture was extracted with ethyl acetate (3×500 mL). The combined organic phases were washed with brine (400 mL), dried over anhydrous Na$_2$SO$_4$, filtered and concentrated in vacuum. The residue was purified via column chromatography on silica gel to give i-106 (10.5 g, 30 mmol) as an oil. $^1$H NMR (400 MHz, Chloroform-d) δ=7.55 (d, J=8.0 Hz, 1H), 7.17 (d, J=8.0 Hz, 2H), 7.07-6.99 (d, J=7.6 Hz, 2H), 6.89 (d, J=8.0 Hz, 4H), 6.08 (d, J=7.6 Hz, 1H), 4.88 (s, 2H), 4.50 (s, 2H), 3.82 (s, 6H).

General Procedure for Preparation of Compound i-107:

To a mixture of i-106 (10.5 g, 30.0 mmol, 1.00 eq) in DMF (100 mL) was added N-iodosuccinimide (6.74 g, 30.0 mmol, 1.00 eq) in portions. The reaction mixture was stirred at 25° C. for 14 h. LCMS showed main peak was the desired product. The reaction mixture was poured into ice-H$_2$O (500 mL). The aqueous phase was extracted with ethyl acetate (3×500 mL). The combined organic phases were dried over anhydrous Na$_2$SO$_4$, filtered and concentrated in vacuum. The residue was purified by pre-HPLC to give i-107 (2.2 g, 4.62 mmol) as an oil which solidified gradually. $^1$H NMR (400 MHz, Chloroform-d) δ=8.31 (s, 1H), 7.14 (d, J=8.8 Hz, 4H), 6.86 (d, J=9.2 Hz, 4H), 4.78 (s, 2H), 4.63 (s, 4H), 3.81 (s, 6H).

Compound 32 was made by the synthetic method outlined in Scheme AL:

Scheme AL

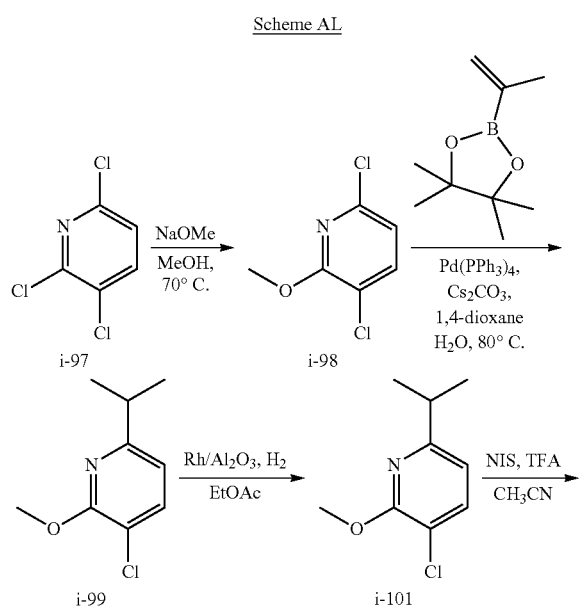

-continued

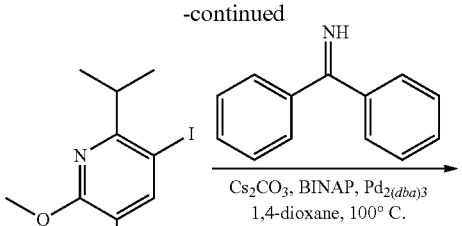
i-101

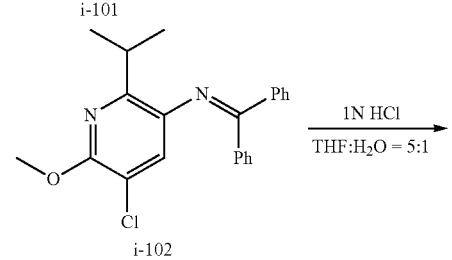
i-102

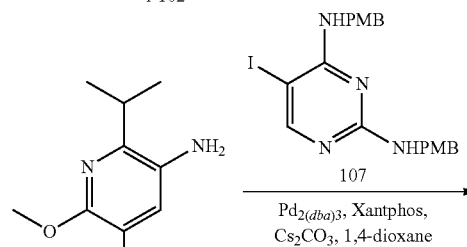
i-103

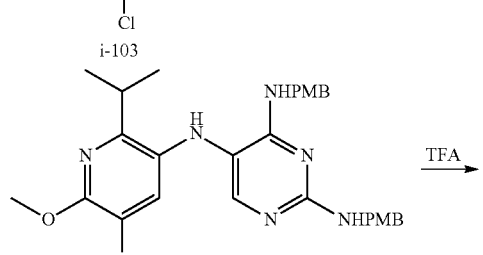
i-104

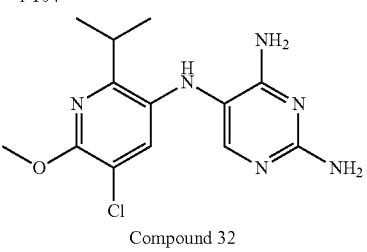
Compound 32

General Procedure for Preparation of Compound i-98:

To the solution of i-97 (30.0 g, 164 mmol, 1.00 eq) in MeOH (300 mL) was added MeONa (10.9 g, 279 mmol, 1.70 eq). The mixture was stirred at 70° C. for 12 h. The mixture was concentrated. Then to the residue was added ethyl acetate (300 mL) and water (100 mL). The two phases were separated and the aqueous phase was extracted with ethyl acetate (2×100 mL). The combined organic phases were dried over anhydrous Na$_2$SO$_4$, filtered and concentrated. The residue was purified via column chromatography on silica to give i-98 (22.7 g, 127 mmol) as a solid which was used in the next step directly. $^1$H NMR (400 MHz, CHLOROFORM-d) δ=7.57 (d, J=7.9 Hz, 1H), 6.88 (d, J=7.9 Hz, 1H), 4.04 (s, 3H).

General Procedure for Preparation of Compound i-99:

To a solution of i-98 (23.0 g, 129 mmol, 1.00 eq) in 1,4-dioxane (500 mL) and H$_2$O (200 mL) was added 2-isopropenyl-4,4,5,5-tetramethyl-1,3,2-dioxaborolane (22.8 g, 135 mmol, 1.05 eq), Cs$_2$CO$_3$ (84.2 g, 258 mmol, 2.00 eq) and Pd(PPh$_3$)$_4$ (14.9 g, 12.9 mmol, 0.10 eq). The mixture was stirred at 80° C. under N$_2$ for 15 h. The mixture was filtered and the solid was washed with petroleum ether (100 mL). The filtrate was separated and the organic phase was extracted with petroleum ether (2×150 mL). The combined organic phases were dried over anhydrous Na$_2$SO$_4$, filtered and concentrated. The residue was purified via column chromatography on silica gel to give i-99 (14.0 g, 75.8 mmol) as a liquid. $^1$H NMR (400 MHz, CHLOROFORM-d) δ=7.58 (d, J=7.9 Hz, 1H), 7.00 (d, J=7.9 Hz, 1H), 5.97 (dd, J=0.8, 1.9 Hz, 1H), 5.27 (quin, J=1.6 Hz, 1H), 4.07-4.03 (m, 3H), 2.18-2.16 (m, 3H).

General Procedure for Preparation of Compound i-100:

To the solution of i-99 (14.0 g, 76.2 mmol, 1.00 eq) in EtOAc (500 mL) was added rhodium on Al$_2$O$_3$ (6.51 g, 63.2 mmol, 0.83 eq). The mixture was stirred at 25° C. under H$_2$ balloon for 5 h. The mixture was filtered and the solid was washed with ethyl acetate (100 mL). Then the filtrate was concentrated to give i-100 (13.1 g, 70.5 mmol) as a liquid.
$^1$H NMR (400 MHz, CHLOROFORM-d) δ=7.51 (d, J=7.7 Hz, 1H), 6.69 (d, J=7.9 Hz, 1H), 4.02 (s, 2H), 4.04-4.01 (m, 1H), 2.94 (spt, J=6.8 Hz, 1H), 1.27 (d, J=6.8 Hz, 6H).

General Procedure for Preparation of Compound i-101:

To the solution of i-100 (5.00 g, 26.9 mmol, 1.00 eq) in CH$_3$CN (50.0 mL) was added NIS (18.2 g, 80.8 mmol, 3.00 eq) and TFA (2 mL, 26.9 mmol, 1.00 eq). The mixture was stirred at 25° C. for 15 h then at 80° C. for 2 h. The mixture was filtered and the filtrate was adjust to pH=8 with saturated NaHCO$_3$ solution. The mixture was partitioned between ethyl acetate (60 mL) and water (30 mL). Then the aqueous layer was extracted with ethyl acetate (2×30 mL). The combined organic layers were washed with saturated Na$_2$SO$_3$ solution (2×30 mL) and dried over Na$_2$SO$_4$, filtered and concentrated. To the residue was added petroleum ether (60 mL). The mixture was stirred at 25° C. for 5 min and white solid was generated. Then the solid was filtered off and the filtrate was concentrated to give i-101 (6.70 g, 21.5 mmol) as a liquid. $^1$H NMR (400 MHz, CHLOROFORM-d) δ=7.91 (s, 1H), 4.01 (s, 3H), 3.34 (spt, J=6.7 Hz, 1H), 1.22 (d, J=6.6 Hz, 6H).

General Procedure for Preparation of Compound i-102:

To the solution of i-101 (920 mg, 2.95 mmol, 1.00 eq) in 1,4-dioxane (16.0 mL) was added diphenylmethanimine (427 mg, 2.36 mmol, 0.80 eq), Cs$_2$CO$_3$ (2.41 g, 7.38 mmol, 2.50 eq), BINAP (368 mg, 590 umol, 0.20 eq) and Pd$_2$(dba)$_3$ (270 mg, 295 umol, 0.10 eq). The mixture was stirred at 100° C. under N$_2$ for 15 h. The reaction mixture was filtered and the filter cake was washed with ethyl acetate (50 mL). To the filtrate was added water (20 mL). The two phases were separated and the aqueous phase was extracted with ethyl acetate (2×20 mL). The combined organic phases were dried over anhydrous Na$_2$SO$_4$, filtered and concentrated. The residue was purified by column chromatography on silica gel to give i-102 (600 mg, 1.64 mmol) as a liquid. $^1$H NMR (400 MHz, CHLOROFORM-d) δ=7.80-7.75 (m, 2H), 7.52-7.47 (m, 1H), 7.45-7.40 (m, 2H), 7.37-7.32 (m, 3H), 7.13-7.08 (m, 2H), 6.67 (s, 1H), 3.97 (s, 3H), 3.30 (quin, J=6.8 Hz, 1H), 1.19 (d, J=6.8 Hz, 6H).

General Procedure for Preparation of Compound i-103:

To a solution of i-102 (600 mg, 1.64 mmol, 1.00 eq) in THF (6.00 mL) and H$_2$O (1.50 mL) was added HCl (1 M, 3.28 mL, 2.00 eq). The mixture was stirred at 25° C. for 2 h. The mixture was adjusted to pH=8 with saturated Na$_2$CO$_3$ solution. To the mixture was added ethyl acetate (5 mL) and H$_2$O (3 mL). The two phases were separated and the aqueous layer was extracted with ethyl acetate (3×10 mL). The combined organic layers were combined, dried over Na$_2$SO$_4$ and concentrated. The residue was purified via column chromatography on silica gel (eluting with petroleum ether:ethyl acetate=100:1 to 50:1) to give i-103 (300 mg, 1.50 mmol) as a liquid. $^1$H NMR (400 MHz, CHLOROFORM-d) δ=7.03 (s, 1H), 3.96 (s, 3H), 3.32 (brs, 2H), 2.95 (spt, J=6.7 Hz, 1H), 1.25 (d, J=6.8 Hz, 6H).

General Procedure for Preparation of Compound i-104:

To a solution of i-103 (250 mg, 1.25 mmol, 1.00 eq) in 1,4-dioxane (5.00 mL) was added i-107 (357 mg, 750 umol, 0.60 eq), Cs$_2$CO$_3$ (1.02 g, 3.13 mmol, 2.50 eq), Xantphos (145 mg, 250 umol, 0.20 eq) and Pd$_2$(dba)$_3$ (114 mg, 125 umol, 0.10 eq). The mixture was stirred at 100° C. under N$_2$ for 15 h. The reaction mixture was filtered and the filter cake was washed with ethyl acetate (20 mL). To the mixture was added water (6 mL). Then the two phases were separated and the aqueous phase was extracted with ethyl acetate (3×10 mL). The combined organic phases were dried over anhydrous Na$_2$SO$_4$, filtered and concentrated. The residue was purified via prep-TLC (petroleum ether:ethyl acetate=1:1) to give i-104 (170 mg, 309 umol) as a solid. $^1$H NMR (400 MHz, CHLOROFORM-d) δ=7.66 (s, 1H), 7.06 (d, J=8.6 Hz, 4H), 6.85 (d, J=8.6 Hz, 4H), 6.77 (s, 1H), 4.82 (s, 2H), 4.67 (s, 4H), 4.49 (s, 1H), 3.94 (s, 3H), 3.80 (s, 6H), 2.52 (quin, J=6.7 Hz, 1H), 1.09 (d, J=6.6 Hz, 6H).

General Procedure for Preparation of Compound 32:

Batch 1: A solution of i-104 (50.0 mg, 91.0 umol, 1.00 eq) in TFA (0.50 mL) was stirred at 80° C. under N$_2$ for 4 h.

Batch 2: A solution of i-104 (150 mg, 273 umol, 1.00 eq) in TFA (1.50 mL) was stirred at 80° C. under N$_2$ for 4 h.

The above two reaction mixtures were combined. The mixture was adjust to pH=8 with saturated Na$_2$CO$_3$ solution at 0° C. To the mixture was added ethyl acetate (15 mL) and water (5 mL). Then the two phases were separated and the aqueous phase was extracted with ethyl acetate (3×10 mL). The combined organic phases were dried over anhydrous Na$_2$SO$_4$, filtered and concentrated. The residue was purified via prep-TLC to give Compound 32 (48.0 mg, 153 umol) as a solid. $^1$H NMR (400 MHz, DMSO-d$_6$) δ=7.48 (s, 1H), 6.54 (s, 1H), 6.35 (s, 1H), 6.07 (br s, 2H), 5.86 (s, 2H), 3.84 (s, 3H), 3.29 (br d, J=6.6 Hz, 1H), 1.21 (br d, J=6.4 Hz, 6H) LCMS: [M+H]$^+$309.1

Example 35: Synthesis of Compound 33

Compound 33 was made by the synthetic method outlined in Scheme AM:

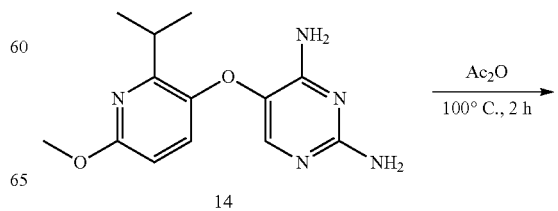

-continued

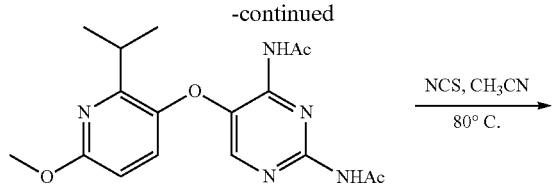

i-108

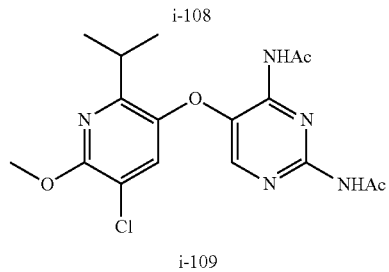

i-109

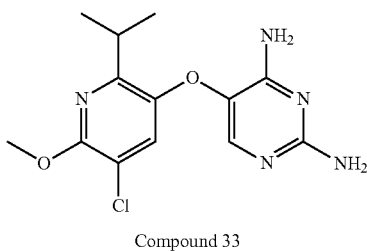

Compound 33

General Procedure for Preparation of Compound i-108:
Compound 14 was prepared as described in Example 16. A mixture of Compound 14 (2.00 g, 7.26 mmol, 1.00 eq) and Ac$_2$O (14.8 g, 145 mmol, 20.0 eq) was stirred at 100° C. for 2 h. To the reaction mixture was added saturated aqueous Na$_2$CO$_3$ to adjust pH to 7. The aqueous layer was extracted with ethyl acetate (3×10 mL). The organic layers were combined, dried over Na$_2$SO$_4$ and concentrated. The residue was purified by prep-HPLC to give i-108 (1.30 g, 3.62 mmol) as a solid. $^1$H NMR (400 MHz, CHLOROFORM-d) δ=8.17 (br s, 1H), 7.90 (br s, 1H), 7.65 (s, 1H), 7.17 (d, J=8.6 Hz, 1H), 6.60 (d, J=8.8 Hz, 1H), 3.96 (s, 3H), 3.15 (td, J=6.8, 13.7 Hz, 1H), 2.67 (s, 3H), 2.40 (s, 3H), 1.24 (d, J=6.8 Hz, 6H).

General Procedure for Preparation of Compound i-109:
To a solution of i-108 (100 mg, 278 umol, 1.00 eq) in CH$_3$CN (1.00 mL) was added NCS (74.3 mg, 557 umol, 2.00 eq). The mixture was stirred at 80° C. for 5 h. The mixture was partitioned between ethyl acetate (5 mL) and water (10 mL). Then the aqueous layer was extracted with ethyl acetate (3×8 mL). The combined organic layers were dried over Na$_2$SO$_4$, filtered and concentrated under reduced pressure. The residue was purified by prep-TLC (petroleum ether:ethyl acetate=1:1) to give i-109 (30.0 mg, 76.1 umol) as a solid. LCMS: [M+H]$^+$ 352.1

General Procedure for Preparation of Compound 33:
To a solution of i-109 (100 mg, 284 umol, 1.00 eq) in MeOH (500 uL) and H$_2$O (500 uL) was added KOH (95.7 mg, 1.71 mmol, 6.00 eq). The mixture was stirred at 50° C. for 2 h. The mixture was partitioned between EtOAc (3 mL) and water (5 mL). Then the aqueous layer was extracted with EtOAc (3×3 mL). The combined organic layers were dried over Na$_2$SO$_4$, filtered and concentrated under reduced pressure. The residue was purified by prep-HPLC to give Compound 33 (5.00 mg, 16.14 umol) as a solid. $^1$H NMR (400 MHz, DMSO-d$_6$) δ=7.35 (s, 1H), 7.09 (s, 1H), 6.42 (br s, 2H), 5.83 (s, 2H), 3.88 (s, 3H), 3.60 (br s, 1H), 1.18 (d, J=6.8 Hz, 6H) LCMS: [M+H]$^+$310.1

Example 36: Synthesis of Compound 34

Compound 34 was made by the synthetic method outlined in Scheme AN:

Scheme AN

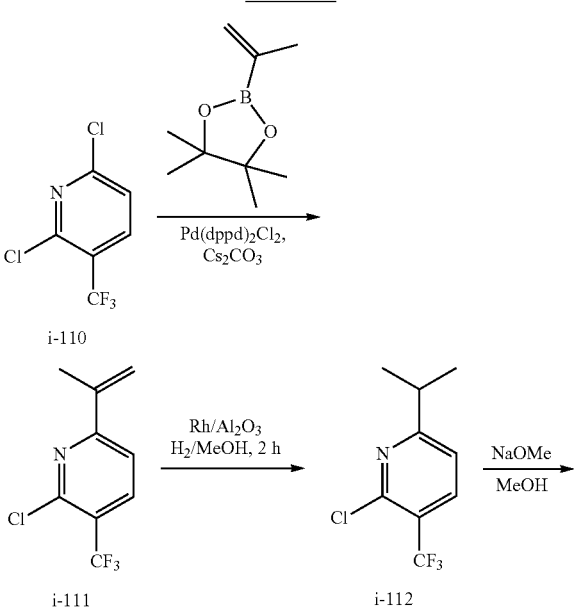

i-110 i-111         i-112

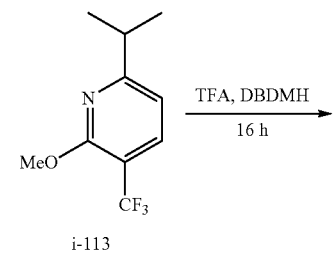

i-113

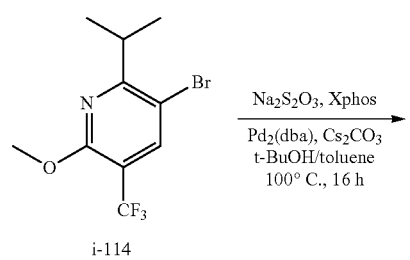

i-114

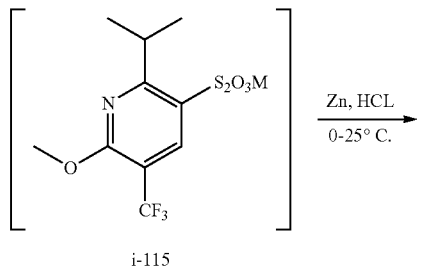

i-115

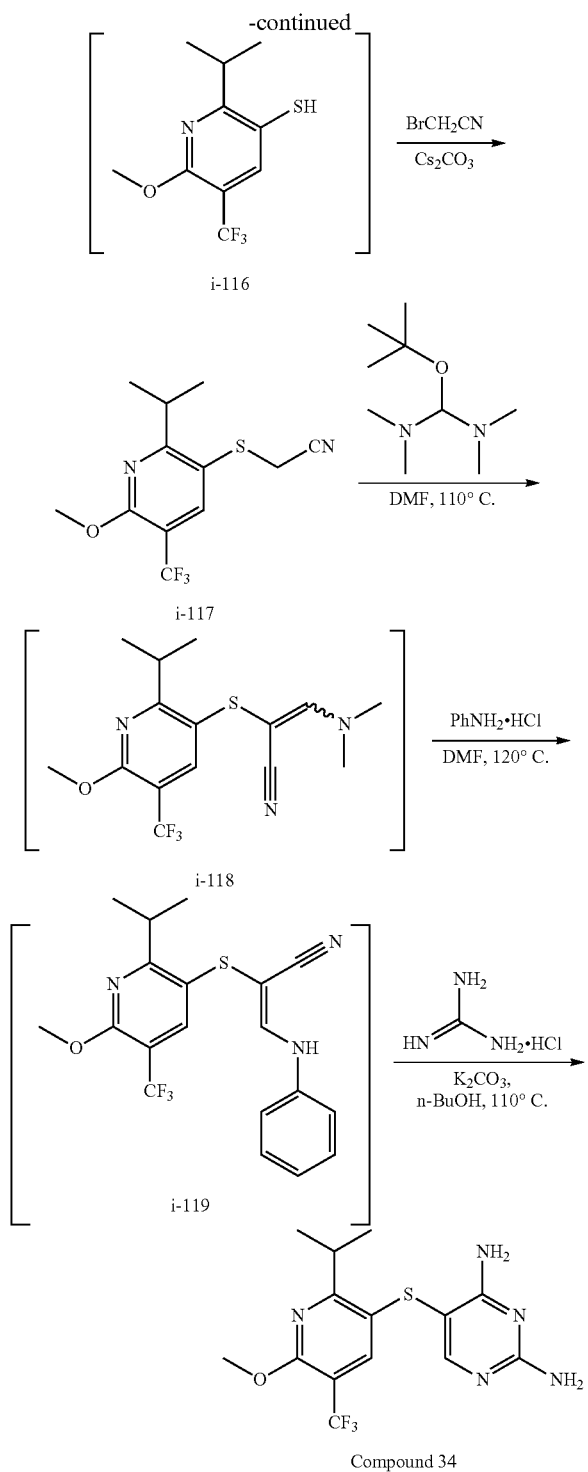

vacuum. To the mixture was added ice water (250 mL) and ethyl acetate (250 mL). The two phases were separated and the aqueous phase was extracted with ethyl acetate (3×100 mL). The combined organic phase was dried with anhydrous $Na_2SO_4$, filtered and concentrated. The residue was purified via column chromatography on silica gel to give i-111 (20 g) as an oil. $^1$H NMR (400 MHz, $CDCl_3$-$D_6$) δ=7.96 (d, J=8.0 Hz, 1H), 7.48 (d, J=8.0 Hz, 1H), 6.06 (s, 1H), 5.47 (s, 1H), 2.12 (s, 3H).

General Procedure for Preparation of Compound i-112:

Compound i-111 (4.0 g, 18 mmol, 1.00 eq) was dissolved in THF (40 mL). $Rh/Al_2O_3$ (1.3 g, 12.8 mmol, 0.71 eq) was added into the solution. The reaction mixture was stirred under $H_2$ balloon at 25° C. for 1 h. Four additional reactions were set up as described above. All five reaction mixtures were combined. The mixture was filtered through a celite pad and the filtrate was concentrated. The residue was purified by column chromatography on silica gel to give i-112 (18 g, 74% yield) as an oil. LCMS: [M+H]$^+$ 223.9

General Procedure for Preparation of Compound i-113:

Compound i-112 (18.0 g, 80.5 mmol, 1.00 eq) and NaOMe (17.4 g, 321 mmol, 4.00 eq) were dissolved in MeOH (200 mL). The suspension was heated to 80° C. for 16 h. The reaction was cooled to RT. To the mixture was added ice water (200 mL) and ethyl acetate (200 mL). The two phases were separated and the aqueous phase was extracted with ethyl acetate (3×100 mL). The combined organic phases were dried with anhydrous $Na_2SO_4$, filtered and concentrated. The residue was purified by column chromatography on silica gel to give i-113 (16.0 g). $^1$H NMR (400 MHz, DMSO-$D_6$) δ=7.94 (d, J=8.0 Hz, 1H), 6.99 (d, J=7.6 Hz, 1H), 3.95 (s, 3H), 3.02-2.95 (m, 1H), 1.23 (d, J=6.8 Hz, 6H).

General Procedure for Preparation of Compound i-114:

Compound i-113 (4 g, 18.3 umol, 1.00 eq) and 1, 3-dibromo-5,5-dimethyl-imidazolidine-2,4-dione (5.5 g, 19.2 mmol, 1.05 eq) were dissolved in TFA (60 mL). The solution was stirred at 25° C. for 16 h. Saturated $NaHCO_3$ was added into the reaction solution at 0° C. to adjust pH=7-8. The aqueous phase was extracted with ethyl acetate (3×25 mL). The combined organic phase was washed with brine (2×25 mL), dried with anhydrous $Na_2SO_4$, filtered and concentrated. The residue was purified by column chromatography on silica gel to give i-114 (3 g) as qn oil. $^1$H NMR (400 MHz, $CDCl_3$-$D_6$) δ=7.89 (s, 1H), 4.03 (s, 3H), 3.51-3.44 (m, 1H), 1.25 (d, J=8.8 Hz, 6H).

General Procedure for Preparation of Compound i-117:

Compound i-114 (0.75 g, 2.52 mmol, 1.00 eq), XPhos (0.12 g, 0.25 mmol, 0.10 eq), $Pd_2(dba)_3$ (0.23 g, 0.250 mmol, 0.10 eq), $Cs_2CO_3$ (1.64 g, 5.04 mmol, 2.00 eq) and $Na_2S_2O_3 \cdot 5H_2O$ (1.25 g, 5.04 mmol, 2.00 eq) were dissolved in t-BuOH (4 mL) and toluene (4 mL). The solution was heated to 80° C. for 16 h and cooled to RT. One additional reaction was set up as described above, and cooled to RT after 16 h. The two reaction mixtures were combined. The reaction mixture was concentrated to dryness to give a residue which was crushed in MTBE (30 mL). The mixture was filtered and the filter cake was washed with MTBE (30 mL). The combined dried filter cake (2 g, crude i-115) was used in next step without purification as brown solid.

Compound i-115 (2.0 g, crude) was dissolved in HCl (4 M, 13 mL, 10.3 eq). The solution was cooled to 0° C. Zn (4.0 g, 60.4 mmol, 12 eq) was added into the solution at 0° C. The solution was warmed to 25° C. and stirred for 2 h. The mixture was filtered and the filtration was added into saturated $NaHCO_3$ to adjust pH to 7-8. The reaction solution was General Procedure for Preparation of Compound i-111:

Compound i-110 (23 g, 106 mmol, 1.00 eq), Pd(dppf)$Cl_2 \cdot CH_2Cl_2$ (8.7 g, 10.7 mmol, 0.10 eq), 2-isopropenyl-4,4,5,5-tetramethyl-1,3,2-dioxaborolane (17.9 g, 106 mmol, 1.00 eq) and $Cs_2CO_3$ (104 g, 319 mmol, 3.00 eq) were dissolved in $H_2O$ (80 mL) and dioxane (250 mL). The solution was heated to 100° C. for 16 h. One additional reaction was set up and identically as described above and heated to 100° C. for 16 h. The two reaction mixtures were cooled to RT and combined. The solvent was removed under extracted with DCM (3×10 mL) to give a solution of crude i-116. The extracted solution was dried and used directly in next step.

To the extracted solution of i-116 in DCM (30 mL) was added DIEA (1.5 g, 11.9 mmol, 1.50 eq) and BrCH₂CN (1.4 g, 11.9 mmol, 1.50 eq). The solution was heated to 50° C. for 16 h and cooled to RT. The reaction mixture was concentrated to give a residue which was purified by column chromatography on silica gel to give i-117 (0.13 g) as an oil. ¹H NMR (400 MHz, CDCl₃-D₆) δ=8.04 (s, 1H), 4.08 (s, 3H), 3.82-3.80 (m, 1H), 3.46 (s, 2H), 1.29 (d, J=6.4 Hz, 6H).

General Procedure for Preparation of Compound 34:

Compound i-117 (120 mg, 413 umol, 1.00 eq) and 1-tert-butoxy-N,N,N',N'-tetramethyl-methane diamine (144 mg, 826 umol, 2.00 eq) were dissolved in DMF (3 mL). The solution was heated to 110° C. for 4 h and cooled to RT. To the mixture was added ethyl acetate (10 mL) and water (10 mL). The two phases were separated and the aqueous phase was extracted with ethyl acetate (3×10 mL). The organic phases were combined and washed with brine (10 mL), dried over anhydrous Na₂SO₄, filtered and concentrated to give i-118 (130 mg, crude) which was used in next step without purification. LCMS: [M+H]⁺ 346.2

Crude i-118 (130 mg, 332 umol, 1.00 eq) and aniline (86 mg, 665 umol, 2.00 eq, HCl) were dissolved in DMF (3 mL). The solution was heated to 120° C. for 45 min and cooled to RT. To the mixture was added ethyl acetate (20 mL) and water (10 mL). The two phases were separated and the aqueous phase was extracted with ethyl acetate (3×10 mL). The organic phases were combined and washed with brine (20 mL), dried over anhydrous Na₂SO₄, filtered and concentrated to give i-119 (130 mg, crude) which was used in next step without purification.

Crude i-119 (130 mg, 330 umol, 1.00 eq) and guanidine hydrochloride (126 mg, 1.32 mmol, 4.00 eq) were dissolved in n-BuOH (3 mL). K₂CO₃ (182 mg, 1.32 mmol, 4.00 eq) was added into the above solution. The suspension was heated to 110° C. for 16 h and cooled to RT. The mixture solution was concentrated. The residue was purified by reverse phase prep-HPLC. MeCN was removed under reduced pressure and then water was removed by lyophillization to give Compound 34 (14 mg, 118 umol) as a solid.

¹H NMR (400 MHz, CDCl₃-D₆) δ=8.11 (s, 1H), 7.33 (s, 1H), 5.24 (br. m., 2H), 4.97 (br. m., 2H), 4.02 (s, 3H), 3.58-3.52 (m, 1H), 1.30 (d, J=6.8 Hz, 6H) LCMS: [M+H]⁺ 360.0

Example 37: Synthesis of Compound 35

Compound 35 was made by the synthetic method outlined in Scheme AO:

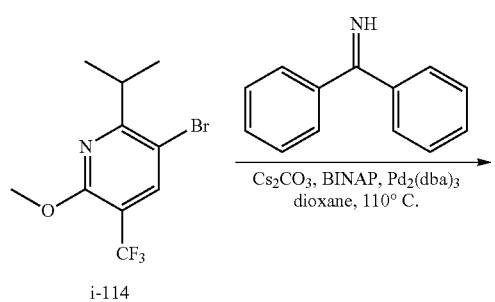

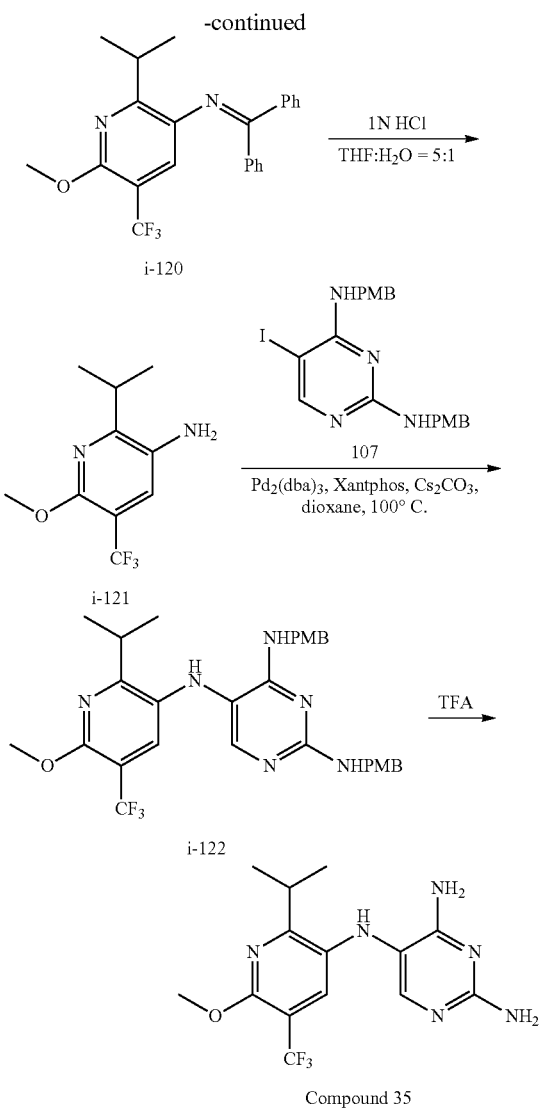

General Procedure for Preparation of Compound i-120:

To a solution of i-114 (1.00 g, 3.35 mmol, 1.00 eq, prepared as described in Example 36) in dioxane (10.0 mL) was added Cs₂CO₃ (2.73 g, 8.38 mmol, 2.50 eq), BINAP (209 mg, 335 umol, 0.10 eq) and Pd₂(dba)₃ (307 mg, 335 umol, 0.10 eq) under N₂. Then diphenylmethanimine (911 mg, 5.03 mmol, 1.50 eq) was added in. The mixture was stirred at 110° C. for 22 h and cooled to RT. Water (25 mL) was added into the mixture. The aqueous phase was extracted with ethyl acetate (4×8 mL). The combined organic phases were dried over anhydrous Na₂SO₄, filtered and concentrated in vacuum to give brown oil. The residue was purified by prep-TLC to give i-120 (800 mg, 2.01 mmol) as an oil. ¹H NMR (400 MHz, Chloroform-d) δ=7.80 (d, J=7.3 Hz, 2H), 7.53-7.47 (m, 1H), 7.46-7.40 (m, 2H), 7.36-7.31 (m, 3H), 7.13-7.06 (m, 2H), 6.85 (s, 1H), 3.99 (s, 3H), 3.40 (spt, J=6.8 Hz, 1H), 1.22 (d, J=6.8 Hz, 6H).

General Procedure for Preparation of Compound i-121:

To a solution of i-120 (800 mg, 2.01 mmol, 1.00 eq) in THF (8.00 mL) and H₂O (1.50 mL) was added HCl (1 mol/L, 4.02 mL, 2.00 eq) slowly at 25° C. The mixture was stirred at 25° C. for 2.5 h. Water (33 mL) was added into the mixture. The aqueous phase was extracted with ethyl acetate (4×25 mL). The combined organic phases were washed with saturated NaHCO$_3$ (40 mL) and dried over anhydrous Na$_2$SO$_4$, filtered and concentrated in vacuum to give an oil. The residue was purified by prep-TLC to give i-121 (390 mg, 1.67 mmol) as a solid. $^1$H NMR (400 MHz, DMSO-d$_6$) δ=7.31 (s, 1H), 4.94 (s, 2H), 3.84 (s, 3H), 3.15 (td, J=6.7, 13.5 Hz, 1H), 1.16 (d, J=6.6 Hz, 6H).

General Procedure for Preparation of Compound i-122:

To a mixture of i-121 (195 mg, 832 umol, 1.00 eq) and i-107 (238 mg, 499 umol, 0.60 eq, prepared as described in example 34) in dioxane (4.00 mL) was added Cs$_2$CO$_3$ (678 mg, 2.08 mmol, 2.50 eq), Xantphos (96.3 mg, 166 umol, 0.20 eq) and Pd$_2$(dba)$_3$ (76.2 mg, 83.2 umol, 0.10 eq) under Na. The mixture was stirred at 100° C. for 12 h and cooled to RT. Water (15 mL) was added. The aqueous phase was extracted with ethyl acetate (4×25 mL). The combined organic phases were dried over anhydrous Na$_2$SO$_4$, filtered and concentrated in vacuum to give a solid. The mixture was purified by prep-TLC to give i-122 (140 mg, 240 umol) as a solid.

$^1$H NMR (400 MHz, Chloroform-d) δ=7.65 (s, 1H), 7.04 (d, J=8.4 Hz, 4H), 6.91 (s, 1H), 6.84 (d, J=8.4 Hz, 4H), 4.85 (s, 2H), 4.68 (s, 4H), 4.55 (s, 1H), 3.95 (s, 3H), 3.80 (s, 6H), 2.60 (td, J=6.9, 13.4 Hz, 1H), 1.11 (d, J=6.6 Hz, 6H).

General Procedure for Preparation of Compound 35:

A mixture of i-122 (140 mg, 240 umol, 1.00 eq) in TFA (1.80 mL) was stirred at 80° C. for 3 h and cooled to RT. Ice-H$_2$O (5 mL) was added in. The pH was adjusted to around 8 by progressively adding saturated Na$_2$CO$_3$ below 10° C. The aqueous phase was extracted with ethyl acetate (4×20 mL). The combined organic phases were dried over anhydrous Na$_2$SO$_4$, filtered and concentrated in vacuum to give a solid. The residue was purified by prep-TLC two times to give Compound 35 (51.7 mg, 151 umol) as a solid. $^1$H NMR (400 MHz, Chloroform-d) δ=7.74 (s, 1H), 6.95 (s, 1H), 4.90 (br s, 2H), 4.81 (br s, 2H), 4.62 (s, 1H), 3.99 (s, 3H), 3.15 (td, J=6.8, 13.3 Hz, 1H), 1.34 (d, J=6.6 Hz, 6H) LCMS: [M+H]$^+$ 343.2

Example 38: Synthesis of Compound 36

Compound 36 was made by the synthetic method outlined in Scheme AP:

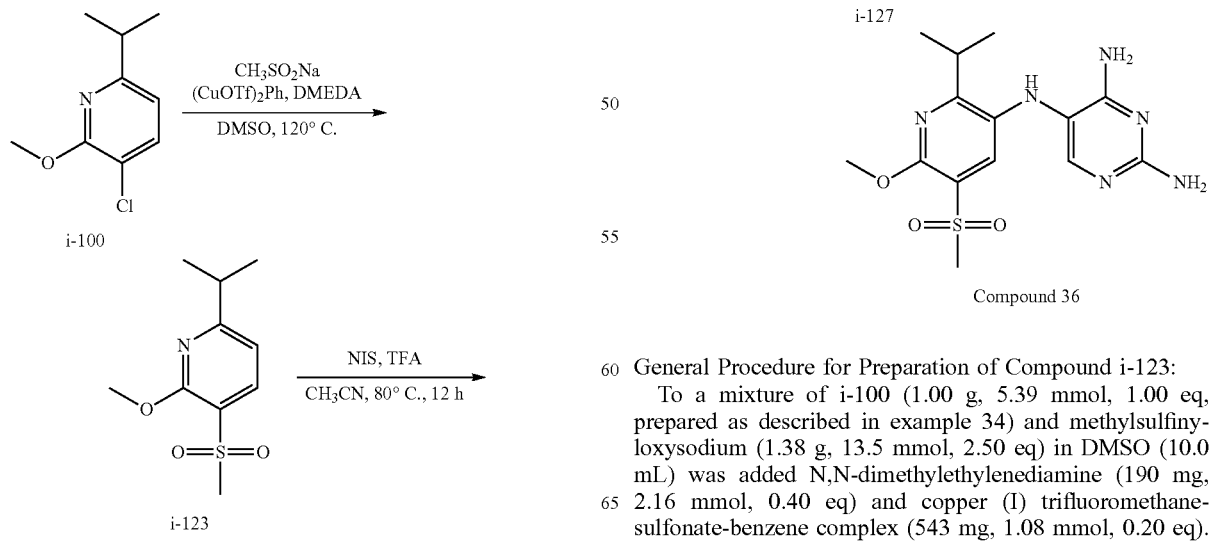

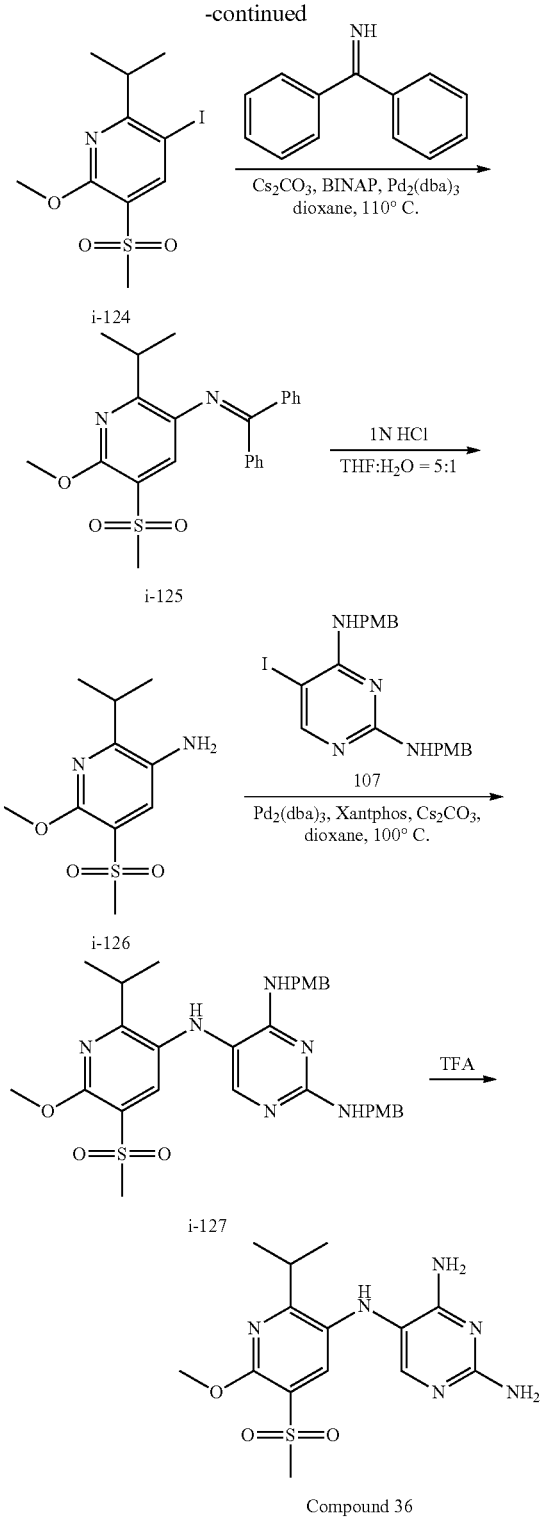

General Procedure for Preparation of Compound i-123:

To a mixture of i-100 (1.00 g, 5.39 mmol, 1.00 eq, prepared as described in example 34) and methylsulfinyloxysodium (1.38 g, 13.5 mmol, 2.50 eq) in DMSO (10.0 mL) was added N,N-dimethylethylenediamine (190 mg, 2.16 mmol, 0.40 eq) and copper (I) trifluoromethanesulfonate-benzene complex (543 mg, 1.08 mmol, 0.20 eq). The resulting reaction mixture was stirred at 120° C. under N$_2$ for 54 h. The reaction mixture was cooled to RT, filtered through a pad of celite and washed with ethyl acetate (50 mL). The filtrate was concentrated and then diluted with ethyl acetate (50 mL) and water (50 mL). The two layers were separated and the aqueous layer was extracted with ethyl acetate (2×50 mL). The combined organic layers were washed with brine (10 mL), dried over Na$_2$SO$_4$, filtered and concentrated under reduced pressure. The residue was purified by prep TLC to give i-123 (240 mg, 1.05 mmol) as an oil. $^1$H NMR (400 MHz, Chloroform-d) δ=8.14 (d, J=7.9 Hz, 1H), 6.91 (d, J=7.7 Hz, 1H), 4.13 (s, 3H), 3.22 (s, 3H), 3.03 (td, J=6.8, 13.7 Hz, 1H), 1.30 (d, J=7.1 Hz, 6H).

General Procedure for Preparation of Compound i-124:

To a solution of i-123 (200 mg, 872 umol, 1.00 eq) in CH$_3$CN (2.00 mL) was added NIS (588 mg, 2.62 mmol, 3.00 eq) and TFA (99.4 mg, 872 umol, 1.00 eq). The mixture was stirred at 80° C. for 15 h. NIS (98.1 mg, 436 umol, 0.50 eq) and TFA (19.9 mg, 174 umol, 0.20 eq) was added in. The mixture was stirred at 80° C. for and additional 16 h and cooled to RT. Saturated Na$_2$SO$_3$ (20 mL) was added in. The aqueous phase was extracted with ethyl acetate (4×20 mL). The combined organic phases were washed with saturated NaHCO$_3$ (40 mL). The organic phase was dried over anhydrous Na$_2$SO$_4$, filtered and concentrated in vacuum. The residue was purified by prep-TLC to give i-124 (270 mg, 760 umol) as a solid. $^1$H NMR (400 MHz, Chloroform-d) δ=8.49 (s, 1H), 4.12 (s, 3H), 3.51-3.40 (m, 1H), 3.22 (s, 3H), 1.26 (d, J=6.8 Hz, 6H).

General Procedure for Preparation of Compound i-125:

To i-124 (200 mg, 563 umol, 1.00 eq) in dioxane (1.60 mL) were added Cs$_2$CO$_3$ (458 mg, 1.41 mmol, 2.50 eq), BINAP (35.1 mg, 56.3 umol, 0.10 eq) and Pd$_2$(dba)$_3$ (51.5 mg, 56.3 umol, 0.10 eq) under Na. Then diphenylmethanimine (153 mg, 844 umol, 142 uL, 1.50 eq) was added in. The mixture was stirred at 110° C. for 16 h and cooled to RT. H$_2$O (5 mL) was added into the mixture. The aqueous phase was extracted with ethyl acetate (4×5 mL). The combined organic phases were dried over anhydrous Na$_2$SO$_4$, filtered and concentrated in vacuum to give an oil. The residue was purified by prep-TLC to afford i-125 (220 mg, 538 umol) as an oil. $^1$H NMR (400 MHz, Chloroform-d) δ=7.80 (d, J=7.0 Hz, 2H), 7.53-7.48 (m, 1H), 7.46-7.40 (m, 2H), 7.36-7.32 (m, 3H), 7.23 (s, 1H), 7.10 (dd, J=2.9, 6.8 Hz, 2H), 4.07 (s, 3H), 3.43 (quin, J=6.8 Hz, 1H), 3.03 (s, 3H), 1.24 (d, J=6.6 Hz, 6H)

General Procedure for Preparation of Compound i-126:

To a mixture of i-125 (220 mg, 538 umol, 1.00 eq) in THF (2.00 mL)/H$_2$O (400 uL) was added HCl (1 M, 38.5 uL, 2.00 eq) slowly at 25° C. The mixture was stirred at 25° C. for 12 h. Water (3 mL) was added into the mixture. The aqueous phase was extracted with ethyl acetate (4×8 mL). The combined organic phases were washed with saturated NaHCO$_3$ (20 mL), dried over anhydrous Na$_2$SO$_4$, filtered and concentrated in vacuum to give an oil. The residue was purified by prep-TLC to give i-126 (100 mg, 409 umol) as a solid. $^1$H NMR (400 MHz, Chloroform-d) δ=7.56 (s, 1H), 4.05 (s, 3H), 3.52 (br s, 2H), 3.21 (s, 3H), 3.03 (td, J=6.7, 13.5 Hz, 1H), 1.28 (d, J=6.6 Hz, 6H)

General Procedure for Preparation of Compound i-127:

To a mixture of i-126 (60.0 mg, 245 umol, 1.00 eq) in dioxane (2.40 mL) was added i-107 (70.2 mg, 147 umol, 0.60 eq, prepared as described in Example 34), Cs$_2$CO$_3$ (200 mg, 614 umol, 2.50 eq), Xantphos (28.4 mg, 49.1 umol, 0.20 eq) and Pd2(dba)$_3$ (22.5 mg, 24.5 umol, 0.10 eq). The mixture was stirred at 100° C. for 12 h under N$_2$. The reaction was cooled to RT and H$_2$O (5 mL) was added. The aqueous phase was extracted with ethyl acetate (4×5 mL). The combined organic phases were dried over anhydrous Na$_2$SO$_4$, filtered and concentrated in vacuum to give an oil. The mixture was purified by prep-TLC to give i-127 (38.0 mg, 64.1 umol) as a solid. $^1$H NMR (400 MHz, Chloroform-d) δ=7.65 (s, 1H), 7.33 (s, 1H), 7.07 (d, J=8.8 Hz, 4H), 6.87 (s, 2H), 6.85 (s, 2H), 4.78 (s, 2H), 4.66 (s, 4H), 4.57 (s, 1H), 4.03 (s, 3H), 3.80 (s, 6H), 3.18 (s, 3H), 2.59-2.46 (m, 1H), 1.09 (d, J=6.6 Hz, 6H)

General Procedure for Preparation of Compound 36:

First batch: A mixture of i-127 (5.00 mg, 8.44 umol, 1.00 eq) in TFA (60.0 uL) was stirred at 80° C. for 3 h. The reaction was cooled to RT.

Second and third batches, two reactions run in parallel: A mixture of i-127 (38.0 mg, 1.00 eq) in TFA (450 uL) was stirred at 80° C. for 3 h. The reactions were cooled to RT.

The above three mixtures were combined and ice-H$_2$O (2 mL) was added in. The pH was adjusted to around 8 by progressively adding saturated Na$_2$CO$_3$ below 10° C. The aqueous phase was extracted with ethyl acetate (4×10 mL). The combined organic phases were dried over anhydrous Na$_2$SO$_4$, filtered and concentrated in vacuum. The residue was purified by prep-HPLC to give Compound 36 (16.8 mg, 36.8 umol, TFA salt) as a solid.

$^1$H NMR (400 MHz, DMSO-d$_6$) δ=11.84 (br s, 1H), 8.39 (br s, 1H), 7.76 (br s, 1H), 7.56 (br s, 1H), 7.48 (s, 1H), 7.20 (s, 1H), 6.82 (s, 1H), 3.99 (s, 3H), 3.31-3.28 (m, 1H), 3.22 (s, 3H), 1.23 (d, J=6.6 Hz, 6H) LCMS: [M+H]$^+$353.1

Example 39: Synthesis of Compound 37

Compound 37 was made by the synthetic method outlined in Scheme AQ:

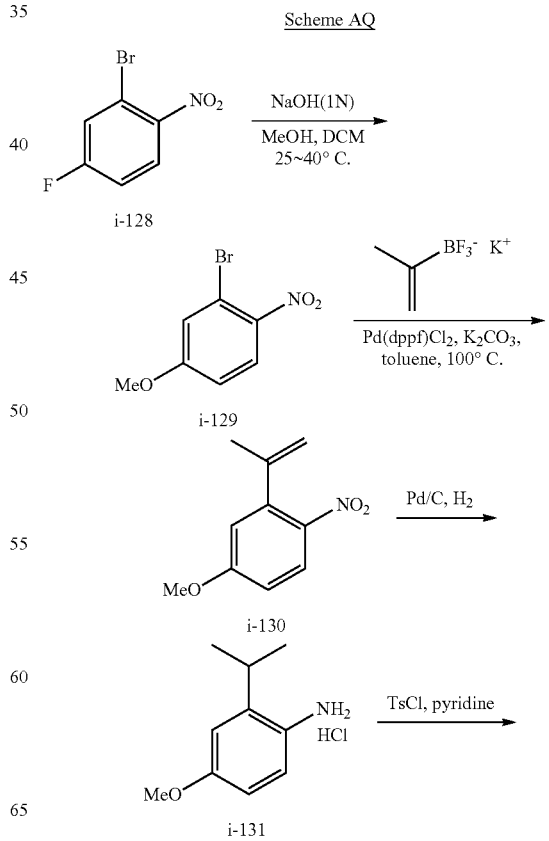

Scheme AQ

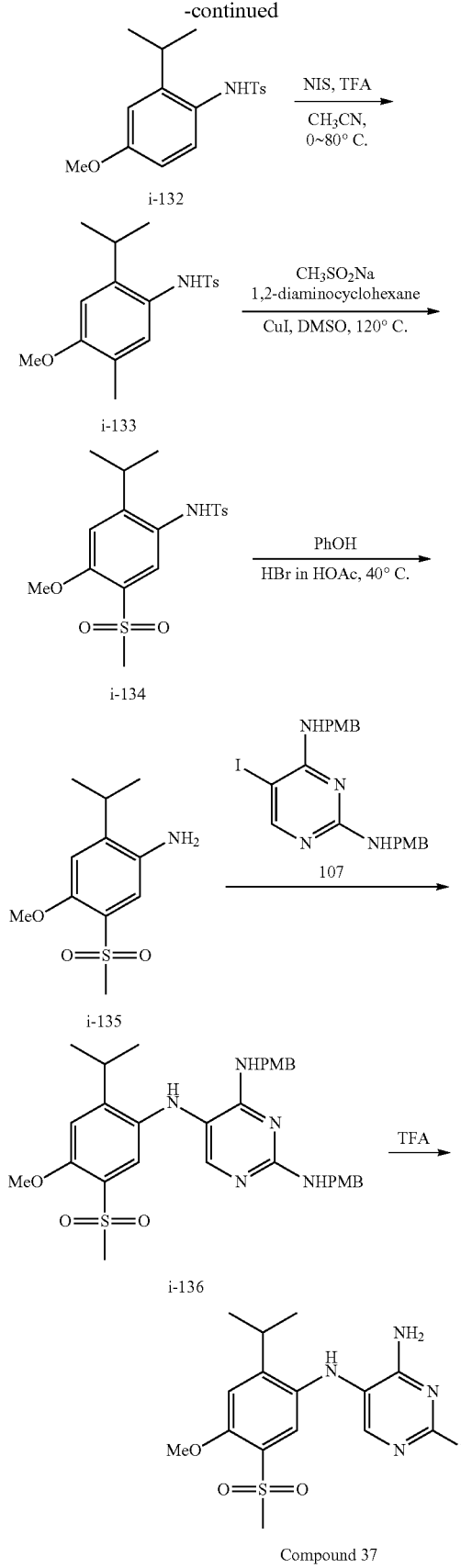

General Procedure for Preparation of Compound i-129:

To a solution of i-128 (60.0 g, 273 mmol, 1.00 eq) in the mixture of dichloromethane (400 mL) and methanol (440 mL) was added 1 M NaOH aqueous solution (1.00 L). Then a catalytic amount of TBAB (360 mg, 1.26 mmol) was added. The reaction was stirred at 40° C. for 16 h and then cooled to RT. The reaction mixture was partitioned between DCM (500 mL) and water (500 mL). Then the aqueous layer was extracted with dichloromethane (3×300 mL). The combined organic layers were dried over $Na_2SO_4$, filtered and concentrated under reduced pressure. The crude product was purified by column chromatography on silica gel to give compound i-129 (43.1 g, 186 mmol) as a solid.

$^1$H NMR (400 MHz, Chloroform-d) δ=8.00 (d, J=9.3 Hz, 1H), 7.23 (d, J=2.6 Hz, 1H), 6.93 (dd, J=2.6, 9.3 Hz, 1H), 3.90 (s, 3H)

General Procedure for Preparation of Compound i-130:

To a solution of i-129 (40.0 g, 172 mmol, 1.00 eq) and potassium 2-propenyltrifluoroborate (51.0 g, 344 mmol, 2.00 eq) in toluene (200 mL) was added $Pd(dppf)Cl_2$ (12.6 g, 17.2 mmol, 0.10 eq) and $K_2CO_3$ (71.5 g, 517 mmol, 3.00 eq). The reaction mixture was stirred at 100° C. for 12 h under $N_2$ atmosphere and cooled to RT. One additional vial was set up as described above and the reaction carried out identically. The two reaction mixtures were combined and were partitioned between ethyl acetate (200 mL) and water (200 mL). The aqueous layer was extracted with ethyl acetate (3×200 mL). Then the combined organic layers were dried over $Na_2SO_4$, filtered and concentrated under reduced pressure. The residue was purified by column chromatography on silica gel to give compound i-130 (45.0 g, 233 mmol) as an oil. $^1$H NMR (400 MHz, Chloroform-d) δ=8.01 (d, J=8.8 Hz, 1H), 6.86 (dd, J=2.9, 9.0 Hz, 1H), 6.76 (d, J=2.6 Hz, 1H), 5.17-5.14 (m, 1H), 4.93 (s, 1H), 3.90 (s, 3H), 2.08 (s, 3H)

General Procedure for Preparation of Compound i-131:

To a solution of i-130 (45.0 g, 233 mmol, 1.00 eq) in methanol (800 mL) was added Pd/C (4.18 g, 1.97 mmol, 5% w.t.). The mixture was stirred at 25° C. under $H_2$ (50 psi) for 12 h. The reaction mixture was filtered through celite under nitrogen and washed with methanol (300 mL). To the filtrate was added 12M HCl (40.0 mL). Then the mixture was concentrated to give compound i-132 (53.7 g, crude, HCl) as a solid which was used for the next step directly. $^1$H NMR (400 MHz, DMSO-$d_6$) δ=10.16 (br. s., 3H), 7.38-7.32 (m, 1H), 6.91 (d, J=2.6 Hz, 1H), 6.86-6.80 (m, 1H), 3.73 (s, 3H), 3.08 (td, J=6.7, 13.6 Hz, 1H), 1.16 (d, J=7.1 Hz, 6H)

General Procedure for Preparation of Compound i-132:

A solution of i-131 (3.00 g, 14.8 mmol, 1.00 eq) and tosyl chloride (3.69 g, 19.3 mmol, 1.30 eq) in pyridine (30 mL) was stirred at 80° C. for 5 h. The reaction mixture was partitioned between ethyl acetate (30 mL) and water (30 mL) and the aqueous layer was extracted with ethyl acetate (3×30 mL). The combined organic layer was washed with 0.5 M HCl (3×50 mL), dried over $Na_2SO_4$, filtered and concentrated under reduced pressure to give i-132 (4.06 g, 12.7 mmol) as a solid which was used in the next step directly.

$^1$H NMR (400 MHz, Chloroform-d) δ=7.59-7.54 (m, 2H), 7.23 (d, J=7.9 Hz, 2H), 7.10 (d, J=8.4 Hz, 1H), 6.71 (d, J=3.1 Hz, 1H), 6.68-6.63 (m, 1H), 6.12 (s, 1H), 3.79 (s, 3H), 2.88-2.77 (m, 1H), 2.40 (s, 3H), 0.96 (d, J=6.6 Hz, 6H)

General Procedure for Preparation of Compound i-133:

To a solution of i-132 (10 g, 31.3 mmol, 1.00 eq) in $CH_3CN$ (100 mL) was added TFA (4.93 g, 43.2 mmol, 3.2 mL, 1.38 eq) and NIS (7.04 g, 31.3 mmol, 1.00 eq) at 0° C. The mixture was stirred at 80° C. for 17 h and cooled to RT.

The reaction mixture was partitioned between ethyl acetate (100 mL) and water (100 mL). Then the aqueous layer was extracted with ethyl acetate (2×50 mL). The combined organic layers were washed with brine (50 mL), dried over $Na_2SO_4$, filtered and concentrated under reduced pressure. The crude product was purified by column chromatography on silica gel to give i-133 (8.20 g, 18.4 mmol) as a solid which was used in the next step. $^1H$ NMR (400 MHz, chloroform-d) δ=7.58-7.54 (m, 2H), 7.24-7.21 (m, 2H), 7.13 (s, 1H), 6.68 (s, 1H), 3.85 (s, 3H), 2.87 (m, 1H), 2.39 (s, 3H), 0.95 (d, J=6.6 Hz, 6H)

General Procedure for Preparation of Compound i-134:

The solution of i-133 (2.00 g, 4.49 mmol, 1.00 eq), sodium methylsulfinate (1.15 g, 11.2 mmol, 2.50 eq), CuI (171 mg, 898 umol, 0.20 eq), (1S,2S)-cyclohexane-1,2-diamine (205 mg, 1.80 mmol, 0.40 eq) in DMSO (20.0 mL) was stirred at 120° C. under Na atmosphere for 20 h and cooled to RT. Water (120 mL) was added in. The aqueous phase was extracted with ethyl acetate (4×50 mL). The combined organic phases were dried over anhydrous $Na_2SO_4$, filtered and concentrated in vacuum to give an oil. The residue was purified by column chromatography on silica gel to give i-134 (1.00 g, 2.52 mmol) as a solid. $^1H$ NMR (400 MHz, DMSO-$d_6$) δ=7.52-7.50 (m, 1H), 7.39-7.34 (m, 3H), 7.24 (s, 1H), 7.08-7.03 (m, 1H), 3.93 (s, 3H), 3.16-3.13 (s, 3H), 2.52 (m, 1H), 2.36 (s, 3H), 0.98 (d, J=6.8 Hz, 6H)

General Procedure for Preparation of Compound i-135:

Compound i-134 (900 mg, 2.26 mmol, 1.00 eq), PhOH (453 mg, 4.81 mmol, 2.13 eq) and hydrogen bromide (28.9 mmol, 4.48 mL, 35%, 12.77 eq) were added to a round bottomed flask. The mixture was stirred for 12 h at 40° C. The pH was adjusted to approximately pH 9-10 by progressively adding NaOH (6 mol/L). Then $H_2O$ (15 mL) was added in. The mixture was extracted with ethyl acetate (4×30 mL). The combined organic phases were dried over anhydrous $Na_2SO_4$, filtered and concentrated under vacuum. The residue was purified by column chromatography on silica gel and further purified by prep-HPLC. The mixture from prep-HPLC was adjusted to pH 9 with saturated $NaHCO_3$. The aqueous phase was extracted with ethyl acetate (4×200 mL). The combined organic phases were dried over anhydrous $Na_2SO_4$, filtered and concentrated in vacuum to give i-135 (290 mg, 1.19 mmol) as a solid.

$^1H$ NMR (400 MHz, Chloroform-d) δ=7.28 (s, 1H), 6.85 (s, 1H), 3.94 (s, 3H), 3.20 (s., 3H), 2.99-2.92 (m, 1H), 1.29-1.27 (d, J=7.1 Hz, 6H)

General Procedure for Preparation of Compound i-135:

To a mixture of i-135 (50 mg, 205 umol, 1.00 eq) and i-107 (58.7 mg, 123 umol, 0.60 eq, prepared as described in example 34) in dioxane (2.00 mL) was added Xantphos (23.8 mg, 41 umol, 0.20 eq) and $Cs_2CO_3$ (134 mg, 0.41 mmol, 2.50 eq). The resulting reaction mixture was degassed with $N_2$ three times and $Pd_2(dba)_3$ (18.8 mg, 20.6 umol, 0.10 eq) was added under $N_2$. The mixture was stirred at 100° C. for 14 h under $N_2$ and cooled to RT. Three additional vials were set up as described above and the reactions carried out in an identical manner. All four reaction mixtures were combined. The reaction mixtures were poured into $H_2O$ (5 mL). The aqueous phase was extracted with ethyl acetate (3×5 mL). The combined organic layers were washed with brine (5 mL), dried over anhydrous $Na_2SO_4$, filtered and concentrated in vacuum. The mixture was purified by prep-TLC to give i-135 (62 mg, crude) as a solid. LCMS: $[M+H]^+$ 592.4

General Procedure for Preparation of Compound 37:

A mixture of i-135 (62 mg, 105 umol, 1.00 eq) in TFA (0.5 mL) was stirred at 80° C. for 14 h under $N_2$, and the reaction cooled to RT. The pH was adjusted to approximately 8 by progressively adding saturated aqueous $Na_2CO_3$ (2 mL) below 10° C. The aqueous phase was extracted with ethyl acetate (2×5 mL). The combined organic layers were washed with brine (2×5 mL), dried over anhydrous $Na_2SO_4$, filtered and concentrated in vacuum. The residue was purified by prep-TLC to give a crude solid which was purified by prep-HPLC to give Compound 37 (5.0 mg, 14 umol) as a solid. $^1H$ NMR (400 MHz, Methanol-$d_4$) δ=7.70 (s, 1H), 7.04 (s, 1H), 6.94 (s, 1H), 4.93 (br s, 2H), 4.82 (br s, 2H), 4.77 (s, 1H), 3.96 (s, 3H), 3.17 (s, 3H), 3.10 (m, 1H), 1.34 (d, J=6.8 Hz, 6H) LCMS: $[M+H]^+$ 352.0

Example 40: Synthesis of Compound 38

Compound 38 was made by the synthetic method outlined in Scheme AR:

Scheme AR

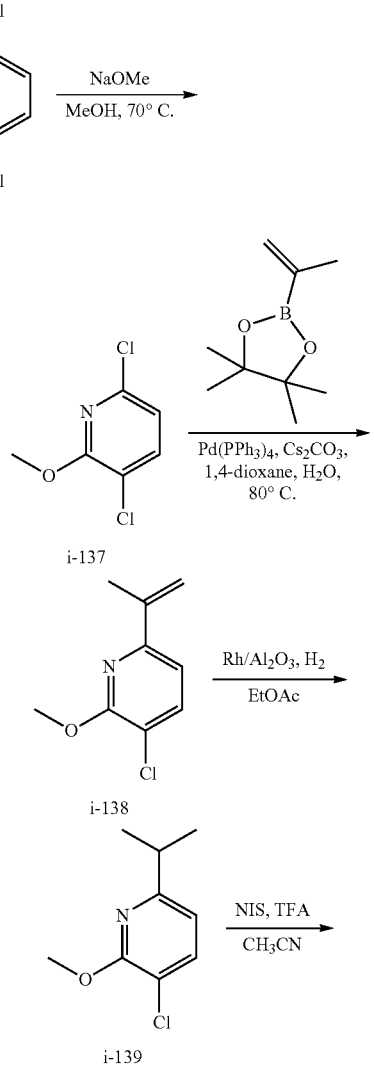

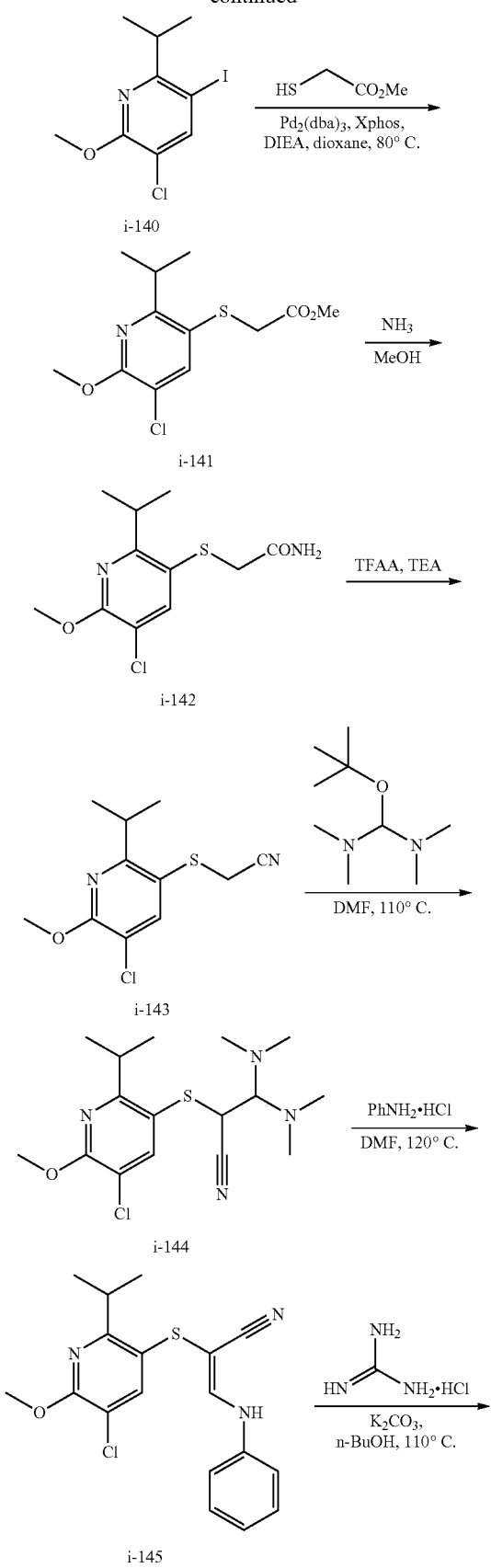

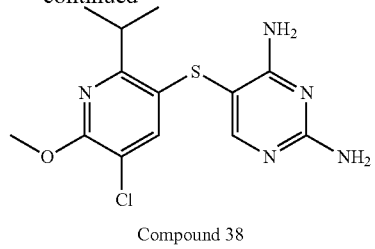

Compound 38

General Procedure for Preparation of Compound i-137:

To the solution of i-136 (30.0 g, 164 mmol, 1.00 eq) in MeOH (300 mL) was added MeONa (10.9 g, 279 mmol, 1.70 eq). The mixture was stirred at 70° C. for 12 h and cooled to RT. The mixture was concentrated under vacuum. Then to the residue was added ethyl acetate (300 mL) and water (100 mL). The two phases were separated and the aqueous phase was extracted with ethyl acetate (2×100 mL). The combined organic phases were dried over anhydrous $Na_2SO_4$, filtered and concentrated. The residue was purified via column chromatography on silica gel to give i-137 (22.7 g, 127 mmol) as a solid which was used for the next step directly. $^1$H NMR (400 MHz, CHLOROFORM-d) δ=7.57 (d, J=7.9 Hz, 1H), 6.88 (d, J=7.9 Hz, 1H), 4.04 (s, 3H)

General Procedure for Preparation of Compound i-138:

To a solution of i-137 (23.0 g, 129 mmol, 1.00 eq) in 1,4-dioxane (500 mL) and $H_2O$ (200 mL) was added 2-isopropenyl-4,4,5,5-tetramethyl-1,3,2-dioxaborolane (22.8 g, 135 mmol, 1.05 eq), $Cs_2CO_3$ (84.2 g, 258 mmol, 2.00 eq) and $Pd(PPh_3)_4$ (14.9 g, 12.9 mmol, 0.10 eq). The mixture was stirred at 80° C. under $N_2$ for 15 h and cooled to RT. The mixture was filtered and the solid was washed with petroleum ether (100 mL). The filtrate was separated and the organic phase was extracted with petroleum ether (2×150 mL). The combined organic phases were dried over anhydrous $Na_2SO_4$, filtered and concentrated. The residue was purified via column chromatography on silica gel (eluting with petroleum ether) to give i-138 (14.0 g, 75.8 mmol) as a liquid. $^1$H NMR (400 MHz, CHLOROFORM-d) δ=7.58 (d, J=7.9 Hz, 1H), 7.00 (d, J=7.9 Hz, 1H), 5.97 (dd, J=0.8, 1.9 Hz, 1H), 5.27 (quin, J=1.6 Hz, 1H), 4.07-4.03 (m, 3H), 2.18-2.16 (m, 3H)

General Procedure for Preparation of Compound i-139:

To the solution of i-138 (14.0 g, 76.2 mmol, 1.00 eq) in EtOAc (500 mL) was added rhodium on $Al_2O_3$ (6.51 g, 63.2 mmol, 0.83 eq). The mixture was stirred at 25° C. under $H_2$ balloon for 5 h. The mixture was filtered and the solid was washed with ethyl acetate (100 mL). Then the filtrate was concentrated to give i-139 (13.1 g, 70.5 mmol) as a liquid.

$^1$H NMR (400 MHz, CHLOROFORM-d) δ=7.51 (d, J=7.7 Hz, 1H), 6.69 (d, J=7.9 Hz, 1H), 4.02 (s, 2H), 4.04-4.01 (m, 1H), 2.94 (spt, J=6.8 Hz, 1H), 1.27 (d, J=6.8 Hz, 6H)

General Procedure for Preparation of Compound i-140:

To the solution of i-139 (5.00 g, 26.9 mmol, 1.00 eq) in $CH_3CN$ (50.0 mL) was added NIS (18.2 g, 80.8 mmol, 3.00 eq) and TFA (2 mL, 26.9 mmol, 1.00 eq). The mixture was stirred at 25° C. for 15 h then at 80° C. for 2 h and cooled to RT. The mixture was filtered and the filtrate was adjust to pH=8 with saturated $NaHCO_3$ solution. The mixture was partitioned between ethyl acetate (60 mL) and water (30 mL). Then the aqueous layer was extracted with ethyl acetate (2×30 mL). The combined organic layers were washed with saturated $Na_2SO_3$ solution (2×30 mL) and dried over $Na_2SO_4$, filtered and concentrated. To the residue was added petroleum ether (60 mL). The mixture was stirred at 25° C. for 5 min and white solid was generated. Then the solid was filtered off and the filtrate was concentrated to give i-140 (6.70 g, 21.5 mmol) as a liquid. $^1$H NMR (400 MHz, CHLOROFORM-d) δ=7.91 (s, 1H), 4.01 (s, 3H), 3.34 (spt, J=6.7 Hz, 1H), 1.22 (d, J=6.6 Hz, 6H)

General Procedure for Preparation of Compound i-141:

Compound i-140 (1.50 g, 4.81 mmol, 1.00 eq), Pd$_2$(dba)$_3$ (440 mg, 481 umol, 0.10 eq), Xantphos (278 mg, 481 umol, 0.10 eq), DIEA (1.24 g, 9.63 mmol, 2.00 eq) and methyl 2-sulfanylacetate (613 mg, 5.78 mmol, 1.20 eq) were dissolved in dioxane (16 mL). The solution was heated to 80° C. for 16 h and cooled to RT. One additional reaction was set up as described above and carried out in an identical manner. The two reaction mixtures were combined. To the mixture was added ethyl acetate (20 mL) and water (20 mL). The two phases were separated and the aqueous phase was extracted with ethyl acetate (3×20 mL). The organic phases were combined and washed with brine (20 mL), dried over anhydrous Na$_2$SO$_4$, filtered and concentrated. The residue was purified by MPLC to give i-141 (2.30 g, 7.94 mmol) as an oil which was used in the next step directly. $^1$H NMR (400 MHz, CDCl$_3$-d) δ=7.73 (s, 1H), 4.02 (s, 3H), 3.70 (s, 3H), 3.68-3.63 (m, 1H), 3.47 (s, 2H), 1.23 (d, J=6.4 Hz, 6H)

General Procedure for Preparation of Compound i-142:

To a solution of NH$_3$ (10 M, 9 mL, 10.00 eq) in MeOH (30 mL) was added i-141 (2.30 g, 9.01 mmol, 1.00 eq). The mixture was stirred at 25° C. for 12 h. The solvent was removed in vacuo to give i-142 (2.00 g, 7.28 mmol) as a solid which was used in next step without purification. $^1$H NMR (400 MHz, CDCl$_3$-d) δ=7.63 (s, 1H), 6.73 (br, 1H), 5.91 (br, 1H), 4.01 (s, 3H), 3.61-3.56 (m, 1H), 3.46 (s, 2H), 1.23 (d, J=6.8 Hz, 6H)

General Procedure for Preparation of Compound i-143:

To a solution of i-142 (2.00 g, 7.28 mmol, 1.00 eq) and TEA (2.95 g, 29.1 mmol, 4.00 eq) in CHCl$_3$ (30 mL) was added TFAA (3.06 g, 14.6 mmol, 2.00 eq) at 0° C. The mixture was warmed to 25° C. and stirred for 1 h. To the mixture was added ice water (25 mL). The two phases were separated and the aqueous phase was extracted with ethyl acetate (3×10 mL). The combined organic phases were dried over anhydrous Na$_2$SO$_4$, filtered and concentrated. The residue was purified via column chromatography on silica gel to give i-143 (1.40 g, 5.45 mmol) as an oil. $^1$H NMR (400 MHz, CDCl$_3$-d) δ=7.83 (s, 1H), 4.05 (s, 3H), 3.76-3.66 (m, 1H), 3.45 (s, 2H), 1.26 (d, J=6.4 Hz, 6H)

General Procedure for Preparation of Compound i-144:

Compound i-143 (600 mg, 2.34 mmol, 1.00 eq) and 1-tert-butoxy-N, N, N', N'-tetramethyl-methanediamine (814 mg, 4.67 mmol, 2.00 eq) were dissolved in DMF (7 mL). The solution was heated to 110° C. for 1 h and cooled to RT. To the mixture was added ethyl acetate (15 mL) and water (15 mL). The two phases were separated and the aqueous phase was extracted with ethyl acetate (3×15 mL). The organic phases were combined and washed with brine (15 mL), dried over anhydrous Na$_2$SO$_4$, filtered and concentrated to give i-144 (600 mg, crude) which was used in next step without purification. LCMS: [M+H]$^+$ 312.2

General Procedure for Preparation of Compound i-145:

Compound i-144 (600 mg, 1.68 mmol, 1.00 eq), aniline hydrochloride (435 mg, 3.36 mmol, 2.00 eq) were dissolved in DMF (8 mL). The solution was heated to 120° C. for 1 h and cooled to RT. To the mixture was added ethyl acetate (20 mL) and water (10 mL). The two phases were separated and the aqueous phase was extracted with ethyl acetate (3×10 mL). The combined organic phases were washed with brine (20 mL), dried over anhydrous Na$_2$SO$_4$, filtered and concentrated to give i-145 (600 mg, crude) which was used in next step without purification.

General Procedure for Preparation of Compound 38:

Compound i-145 (600 mg, 1.67 mmol, 1.00 eq) and guanidine hydrochloride (638 mg, 6.68 mmol, 4.00 eq) were dissolved in n-BuOH (8 mL). Then K$_2$CO$_3$ (923 mg, 6.68 mmol, 4.00 eq) was added. The suspension was heated to 110° C. for 16 h, and then cooled to RT. To the mixture was added ethyl acetate (20 mL) and water (20 mL). The two phases were separated and the aqueous phase was extracted with ethyl acetate (3×20 mL). The organic phases were combined and dried over anhydrous Na$_2$SO$_4$, filtered and concentrated. The residue was purified by reverse phase prep-HPLC. MeCN was removed under reduced pressure and then water was removed by lyophillization to give Compound 38 (65.1 mg, 0.20 mmol) as a solid.

$^1$H NMR (400 MHz, DMSO-d$_6$) δ=7.92 (s, 1H), 7.16 (s, 1H), 6.61 (br, 2H), 6.43 (s, 2H), 3.91 (s, 3H), 3.47-3.41 (m, 1H), 1.21 (d, J=6.8 Hz, 6H) LCMS: [M+H]$^+$ 325.9

Example 41: Synthesis of Compound 39

Compound 39 was made by the synthetic method outlined in Scheme AS:

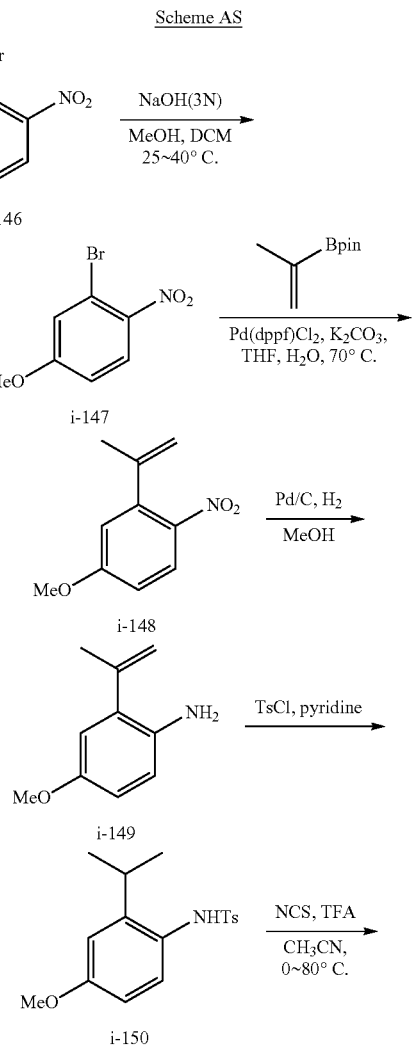

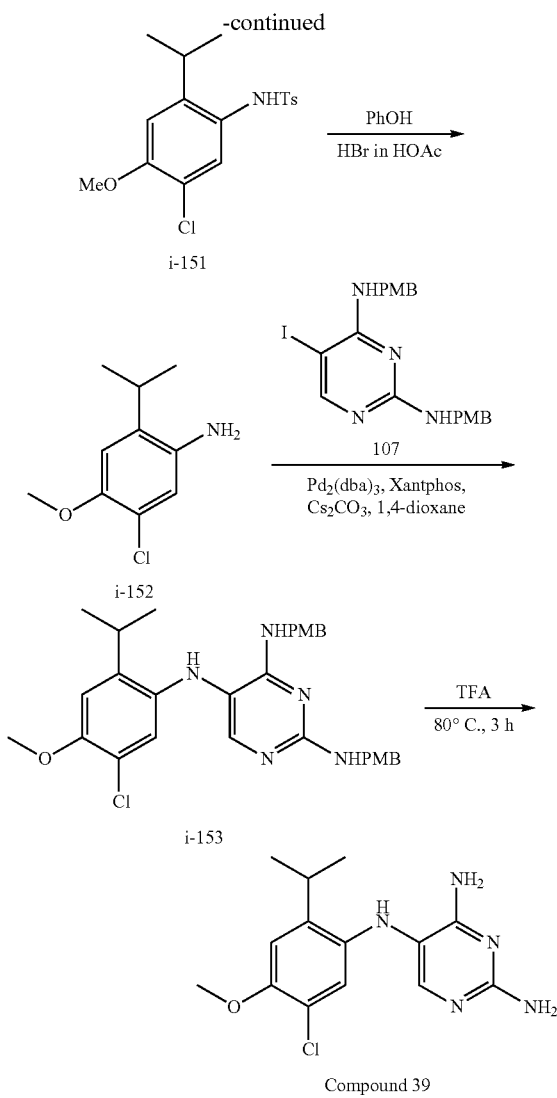

General Procedure for Preparation of Compound i-147:

To a solution of i-146 (50.0 g, 227 mmol, 1.00 eq) in dichloromethane (500 mL) and methanol (500 mL) was added the solution of NaOH (36.4 g, 909 mmol, 4.00 eq) in $H_2O$ (360 mL). The reaction was stirred at 40° C. for 16 h and cooled to RT. The reaction mixture was partitioned between dichloromethane (500 mL) and water (500 mL). Then the aqueous layer was extracted with dichloromethane (3×300 mL). The combined organic layers were dried over $Na_2SO_4$, filtered and concentrated under reduced pressure. The crude product was purified by column chromatography on silica gel to give i-147 (50 g, 215 mmol) as a solid.

$^1H$ NMR (400 MHz, Chloroform-d) δ=8.00 (d, J=9.3 Hz, 1H), 7.23 (d, J=2.8 Hz, 1H), 6.93 (dd, J=2.7, 9.2 Hz, 1H), 3.90 (s, 3H)

General Procedure for Preparation of Compound i-148:

To a solution of i-147 (50.0 g, 215 mmol, 1.00 eq), $K_2CO_3$ (59.6 g, 431 mmol, 2.00 eq) and isopropenylboronic acid pinacol ester (33.5 g, 226 mmol, 1.05 eq) in THF (800 mL) and $H_2O$ (200 mL) was added $Pd(dppf)Cl_2$ (1.58 g, 2.15 mmol, 0.01 eq) under Na. The resulting reaction mixture was degassed four times back filling with Na each time and the mixture was stirred at 70° C. for 15 h under Na atmosphere. The reaction mixture was cooled to RT, filtered through a pad of celite and washed with ethyl acetate (500 mL). The filtrate was concentrated and then diluted with ethyl acetate (500 mL) and water (500 mL). The two layers were separated and the aqueous layer was extracted with ethyl acetate (2×500 mL). The combined organic layers were washed with brine (500 mL), dried over $Na_2SO_4$, filtered and concentrated under reduced pressure. The residue was dissolved with petroleum ether (250 mL). Then the mixture was filtered and the filtrate was concentrated to give compound i-148 (40.0 g, 207 mmol) as an oil. LCMS: $[M+H]^+$ 193.7

General Procedure for Preparation of Compound i-149:

To a solution of i-148 (30.0 g, 155 mmol, 1.00 eq) in methanol (300 mL) was added Pd/C (3.0 g, 5% w.t.). The mixture was stirred at 50° C. under $H_2$ (50 psi) for 5 h. The reaction mixture was cooled and filtered through celite and washed with methanol (500 mL). The mixture was concentrated under reduced pressure. The crude product was purified by column chromatography on silica gel to give i-149 (25.0 g, 151 mmol) as a solid which was used in the next step directly. LCMS: $[M+H]^+$ 165.8

General Procedure for Preparation of Compound i-150:

A solution of i-149 (30.0 g, 182 mmol, 1.00 eq) and TosCl (45.0 g, 236 mmol, 1.30 eq) in pyridine (300 mL) was stirred at 80° C. for 5 h and cooled to RT. The reaction mixture was partitioned between ethyl acetate (300 mL) and water (300 mL) and the aqueous layer was extracted with ethyl acetate (2×500 mL). The combined organic layers were washed with 0.5 M HCl (2×500 mL), dried over $Na_2SO_4$, filtered and concentrated under reduced pressure. The crude product was purified by column chromatography on silica gel to give i-150 (50 g, 156 mmol) as an oil. $^1H$ NMR (400 MHz, Chloroform-d) δ=7.59-7.54 (m, 2H), 7.23 (d, J=7.9 Hz, 2H), 7.10 (d, J=8.4 Hz, 1H), 6.71 (d, J=3.1 Hz, 1H), 6.68-6.63 (m, 1H), 6.12 (s, 1H), 3.79 (s, 3H), 2.88-2.77 (m, 1H), 2.40 (s, 3H), 0.96 (d, J=6.6 Hz, 6H)

General Procedure for Preparation of Compound i-151:

To a solution of i-150 (10.0 g, 31.3 mmol, 1.00 eq) in $CH_3CN$ (100 mL) was added TFA (4.93 g, 43.2 mmol, 1.38 eq) and NCS (4.18 g, 31.3 mmol, 1.00 eq) at 0° C. Then the mixture was stirred at 80° C. for 5 h. The reaction mixture was cooled to RT and partitioned between ethyl acetate (200 mL) and water (200 mL). Then the aqueous layer was extracted with ethyl acetate (2×100 mL). The combined organic layers were dried over $Na_2SO_4$, filtered and concentrated under reduced pressure. The crude product was purified by column chromatography on silica gel to give i-151 (10 g, crude) as a solid. $^1H$ NMR (400 MHz, chloroform-d) δ=7.59-7.54 (m, 2H), 7.27-7.21 (m, 2H), 7.15 (s, 1H), 6.71 (s, 1H), 3.88 (s, 3H), 2.91 (quin, J=6.8 Hz, 1H), 2.41 (s, 3H), 0.99 (d, J=6.8 Hz, 6H)

General Procedure for Preparation of Compound i-152:

To a mixture of i-151 (9.0 g, 25.4 mmol, 1.00 eq) and phenol (2.39 g, 25.4 mmol, 1.0 eq) was added hydrogen bromide in HOAc (70 mL). The mixture was stirred for 15 h at 40° C. The reaction mixture was cooled to RT, and adjusted to pH 9 by progressively adding aqueous NaOH (6 mol/L, 200 mL). The mixture was extracted with ethyl acetate (200 mL). The two layers were separated and the aqueous layers were extracted with ethyl acetate (2×100 mL). The combined organic phases were dried over anhydrous $Na_2SO_4$, filtered and concentrated in vacuum. The residue was purified by prep-HPLC to give i-152 (2.0 g, 10.0 mmol) as an oil. $^1H$ NMR (400 MHz, Chloroform-d) δ=6.77 (s, 1H), 6.75 (s, 1H), 3.85 (s, 3H), 2.93-2.85 (m, 1H), 2.55 (br s, 2H), 1.26 (d, J=6.8 Hz, 6H)

General Procedure for Preparation of Compound i-153:

To a mixture of i-152 (40.0 mg, 200 umol, 1.00 eq) in 1,4-dioxane (2.00 mL) was added i-107 (57.2 mg, 120 umol, 0.60 eq, prepared as described in example 34), $Cs_2CO_3$ (163 mg, 500 umol, 2.50 eq), Xantphos (23.2 mg, 40.1 umol, 0.20 eq) and $Pd_2(dba)_3$ (18.3 mg, 20.0 umol, 0.10 eq). The mixture was stirred at 100° C. for 12 h under $N_2$. One additional vial was set up as described above and the reaction run in an identical manner. The two reaction mixtures were combined. The mixture was filtered and concentrated in vacuum to give an oil. The mixture was then purified by prep-HPLC to give i-153 (22.0 mg, 40.1 umol) as a solid. $^1$H NMR (400 MHz, chloroform-d) δ=7.32 (s, 1H), 7.06 (d, J=8.6 Hz, 4H), 6.90 (d, J=8.6 Hz, 4H), 6.77-6.71 (m, 1H), 6.52 (s, 1H), 4.85 (s, 4H), 3.86 (s, 3H), 3.82 (s, 6H), 3.79 (s, 2H), 2.39-2.33 (m, 1H), 1.02 (d, J=6.8 Hz, 6H)

General Procedure for Preparation of Compound 39:

A mixture of i-153 (18.0 mg, 32.8 umol, 1.00 eq) in TFA (1.0 mL) was stirred at 80° C. for 14 h and cooled to RT. The pH was adjusted to approximately 8 by progressively adding saturated $Na_2CO_3$ (2 mL) below 10° C. The aqueous phase was extracted with ethyl acetate (2×5 mL). The combined organic phases were dried over anhydrous $Na_2SO_4$, filtered and concentrated in vacuum. The residue was purified by prep-HPLC to give Compound 39 (4.1 mg, 13.3 umol, TFA) as a solid. $^1$H NMR (400 MHz, Methanol-$d_4$) δ=6.99 (s, 1H), 6.97 (s, 1H), 6.80 (s, 1H), 3.86 (s, 3H), 3.18-3.04 (m, 1H), 1.26 (d, J=6.8 Hz, 6H) LCMS: [M+H]$^+$308.1

Example 42: Synthesis of Compound 40

Compound 40 was made by the synthetic method outlined in Scheme AT:

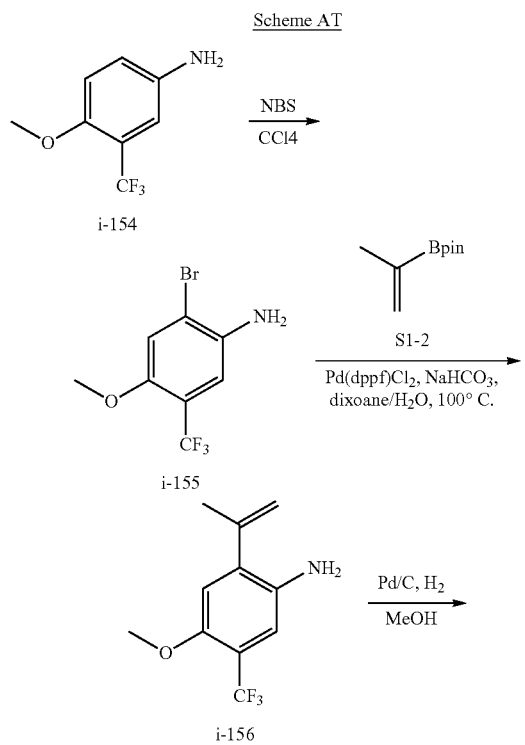

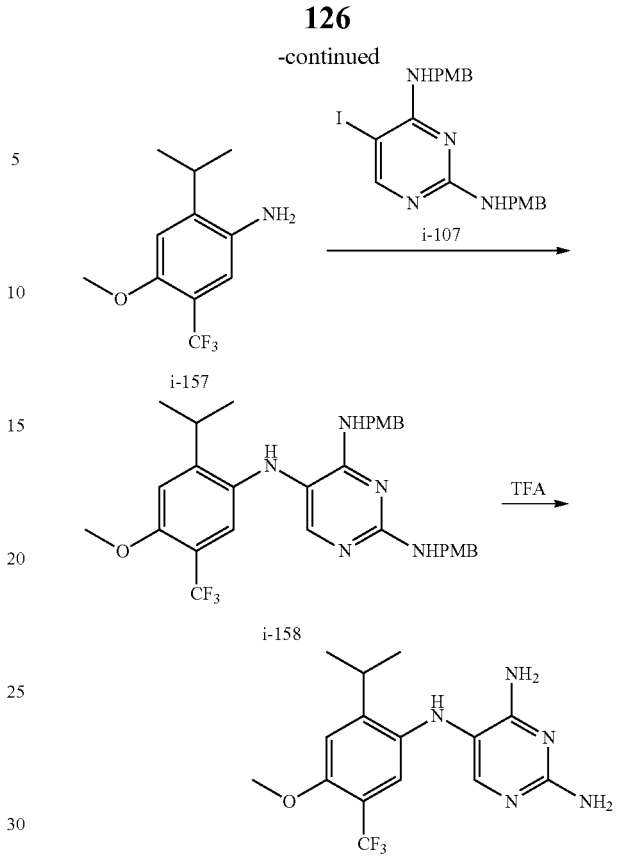

General Procedure for Preparation of Compound i-155:

To a solution of i-154 (5.0 g, 26.2 mmol, 1.00 eq) in $CCl_4$ (40.0 mL) was added NBS (4.66 g, 26.2 mmol, 1.00 eq). Then the mixture was stirred at 80° C. for 4 h and cooled to RT. The reaction mixture was quenched by addition aqueous NaOH (50 mL, 1M) at 25° C. Then the aqueous layer was extracted with ethyl acetate (2×50 mL). The combined organic layers were dried over $Na_2SO_4$, filtered and concentrated under reduced pressure. The crude product was purified by column chromatography on silica gel (eluted from petroleum ether/ethyl acetate=20/1 to petroleum ether/ethyl acetate=15/1) to give i-155 (2.8 g, 10.4 mmol) as a solid. $^1$H NMR (400 MHz, chloroform-d) δ=7.11 (s, 1H), 7.00 (s, 1H), 3.93 (br s, 2H), 3.83 (s, 3H)

General Procedure for Preparation of Compound i-156:

To a solution of i-155 (1.5 g, 5.55 mmol, 1.00 eq), $NaHCO_3$ (0.93 g, 11.1 mmol, 2.00 eq) and isopropenylboronic acid pinacol ester (1.12 g, 6.67 mmol, 1.20 eq) in 1,4-dioxane (10 mL) and $H_2O$ (2.5 mL) was added Pd(dppf)$Cl_2$ (90 mg, 0.11 mmol, 0.02 eq) under Na atmosphere. The reaction mixture was stirred at 100° C. for 14 h. The reaction mixture cooled and poured into water (20 mL). The mixture was extracted with ethyl acetate (3×10 mL). Then the combined organic layers were washed with brine (10 mL), dried over $Na_2SO_4$, filtered and concentrated under reduced pressure. The residue was purified by column chromatography on silica gel to give compound i-156 (0.9 g, 3.9 mmol) as an oil. $^1$H NMR (400 MHz, Chloroform-d) δ=6.92 (s, 1H), 6.72 (s, 1H), 5.35 (s, 1H), 5.09 (s, 1H), 3.83 (s, 3H), 2.18 (s, 2H), 1.28 (s, 3H)

General Procedure for Preparation of Compound i-157:

To a solution of i-156 (0.9 g, 3.9 mmol, 1.00 eq) in methanol (10 mL) was added Pd/C (0.3 g, 5% w.t.). The mixture was stirred at 50° C. under H$_2$ (50 psi) for 4 h and cooled to RT. The reaction mixture was filtered through celite. Then the mixture was concentrated to give crude i-157 which was purified by column chromatography on silica gel to give i-157 (0.4 g, 1.7 mmol) as an oil. $^1$H NMR (400 MHz, Chloroform-d) δ=6.90 (s, 1H), 6.83 (s, 1H), 3.86 (s, 3H), 2.95 (m, 1H), 1.28 (d, J=6.8 Hz, 6H) δ=6.90 (s, 1H), 6.83 (s, 1H), 3.86 (s, 3H), 2.95 (m, 1H), 1.28 (d, J=6.8 Hz, 6H)

General Procedure for Preparation of Compound i-158:

To a mixture of i-157 (80 mg, 343 umol, 1.00 eq) and i-107 (98 mg, 206 umol, 0.60 eq, prepared as described in example 34) in dioxane (3.00 mL) was added Xantphos (40 mg, 69 umol, 0.20 eq) and Cs$_2$CO$_3$ (279 mg, 0.86 mmol, 2.50 eq). The resulting reaction mixture was degassed with N$_2$ three times and Pd$_2$(dba)$_3$ (76.2 mg, 83.2 umol, 0.10 eq) was added under N$_2$. Then the mixture was stirred at 100° C. for 14 h under N$_2$ and cooled to RT. Three additional vials were set up as described above and the reactions carried out in an identical manner. The four reaction mixtures were combined. The reaction mixtures were poured into H$_2$O (50 mL). The aqueous phase was extracted with ethyl acetate (3×50 mL). The combined organic phases were washed with brine (50 mL), dried over anhydrous Na$_2$SO$_4$, filtered and concentrated in vacuum. The mixture was purified by prep-TLC to give i-158 (130 mg, 223 umol) as a solid. $^1$H NMR (400 MHz, Chloroform-d) δ=7.64 (s, 1H), 7.05 (d, J=8.3 Hz, 4H), 6.84 (d, J=8.3 Hz, 4H), 6.80 (s, 1H), 6.64 (s, 1H), 4.69 (s, 4H), 3.84 (s, 3H), 3.80 (s, 6H), 2.49 (m, 1H), 1.09 (d, J=7.0 Hz, 6H)

General Procedure for Preparation of Compound 40:

A mixture of i-158 (130 mg, 223 umol, 1.00 eq) in TFA (4 mL) was stirred at 80° C. for 14 h. The reaction mixture was cooled, and concentrated to remove TFA under N$_2$. The residue was diluted with ethyl acetate (10 mL). The combined organic layers were washed with saturated NaHCO$_3$ (2×3 mL). The aqueous phase was extracted with ethyl acetate (2×5 mL). The combined organic phases were dried over anhydrous Na$_2$SO$_4$, filtered and concentrated in vacuum. The residue was purified by prep-HPLC to give Compound 40 (9.8 mg, 21.5 umol, TFA) as a solid. $^1$H NMR (400 MHz, Methanol-d$_4$) δ=7.09 (s, 1H), 6.97 (d, J=5.1 Hz, 2H), 3.89 (s, 3H), 3.25-3.10 (m, 1H), 1.28 (d, J=6.8 Hz, 6H) LCMS: [M+H]$^+$ 341.9

Example 43: Synthesis of Compound 41

Compound 41 was made by the synthetic method outlined in Scheme AU:

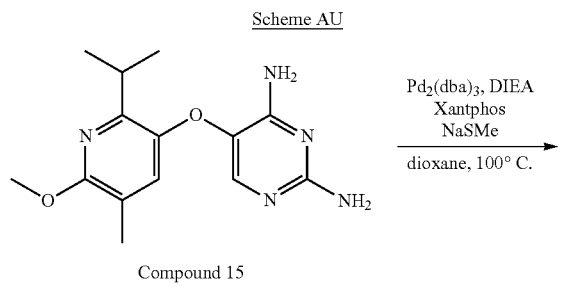

Scheme AU

Compound 15

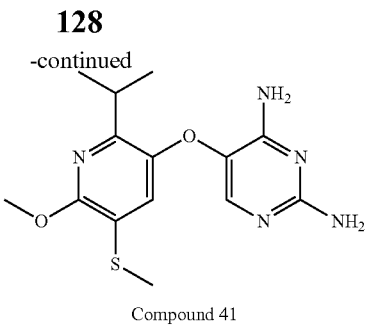

Compound 41

General Procedure for Preparation of Compound 41:

The solvent (dioxane) was degassed for 30 min by sparging with N$_2$. A solution of DIEA (644 mg, 4.99 mmol, 1.00 eq) in dioxane (30 mL) was added to a mixture of Compound 15 (2.00 g, 4.99 mmol, 1.00 eq, prepared as described in example 17), Pd$_2$(dba)$_3$ (137 mg, 150 umol, 0.03 eq), Xantphos (144 mg, 250 umol, 0.05 eq) and NaSMe (367 mg, 5.24 mmol, 1.05 eq) under Ar. The reaction was heated to 100° C. for 36 h under Ar. Upon cooling the reaction mixture was filtered and the filter cake was washed with dioxane (4×20 mL). The filtrate was concentrated in vacuum to leave a residue. Then the residue was purified via column chromatography on silica gel to give Compound 41 (1.40 g, 4.36 mmol) as a solid.

$^1$H NMR (400 MHz, DMSO-d$_6$) δ=7.23 (s, 1H), 6.95 (s, 1H), 6.47 (br s, 2H), 5.78 (s, 2H), 3.89 (s, 3H), 3.32-3.25 (m, 1H), 2.30 (s, 3H), 1.19 (d, J=6.6 Hz, 6H) LCMS: [M+H]$^+$ 322.0

Example 44: Synthesis of Compound 42

Compound 42 was made by the synthetic method outlined in Scheme AV:

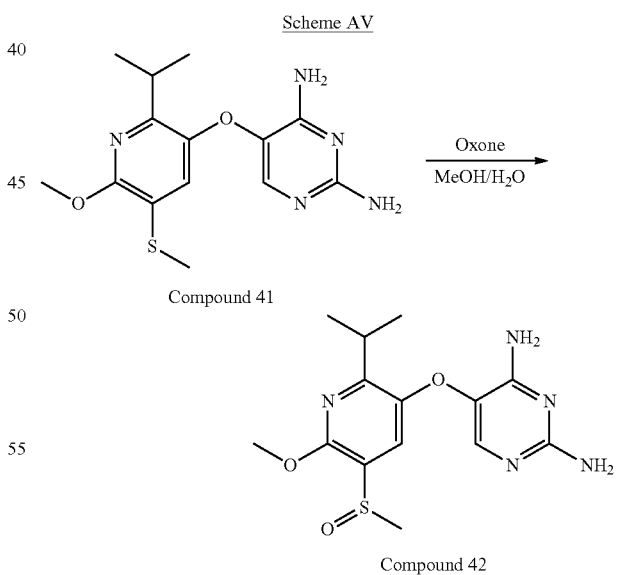

Scheme AV

Compound 41

Compound 42

General Procedure for Preparation of Compound 42:

A solution of oxone (762 mg, 1.24 mmol, 1.00 eq) in H$_2$O (10 mL) was added to a solution of Compound 41 (400 mg, 1.24 mmol, 1.00 eq) in methanol (10 mL) at −10-0° C. The reaction mixture was stirred below 0° C. for 20 minutes. The reaction mixture was filtered and the filter cake was washed with ethyl acetate (3×50 mL). Ethyl acetate (450 mL) and saturated aqueous sodium sulfite (100 mL) were added to the filtrate. The two phases were separated. The organic phase was washed with saturated sodium sulfite solution (100 mL) and brine (2×100 mL), dried over Na$_2$SO$_4$ and concentrated in vacuum to give compound 42 (0.43 g, crude) as yellow solid. $^1$H NMR (400 MHz, DMSO-d$_6$) δ=7.46 (s, 1H), 7.25 (s, 1H), 6.51 (br s, 2H), 5.95 (br s, 2H), 3.94 (s, 3H), 3.51 (td, J=6.6, 13.3 Hz, 1H), 2.72 (s, 3H), 1.26 (br d, J=6.7 Hz, 6H) LCMS: [M+H]$^+$ 338.0

Example 45: Synthesis of Compound 43

Compound 43 was made by the synthetic method outlined in Scheme AW:

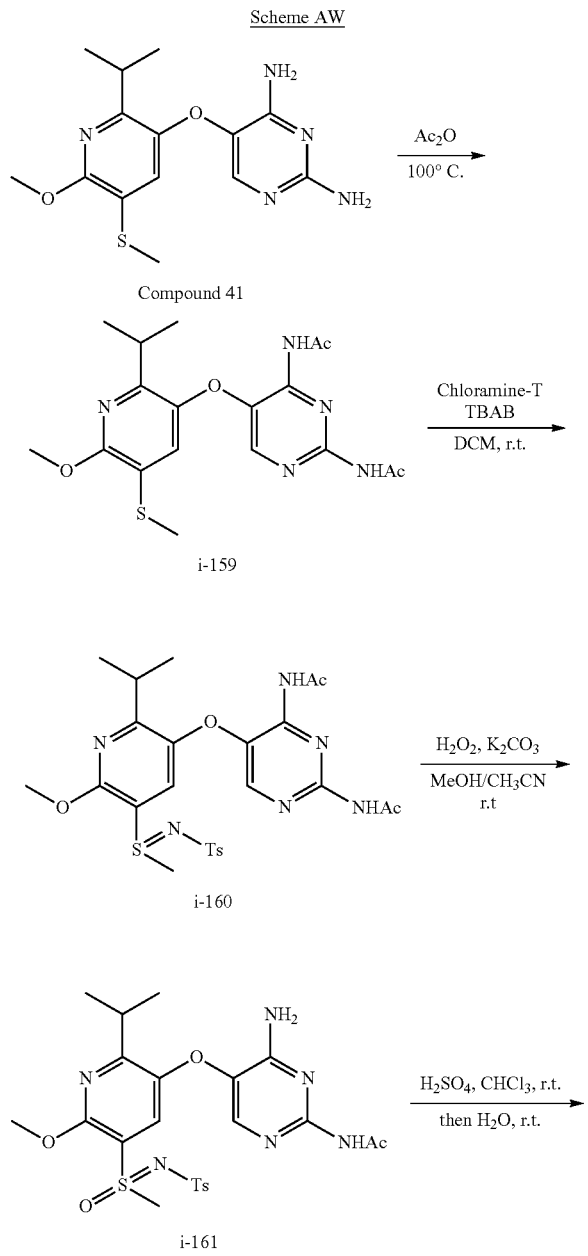

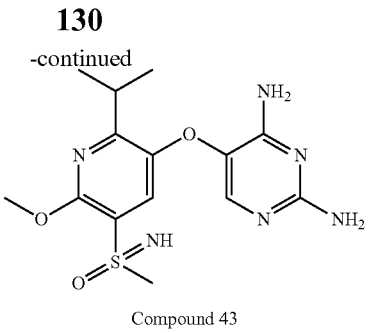

Compound 43

General Procedure for Preparation of Compound i-159:
A mixture of Compound 41 (500 mg, 1.56 mmol, 1.00 eq) and Ac$_2$O (1.63 g, 16.0 mmol, 1.50 mL, 10.29 eq) was stirred at 100° C. for 1 h. The reaction mixture was cooled to RT, and concentrated in vacuum to remove excessive Ac$_2$O. Cooled saturated sodium bicarbonate solution (100 mL) was added and the mixture was extracted with dichloromethane (3×100 mL). The combined organic layers were washed with brine (2×100 ml), dried with anhydrous Na$_2$SO$_4$, filtered and concentrated in vacuum to leave a residue. The residue was purified via column chromatography on silica gel to give i-159 (420 mg, 1.04 mmol) as a solid. $^1$H NMR (400 MHz, CHLOROFORM-d) δ=8.18 (s, 1H), 7.91 (br s, 1H), 7.63 (s, 1H), 6.96 (s, 1H), 4.04 (s, 3H), 3.03-3.14 (m, 1H), 2.67 (s, 3H), 2.39 (br s, 3H), 2.36 (s, 3H), 1.21 (br d, J=6.8 Hz, 6H)

General Procedure for Preparation of Compound i-160:
A mixture of i-159 (200 mg, 493 umol, 1.00 eq), Chloramine-T (337 mg, 1.48 mmol, 3.00 eq) and TBAB (318 mg, 987 umol, 2.00 eq) in dichloromethane (8 mL) was stirred at 20-30° C. for 3 h. The reaction mixture was filtered and the filter cake was washed with dichloromethane (3×15 mL). The filtrate was concentrated in vacuum to leave a residue as an oil. The residue was purified by prep-TLC to give i-160 (200 mg, 348 umol) as a solid.
$^1$H NMR (400 MHz, CHLOROFORM-d) δ=8.10 (s, 1H), 7.94 (s, 1H), 7.75 (d, J=7.8 Hz, 2H), 7.66 (s, 1H), 7.23 (d, J=7.8 Hz, 2H), 6.98 (s, 1H), 4.07 (s, 3H), 3.32-3.24 (m, 1H), 2.83 (s, 3H), 2.64 (s, 3H), 2.44 (s, 3H), 2.39 (s, 3H), 1.26 (d, J=5.6 Hz, 6H)

General Procedure for Preparation of Compound i-161:
H$_2$O$_2$ (355 mg, 10.4 mmol, 300 uL, 60.00 eq) was added to a solution of i-160 (100 mg, 174 umol, 1.00 eq) and K$_2$CO$_3$ (241 mg, 1.74 mmol, 10.00 eq) in methanol (2 mL) and acetonitrile (0.2 mL). The reaction mixture was stirred for 20 h at 20-30° C. The reaction mixture was concentrated in vacuum to remove the solvents. Water (25 mL) and dichloromethane (25 mL) were added. Then the two phases were separated and the aqueous phase was extracted with dichloromethane (2×25 mL). The combined organic layers were washed with brine (2×25 mL), dried over anhydrous Na$_2$SO$_4$, filtered and concentrated in vacuum to give i-161 (80 mg, 146 umol) as an oil which was used in the next step without further purification. $^1$H NMR (400 MHz, CHLOROFORM-d) δ=9.40 (br s, 1H), 7.85 (s, 1H), 7.70 (d, J=8 Hz, 2H), 7.53 (s, 1H), 7.21 (d, J=8 Hz, 2H), 6.16 (br s, 2H), 4.04 (s, 3H), 3.49 (s, 3H), 3.39 (td, J=7.0, 13.6 Hz, 1H), 2.50 (br s, 3H), 2.38 (s, 3H), 1.29 (d, J=7.2 Hz, 6H)

General Procedure for Preparation of Compound 43:
Compound i-161 (50 mg, 91.1 umol, 1.00 eq) was dissolved in CHCl$_3$ (1.00 mL). H$_2$SO$_4$ (442 mg, 4.50 mmol, 49.4 eq) was added at 0° C. The mixture was stirred for 24 h at 25° C. H$_2$O (1.00 mL) was added. The reaction mixture was stirred for 5 h at 25° C. The reaction mixture was poured into saturated sodium bicarbonate solution (20 mL) and the pH was around 8-9. The aqueous phase was extracted with dichloromethane (3×20 mL). The combined organic layers were washed with brine (3×20 mL), dried over $Na_2SO_4$, filtered and concentrated in vacuum to leave a residue. The residue was purified by prep-HPLC to give the Compound 43 (8 mg, 22.7 umol, 25% yield) as white solid. $^1$H NMR (400 MHz, METHANOL-$d_4$) δ=7.66 (s, 1H), 7.35 (s, 1H), 4.59 (br s, 1H), 4.10 (s, 3H), 3.54 (td, J=6.8, 13.5 Hz, 1H), 3.24 (s, 3H), 1.32 (dd, J=1.8, 6.7 Hz, 6H) LCMS: [M+H]$^+$ 353.0

Example 46: Synthesis of Compound 44

Compound 44 was made by the synthetic method outlined in Scheme AX:

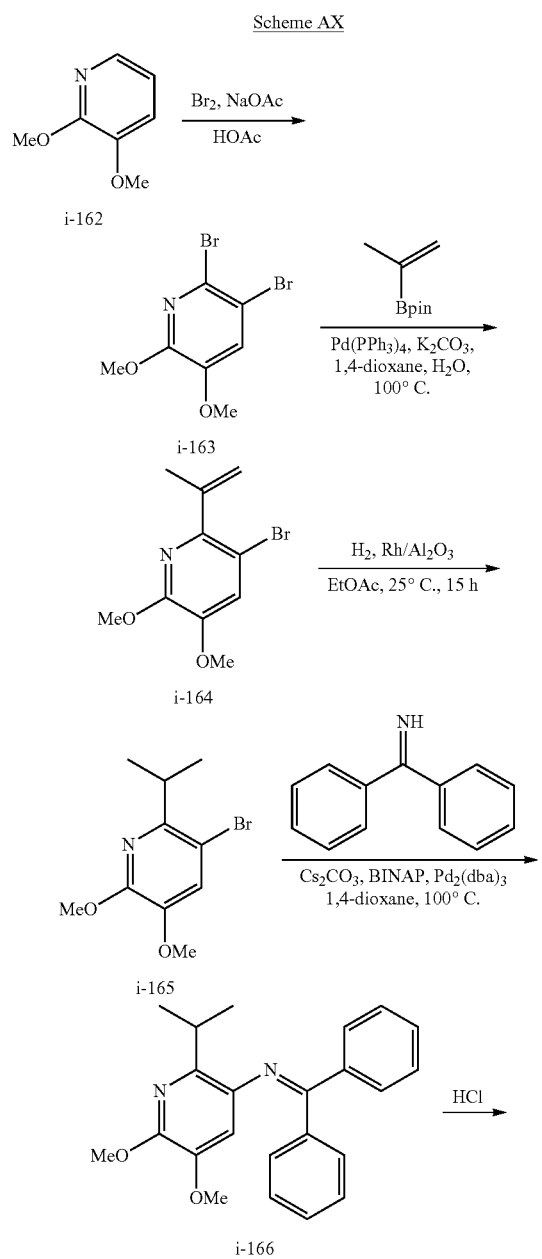

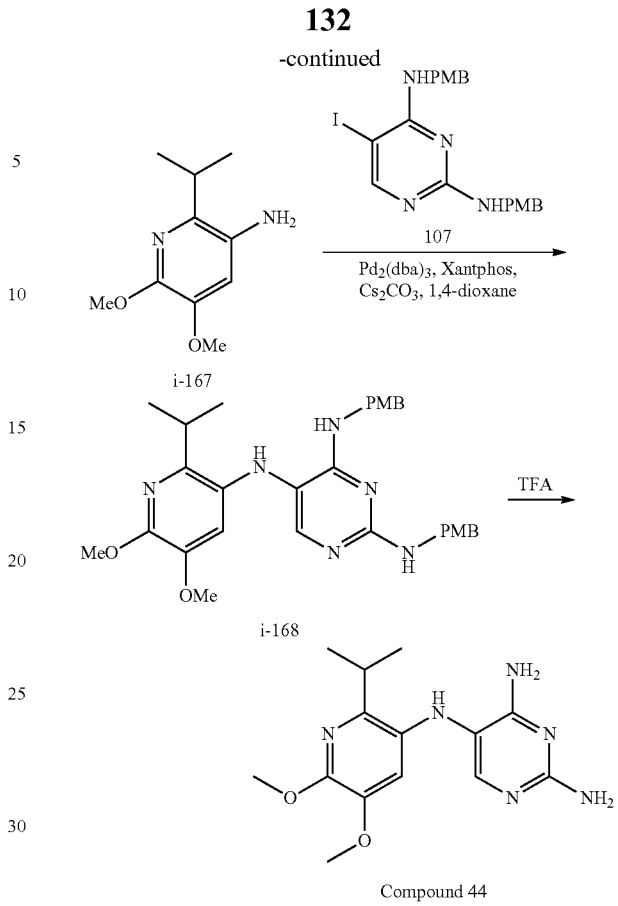

General Procedure for Preparation of Compound i-163:

To a solution of i-162 (5.00 g, 35.9 mmol, 1.00 eq) and NaOAc (8.84 g, 108 mmol, 3.00 eq) in HOAc (65.0 mL) was added Bra (20.1 g, 126 mmol, 6.48 mL, 3.50 eq) while maintaining the inner temperature below 25° C. The mixture was stirred at 25° C. for 20 h. The mixture was adjusted to pH 7 with 25% aqueous NaOH solution. The aqueous phase was extracted with DCM (3×100 mL). The organic phases were combined and washed with brine (100 mL), dried over anhydrous $Na_2SO_4$, filtered and concentrated to give i-163 (8.78 g, 29.6 mmol) as a solid. This product was used in the next step directly. $^1$H NMR (400 MHz, CHLOROFORM-d) δ=7.22 (s, 1H), 4.01 (s, 3H), 3.87 (s, 3H)

General Procedure for Preparation of Compound i-164:

To a mixture of i-163 (8.78 g, 29.6 mmol, 1.00 eq) and isopropenylboronic acid pinacol ester (4.97 g, 29.6 mmol, 1.00 eq) in 1,4-dioxane (100 mL) and $H_2O$ (25.0 mL) was added $K_2CO_3$ (8.17 g, 59.1 mmol, 2.00 eq) and Pd(PPh$_3$)$_4$ (4.10 g, 3.55 mmol, 0.12 eq) under Na. The mixture was stirred at 100° C. for 6 h. The mixture was filtered and the solid was washed with EtOAc (100 mL). The two phases were separated and the aqueous phase was extracted with EtOAc (3×100 mL). The combined organic phases were dried over anhydrous $Na_2SO_4$, filtered and concentrated. The residue was purified by column chromatography on silica gel to give i-164 (3.50 g, 13.6 mmol) as an oil. $^1$H NMR (400 MHz, CHLOROFORM-d) 6=7.20 (s, 1H), 5.40 (s, 1H), 5.33 (s, 1H), 4.00 (s, 3H), 3.88 (s, 3H), 2.14 (s, 3H)

General Procedure for Preparation of Compound i-165:

To a solution of i-164 (2.50 g, 9.69 mmol, 1.00 eq) in EtOAc (10.0 mL) was added rhodium/$Al_2O_3$ (1.40 g, 678 umol, 5% purity, 0.07 eq). The mixture was stirred at 25° C.

under H$_2$ balloon for 15 h. The mixture was filtered and the solid washed with EtOAc (3×10 mL). The combined organic layers were concentrated under reduced pressure to give i-165 (2.10 g, 8.07 mmol, 83% yield) as light yellow oil which was used in the next step directly.

$^1$H NMR (400 MHz, CHLOROFORM-d) δ=7.13 (s, 1H), 4.02-3.97 (m, 3H), 3.85 (s, 3H), 3.38 (spt, J=6.7 Hz, 1H), 1.22 (d, J=6.8 Hz, 6H)

General Procedure for Preparation of Compound i-166:

To a solution of i-165 (2.70 g, 10.4 mmol, 1.00 eq) in 1,4-dioxane (20.0 mL) was added diphenylmethanimine (2.82 g, 15.6 mmol, 1.50 eq), Cs$_2$CO$_3$ (8.45 g, 26.0 mmol, 2.50 eq), BINAP (1.29 g, 2.08 mmol, 0.20 eq) and Pd$_2$(dba)$_3$ (1.14 g, 1.25 mmol, 0.12 eq) under N$_2$. The mixture was stirred at 100° C. for 12 h. The mixture was cooled to RT, and filtered, and the solid washed with EtOAc (30 mL). To the filtrate was added H$_2$O (50 mL). The two phases were separated and the aqueous phase was extracted with EtOAc (2×30 mL). The combined organic phases were dried over anhydrous Na$_2$SO$_4$, filtered and concentrated. The residue was purified by column chromatography on silica gel to give i-166 (1.80 g, 4.99 mmol) as a solid.

$^1$H NMR (400 MHz, CHLOROFORM-d) δ=7.85-7.77 (m, 2H), 7.52-7.39 (m, 3H), 7.36-7.29 (m, 3H), 7.17-7.09 (m, 2H), 6.15 (s, 1H), 3.97 (s, 3H), 3.46 (s, 3H), 3.32 (spt, J=6.7 Hz, 1H), 1.17 (d, J=6.8 Hz, 6H)

General Procedure for Preparation of Compound i-167:

To a solution of i-166 (1.80 g, 4.99 mmol, 1.00 eq) in THF (15.0 mL) and H$_2$O (3.00 mL) was added HCl (1 M, 9.98 mL, 2.00 eq). The mixture was stirred at 25° C. for 2 h. The mixture was adjusted to pH 8 with saturated Na$_2$CO$_3$ solution. To the mixture was added EtOAc (30 mL) and H$_2$O (30 mL). The two phases were separated and the aqueous layer was extracted with EtOAc (3×30 mL). The combined organic layers were combined, dried over Na$_2$SO$_4$ and concentrated. The residue was purified by column chromatography on silica gel to give i-167 (900 mg, 4.59 mmol) as an oil. $^1$H NMR (400 MHz, CHLOROFORM-d) δ=6.53 (s, 1H), 3.96 (s, 3H), 3.82 (s, 3H), 2.93 (td, J=6.7, 13.3 Hz, 1H), 1.24 (d, J=6.8 Hz, 6H)

General Procedure for Preparation of Compound i-168:

To a solution of i-167 (450 mg, 2.29 mmol, 1.00 eq) and i-107 (655 mg, 1.38 mmol, 0.60 eq, prepared as described in Example 34) in 1,4-dioxane (5.00 mL) was added Xantphos (265 mg, 459 umol, 0.20 eq), Cs$_2$CO$_3$ (1.87 g, 5.73 mmol, 2.50 eq) and Pd$_2$(dba)$_3$ (210 mg, 229.30 umol, 0.10 eq) under N$_2$. The mixture was stirred at 100° C. for 12 h and cooled to RT. The mixture was filtered and the solid was washed with EtOAc (15 mL). To the filtrate was added H$_2$O (20 mL). The two phases were separated and the aqueous phase was extracted with EtOAc (3×15 mL). The combined organic phases were dried over anhydrous Na$_2$SO$_4$, filtered and concentrated. The residue was purified by column chromatography on silica gel to give i-168 (150 mg, 275 umol) as a solid. $^1$H NMR (400 MHz, CHLOROFORM-d) δ=7.47 (s, 1H), 7.10 (d, J=8.6 Hz, 4H), 6.89-6.84 (m, 4H), 6.29 (s, 1H), 4.80 (s, 4H), 3.95 (s, 3H), 3.81 (s, 6H), 3.68 (s, 3H), 2.50-2.44 (m, 1H), 1.04 (d, J=6.6 Hz, 6H)

General Procedure for Preparation of Compound 44:

Compound 168 (150 mg, 275 umol, 1.00 eq) was added to TFA (2.00 mL) and the mixture was stirred at 80° C. for 4 h and cooled to RT. The mixture was adjusted to pH 8 with saturated Na$_2$CO$_3$ solution at 0° C. To the mixture was added EtOAc (5 mL) and H$_2$O (5 mL). Then the two phases were separated and the aqueous phase was extracted with EtOAc (3×5 mL). The combined organic phases were dried over anhydrous Na$_2$SO$_4$, filtered and concentrated. The mixture was purified by prep-HPLC to give Compound 44 (22.0 mg, 72.3 umol) as a solid.

$^1$H NMR (400 MHz, METHANOL-d$_4$) δ=6.84 (s, 1H), 6.81 (s, 1H), 3.94 (s, 3H), 3.77 (s, 3H), 3.17-3.07 (m, 1H), 1.20 (d, J=6.8 Hz, 6H) LCMS: [M+H]$^+$ 305.2

Example 47: Synthesis of Compound 45

Compound 45 was made by the synthetic method outlined in Scheme AY:

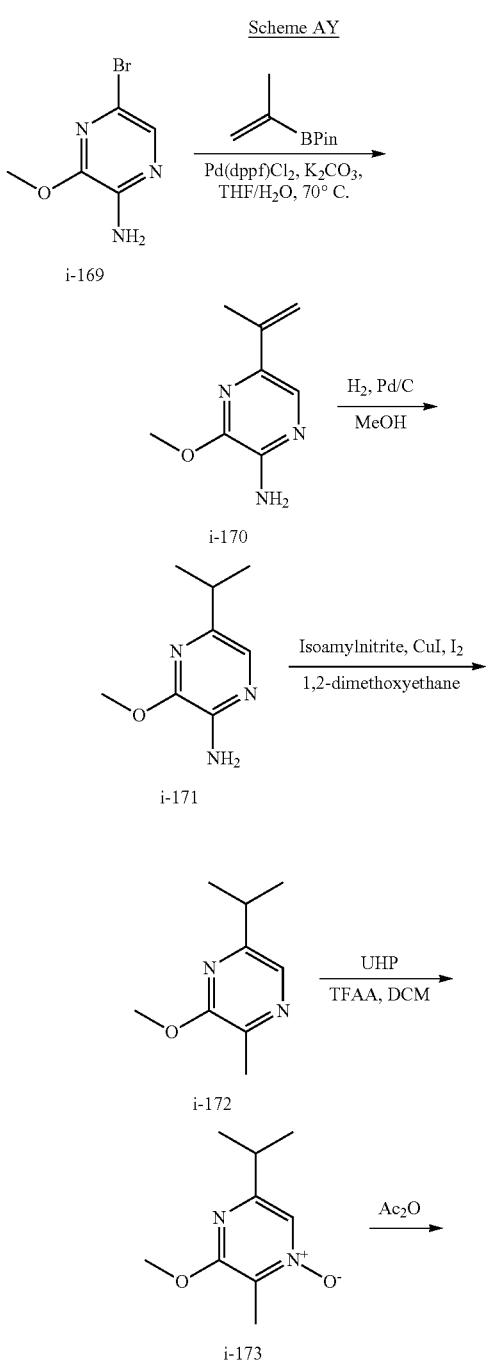

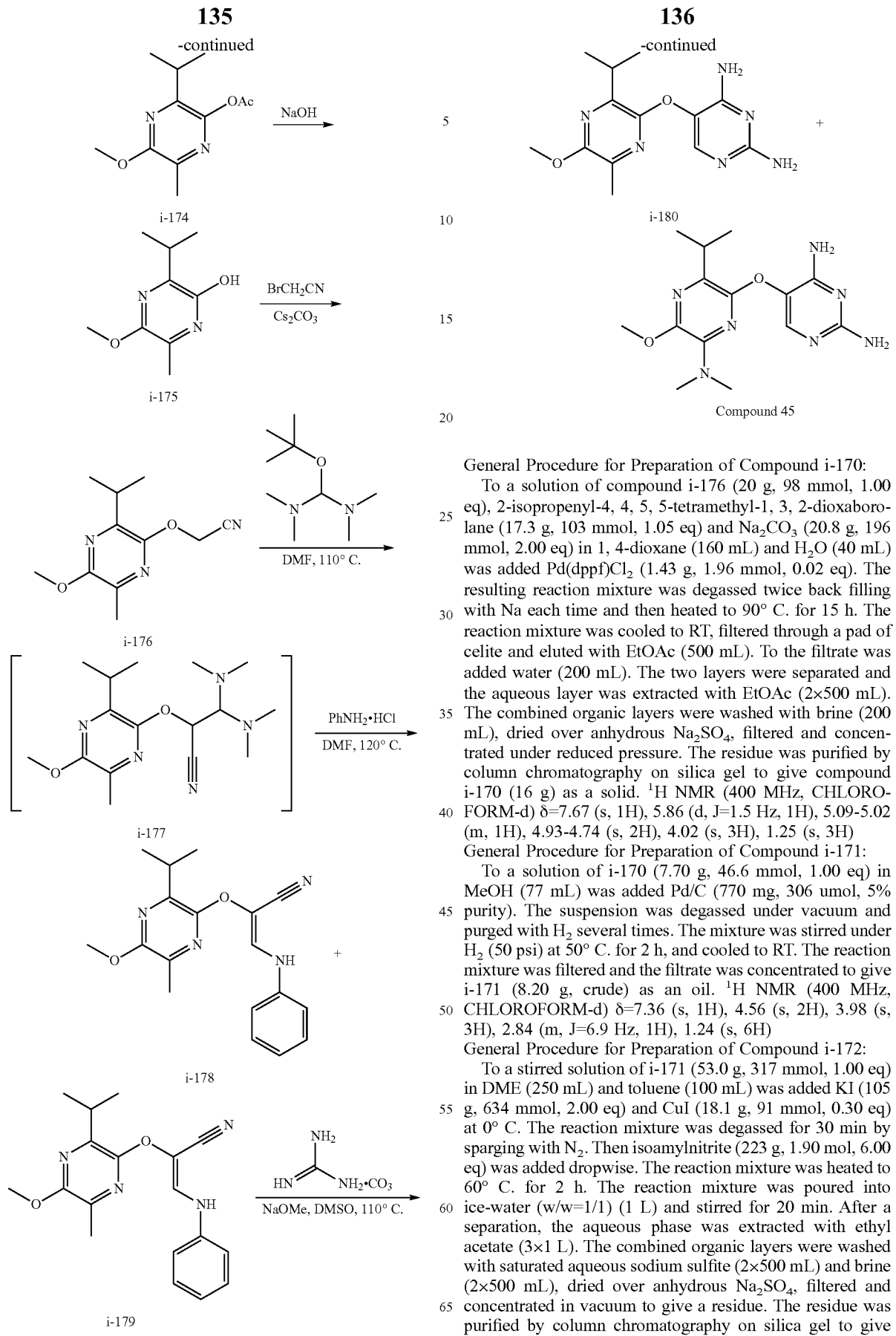

General Procedure for Preparation of Compound i-170:

To a solution of compound i-176 (20 g, 98 mmol, 1.00 eq), 2-isopropenyl-4, 4, 5, 5-tetramethyl-1, 3, 2-dioxaborolane (17.3 g, 103 mmol, 1.05 eq) and $Na_2CO_3$ (20.8 g, 196 mmol, 2.00 eq) in 1, 4-dioxane (160 mL) and $H_2O$ (40 mL) was added Pd(dppf)$Cl_2$ (1.43 g, 1.96 mmol, 0.02 eq). The resulting reaction mixture was degassed twice back filling with Na each time and then heated to 90° C. for 15 h. The reaction mixture was cooled to RT, filtered through a pad of celite and eluted with EtOAc (500 mL). To the filtrate was added water (200 mL). The two layers were separated and the aqueous layer was extracted with EtOAc (2×500 mL). The combined organic layers were washed with brine (200 mL), dried over anhydrous $Na_2SO_4$, filtered and concentrated under reduced pressure. The residue was purified by column chromatography on silica gel to give compound i-170 (16 g) as a solid. $^1$H NMR (400 MHz, CHLOROFORM-d) δ=7.67 (s, 1H), 5.86 (d, J=1.5 Hz, 1H), 5.09-5.02 (m, 1H), 4.93-4.74 (s, 2H), 4.02 (s, 3H), 1.25 (s, 3H)

General Procedure for Preparation of Compound i-171:

To a solution of i-170 (7.70 g, 46.6 mmol, 1.00 eq) in MeOH (77 mL) was added Pd/C (770 mg, 306 umol, 5% purity). The suspension was degassed under vacuum and purged with $H_2$ several times. The mixture was stirred under $H_2$ (50 psi) at 50° C. for 2 h, and cooled to RT. The reaction mixture was filtered and the filtrate was concentrated to give i-171 (8.20 g, crude) as an oil. $^1$H NMR (400 MHz, CHLOROFORM-d) δ=7.36 (s, 1H), 4.56 (s, 2H), 3.98 (s, 3H), 2.84 (m, J=6.9 Hz, 1H), 1.24 (s, 6H)

General Procedure for Preparation of Compound i-172:

To a stirred solution of i-171 (53.0 g, 317 mmol, 1.00 eq) in DME (250 mL) and toluene (100 mL) was added KI (105 g, 634 mmol, 2.00 eq) and CuI (18.1 g, 91 mmol, 0.30 eq) at 0° C. The reaction mixture was degassed for 30 min by sparging with $N_2$. Then isoamylnitrite (223 g, 1.90 mol, 6.00 eq) was added dropwise. The reaction mixture was heated to 60° C. for 2 h. The reaction mixture was poured into ice-water (w/w=1/1) (1 L) and stirred for 20 min. After a separation, the aqueous phase was extracted with ethyl acetate (3×1 L). The combined organic layers were washed with saturated aqueous sodium sulfite (2×500 mL) and brine (2×500 mL), dried over anhydrous $Na_2SO_4$, filtered and concentrated in vacuum to give a residue. The residue was purified by column chromatography on silica gel to give compound i-172 (33 g) as an oil. $^1$H NMR (400 MHz, CHLOROFORM-d) δ=7.83 (s, 1H), 4.01 (s, 3H), 2.93-3.02 (m, 1H), 1.29 (d, J=7.2 Hz, 6H)

General Procedure for Preparation of Compound i-173:

To a stirred solution of i-172 (5.00 g, 18 mmol, 1.00 eq) in DCM (50 mL) was added urea hydrogen peroxide (16.9 g, 180 mmol, 10 eq) and TFAA (25 mL) at 0° C. The reaction mixture was heated to 40° C. for 3 h. The reaction mixture were poured into ice-water (w/w=1/1) (100 mL). After a separation, the aqueous phase was extracted with DCM (3×100 mL). The combined organic layers were washed with saturated aqueous sodium metabisulfite (2×50 mL) and brine (2×50 mL), dried over anhydrous $Na_2SO_4$, filtered and concentrated in vacuum to give a residue. The residue was purified by column chromatography on silica gel to give compound i-173 (3 g, crude) as an oil. $^1$H NMR (400 MHz, CHLOROFORM-d) δ=7.88 (s, 1H), 4.06 (s, 3H), 3.14-3.07 (m, 1H), 1.28 (d, J=6.8 Hz, 6H)

General Procedure for Preparation of Compound i-174:

A solution of i-173 (1.25 g, 4.25 mmol, 1.00 eq) in $Ac_2O$ (10 mL) was stirred and heated to 110° C. for 15 h under Ar. The reaction mixture was concentrated to dryness and then diluted with ice water (5 mL) and extracted with EtOAc (2×5 mL). The combined organic layers were washed with brine (5 mL), dried over $Na_2SO_4$, filtered and concentrated under reduced pressure. The residue was purified by column chromatography on silica gel to give i-174 (200 mg, 0.59 mmol) as an oil which was used in the next step directly. $^1$H NMR (400 MHz, CHLOROFORM-d) δ=4.03 (s, 3H), 3.01-2.94 (m, 1H), 2.35 (s, 3H), 1.24 (d, J=6.8 Hz, 6H)

General Procedure for Preparation of Compound i-175:

To a stirred solution of i-174 (90 mg, 0.27 mmol, 1.00 eq) in MeOH (1 mL) was added NaOH (21 mg, 0.54 mmol, 2 eq). The mixture was stirred at 0° C. for 3 h. The reaction mixture was concentrated to dryness. Then the residue was diluted with $H_2O$ (5 mL) and extracted with EtOAc (3×5 mL). The combined organic layers were washed with brine (2×5 mL), dried over $Na_2SO_4$, filtered and concentrated under reduced pressure. The residue was purified by prep-TLC to give i-175 (40 mg, 0.14 mmol) as a solid which was used for the next step directly. $^1$H NMR (400 MHz, DMSO-$d_6$) δ=11.36 (s, 1H), 3.81 (s, 3H), 3.14-3.07 (m, 1H), 1.17 (d, J=6.8 Hz, 6H)

General Procedure for Preparation of Compound i-176:

To a stirred solution of i-175 (200 mg, 0.68 mmol, 1.00 eq) in $CH_3CN$ (2 mL) was added $Cs_2CO_3$ (443 mg, 1.36 mmol, 2.00 eq) and $BrCH_2CN$ (98 mg, 0.82 mmol, 1.20 eq). The mixture was stirred at 90° C. for 15 h under Ar. The reaction mixture was concentrated to dryness and diluted with $H_2O$ (5 mL) and extracted with EtOAc (3×5 mL). The combined organic layers were washed with brine (2×5 mL), dried over $Na_2SO_4$, filtered and concentrated. The residue was purified by prep-TLC to give i-176 (80 mg, 0.24 mmol, 35% yield) as an oil.

$^1$H NMR (400 MHz, CHLOROFORM-d) δ=5.01 (s, 2H), 3.99 (s, 3H), 3.29-3.14 (m, 1H), 1.25 (d, J=6.8 Hz, 6H)

General Procedure for Preparation of Compound i-177:

To a stirred solution of i-176 (80 mg, 0.24 mmol, 1.00 eq) in DMF (2 mL) was added 1-tert-butoxy-N,N,N',N'-tetramethyl-methane diamine (84 mg, 0.48 mmol, 2.00 eq). The solution was heated to 110° C. for 2 h. The solution was cooled to RT, and used in the next step without purification.

General Procedure for Preparation of Compounds i-178 and i-179:

To a stirred solution of i-177 (80 mg, 0.18 mmol, 1.00 eq) in DMF (1 mL) was added aniline hydrochloride (120 mg, 0.9 mmol, 5.00 eq). The reaction mixture was heated to 120° C. for 15 h. The reaction mixture was concentrated to dryness, and diluted with $H_2O$ (10 mL) and extracted with methyl t-Butyl ether (3×5 mL). The combined organic layers were washed with brine (2×5 mL), dried over $Na_2SO_4$, filtered and concentrated to give a mixture of i-178 and i-179 (200 mg, crude) as solids which were used directly in the next step without purification.

General Procedure for Preparation of Compound 45:

To a stirred solution of i-178 and i-179 (200 mg, 69 mmol, 1.00 eq) in DMSO (1.0 mL) was added NaOMe (3.7 mg, 69 mmol, 1.0 eq) and guanidine carbonate (16.4 mg, 138 umol, 2.00 eq). The reaction mixture was degassed for 3 times by sparging with $N_2$. The reaction mixture was heated to 110° C. for 15 h. The reaction mixture was cooled, and purified by prep-HPLC to give compound 45 (2 mg) as a solid. Compound i-180 was not isolated but was detected in the crude. $^1$H NMR (400 MHz, CHLOROFORM-d) δ=7.39 (s, 1H), 6.13-5.58 (m, 2H), 3.97 (s, 3H), 3.13 (s, 1H), 3.02 (s, 6H), 1.23 (d, J=6.8 Hz, 6H) LCMS: [M+H]$^+$ 320.1

Example 48: Synthesis of Compound 46

Compound 46 was made by the synthetic method outlined in Scheme AZ:

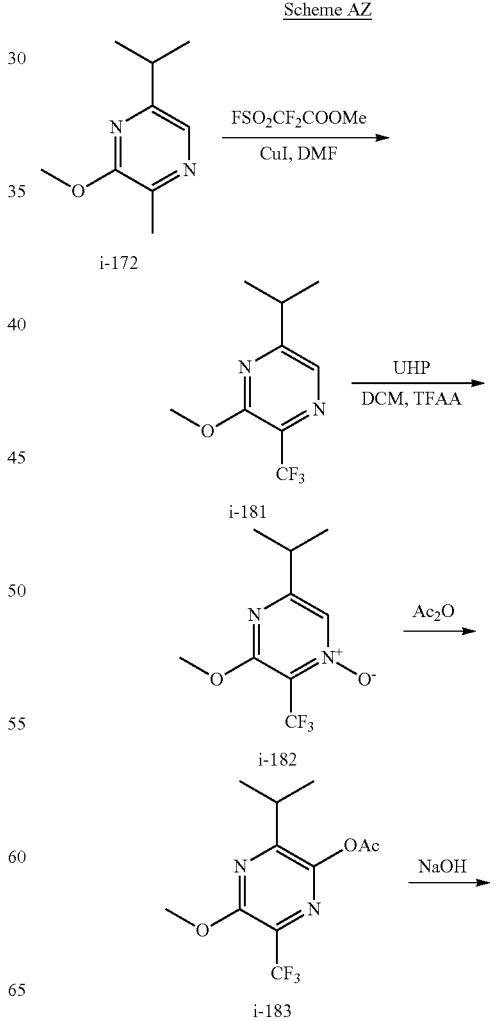

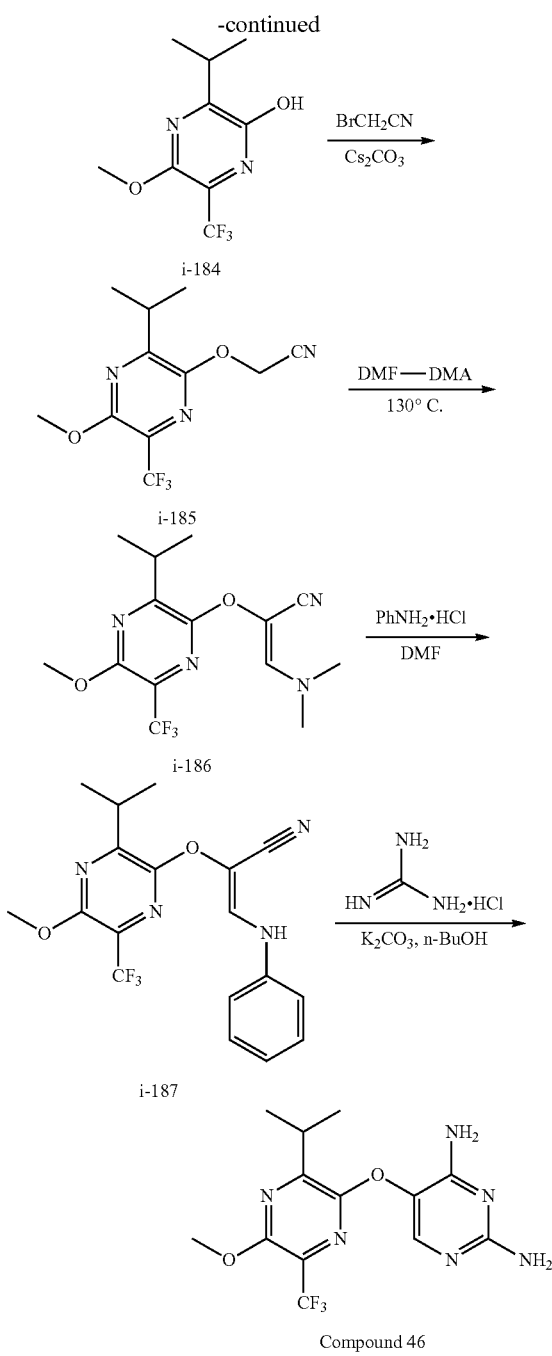

General Procedure for Preparation of Compound i-181:

To a solution of i-172 (10 g, 36.0 mmol, 1.00 eq, prepared as described in example 47) in DMF (100 mL) was added CuI (6.8 g, 36.0 mmol, 1.00 eq) and methyl-2, 2-difluoro-2-2(fluorosulfonyl)-acetate (13.8 g, 71.9 mmol, 2.00 eq) under $N_2$. The resulting reaction mixture was degassed 2 times back filling with $N_2$ each time and then heated to 120° C. for 17 h. The reaction mixture was cooled to 20° C. The reaction mixture was diluted with $H_2O$ (250 mL) and extracted with EtOAc (3×100 mL). The combined organic layers were washed with brine (2×50 mL), dried over $Na_2SO_4$, filtered and concentrated under reduced pressure. The residue was purified by column chromatography on silica gel (petroleum ether/ethyl acetate=100:1 to 50:1) to give compound i-181 (10 g, 45.4 mmol) as an oil.

$^1$H NMR (400 MHz, CHLOROFORM-d) δ=8.08 (s, 1H), 4.08 (s, 3H), 3.17-3.03 (m, 1H), 1.34 (d, J=6.8 Hz, 6H)

General Procedure for Preparation of Compound i-182:

To a stirred solution of i-181 (9.00 g, 40.9 mmol, 1.00 eq) in DCM (90 mL) was added urea hydrogen peroxide (19.2 g, 204 mmol, 5 eq) and TFAA (45 mL) at 0° C. The reaction mixture was stirred at 0° C. for 5 h. The reaction mixture was poured into ice-water (w/w=1/1) (500 mL). After as separation, the aqueous phase was extracted with EtOAc (3×500 mL). The combined organic phase were washed with brine (2×100 mL), dried over anhydrous $Na_2SO_4$, filtered and concentrated in vacuum. The residue was purified by column chromatography on silica gel (petroleum ether:ethyl acetate=20:1) to give compound i-182 (6 g, 25.4 mmol) as an oil which was used in the next step without purification. LCMS: [M+H]$^+$ 226.9

General Procedure for Preparation of Compound i-183:

The solution of i-182 (3.00 g, 12.7 mmol, 1.00 eq) in $Ac_2O$ (30 mL) was stirred and heated to 110° C. for 5 h under Ar. The reaction mixture was concentrated to dryness and then diluted with ice $H_2O$ (50 mL) and extracted with EtOAc (2×50 mL). The combined organic layers were washed with brine (50 mL), dried over $Na_2SO_4$, filtered and concentrated under reduced pressure. The residue was purified by silica column chromatography on silica gel to give i-183 (1.2 g, 4.31 mmol) as an oil which was used in the next step directly. LCMS: [M+H]$^+$ 279.0

General Procedure for Preparation of Compound i-184:

To a stirred solution of i-183 (3.00 g, 10.8 mmol, 1.00 eq) in MeOH (30 mL) was added NaOH (431 mg, 10.8 mmol, 1.00 eq). The mixture was stirred at 0° C. for 5 h. The reaction mixture was concentrated to dryness, diluted with $H_2O$ (50 mL) and extracted with EtOAc (3×50 mL). The combined organic layers were washed with brine (2×5 mL), dried over $Na_2SO_4$, filtered and concentrated under reduced pressure to give i-184 (3 g, crude) as an oil which was used in the next step directly. LCMS: [M+H]$^+$ 236.9

General Procedure for Preparation of Compound i-185:

To a stirred solution of i-184 (3.00 g, 12.7 mmol, 1.00 eq) in $CH_3CN$ (30 mL) was added $Cs_2CO_3$ (8.28 g, 25.4 mmol, 2.00 eq) and $BrCH_2CN$ (1.83 g, 15 mmol, 1.20 eq). The mixture was stirred at 90° C. for 15 h under Ar. The reaction mixture was cooled and concentrated to dryness, diluted with $H_2O$ (50 mL) and extracted with EtOAc (3×50 mL). The combined organic layers were washed with brine (50 mL), dried over $Na_2SO_4$, filtered and concentrated. The residue was purified by prep-TLC to give i-185 (600 mg, 2.18 mmol) as an oil. $^1$H NMR (400 MHz, CHLOROFORM-d) δ=5.04 (s, 2H), 4.06 (s, 3H), 3.48-3.24 (m, 1H), 1.29 (dd, J=6.8 Hz, 6H)

General Procedure for Preparation of Compound i-186:

A stirred solution of i-185 (100 mg, 317 mmol, 1.00 eq) in DMF-DMA (1.0 mL) was degassed for 3 times by sparging with $N_2$. The reaction mixture was heated to 130° C. for 13 h. The reaction mixture was cooled to RT and concentrated in vacuum to give i-186 (100 mg, crude) as an oil which was used without purification in the next step. LCMS: [M+H]$^+$ 331.0

General Procedure for Preparation of Compound i-187:

To a stirred solution of crude i-186 (100 mg, 0.30 mmol, 1.00 eq) in DMF (0.2 mL) was added aniline hydrochloride (78 mg, 0.6 mmol, 2.00 eq). The reaction mixture was heated to 120° C. for 2 h. The reaction mixture was cooled to RT, and concentrated to dryness, and diluted with $H_2O$ (5 mL) and extracted with methyl t-Butyl ether (3×5 mL). The combined organic layers were washed with brine (2×5 mL), dried over $Na_2SO_4$, filtered and concentrated to give i-187

(100 mg, crude) as an oil which was used directly without purification. LCMS: [M+H]+ 379.0

General Procedure for Preparation of Compound 46:

To a stirred solution of i-187 (100 mg, 0.26 mmol, 1.00 eq) in n-BuOH (1 mL) was added $K_2CO_3$ (73 mg, 0.53 mmol, 2.00 eq) and guanidine hydrochloride (50 mg, 0.53 mmol, 2.00 eq.) at 0° C. The reaction mixture was degassed for 3 times by sparging with $N_2$. The reaction mixture was heated to 100° C. for 15 h and cooled to RT. The reaction mixture was filtered and the filtrate was concentrated in vacuum. The residue was purified by prep-HPLC to give Compound 46 (9.0 mg, TFA) as a solid. $^1$H NMR (400 MHz, CHLOROFORM-d) δ=7.62 (s, 1H), 5.77 (br s, 2H), 4.10 (s, 3H), 3.45-3.33 (m, 1H), 1.37 (d, J=6.6 Hz, 6H) LCMS: [M+H]+ 345.0

Example 49: Synthesis of Compound 47

Compound 47 was made by the synthetic method outlined in Scheme BA:

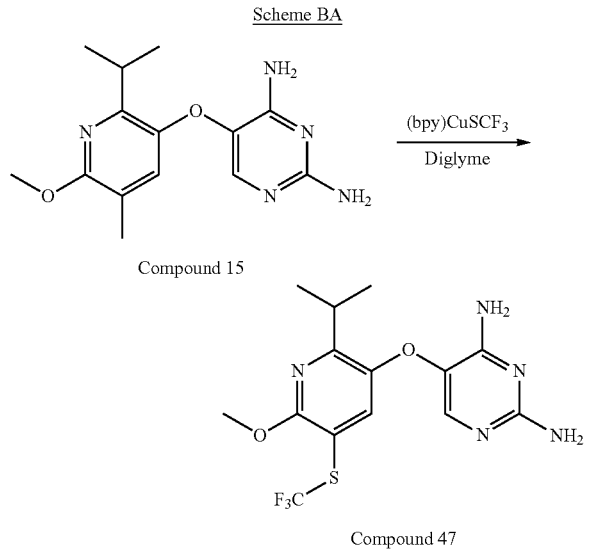

General Procedure for Preparation of Compound 47:

A suspension of compound 15 (1 g, 2.49 mmol, 1 equiv) and (bpy)CuSCF$_3$ (1.2 g, 3.74 mmol, 1.5 equiv) in diglyme (10 m) was placed in a sealed tube and heated to 130° C. for 24 h. After cooling to RT, tetrahydrofuran (100 mL) was added and the reaction was filtered through a Celite pad. The filter cake was rinsed with tetrahydrofuran (100 mL) and the filtrate was concentrated under reduced pressure. The residue was diluted with water (200 mL) and concentrated ammonium hydroxide (20 mL). After stirring at RT for 20 min, the solid was filtered off and dried and dried under vacuum at 40° C. overnight. The solid was purified by silica gel chromatography to give partially purified Compound 47 (100 mg, 80% purity by LCMS). Further purification by prep-TLC afforded Compound 47 (22 mg, >95% purity) as a solid. $^1$H NMR (400 MHz, THF-d$_8$) δ=7.45 (s, 1H), 7.43 (s, 1H), 5.91 (br s, 2H), 5.38 (br s, 2H), 4.05 (s, 3H), 3.55 (m, 1H), 2.55 (s, 1H), 1.33 (d, 6H). LCMS: [M+H]+ 376.1

Biological Assay

1321N1 human astrocytoma and HEK293 human embryonic kidney cells were stably transfected with human P2X2 and P2X3 receptor subunits to form heteromeric P2X2/3 channels and passaged in flasks. Additionally, HEK293 cells were stably transfected with human P2X3 receptor subunits to form homomeric P2X3 channels.

Approximately 24 hours before the FlexStation calcium fluorescence experiment, cells were released from their flasks, centrifuged and re-suspended in nutrient medium. The cells were aliquoted into black-wall, clear-bottom 96 well plates at a density of 25,000 cells per well and incubated overnight in a humidified, CO$_2$-enriched (5%) atmosphere at 37° C.

On the day of the experiment, cells were washed with assay buffer (calcium- and magnesium-free Hank's balanced salt solution, 20 mM HEPES, 2 mM CaCl$_2$; AB) and loaded with 4 μM Fluo-4 (P2X2/3) or Calcium 6 (Molecular Devices, according to manufacturer's instructions; P2X3) calcium-sensitive fluorescent dye in 100 μL AB.

After 1 hour of dye loading at 37° C., 1321N1-hP2X2/3 cells were washed two times with AB and test compound or vehicle added to each well in a total volume of 150 μL AB. HEK-hP2X3 cells were not washed because the Calcium 6 dye kit includes an extracellular dye that quenches unabsorbed Calcium 6 dye; test compound or vehicle were added directly to the assay plates to achieve the appropriate concentration of test compound in a total volume of 150 μL AB.

After 20 minutes incubation at RT and protected from light, the assay plates were loaded into the FlexStation microplate reader and baseline fluorescence measured with an excitation wavelength of 485 nm and emission wavelength readings centered at 525 nm (515 nm cut off).

The agonist was dispensed by the FlexStation during fluorescence measurement to construct agonist activation and antagonist inhibition curves. The final agonist concentration for inhibition was 1 μM α,β-meATP for P2X3 and 3 μM ATP for P2X2/3. Peak fluorescence was measured and curves generated using a four parameter nonlinear regression equation.

The data in Table 2 were obtained using the assay referred to above:

TABLE 2

| Compound # | Average pIC$_{50}$ | | Selectivity |
| | P2X3 | P2X2/3 | P2X3/P2X2/3 |
|---|---|---|---|
| 1 | 7.0 | <5 | >100 |
| 2 | 6.3 | <5 | >18 |
| 3 | 6.8 | <5 | >67 |
| 4 | 6.9 | 5.2 | 48 |
| 5 | 7.4 | 5.4 | 97 |
| 6 | 6.1 | <5 | >13 |
| 7 | 6.5 | <5 | >34 |
| 8 | 6.7 | <5 | >47 |
| 9 | 6.8 | <5 | >56 |
| 10 | <5 | <5 | NA |
| 11 | 6.8 | <5 | >58 |
| 12 | 5.3 | <5 | >2 |
| Comparative Compound 1 | <5 | <5 | NA |
| Comparative Compound 2 | <5 | <5 | NA |
| 13 | 7.4 | 6.7 | 5.2 |
| 14 | 5.9 | <5 | >7.1 |
| 15 | 7.2 | 6.4 | 6.5 |
| 16 | 7.2 | <5 | >145 |
| 17 | 6.0 | <5 | >10 |
| 18 | 7.2 | 5.8 | 23 |
| 19 | 8.2 | 6.7 | 28 |
| 20 | 7.7 | 6.4 | 19 |
| 21 | 6.4 | <5 | >24 |
| 22 | 5.4 | <5 | >3 |
| 23 | 5.4 | <5 | >3 |

TABLE 2-continued

| Compound # | Average pIC$_{50}$ | | Selectivity |
| | P2X3 | P2X2/3 | P2X3/P2X2/3 |
| --- | --- | --- | --- |
| 24 | 7.0 | 6.4 | 4 |
| 25 | 6.7 | <5 | >52 |
| 26 | 5.1 | <5 | >1 |
| 27 | 7.1 | 6.2 | 7.3 |
| 28 | 6.1 | 5.2 | 7.2 |
| 29 | 7.3 | 6.7 | 3.9 |
| 30 | 7.2 | 5.8 | 28 |
| 31 | 5.4 | <5 | >2.5 |
| 32 | 8.0 | 6.4 | 34 |
| 33 | 7.6 | 6.1 | 26 |
| 34 | 6.1 | 5.2 | 8.3 |
| 35 | 7.4 | 5.1 | 198 |
| 36 | 7.6 | <5 | >370 |
| 37 | 6.9 | <5 | >73 |
| 38 | 6.7 | <5 | >48 |
| 39 | 7.6 | 5.3 | 208 |
| 40 | 7.1 | <5 | >123 |
| 41 | 7.9 | 6.3 | 41 |
| 42 | 6.5 | <5 | >33 |
| 43 | 5.5 | <5 | >3.4 |
| 44 | 8.0 | 5.7 | 225 |
| 45 | 5.8 | <5 | >6.0 |
| 46 | 7.0 | 6.0 | 10 |
| 47 | 6.2 | 5.9 | 2.1 |

The potential tolerability benefits of P2X3 channel selectivity have become evident with experience from clinical studies using novel drug-like antagonists. Previously reported carbon- and oxygen-linked diaminopyrimidine analogs display either no or only modest potency selectivity favoring homotrimeric P2X3 over heterotrimeric P2X2/3 channels.

For example the most selective carbon-linked analog displays a 16 fold selectivity ratio. Oxygen-linked examples shown in Table 1 (X=O) exhibit an average P2X3-to-P2X2/3 selectivity ratio of 10 (potencies shown as pIC$_{50s}$).

The data in Table 3 shows the pIC$_{50s}$ and selectivity of diaminopyrimidine antagonists of the P2X3 and P2X2/3 ion channels of previously disclosed oxygen-linked versus sulfur linked analogs of the present disclosure.

TABLE 3

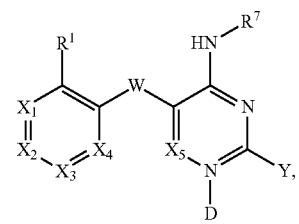

| | | X = O[1] | | | X = S | | |
| Row | R | P2X3 | P2X2/3 | Selectivity | P2X3[2] | P2X2/3[3] | Selectivity |
| --- | --- | --- | --- | --- | --- | --- | --- |
| A | OCH$_3$ | 7.6 | 6.3 | 20 | 7.0 | <5 | >100 |
| B | I | 8.0 | 7.1 | 8 | 6.8 | 5.2 | 48 |
| C | S(O)$_2$CH$_3$ | 7.0 | 6.0 | 10 | 6.3 | <5 | >18 |
| D | Cl | 7.6 | 7.0 | 4 | 6.8 | <5 | >50 |
| | Average selectivity: | | | 10 | | | >50 |

1. Mean pIC$_{50s}$ from Carter et al, Bioorg Med Chem Lett 2009 Mar 15;19(6):1628-31.
2. Mean pIC$_{50}$, hP2X3, HEK293 cells
3. Mean pIC$_{50}$, hP2X2/3, 1321N1 (astrocytoma) cells One of the most selective diaminopyrimidine inhibitors previously known, the oxygen-linked analog in row A, has pIC$_{50s}$ of 7.6 and 6.3 for the P2X3 and P2X2/3 receptors, respectively, a potency ratio of 20 (pIC$_{50}$=−log IC$_{50}$, Ratio=10^(P2X2/3pIC$_{50}$−P2X2/3pIC$_{50}$)). The corresponding sulfur-linked analog (Row A, X=S; compound 1) exhibits pIC$_{50s}$ of 7.00 and <5 (highest concentration tested is 10 µM) at P2X3 and P2X2/3, respectively, or a selectivity ratio that is greater than 100.

All other pairs of analogs shown in Table 3 exhibit a significant increase in the selectivity ratio for the sulfur-linked analog relative to the corresponding oxygen- or carbon-linked compound.

Importantly, the average selectivity for sulfur-linked compounds in Table 3 is more than 5 times greater than the average selectivity of the oxygen-linked compounds.

The trend extends beyond these four examples to all diaminopyrimidine analogs that have published inhibition activity at the P2X3 and P2X2/3 receptors for oxygen- and carbon-linked analogs the average selectivity=4, while for the sulfur-linked analogs of the present disclosure, the average selectivity is 45.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective spirit and scope of the present disclosure. All such modifications are intended to be within the scope of the claims appended hereto.

The invention claimed is:
1. A compound of Formula 1:

Formula 1 or a pharmaceutically acceptable salt thereof, wherein:
W is selected from O, S and NH;
X$_1$ is N or CR$^2$;
X$_2$ is CR$^3$;
X$_3$ is CR$^4$;
X$_4$ is CR$^5$;
X$_5$ is N or CR$^6$, provided, however, when X$_1$ is CR$^2$, W is not O;
Y is —NR$^d$R$^e$, wherein one of R$^d$ and R$^e$ is hydrogen, and the other is selected from hydrogen and C$_{1-12}$-alkyl;
D is absent;
R$^1$ is selected from C$_{1-12}$-alkyl, C$_{2-12}$-alkenyl, C$_{2-12}$-alkynyl, C$_{3-12}$-cycloalkyl, C$_{3-12}$-cycloalkenyl, C$_{1-12}$-haloalkyl, and C$_{1-12}$-hydroxyalkyl;
R$^2$, R$^3$, and R$^4$ are each independently selected from hydrogen, C$_{1-12}$-alkyl, C$_{2-12}$-alkenyl, C$_{2-12}$-alkynyl, amino, halo, amido, C$_{1-12}$-haloalkyl, C$_{1-12}$-alkoxy, hydroxy, C$_{1-12}$-haloalkoxy, nitro, C$_{1-12}$-hydroxyalkyl, C$_{2-12}$-alkoxyalkyl, C$_{1-12}$-hydroxyalkoxy, C$_{3-12}$-alkynylalkoxy, C$_{1-12}$-alkylsulfonyl, C$_{5-12}$-arylsulfonyl, cyano, C$_{6-12}$-aryl, C$_{5-12}$-heteroaryl, C$_{3-12}$-heterocyclyl, C$_{4-12}$-heterocyclylalkoxy, C$_{6-12}$-aryloxy, C$_{5-12}$-heteroaryloxy, $C_{7-12}$-arylalkyloxy, $C_{6-12}$-heteroaralkyloxy, optionally substituted phenoxy, $-(CH_2)_m-(Z)_n-(CO)-R^f$ and $-(CH_2)_m-(Z)_n-SO_2-(NR^g)_{n'}-R^f$, where m, n and n' are each independently 0 or 1;

$R^5$ is selected from hydrogen, $C_{1-12}$-alkyl, $C_{2-12}$-alkenyl, $C_{2-12}$-alkynyl, amino, amido, $C_{1-12}$-haloalkyl, $C_{1-12}$-alkoxy, hydroxy, $C_{1-12}$-haloalkoxy, nitro, $C_{1-12}$-hydroxyalkyl, $C_{2-12}$-alkoxyalkyl, $C_{1-12}$-hydroxyalkoxy, $C_{3-12}$-alkynylalkoxy, $C_{1-12}$-alkylsulfonyl, $C_{5-12}$-arylsulfonyl, cyano, $C_{6-12}$-aryl, $C_{5-12}$-heteroaryl, $C_{3-12}$-heterocyclyl, $C_{4-12}$-heterocyclylalkoxy, $C_{6-12}$-aryloxy, $C_{5-12}$-heteroaryloxy, $C_{7-12}$-arylalkyloxy, $C_{6-12}$-heteroaralkyloxy, optionally substituted phenoxy, $-(CH_2)_m-(Z)_n-(CO)-R^f$ and $-(CH_2)_m-(Z)_n-SO_2-(NR^g)_{n'}-R^f$, where m, n and n' are each independently 0 or 1;

Z is O or $NR^g$;

$R^f$ is selected from hydrogen, $C_{1-12}$-alkyl, hydroxy, $C_{1-12}$-alkoxy, amino, $C_{1-12}$-hydroxyalkyl and $C_{2-12}$-alkoxyalkyl;

each $R^g$ is independently selected from hydrogen and $C_{1-12}$-alkyl;

$R^6$ is hydrogen; and $R^7$ is hydrogen.

2. The compound of claim 1, or a pharmaceutically acceptable salt thereof, wherein $X_1$ is $CR^2$ and W is S, providing compounds of Formula 1a as follows:

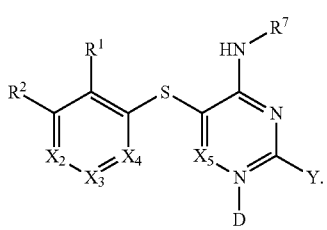

Formula 1a

3. The compound of claim 1, or a pharmaceutically acceptable salt thereof, wherein $X_1$ is N, providing compounds of Formula 1b, as follows:

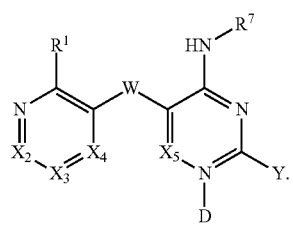

Formula 1b

4. The compound of claim 1, or a pharmaceutically acceptable salt thereof, wherein $X_5$ is N, providing compounds of Formula 1l, as follows:

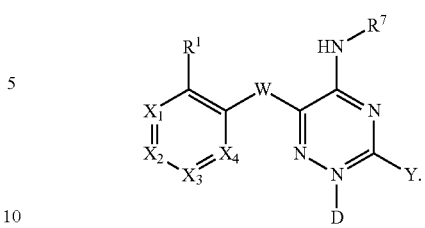

Formula 1l

5. The compound of claim 1, or a pharmaceutically acceptable salt thereof, wherein $X_5$ is $CR^6$, providing compounds of Formula 1m, as follows

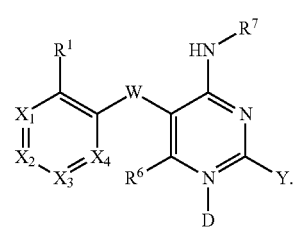

Formula 1m

6. The compound of claim 1, or a pharmaceutically acceptable salt thereof, wherein W is O.

7. The compound of claim 1, or a pharmaceutically acceptable salt thereof, wherein W is S.

8. The compound of claim 1, or a pharmaceutically acceptable salt thereof, wherein W is NH.

9. The compound of claim 1 of Formula 2, or a pharmaceutically acceptable salt thereof:

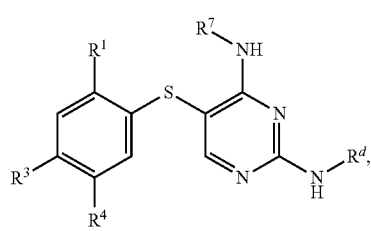

Formula 2 wherein:

$R^1$ is selected from $C_{1-12}$-alkyl, $C_{2-12}$-alkenyl, $C_{3-12}$-cycloalkyl, and $C_{3-12}$-cycloalkenyl.

10. The compound of claim 1 of Formula 3, or a pharmaceutically acceptable salt thereof:

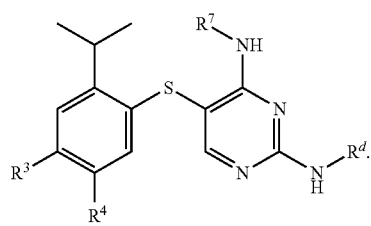

Formula 3

11. The compound of claim 1, or a pharmaceutically acceptable salt thereof, selected from:

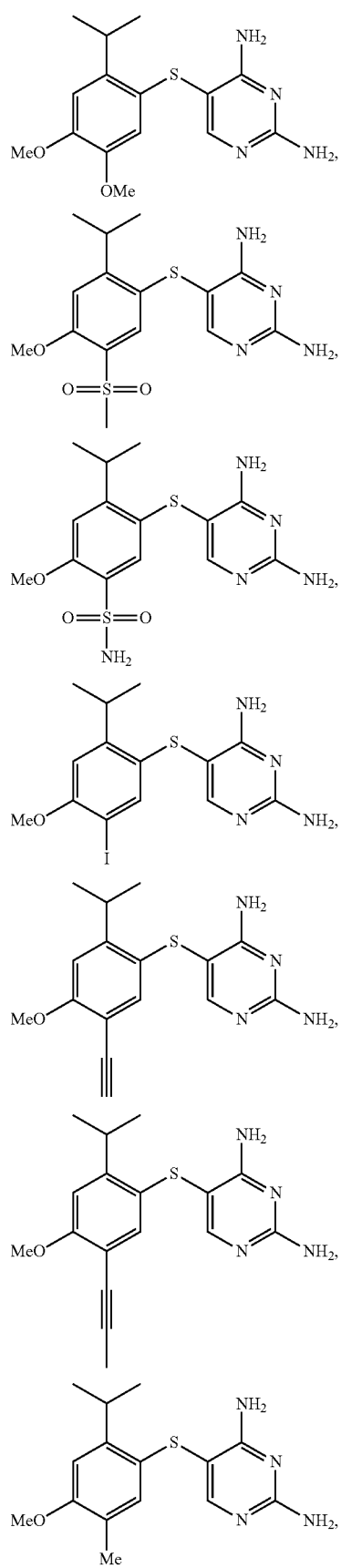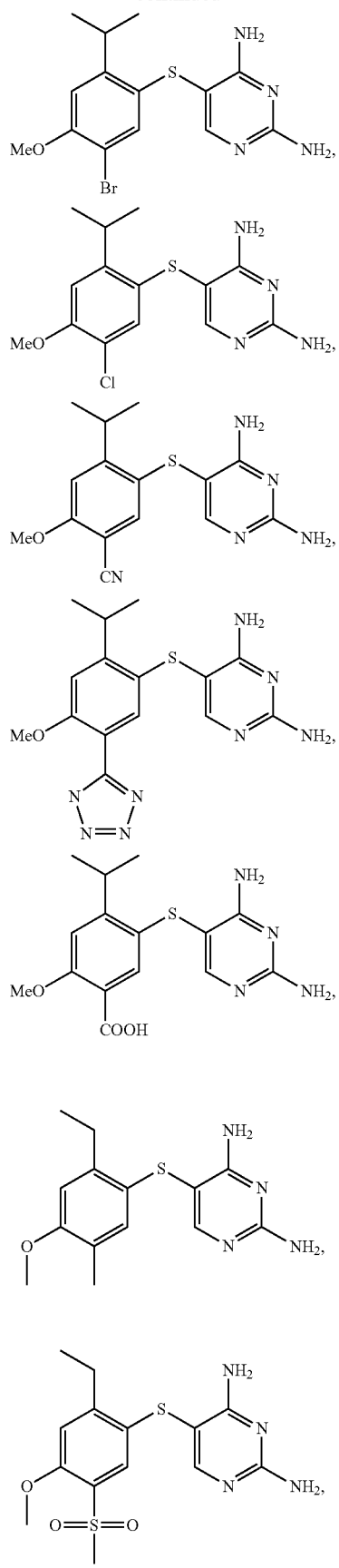

149
-continued
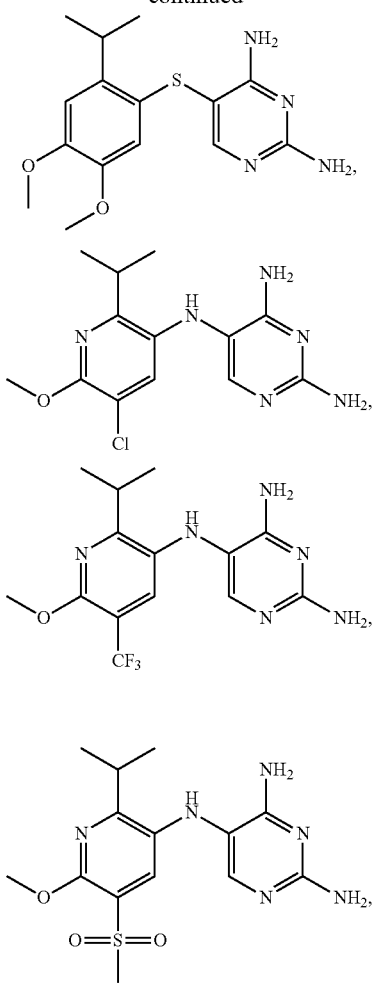
150
-continued
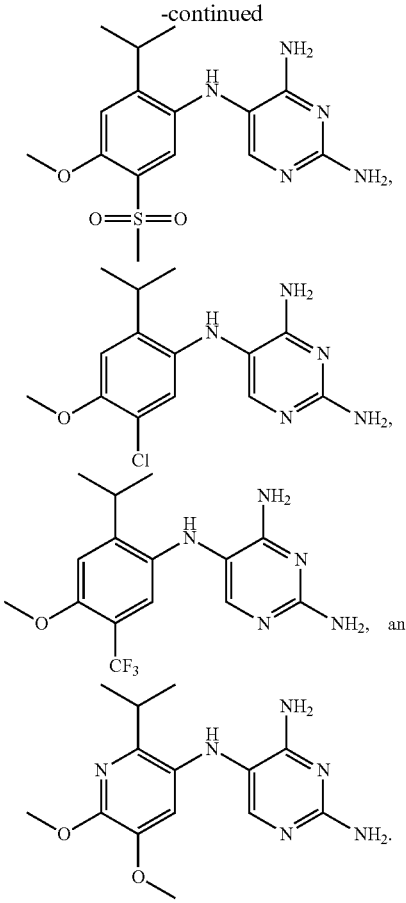
12. A composition which comprises an inert carrier and a compound of claim 1, or a pharmaceutically acceptable salt thereof.
* * * * *